US012252527B2

(12) United States Patent
Farzan et al.

(10) Patent No.: US 12,252,527 B2
(45) Date of Patent: Mar. 18, 2025

(54) CD4 MUTEINS AND METHODS OF USING THE SAME

(71) Applicants: UNIVERSITY OF FLORIDA RESEARCH FOUNDATION, INCORPORATED, Gainesville, FL (US); Emmune, Inc., Juno Beach, FL (US)

(72) Inventors: Michael Farzan, Juno Beach, FL (US); Matthew Gardner, Jupiter, FL (US); Ina Fetzer, Palm Beach Gardens, FL (US); Michael Alpert, Jupiter, FL (US); Charles Bailey, Jupiter, FL (US)

(73) Assignees: UNIVERSITY OF FLORIDA RESEARCH FOUNDATION, INCORPORATED, Gainesville, FL (US); EMMUNE, INC., Juno Beach, FL (US)

( * ) Notice: Subject to any disclaimer, the term of this patent is extended or adjusted under 35 U.S.C. 154(b) by 1126 days.

(21) Appl. No.: 16/982,134

(22) PCT Filed: Mar. 21, 2019

(86) PCT No.: PCT/US2019/023422
§ 371 (c)(1),
(2) Date: Sep. 18, 2020

(87) PCT Pub. No.: WO2019/183387
PCT Pub. Date: Sep. 26, 2019

(65) Prior Publication Data

US 2023/0159616 A1 May 25, 2023

Related U.S. Application Data

(60) Provisional application No. 62/645,903, filed on Mar. 21, 2018.

(51) Int. Cl.

| | |
|---|---|
| *C07K 14/73* | (2006.01) |
| *A61P 31/18* | (2006.01) |
| *C12N 15/86* | (2006.01) |

(52) U.S. Cl.
CPC ........ *C07K 14/70514* (2013.01); *A61P 31/18* (2018.01); *C12N 15/86* (2013.01); *C07K 2319/30* (2013.01); *C12N 2750/14143* (2013.01)

(58) Field of Classification Search
CPC .......... C07K 14/70514; C07K 2319/30; A61P 31/18; A61P 31/12; C12N 15/86; C12N 2750/14143; A61K 38/00; A61K 38/1774
See application file for complete search history.

(56) References Cited

U.S. PATENT DOCUMENTS

| | | | | |
|---|---|---|---|---|
| 5,387,484 | A | 2/1995 | Doany et al. | |
| 5,688,676 | A | 11/1997 | Zhou et al. | |
| 5,691,176 | A | 11/1997 | Lebkowski et al. | |
| 5,741,683 | A | 4/1998 | Zhou et al. | |
| 5,851,828 | A | 12/1998 | Seed et al. | |
| 6,156,303 | A | 12/2000 | Russell et al. | |
| 7,587,281 | B2 * | 9/2009 | Gershoni | G16B 20/50 435/7.1 |
| 8,163,543 | B2 | 4/2012 | Urabe et al. | |
| 2002/0081721 | A1 | 6/2002 | Allen et al. | |
| 2007/0005262 | A1 * | 1/2007 | Gershoni | G16B 20/50 702/19 |
| 2009/0247734 | A1 | 10/2009 | Hendrickson et al. | |
| 2011/0305670 | A1 | 12/2011 | Farzan | |
| 2016/0008374 | A1 | 1/2016 | Geleziunas et al. | |
| 2016/0340405 | A1 | 11/2016 | Gardner et al. | |
| 2019/0247734 | A1 | 8/2019 | Wood, V | |

FOREIGN PATENT DOCUMENTS

| | | | |
|---|---|---|---|
| WO | 92/00985 | A1 | 1/1992 |
| WO | 96/17947 | A1 | 6/1996 |
| WO | 00/24916 | A1 | 5/2000 |
| WO | 00/47757 | A1 | 8/2000 |
| WO | 2011/077093 | A1 | 6/2011 |
| WO | 2014/150748 | A2 | 9/2014 |

OTHER PUBLICATIONS

Piatier-Tonneau et al. Mutations in the D strand of the human CD4 V1 domain affect CD4 interactions with human immunodeficiency virus envelope glycoprotein gp120 and HLA class II antigens similarity. PNAS (1991), 88: 6858-6862.*
Meyerson et al. (Positive selection of primate genes that promoter HIV-1 replication. Virology (2014), 455-455: 291-298). (Year: 2014).*
African Application No. AP/P/2020/012733, African Search Report, mailed Oct. 18, 2022.
Altschul et al., Gapped BLAST and PSI-BLAST: a new generation of protein database search programs, Nucleic Acids Res., 25(17):3389-3402 (1997).
Altschul et al., Issues in searching molecular sequence databases, Nat. Genet., 6:119-129 (1994).
Altschul, A protein alignment scoring system sensitive at all evolutionary distances, J. Mol. Evol., 36:290-300 (1993).
Anselmo et al., Nanoparticles in the clinic, Bioeng. Transl. Med., 1(1):10-29 (2016).
Ashkenazi et al., Resistance of primary isolates of human immunodeficiency virus type 1 to soluble CD4 is independent of CD4-rgp120 binding affinity, Proc. Natl. Acad. Sci. USA., 88(16):7056-60 (1991).

(Continued)

*Primary Examiner* — Iqbal H Chowdhury
(74) *Attorney, Agent, or Firm* — MARSHALL, GERSTEIN & BORUN LLP

(57) ABSTRACT

The invention relates to proteins that contain the CD4 domain 1 and the CD4 domain 2 (CD4 D1D2), wherein the CD4 D1D2 contains one or more mutations compared to wild-type human CD4 D1D2, and to methods of using the proteins for treating a human immunodeficiency virus (HIV) infection in a subject.

23 Claims, 41 Drawing Sheets

Specification includes a Sequence Listing.

(56) References Cited

OTHER PUBLICATIONS

Byrn et al., Biological properties of a CD4 immunoadhesin, Nature, 344(6267):667-70 (1990).
Capon et al., Designing CD4 immunoadhesins for AIDS therapy, Nature, 337(6207):525-31 (1989).
Chamow et al., CD4 immunoadhesins in anti-HIV therapy: new developments, Int. J. Cancer Suppl., 7:69-72 (1992).
Chamow et al., Modification of CD4 immunoadhesin with monomethoxypoly(ethylene glycol) aldehyde via reductive alkylation, Bioconjug Chem., 5(2):133-40 (1994).
Chen et al., Engineered Single Human CD4 Domains as Potent HIV-1 Inhibitors and Components of Vaccine Immunogens, Journal of Virology, 85:(18):9395-9405 (2011).
Daar et al., High concentrations of recombinant soluble CD4 are required to neutralize primary human immunodeficiency virus type 1 isolates, Proc. Natl. Acad. Sci. USA., 87(17): 6574-8 (1990).
Deen et al., A soluble form of CD4 (T4) protein inhibits AIDS virus infection, Nature, 331(6151):82-4 (1988).
European Application No. 19771245.8, European Search Report and Opinion, mailed Jun. 9, 2022.
Fisher et al., HIV infection is blocked in vitro by recombinant soluble CD4, Nature, 331(6151):76-8 (1988).
Gao et al., Clades of Adeno-associated viruses are widely disseminated in human tissues, J. Virol., 78(12):6381-6388 (2004).
Gardner et al., AAV-expressed eCD4-Ig provides durable protection from multiple SHIV challenges, Nature, 519(7541):87-91 (2015).
Harris et al., Characterization of a soluble form of human CD4. Peptide analyses confirm the expected amino acid sequence, identify glycosylation sites and demonstrate the presence of three disulfide bonds, European Journal of Biochemistry, 188(2):291-300 (1990).
Henikoff et al., Amino acid substitution matrices from protein blocks, Proc. Natl. Acad. Sci. USA., 89:10915-10919 (1992).
Hessell et al., Fc receptor but not complement binding is important in antibody protection against HIV, Nature, 449(7158):101-4 (2007).
Hodges et al., Phase 1 study of recombinant human CD4-immunoglobulin G therapy of patients with AIDS and AIDS-related complex, Antimicrob Agents Chemother, 35(12):2580-6 (1991).
Hussey et al., A soluble CD4 protein selectively inhibits HIV replication and syncytium formation, Nature, 331(6151):78-81 (1988).
International Application No. PCT/US19/23422, International Preliminary Report on Patentability, mailed Oct. 1, 2020.
International Application No. PCT/US19/23422, International Search Report and Written Opinion, mailed Aug. 27, 2019.
Kahn et al., The safety and pharmacokinetics of recombinant soluble CD4 (rCD4) in subjects with the acquired immunodeficiency syndrome (AIDS) and AIDS-related complex. A phase 1 study, Ann. Intern. Med., 112(4):254-61 (1990).
Karlin et al., Methods for assessing the statistical significance of molecular sequence features by using general scoring schemes, Proc. Natl. Acad. Sci. USA., 87:2264-2268 (1990).
Mueller et al., Production and discovery of novel recombinant adeno-associated viral vectors, Curr. Protoc. Microbiol., Chapter 14:Unit14D.1 (2012).
Nobbmann et al., Dynamic light scattering as a relative tool for assessing the molecular integrity and stability of monoclonal antibodies, Biotechnol. Genet. Eng. Rev., 24:117-28 (2007).
O'Brien et al., Mapping genetic determinants for human immunodeficiency virus type 1 resistance to soluble CD4, J. Virol., 66(5):3125-30 (1992).
Saha et al., Design and Characterization of Stabilized Derivatives of Human CD4D12 and CD4D1, Biochemistry, 50(37):7891-7900 (2011).
Schooley et al., Recombinant soluble CD4 therapy in patients with the acquired immunodeficiency syndrome (AIDS) and AIDS-related complex. A phase I-II escalating dosage trial, Ann. Intern. Med., 112(4):247-53 (1990).
Smith et al., Blocking of HIV-1 infectivity by a soluble, secreted form of the CD4 antigen, Science, 238(4834):1704-7 (1987).
Srivastava, Adeno-associated virus-mediated gene transfer, J. Cell Biochem., 105(1):17-24 (2008).
Traunecker et al., Soluble CD4 molecules neutralize human immunodeficiency virus type 1, Nature, 331(6151):84-6 (1988).
Tsui et al., An efficient phage plaque screen for the random mutational analysis of the interaction of HIV-1 gp120 with human CD4., JBC., 267(13): 9361-9367 (1992).
Watanabe et al., Effect of recombinant soluble CD4 in rhesus monkeys infected with simian immunodeficiency virus of macaques, Nature, 337(6204):267-70 (1989).
Weitzman et al., Adeno-associated virus biology, Adeno-Associated Virus: Methods and Protocols, 807:1-23 (2011).
Xie et al., Structure-Activity Relationships in the Binding of Chemically Derivatized CD4 to gp120 from Human Immunodeficiency Virus, J. Med. Chem., 50(20):4898-4908 (2007).
R. Murray et al., Biochimiya cheloveka (Human Biochemistry), Mir. 1993, vol. 1, p. 34 (translated preface provided).

* cited by examiner

FIGURE 4
A.

```
                                            10s       20s       30s       40s       50s
Apes                                 123456789012345678901234567890123456789012--345678901234567 8
Human                                KKVVLGKKGDTVELTCTASQKKSIQFHWKNSNQIKILGNQGS---FLTKGPSKLNDRVDSR
Chimp                                KKVVLGKKGDTVELTCTASQKKSIQFHWKNSNQTKILGNQGS---FLTKGPSKLNDRVDSR
Bonobo                               KKVVLGKKGDTVELTCTASQKKSIQFHWKNSNQTKILGNQGS---FLTKGPSKLNDRVDSR
Gorilla                              NKVVLGKKGDTVELNCTASQKKSIQFHWKNSNQMKILGNQGS---FLTKGPSKLSDRADSR
Bornean orangutan                    KKVVLGKKGDTVELTCTASQKKSIQFHWKNSNQTKILGNQGS---FLTKGPSKLSNRADSR
White-cheeked gibbon                 KKVVLGKKGDTVELTCTASPKKSIQFHWKNSNQIKILGNQGS---FLTKGPSKLSDRADSR
Agile gibbon                         KKVVLGKKGDTVELTCTASPKKSIQFHWKNSNQIKILGNQGS---FLTKGPSKLSDRADSR
Siamang                              KKVVLGKKGDTVELTCIASPKKSIQFHWKNSNQIKILGNQGS---FLTKGPSKLSDRADSR 10s       20s       30s       40s       50s
Old World Monkeys                    123456789012345678901234567890123456789012--345678901234567 8
Colobus monkey                       KNVVLGKKGDTVELTCNAPSKKNIQFHWKNSNQIKILGNQGS---FLTKGPSKLSDRADSR
Colobus guereza                      KNVVLGKKGDTVELTCNAPSKKNIQFHWKNSNQIKILGNQGS---FLTKGPSKLSDRADSR
Angolan colobus                      KNVVLGKKGDTVELTCNAPPKKNIQFHWKNSNQIKILGNQGS---FLTKGPSKLSDRADSR
African green monkey                 XXVVLGKKGDTVELTCNASQKTTTQFHWKNSNQTKILGKQGS---FLTKGSSKLRDRIDSR
Vervet monkey                        KKVVLGKKGDTVELTCNASQKTTTQFHWKNSNQTKILGKQGS---FLTKGSSKLRDRIDSR
Sabaeus monkey                       KKVVLGKKGDTVELTCNASQNTTTQFHWKNSNQIKILGKQGS---FLTKGSSKLRDRIDSR
Tantalus monkey                      XXVVLGKKGDTVELTCNASQNTTTQFHWKNSNQIKILGKQGS---FLTKGSSKLRDRIDSR
Red guenon                           XXVVLGKKGDTVELTCNASQKTTTQFHWKNSNQMKILGKQGS---FLTKGPSKLRDRTDSR
Sooty mangabey                       KNVVLGKKGDTVELACNASQKKSTQFHWKNSRQIKILGNQGS---FLTKGSSKLSDRADSR
Mandrill                             RNVVLGKKGDTVELTCNASQKKNTPFHWKNSRQIKILGNQGSS--FLTKGPSKLSDRIDSR
Black snub-nose monkey               KKVVLGKKGDTVELTCSASQKKNIQFHWKNSNQIKILGNQGS---FLTKGPSKLSDRADSR
Golden snub-nose                     KKVVLGKKGDTVELTCSASQKKNIQFHWKNSNQIKILGNQGS---FLTKGPSKLSDRADSR
Leaf monkey                          KKVVLGKKGDTVELTCSASQKKNIQFHWKNSRQIKILGNQGS---FLTKGPSKLSDRADSR
Francoi's langur                     KKVVLGKKGDTVELTCSASQKKNIQFHWKNSRQIKILGNQGS---FLTKGPSKLSDRADSR
Pig-tailed macaque                   KKVVLGKKGDTVELTCNASQKKNIQFHWKNSNQIKILGNQGS---FLTKGPSKLSDRADSR
Rhesus macaque                       KKVVLGKKGDTVELTCNASQKKNTQFHWKNSNQIKILGIQGS---FLTKGPSKLSDRADSR
Cynomolgus macaque                   KKVVLGKKGDTVELTCNASQKKNTQFHWKNSNQIKILGIQGS---FLTKGPSKLSDRADSR
Japanese macaque                     KKVVLGKKGDTVELTCNASQKKNTQFHWKNSNQIKILGIQGS---FLTKGPSKLSDRADSR
Wolf's guenon                        KKVVLGKKGGTVELTCNATQKKNTQFHWKNSNQIKILGNQGS---FLTKGPSKLSDRADSR
Talapoin                             KKVVLGKKGDTVELTCNASQKKSTQFHWKNSNQIKILGNQGS---FLTKGPSKLSDRADSR
Gray-cheeked mangabey                KKVVLGKKGDTVELTCNASQKKSTQFHWKNSNQIKILGNQGS---FLTKGPSKLSDRADSR
Olive baboon                         KKVVLGKKGDTVELTCNASQKKSTQFHWKNSNQIKILGNQGS---FLTKGPSKLSDRADSR 10s       20s       30s       40s       50s
New World Monkeys                    123456789012345678901234567890123456789012--345678901234567 8
Coppery titi                         KTVVLGKKGETVELSCETSLKKTLQFYWKTSDQIKILGIQGF--LLTKGQSKLADRIDSK
Marmoset                             KTVVLGKKGEMVELPCETSLKKKLQFHWKTSNQIKILGIQGS--FVTKGQSKLANRIDSK
Squirrel monkey                      KTVVLGKKGEVVELPCETSLKKNVPFHWKTSDRIKILGVQNY--FVTRGQSKLTDRIDSK
Bolivian squirrel monkey             RTVVLGKKGETVELPCETSLKKNVPFHWKTSDQIKILGVQNY--FVTRGQSKLTDRIDSK
Howler monkey                        KTVVLGRKGETVELSCETSPKKNLQFHWKTSNQIKILGVQGS--SLTKGQSKLADRIDSK
Bolivian red howler monkey           KTVVLGRKGETVELSCETSPKKNLQFHWKTSNQIKILGVQGS--SLTKGQSKLADRIDSK
Panamanian white-throated capuchin   RTVVLGKKGEMVELPCETSLKKNTQFHWKTSDQIKILGIQNS--FLTRGQSKLADRIDSK
Nancy Ma's owl monkey                KTVVLGEKGETVELPCETSLKKNVQFHWKTSDQIKILGNQGS--FLTRGQSKLADRIDSK
Azara's owl monkey                   KTVVLGEKGETVELPCETSLKKNVQFHWKTSDQIKILGIQGS--FLTRGQSKLADRIDSK
Spix's owl monkey                    KTVVLGEKGETVELPCETSLKKNVQFHWKTSDQIKILGIQGS--FLTRGQSKLADRIDSK 10s       20s       30s       40s       50s
Prosimians                           123456789012345678901234567890123456789012--345678901234567 8
Tarsier                              KEVVLAKKGETGELPCQGSPKKSMSFSWKYSNQVMILRNQGS--PWITGSSRLKPRVESK
Sunda flying lemur                   KEVILGKKGDMVELPCKASEKRYLLFSWKHSDQIKILGNQGS--PWITGSSKLKHRVESR
Gray mouse lemur                     KEVVLGRKGDTVELPCKASQKKAIPFAWKHSNQTRILGKQGSSYFETTGPSMKKNRVESK
Coquerel's sifaka                    KEVVLGRKGDTVELPCKASQKKSMPFAWKHSNQTRILGKQGSSYFETTGPSMKKNRVESK
```

```
                                  60s       70s       80s       90s       100s      110s
                          9012345678901234567890123456789012345678901234567890123456789012345678
Apes
Human                     RSLWDQGNFPLIIKNLKIEDSDTYICEVEDQKEEVQLLVFGLTANSDTHLLQGQSLTLTL
Chimp                     RSLWDQGNFTLIIKNLKIEDSDTYICEVGDQKEEVQLLVFGLTANSDTHLLQGQSLTLTL
Bonobo                    RSLWDQGNFPLIIKNLKIEDSDTYICEVGDQKEEVQLLVFGLTANSDTHLLQGQSLTLTL
Gorilla                   RSLWDQGNFPLIIKNLKIEDSDTYICEVEGQKEEVQLLVFGLTANSDTHLLQGQSLTLTL
Bornean orangutan         RSLWDQGNFPLIIKNLKIEDSDTYICEVEDQKEEVQLLVFGLTANSDTHLLQGQSLTLAL
White-cheeked gibbon      KSLWDQRNFPLIIKNLKIEDSDTYICEVEDQKEEVQLLVFGLTANSDTHLLQGQSLTLTL
Agile gibbon              KSLWDQRNFPLIIKNLKIEDSDTYICEVEDQKEEVQLLVFGLTANSDTHLLQGQSLTLTL
Siamang                   KSLWDQGNFPLIIKNLKIEDSDTYICEVEDQKEEVQLLVFGLTANSDTHLLQGQSLTLTL 60s       70s       80s       90s       100s      110s
                          9012345678901234567890123456789012345678901234567890123456789012345678
Old World Monkeys
Colobus monkey            KSLWDQGCFSMIIKNLKIEDSDTYICEVEDKKEEVELLVFGLTASSDTHLLQGQSLTLTL
Colobus guereza           KSLWDQGCFSMIIKNLKIEDSDTYICEVEDKKEEVELLVFGLTASSDTHLLQGQSLTLTL
Angolan colobus           KSLWDQGCFSMIIKNLKIEDSDTYICEVEDKKEEVELLVFGLTASSDTHLLQGQSLTLTL
African green monkey      KSLWDQGCFSMIIKNLKIEDSETYICEVENKKEEVELLVFGLTASSDTHLLQGQSLTLTL
Vervet monkey             KSLWDQGCFSMIIKNLKIEDSETYICEVENKKEEVELLVFGLTASSDTHLLQGQSLTLTL
Sabaeus monkey            KSLWDQGCFSMIIKNLKIEDSETYICEVENKKEEVELLVFGLTASSDTHLLQGQSLTLTL
Tantalus monkey           KSLWDQGCFSMIIKNLKIEDSETYICEVENKKEEVELLVFGLTASSDTHLLQGQSLTLTL
Red guenon                KSLWDQGCFSMIIKNLKIEDSETYICEVENKKEEVELLVFGLTASSDTHLLQGQSLTLTL
Sooty mangabey            KSLWDQGCFSMIIKNLKIEDSETYICEVENKKEEVELLVFGLTASSDTHLLEGQSLTLTL
Mandrill                  KSLWDQGCFSMIIKNLKIEDSETYICEVEDKKEEVELLVFGLTASSDTHLLEGQSLTLTL
Black snub-nose monkey    KSLWDQGCFSMIIKNLKIEDSETYICEVEDKKEEVELLVFGLTASSDTHLLQGQSLTLTL
Golden snub-nose          KSLWDQGCFSMIIKNLKIEDSETYICEVEDKKEEVELLVFGLTASSDTHLLQGQSLTLTL
Leaf monkey               KSLWDQGCFSMIIKNLKIEDSETYICEVEDKKEEVELLVFGLTASSDTHLLQGQSLTLTL
Francoi's langur          KSLWDQGCFSMIIKNLKIEDSETYICEVEDKKEEVELLVFGLTASSDTHLLQGQSLTLTL
Pig-tailed macaque        KSLWDQGCFSMIIKNLKIEDSNTYICEVENKKEEVELLVFGLTASSDTHLLEGQSLTLTL
Rhesus macaque            KSLWDQGCFSMIIKNLKIEDSDTYICEVENKKEEVELLVFGLTASSDTHLLEGQSLTLTL
Cynomolgus macaque        KSLWDQGCFSMIIKNLKIEDSDTYICEVENKKEEVELLVFGLTASSDTHLLEGQSLTLTL
Japanese macaque          KSLWDQGCFSMIIKNLKIEDSDTYICEVENKKEEVELLVFGLTASSDTHLLEGQSLTLTL
Wolf's guenon             KSLWDQGCFSMIIKNLKIEDSETYICEVEDKKEEVELLVFGLTASSDTHLLQGQSLTLTL
Talapoin                  KSLWDQGCFSMIIKNLKIEDSETYICEVEDKKEEVELLVFGLTASSDTHLLQGQSLTLTL
Gray-cheeked mangabey     KSLWDQGCFSMIIKNLKIEDSETYICEVEDKKEEVELLVFGLTASSDTHLLEGQSLTLTL
Olive baboon              KSLWDQGCFSMIIKNLKIEDSETYICEVEDKKEEVELLVFGLTASSDTHLLEGQSLTLTL 60s       70s       80s       90s       100s      110s
                          9012345678901234567890123456789012345678901234567890123456789012345678
New World Monkeys
Coppery titi              KSSWDRGSFPLIIKNVQVEDSETYICEVESKKEEVELQVFGLTATPDTHLLQGNLTLTL
Marmoset                  QSSWDRGSFPLIIRNVQVEDSETYICEVESKKEEVELQVFGLTVNPDTHLLQGQSLTLTL
Squirrel monkey           RSSWDRGSFPLLIKDARIEDSETYICEVESKKEEVELQVFGLTANPDTHLLQGQSLTLTL
Bolivian squirrel monkey  KSSWDRGSFPLLIKDARIEDSETYICEVESKKEEVELQVFGLTANPDTHLLQGQSLTLTL
Howler monkey             KSSWDRGSFPLIIKNVQVEDSETYICEVESKKEEVELQVFGLTANPDTHLLQGQSLTLTL
Bolivian red howler monkey KSSWDRGSFPLIIKNVQVEDSETYICEVESKKEEVELQVFGLTANPDTHLLQGQSLTLTL
Panamanian white-throated capuchin KSSWDRGSFPLLIKNVQVEDSETYICEVESKKEEVELQVFGLTANPDTHLLQGQSLTLTL
Nancy Ma's owl monkey     KSSWDRGSFPLIIKNVQVEDSETYICEVERKKEEVELQVFGLTASPDTHLLQGQSLTLTL
Azara's owl monkey        KSSWDRGSFPLIIKNVRVEDSETYICEVERKKEEVELQVFGLTASPDTHLLQGQSLTLTL
Spix's owl monkey         KSSWDRGSFPLIIKNVQVEDSETYICEVERKKEEVELQVFGLTASPDTHLLQGQSLTLTL 60s       70s       80s       90s       100s      110s
                          9012345678901234567890123456789012345678901234567890123456789012345678
Prosimians
Tarsier                   KSLWDQGSFPLIIRNLEVGDSGTYICEVQDRKTEVELLVFALTANSNTRLLQGQSLTLSL
Sunda flying lemur        KNLWDQGSFPLVIKNLEVEDSGMYICEVENRKIEVELLVFGLIANSDTRLLQGQSLTLTL
Gray mouse lemur          KNLWDQGSFPLVIKNLEMKDSGSYICEVEDKK-EVELLVFGLTANSGTRVLEGQSLTLTL
Coquerel's sifaka         KNLWDQGSFPLIIKNLEMQDSGTYICEVEDKK-EVELLVFGLTANSGTRVLEGQSLTLTL
```

```
                                              120s      130s      140s      150s      160s      170s
                                    901234567890123456789012345678901234567890123456789012345678
Apes
Human                               ESPPGSSPSVQCRSPRGKNIQGGKTLSVSQLELQDSGTWTCTVLQNQKKVEFKIDIVVLA
Chimp                               ESPPGSSPSVQCRSPRGKNIQGGKTLSVSQLELQDSGTWTCTVLQNQKKVEFKIDIVVLA
Bonobo                              ESPPGSSPSVQCRSPRGKNIQGGKTLSVSQLELQDSGTWTCTVLQNQKKVEFKIDIVVLA
Gorilla                             ESPPGSSPSVQCRSPRGKNIQGGKTLSVSQLELQDSGTWTCTVLQNQEKVEFKIDIVVLA
Bornean orangutan                   ESPPGSSPSVQCRSPTGKNIQAGKTLSVSQLELQDSGTRTCAVLQDQKKVEFKIDIVVLA
White-cheeked gibbon                EGPPGSSPSVQCRSPRGKNIQGGKTLSVSQLELQDSGTWTCTVLQDQKKVEFKIDIVVLA
Agile gibbon                        ESPPGSSPSVQCRSPRGKNIQGGKTLSVPQLELQDSGTWTCTVLQDQKKVEFKIDIVVLA
Siamang                             EGPPGSSPSVQCRSPRGKNIQGGKTLSVPQLELQDSGTWTCTVLQDQKKVEFKIDIVVLA 120s      130s      140s      150s      160s      170s
                                    901234567890123456789012345678901234567890123456789012345678
Old World Monkeys
Colobus monkey                      ESPPGTSPSVQCRSPRGKNIQGGKTLSVPQLERQDSGTWTCTVSQDQKRVEFKIDIVVLA
Colobus guereza                     ESPPGTSPSVQCRSPRGKNIQGGKTLSVPQLERQDSGTWTCTVSQDQKRVEFKIDIVVLA
Angolan colobus                     ESPPGTSPSVQCRSPRGKNIQGGKTLSVPQLERQDSGTWTCTISQDQKRVEFKIDIVVLA
African green monkey                ESPPGSSPSVKCRSPRGKNIQGGKTLSVPQLERQDSGTWTCTVSQDQNTVEFKIDIVVLA
Vervet monkey                       ESPPGSSPSVKCRSPRGKNIQVGRTLSVPQLERQDSGTWTCTVSQDQNTVEFKIDIVVLA
Sabaeus monkey                      ESPPGSSPSVKCRSPRGKNIQGGRTLSVPQLERQDSGTWTCTVSQDQNTVEFKIDIVVLA
Tantalus monkey                     ESPPGSSPSVKCRSPRGKNIQGGRTLSVPQLERQDSGTWTCTVSQDQNTVEFKIDIVVLA
Red guenon                          ESPPGSSPSVKCRSPRGKNIQGGRTLSVPQLERQDSGTWTCTVSQDQNTVEFKIDIVVLA
Sooty mangabey                      ESPPGSSPSVKCRSPRGKNIQGGRTLSVPQLERQDSGTWTCTVSQDQKTVEFKIDIVVLA
Mandrill                            ESPPGSSPSVKCRSPRGKNIQGGRTLSVPQLERQDSGTWTCTVSQDQRTVEFKIDIVVLA
Black snub-nose monkey              ESPPGSSPSVQCRSPRGKNIQGGKTLSVPQLERQDSGIWTCTVSQDQKTVEFKIDIMVLA
Golden snub-nose                    ESPPGSSPSVQCRSPRGKNIQGGKTLSVPQLERQDSGIWTCTVSQDQKTVEFKIDIMVLA
Leaf monkey                         ESPPGSSPSVQCRSPRGKNIQGGKTLSVPQLERQDSGIWTCTVSQDQNTVEFKIDIVVLA
Francoi's langur                    ESPPGSSPSVQCRSPRGKNIQGGKTLSVPQLERQDSGIWTCTVSQDQKTVEFKIDIVVLA
Pig-tailed macaque                  ESPPGSSPSVKCRSPGGKNIQGGRTLSVPQLERQDSGTWTCTVSQDQKTVEFKIDIVVLA
Rhesus macaque                      ESPPGSSPSVKCRSPGGKNIQGGRTLSVPQLERQDSGTWTCTVSQDQKTVEFKIDIVVLA
Cynomolgus macaque                  ESPPGSSPSVKCRSPGGKNIQGGRTLSVPQLERQDSGTWTCTVSQDQKTVEFKIDIVVLA
Japanese macaque                    ESPPGSSPSVKCRSPGGKNIQGGRTISVPQLERQDSGTWTCTVSQDQKTVEFKIDIVVLA
Wolf's guenon                       ESPPGSSPSVKCRSPRGKNIQRGRTLSVPQLERQDSGTWTCTVSQDQKTVEFNIDIVVLA
Talapoin                            ESPPGSSPSVKCRSPRGKNIQGGRTLSVPQLERQDSGTWTCTVSQDQNTVEFKIDIVVLA
Gray-cheeked mangabey               ESPPGTSPSVKCRSPRGKNIQVGRTLSVPQLERQDSGTWTCNVSQDQKTVEFKIDIVVLA
Olive baboon                        ESPPGTSPSVKCRSPRGKNIQGGRTLSVPQLERQDSGTWTCNVSQDQKTVEFKIDIVVLA 120s      130s      140s      150s      160s      170s
                                    901234567890123456789012345678901234567890123456789012345678
New World Monkeys
Coppery titi                        ESPPGSSPSVECTSPRGKRISGMKTLFLSQLVIQDSGTGRCALCQBRELV-FQINIVVLA
Marmoset                            ESPPGSSPSVKCMSPRGKTIRGMKTLFMSQLEIPDSGTWKCTVSQBLELV-FKINIVVLA
Squirrel monkey                     ESPPGSSPSVECTSPRGKRIRGKKTLSVSQLGIPDSGTWKCTVFQBLELV-FEINIVVLA
Bolivian squirrel monkey            ESPPGSSPSVECTSPRGKRIRGKKTLSVSQLGIPDSGTWKCTVFQBLELV-FEINIVVLA
Howler monkey                       ESPPGSSPSVECTSPRGKRIQGMKSLSLSQLEIQDSGTWKCTVSQBPQLV-FKINIVVLA
Bolivian red howler monkey          ESPPGSSPSVECTSPRGKRIQGMKSLSLSQLEIQDSGTWKCTVSQBPQLV-FKINIVVLA
Panamanian white-throated capuchin  ESPPGSSPSVECTSPRGKRIQGMKSLSLSQLEIQDSGTWKCTVSQBLELV-FKINIVVLA
Nancy Ma's owl monkey               ESPPGSSPSVECTSPRGKRIQGMKNLSVSQLEIQDSGTWKCTVSQRPELL-FKINVVLA
Azara's owl monkey                  ESPPGSSPSVECTSPRGKRIQGMKTLSVSQLEIQDSGTWKCTVSQBPELL-FKINVVLA
Spix's owl monkey                   ESPPGSSPSVECTSPRGKRIQGMKTLSVSQLEIQDSGTWKCTVSQBPELL-FKINVVLA 120s      130s      140s      150s      160s      170s
                                    901234567890123456789012345678901234567890123456789012345678
Prosimians
Tarsier                             EGPQGRNPSLQCQGPGNKKISGVGSLSLSQLGPQRSGRWTCAVSQDQKTLEFSKDVVVLV
Sunda flying lemur                  ESPPDSNPSVQWKSPGNKETNGVKTLSVSQLGSQESGTWTCTVSKDQRTLALNINILVLA
Gray mouse lemur                    ESPRGSSPSVKCKSPGNKNINGVSLLSLPQLIQDSGTWTCTVSQDRQTLAFKIHISVLA
Coquerel's sifaka                   ESPRGSSPSVQCKSPRNKNINGVSVLSVSQLGLQDSGTWTCTVSQDRHTLAFKIHISVLA
```

FIGURE 6, continued
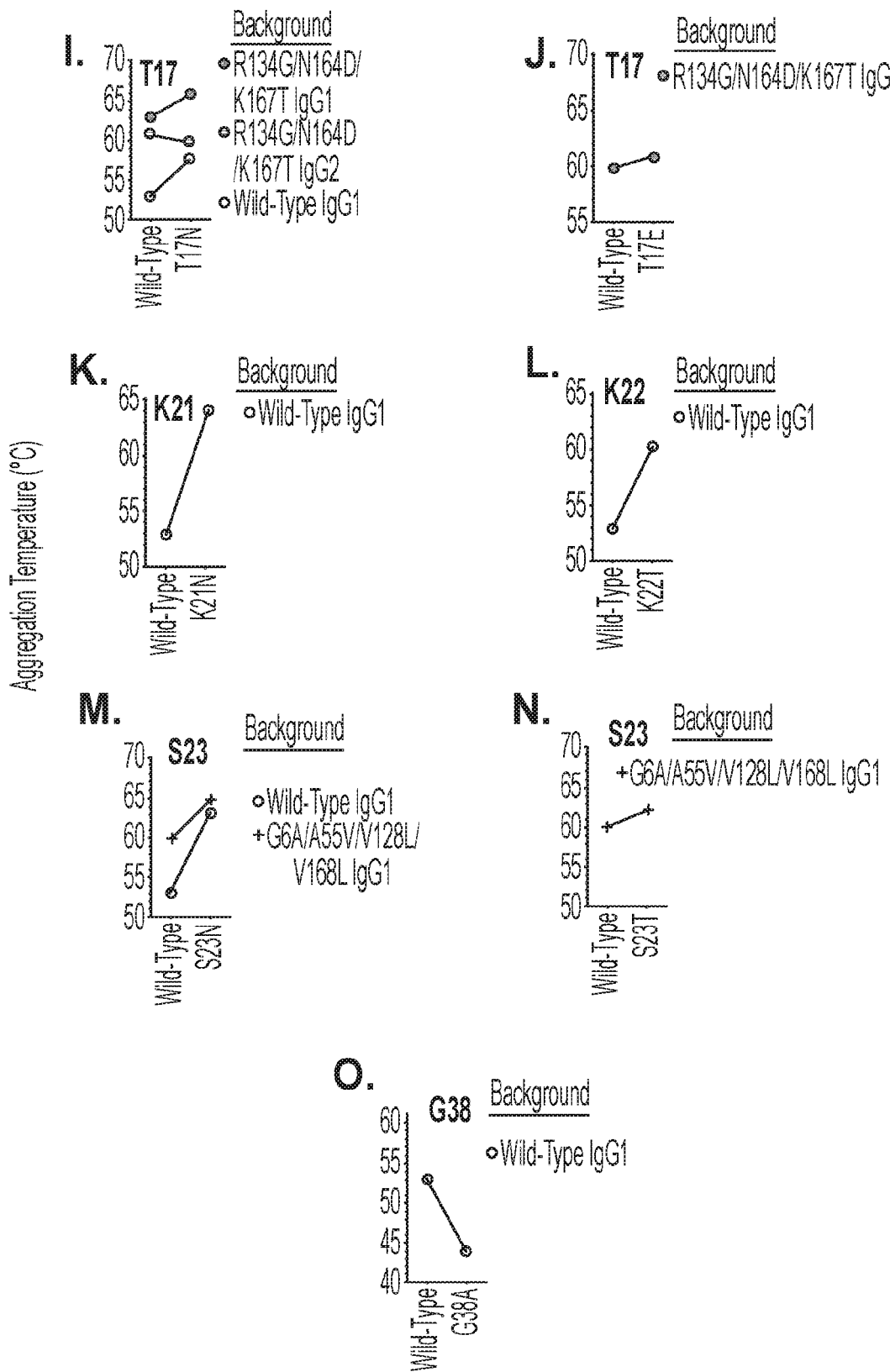

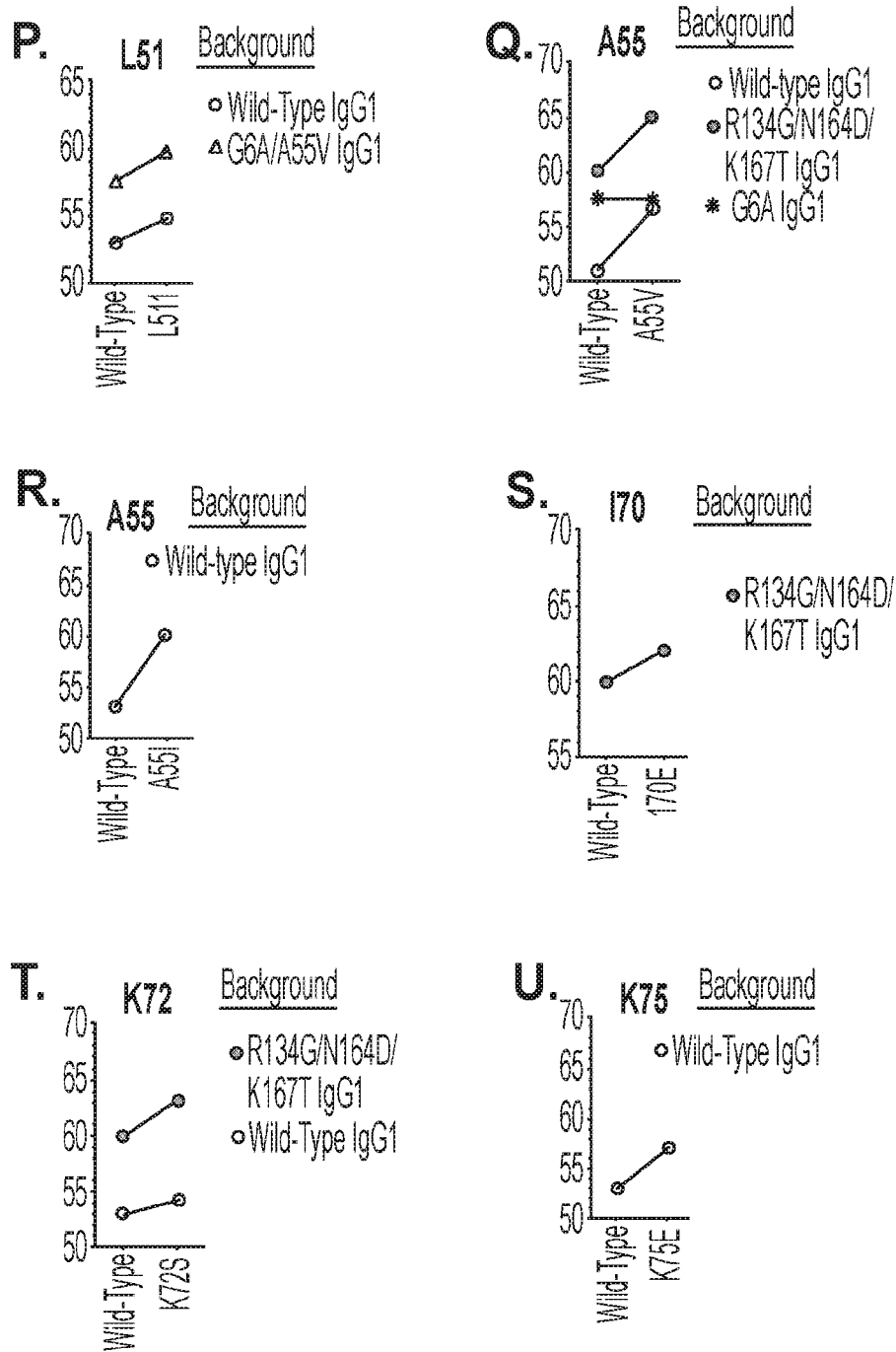
FIGURE 6, continued

FIGURE 6, continued
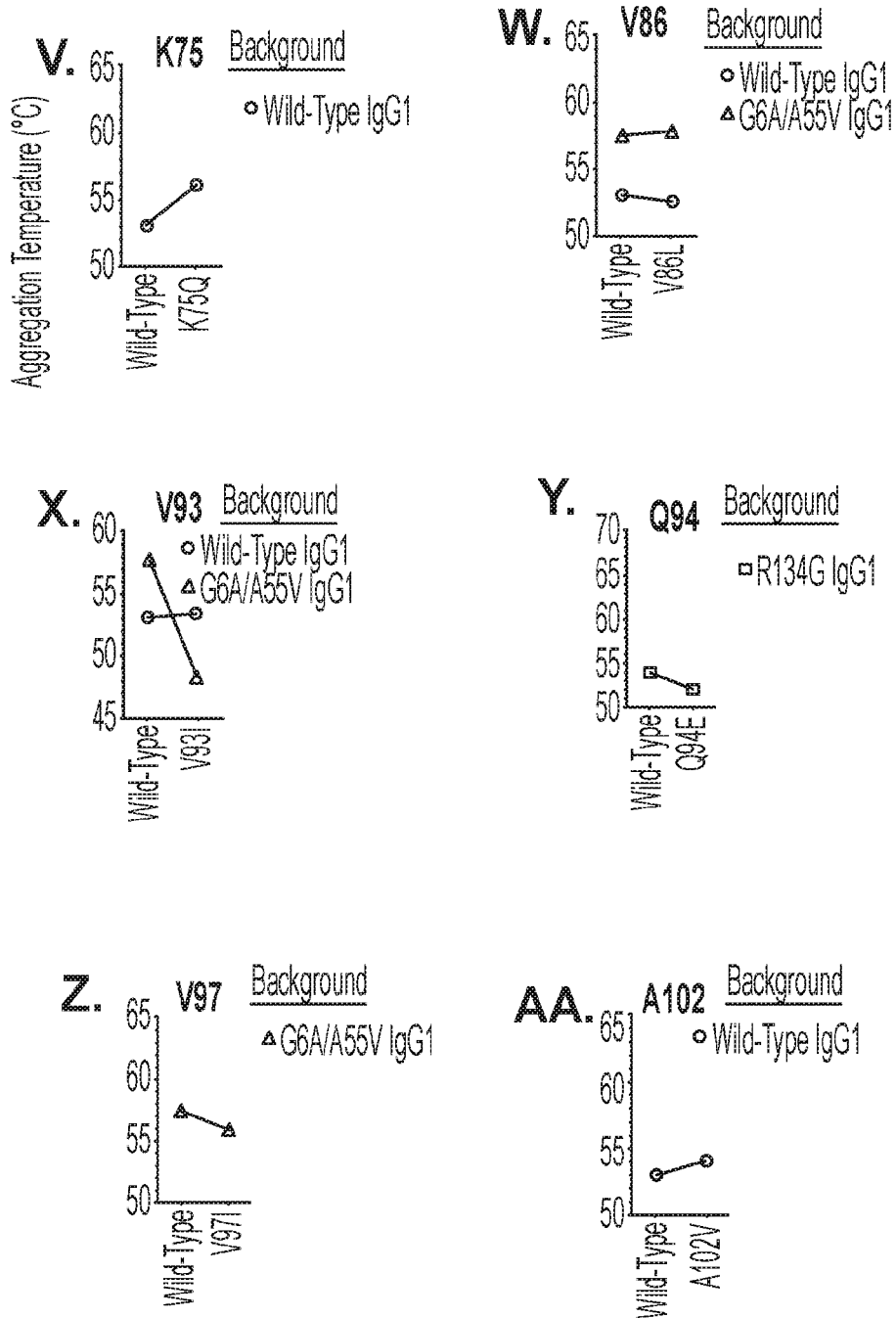

FIGURE 6, continued
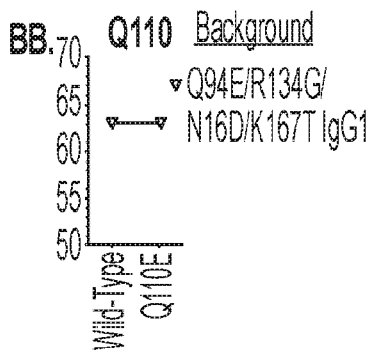
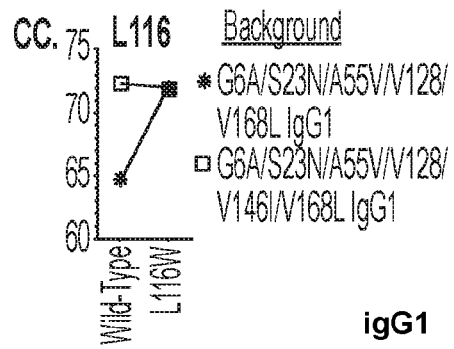
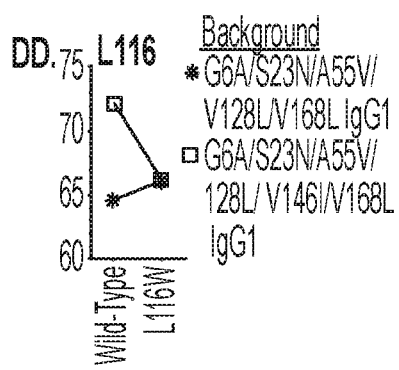
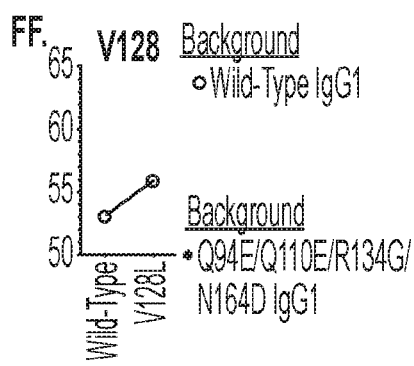
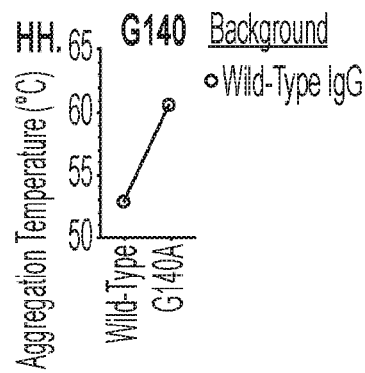
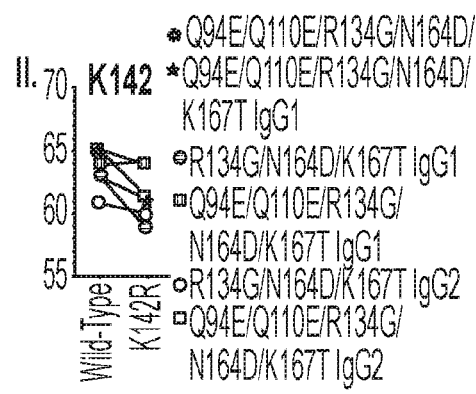

FIGURE 6, continued
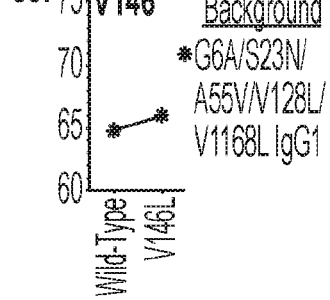
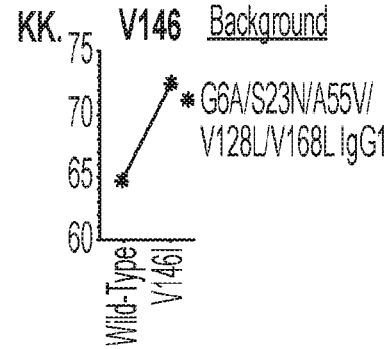
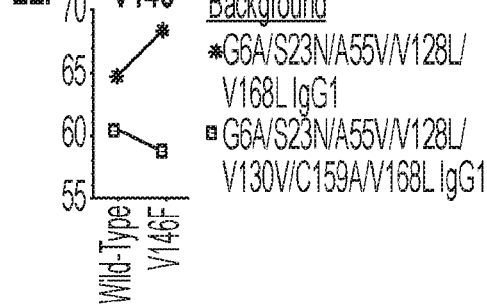
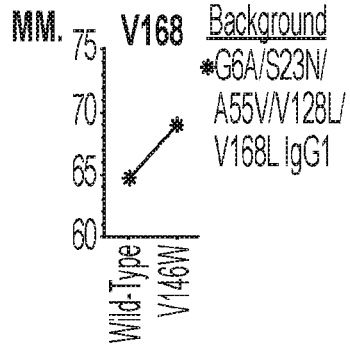
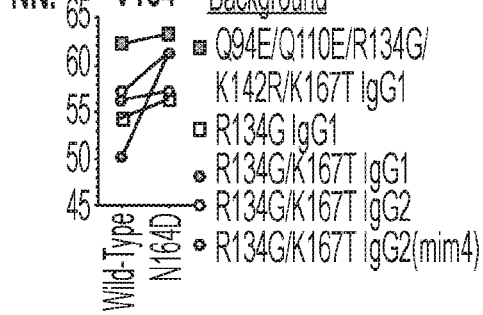
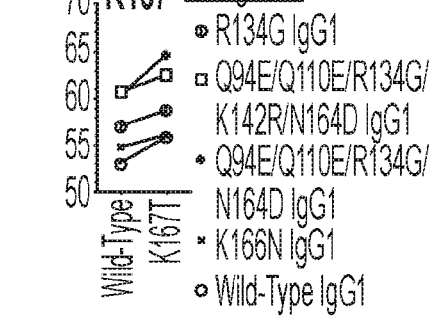
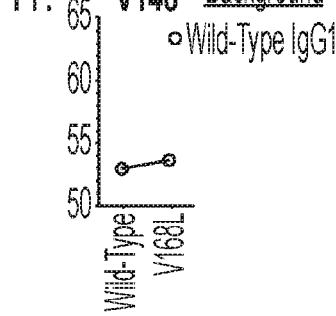

FIGURE 6, continued
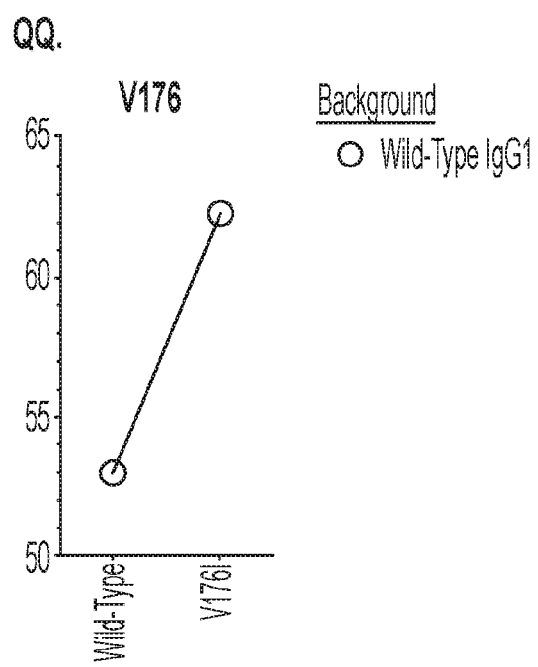

FIGURE 7, continued
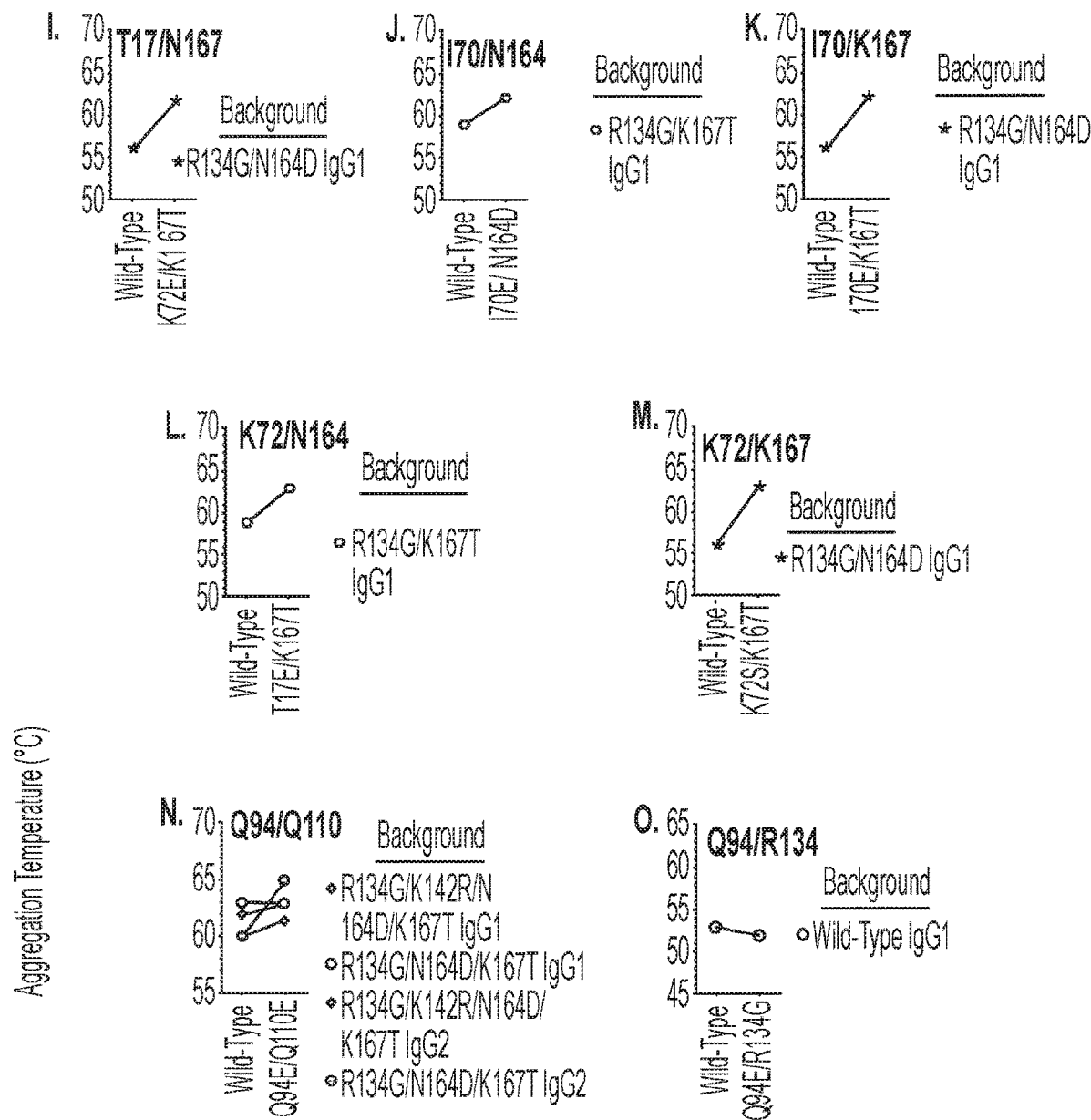

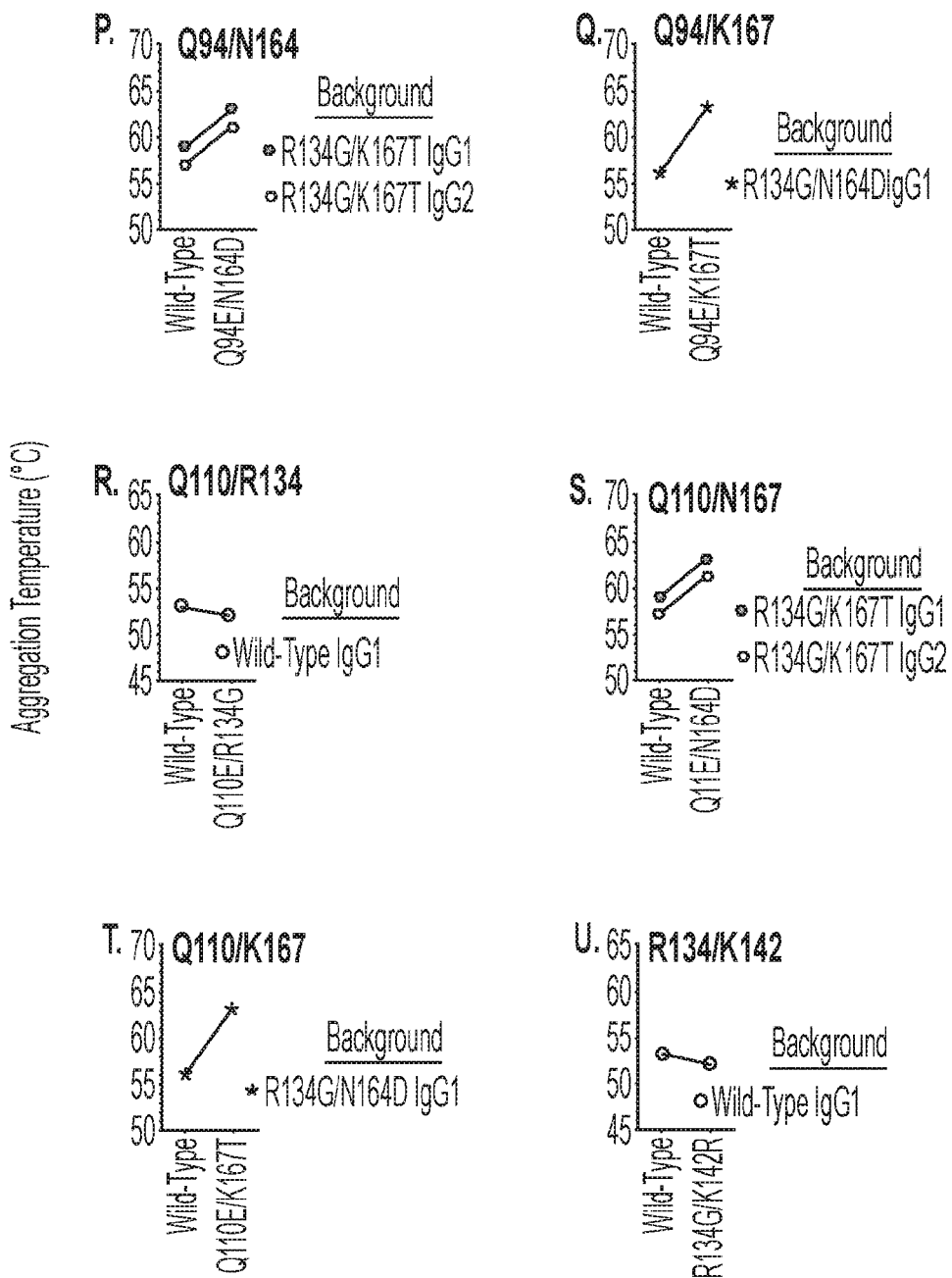
FIGURE 7, continued

FIGURE 7, continued
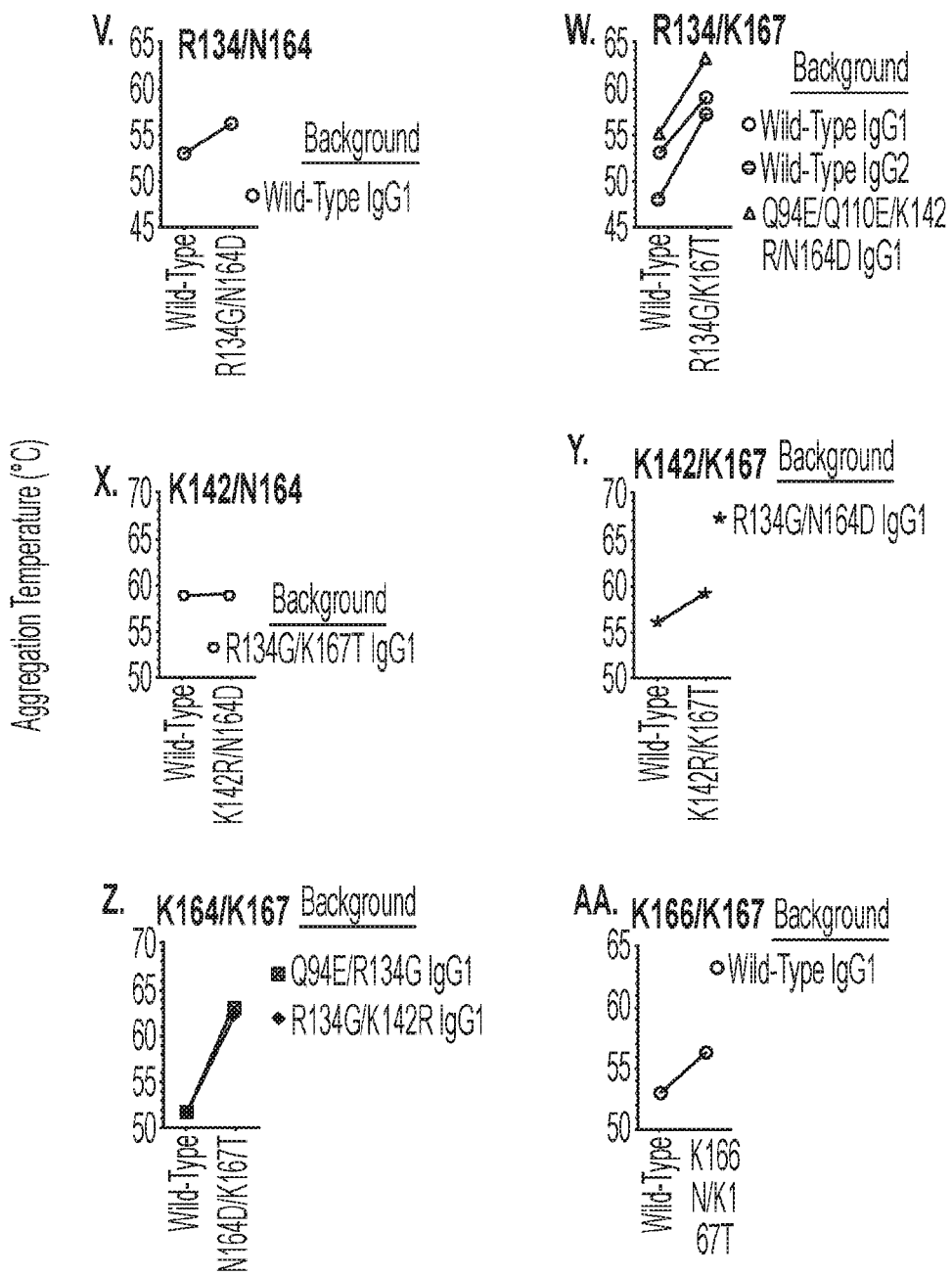

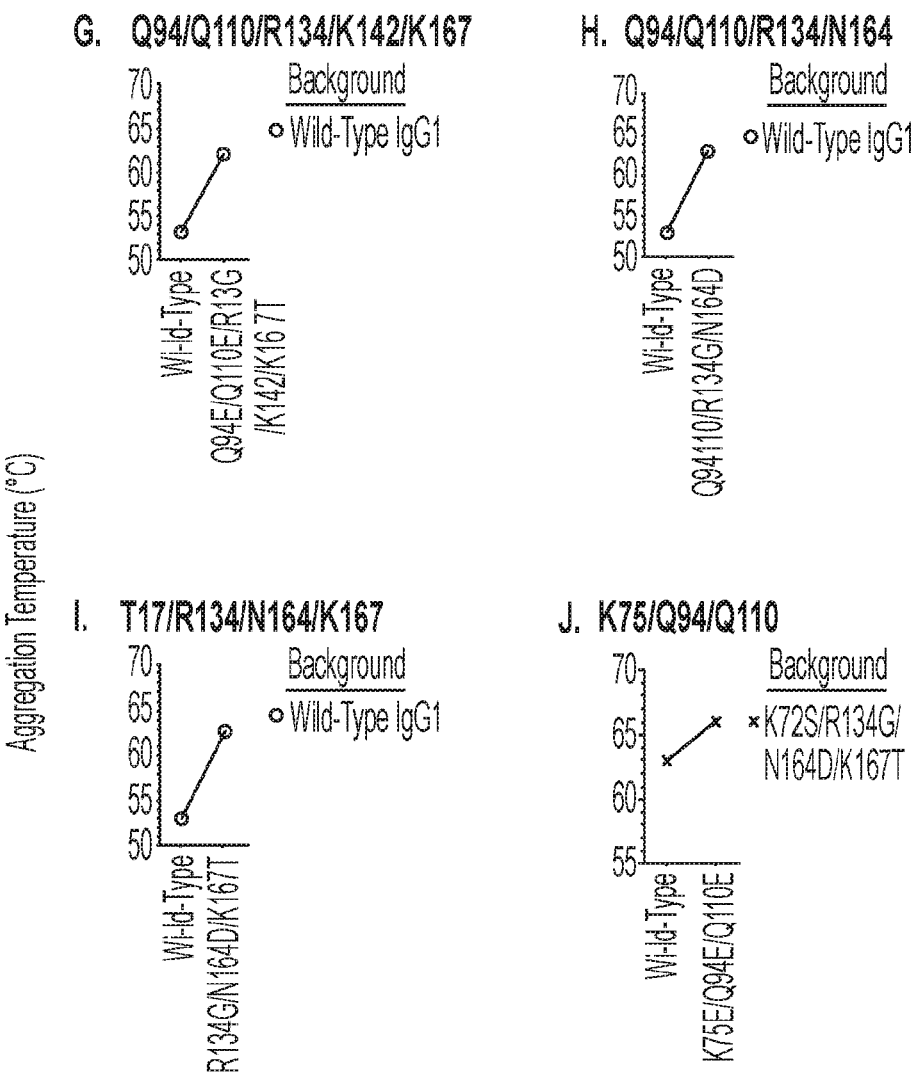

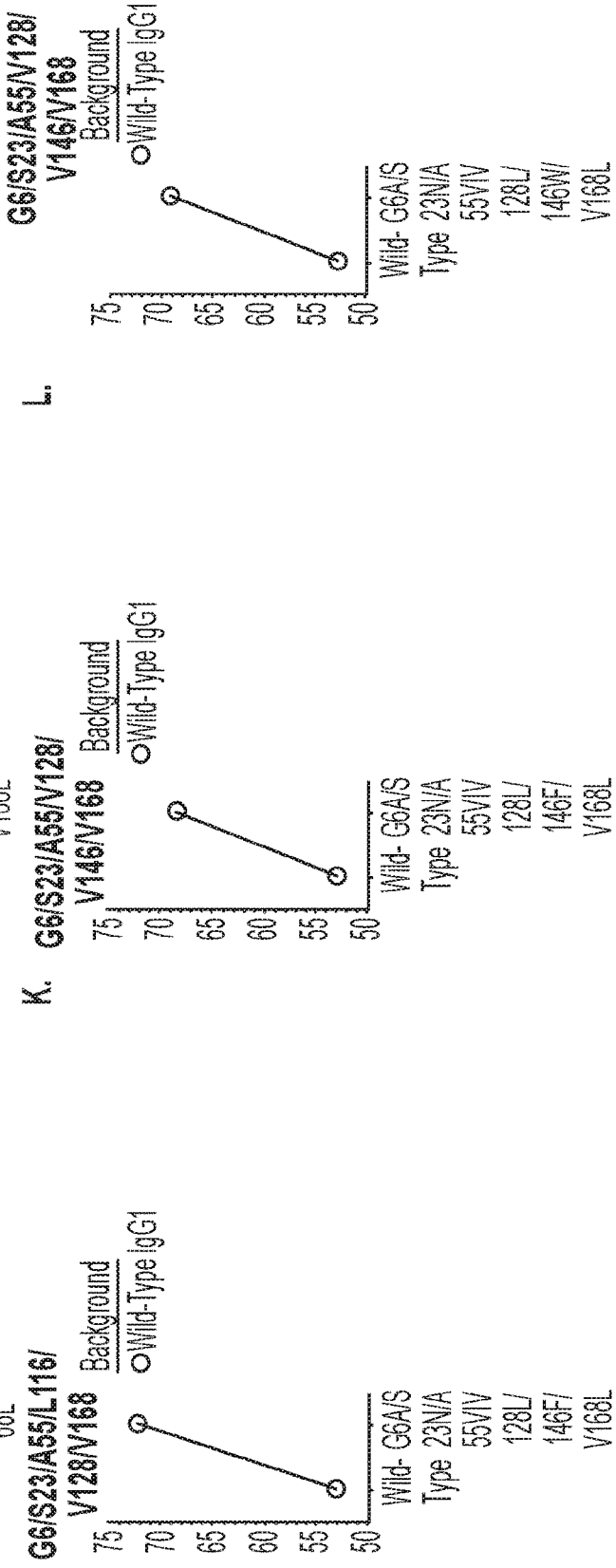
FIGURE 10, continued

FIGURE 15
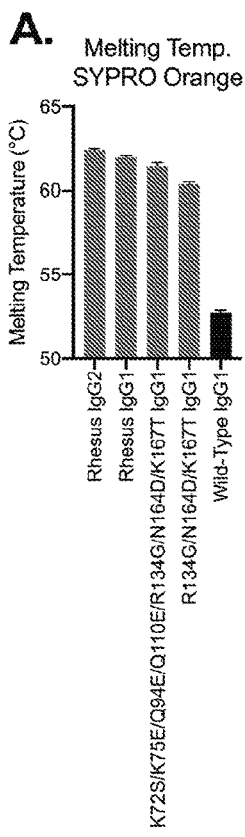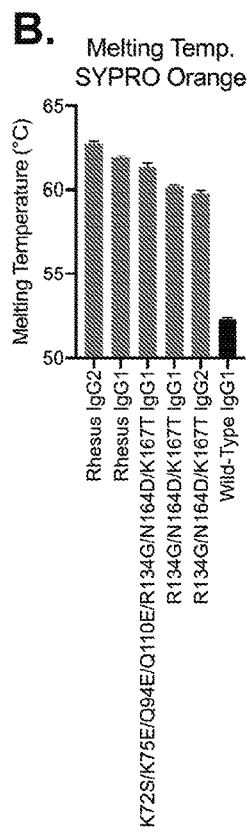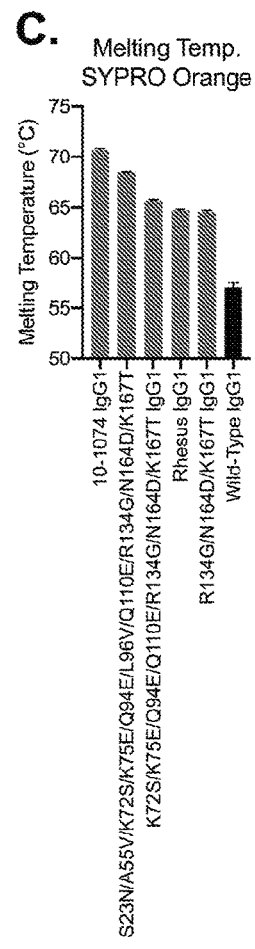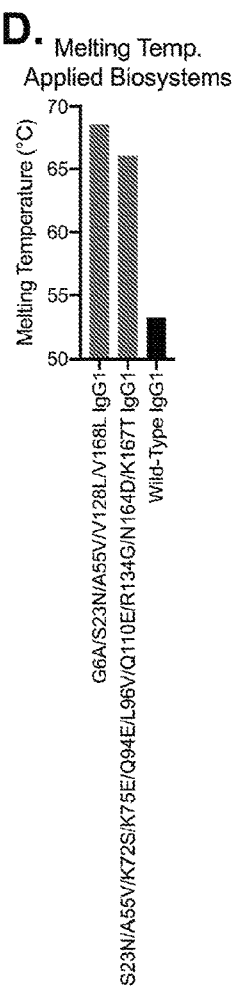

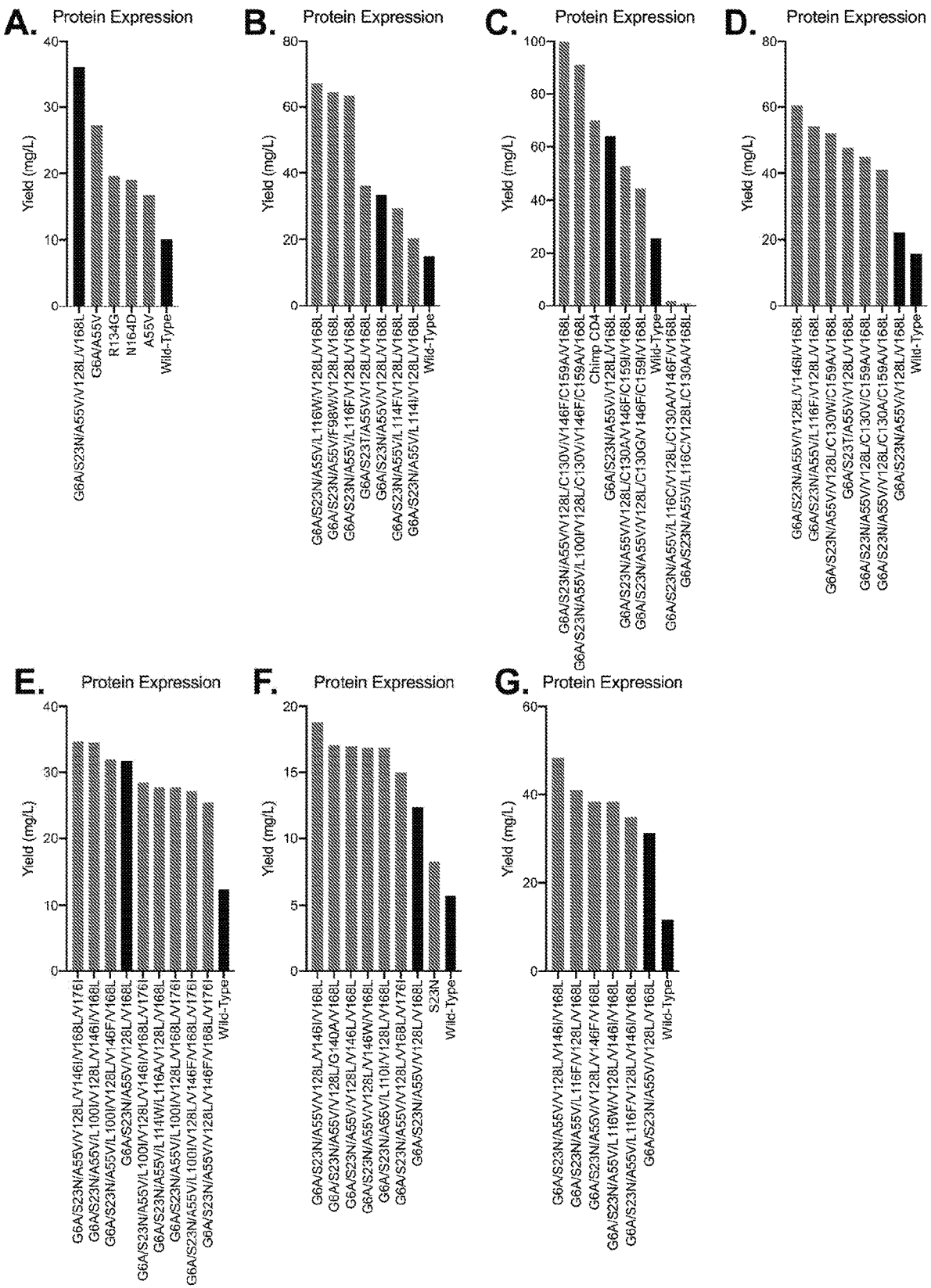

FIGURE 17, continued
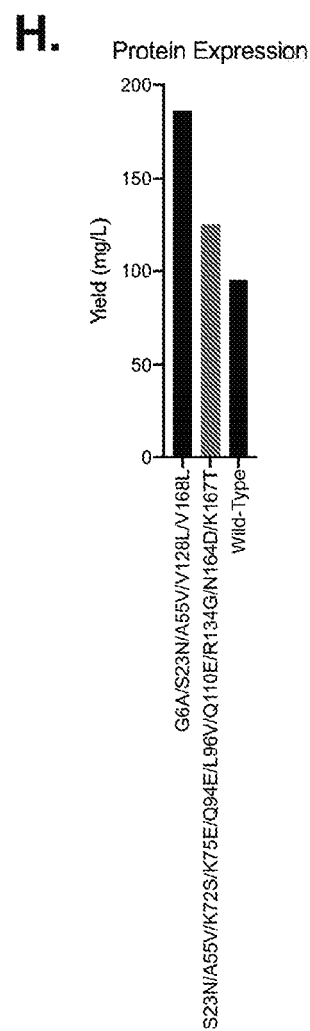

FIGURE 18
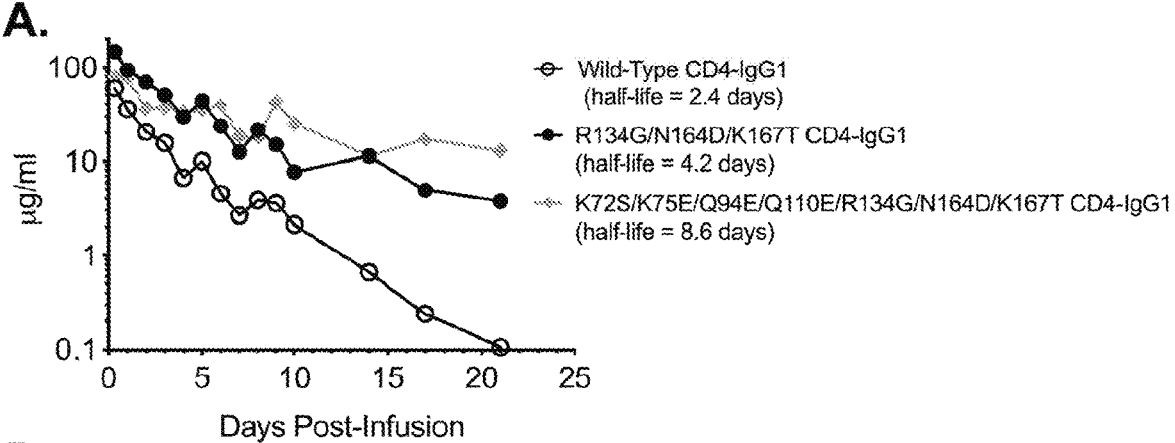
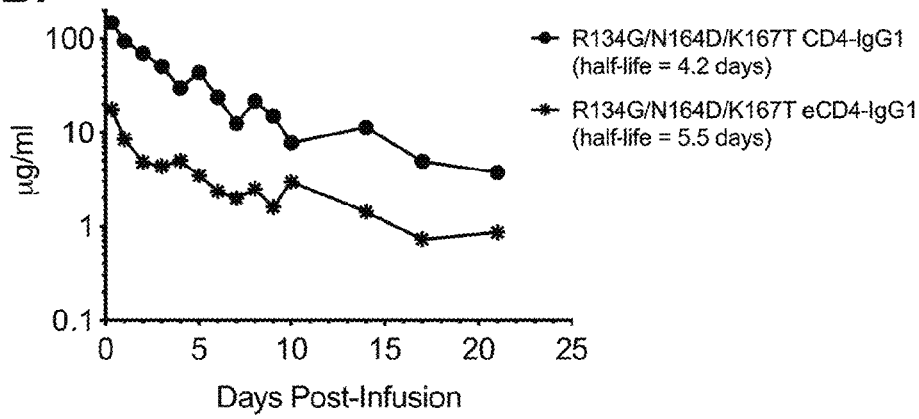
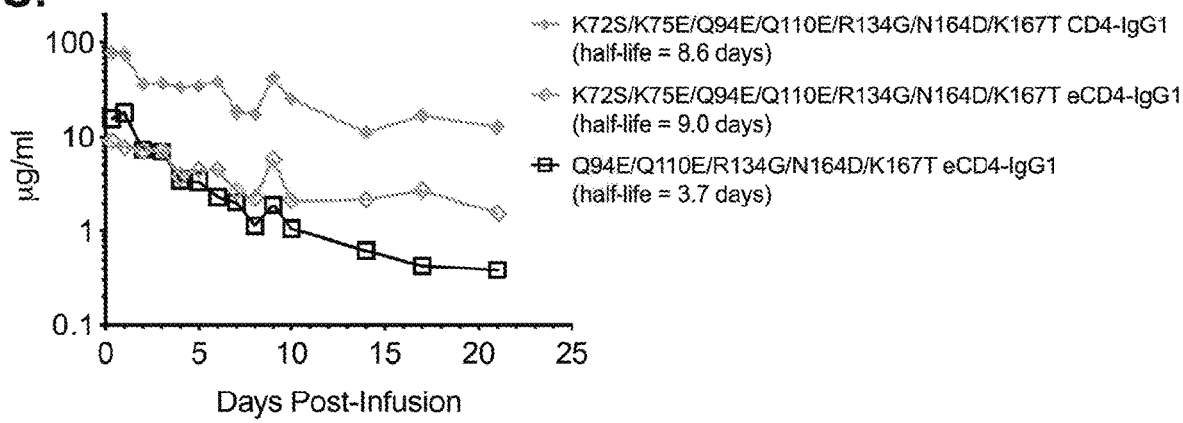

FIGURE 20
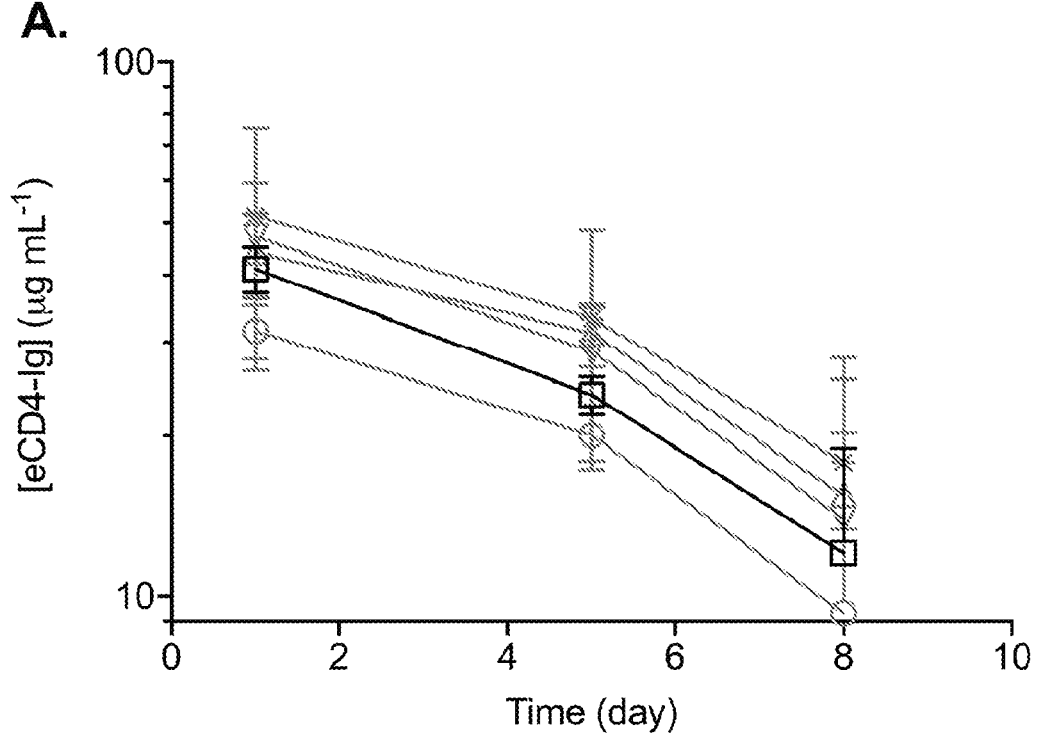
- S23N/A55V/K72S/K75E/Q94E/L96V/Q110E/R134G/N164D/K167T
- G6A/S23N/A55V/V128L/V168L
- G6A/S23N/A55V/V128L/R134G/V168L
- G6A/S23N/A55V/V128L/K167T/V168L
- G6A/S23N/A55V/V128L/R134G/N164D/K167T/V168L
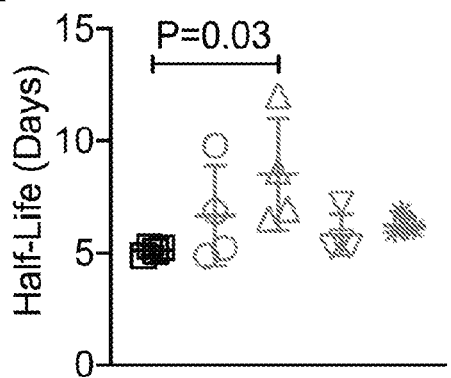

SEQUENCE LISTING

<160> NUMBER OF SEQ ID NOS: 90

<210> SEQ ID NO 1
<211> LENGTH: 178
<212> TYPE: PRT
<213> ORGANISM: Homo sapiens

<400> SEQUENCE: 1

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80
```

```
                    -continued
Thr Tyr Ile Cys Glu Val Glu Asp Gln Lys Glu Val Gln Leu Leu
                 85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 2
<211> LENGTH: 14
<212> TYPE: PRT
<213> ORGANISM: Artificial sequence
<220> FEATURE:
<223> OTHER INFORMATION: Synthetic sequence

<400> SEQUENCE: 2

Asp Tyr Ala Asp Tyr Asp Gly Gly Tyr Tyr Asp Met Asp
1               5                   10

<210> SEQ ID NO 3
<211> LENGTH: 14
<212> TYPE: PRT
<213> ORGANISM: Artificial sequence
<220> FEATURE:
<223> OTHER INFORMATION: Synthetic sequence

<400> SEQUENCE: 3

Asp Tyr Tyr Asp Tyr Asp Gly Gly Tyr Tyr Asp Met Asp
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic sequence

<400> SEQUENCE: 4

Asp Tyr Tyr Asp Tyr Asp Gly Gly Tyr Tyr Asp Asp Asp
1               5                   10

<210> SEQ ID NO 5
<211> LENGTH: 14
<212> TYPE: PRT
<213> ORGANISM: Artificial sequence
<220> FEATURE:
<223> OTHER INFORMATION: Synthetic sequence

<400> SEQUENCE: 5

Asp Tyr Tyr Asp Tyr Asp Gly Gly Tyr Tyr Asp Asn Asp
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic sequence
```

<400> SEQUENCE: 6

Asp Tyr Tyr Asp Tyr Asp Gly Gly Tyr Tyr Asp Gly Asp
1               5                   10

<210> SEQ ID NO 7
<211> LENGTH: 14
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(13)
<223> OTHER INFORMATION: X is any amino acid

<400> SEQUENCE: 7

Asp Tyr Xaa Asp Tyr Asp Gly Gly Tyr Tyr Asp Xaa Asp
1               5                   10

<210> SEQ ID NO 8
<211> LENGTH: 177
<212> TYPE: PRT
<213> ORGANISM: Artificial sequence
<220> FEATURE:
<223> OTHER INFORMATION: Synthetic sequence

<400> SEQUENCE: 8

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Gln Lys Glu Glu Val Gln Leu Leu Val
                85                  90                  95

Phe Gly Leu Thr Ala Asn Ser Asp Thr His Leu Leu Gln Gly Gln Ser
            100                 105                 110

Leu Thr Leu Thr Leu Glu Ser Pro Pro Gly Ser Ser Pro Ser Val Gln
        115                 120                 125

Cys Arg Ser Pro Gly Gly Lys Asn Ile Gln Gly Gly Lys Thr Leu Ser
    130                 135                 140

Val Ser Gln Leu Glu Leu Gln Asp Ser Gly Thr Trp Thr Cys Thr Val
145                 150                 155                 160

Leu Gln Asp Gln Lys Thr Val Glu Phe Lys Ile Asp Ile Val Val Leu
                165                 170                 175

Ala

<210> SEQ ID NO 9
<211> LENGTH: 534
<212> TYPE: DNA
<213> ORGANISM: Artificial sequence
<220> FEATURE:
<223> OTHER INFORMATION: Synthetic sequence

<400> SEQUENCE: 9
aagaaggtgg tgctgggcaa gaagggcgac accgtggagc tgacctgcac cgccagccag     60

```
aagaagagca tccagttcca ctggaagaac agcaaccaga tcaagatcct gggcaaccag    120
ggcagcttcc tgaccaaggg ccccagcaag ctgaacgaca gagccgacag cagaagaagc    180
ctgtgggacc agggcaactt ccccctgatc atcaagaacc tgaagatcga ggacagcgac    240
acctacatct gcgaggtgga ggaccagaag gaggaggtgc agctgctggt gttcggcctg    300
accgccaaca gcgacaccca cctgctgcag ggccagagcc tgaccctgac cctggagagc    360
ccccccggca gcagcccag cgtgcagtgc agaagcccg gcggcaagaa catccagggc    420
ggcaagaccc tgagcgtgag ccagctggag ctgcaggaca gcggcacctg gacctgcacc    480
gtgctgcagg accagaagac cgtggagttc aagatcgaca tcgtggtgct ggcc         534
```

<210> SEQ ID NO 10
<211> LENGTH: 178
<212> TYPE: PRT
<213> ORGANISM: Artificial sequence
<220> FEATURE:
<223> OTHER INFORMATION: Synthetic sequence

<400> SEQUENCE: 10

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala
```

<210> SEQ ID NO 11
<211> LENGTH: 534
<212> TYPE: DNA
<213> ORGANISM: Artificial sequence
<220> FEATURE:
<223> OTHER INFORMATION: Synthetic sequence

<400> SEQUENCE: 11

```
aagaaggtgg tgctgggcaa gaagggcgac accgtggagc tgacctgcac cgccagccag    60
aagaagagca tccagttcca ctggaagaac agcaaccaga tcaagatcct gggcaaccag    120
ggcagcttcc tgaccaaggg ccccagcaag ctgaacgaca gagtggacag cagaagaagc    180
ctgtgggacc agggcaactt ccccctgatc atcaagaacc tgaagatcga ggacagcgac    240
```

```
acctacatct gcgaggtgga ggaccagaag gaggaggtgc agctgctggt gttcggcctg    300
accgccaaca gcgacaccca cctgctgcag ggccagagcc tgaccctgac cctggagagc    360
ccccccggca gcagcccag cgtgcagtgc agaagcccca gaggcaagaa catccagggc    420
ggcaagaccc tgagcgtgag ccagctggag ctgcaggaca gcggcacctg gacctgcacc    480
gtgctgcaga ccagaagaa ggtggagttc aagatcgaca tcgtggtgct ggcc           534
```

<210> SEQ ID NO 12
<211> LENGTH: 178
<212> TYPE: PRT
<213> ORGANISM: Artificial sequence
<220> FEATURE:
<223> OTHER INFORMATION: Synthetic sequence

<400> SEQUENCE: 12

```
Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Gly Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala
```

<210> SEQ ID NO 13
<211> LENGTH: 534
<212> TYPE: DNA
<213> ORGANISM: Artificial sequence
<220> FEATURE:
<223> OTHER INFORMATION: Synthetic sequence

<400> SEQUENCE: 13

```
aagaaggtgg tgctgggcaa gaagggcgac accgtggagc tgacctgcac cgccagccag    60
aagaagagca tccagttcca ctggaagaac agcaaccaga tcaagatcct gggcaaccag    120
ggcagcttcc tgaccaaggg ccccagcaag ctgaacgaca gagtggacag cagaagaagc    180
ctgtgggacc agggcaactt ccccctgatc atcaagaacc tgaagatcga ggacagcgac    240
acctacatct gcgaggtgga ggaccagaag gaggaggtgc agctgctggt gttcggcctg    300
accgccaaca gcgacaccca cctgctgcag ggccagagcc tgaccctgac cctggagagc    360
ccccccggca gcagcccag cgtgcagtgc agaagcccg gcggcaagaa catccagggc    420
```

| ggcaagaccc tgagcgtgag ccagctggag ctgcaggaca gcggcacctg gacctgcacc | 480 |
| gtgctgcagg accagaagac cgtggagttc aagatcgaca tcgtggtgct ggcc | 534 |

<210> SEQ ID NO 14
<211> LENGTH: 178
<212> TYPE: PRT
<213> ORGANISM: Artificial sequence
<220> FEATURE:
<223> OTHER INFORMATION: Synthetic sequence

<400> SEQUENCE: 14

```
Lys Lys Val Val Leu Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Gly Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala
```

<210> SEQ ID NO 15
<211> LENGTH: 534
<212> TYPE: DNA
<213> ORGANISM: Artificial sequence
<220> FEATURE:
<223> OTHER INFORMATION: Synthetic sequence

<400> SEQUENCE: 15

| aagaaggtgg tgctgggcaa gaagggcgac accgtggagc tgacctgcac cgccagccag | 60 |
| aagaagaaca tccagttcca ctggaagaac agcaaccaga tcaagatcct gggcaaccag | 120 |
| ggcagcttcc tgaccaaggg ccccagcaag ctgaacgaca gagtggacag cagaagaagc | 180 |
| ctgtgggacc agggcaactt ccccctgatc atcaagaacc tgaagatcga ggacagcgac | 240 |
| acctacatct gcgaggtgga ggaccagaag gaggaggtgc agctgctggt gttcggcctg | 300 |
| accgccaaca gcgacaccca cctgctgcag ggccagagcc tgaccctgac cctggagagc | 360 |
| cccccccggca gcagccccag cgtgcagtgc agaagcccccg gcggcaagaa catccagggc | 420 |
| ggcaagaccc tgagcgtgag ccagctggag ctgcaggaca gcggcacctg gacctgcacc | 480 |
| gtgctgcagg accagaagac cgtggagttc aagatcgaca tcgtggtgct ggcc | 534 |

```
<210> SEQ ID NO 16
<211> LENGTH: 178
<212> TYPE: PRT
<213> ORGANISM: Artificial sequence
<220> FEATURE:
<223> OTHER INFORMATION: Synthetic sequence

<400> SEQUENCE: 16

Asn Glu Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 17
<211> LENGTH: 534
<212> TYPE: DNA
<213> ORGANISM: Artificial sequence
<220> FEATURE:
<223> OTHER INFORMATION: Synthetic sequence

<400> SEQUENCE: 17
aacgaggtgg tgctgggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gagccgacag cagaagaagc     180
ctgtgggacc agggcaactt ccccctgatc atcaagaacc tgaagatcga ggacagcgac     240
acctacatct gcgaggtgga ggaccagaag gaggaggtgc agctgctggt gttcggcctg     300
accgccaaca gcgacaccca cctgctgcag ggccagagcc tgaccctgac cctggagagc     360 cccccccggca gcagccccag cgtgcagtgc agaagcccca gaggcaagaa catccagggc     420
ggcaagaccc tgagcgtgag ccagctggag ctgcaggaca gcggcacctg gacctgcacc     480
gtgctgcaga accagaagaa ggtggagttc aagatcgaca tcgtggtgct ggcc           534

<210> SEQ ID NO 18
<211> LENGTH: 178
<212> TYPE: PRT
<213> ORGANISM: Artificial sequence
<220> FEATURE:
<223> OTHER INFORMATION: Synthetic sequence
```

<400> SEQUENCE: 18

Lys Lys Val Val Leu Gly Glu Glu Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 19
<211> LENGTH: 534
<212> TYPE: DNA
<213> ORGANISM: Artificial sequence
<220> FEATURE:
<223> OTHER INFORMATION: Synthetic sequence

<400> SEQUENCE: 19
aagaaggtgg tgctgggcga ggagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gagccgacag cagaagaagc     180
ctgtgggacc agggcaactt ccccctgatc atcaagaacc tgaagatcga ggacagcgac     240
acctacatct gcgaggtgga ggaccagaag gaggaggtgc agctgctggt gttcggcctg     300
accgccaaca gcgacaccca cctgctgcag ggccagagcc tgaccctgac cctggagagc     360
ccccccggca gcagcccccag cgtgcagtgc agaagcccca gaggcaagaa catccagggc     420
ggcaagaccc tgagcgtgag ccagctggag ctgcaggaca gcggcacctg gacctgcacc     480
gtgctgcaga accagaagaa ggtggagttc aagatcgaca tcgtggtgct ggcc           534

<210> SEQ ID NO 20
<211> LENGTH: 178
<212> TYPE: PRT
<213> ORGANISM: Artificial sequence
<220> FEATURE:
<223> OTHER INFORMATION: Synthetic sequence

<400> SEQUENCE: 20

Asn Glu Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Val Asp Ser Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Gly Gly Lys Asn Ile Gln Gly Gly Lys Thr Leu
            130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala

<210> SEQ ID NO 21
<211> LENGTH: 534
<212> TYPE: DNA
<213> ORGANISM: Artificial sequence
<220> FEATURE:
<223> OTHER INFORMATION: Synthetic sequence

<400> SEQUENCE: 21
aacgaggtgg tgctgggcaa gaagggcgac accgtggagc tgacctgcac cgccagccag    60
aagaagagca tccagttcca ctggaagaac agcaaccaga tcaagatcct gggcaaccag   120
ggcagcttcc tgaccaaggg ccccagcaag ctgaacgaca gagtggacag cagaagaagc   180
ctgtgggacc agggcaactt ccccctgatc atcaagaacc tgaagatcga ggacagcgac   240
acctacatct gcgaggtgga ggaccagaag gaggaggtgc agctgctggt gttcggcctg   300
accgccaaca gcgacaccca cctgctgcag ggccagagcc tgaccctgac cctggagagc   360 cccccggca gcagccccag cgtgcagtgc agaagccccg gcggcaagaa catccagggc   420
ggcaagaccc tgagcgtgag ccagctggag ctgcaggaca gcggcacctg gacctgcacc   480
gtgctgcagg accagaagac cgtggagttc aagatcgaca tcgtggtgct ggcc         534

<210> SEQ ID NO 22
<211> LENGTH: 178
<212> TYPE: PRT
<213> ORGANISM: Artificial sequence
<220> FEATURE:
<223> OTHER INFORMATION: Synthetic sequence

<400> SEQUENCE: 22

Lys Lys Val Val Leu Gly Glu Glu Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

```
Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Gly Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala
```

<210> SEQ ID NO 23
<211> LENGTH: 534
<212> TYPE: DNA
<213> ORGANISM: Artificial sequence
<220> FEATURE:
<223> OTHER INFORMATION: Synthetic sequence

<400> SEQUENCE: 23

```
aagaaggtgg tgctgggcga ggagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gagtggacag cagaagaagc     180
ctgtgggacc agggcaactt ccccctgatc atcaagaacc tgaagatcga ggacagcgac     240
acctacatct gcgaggtgga ggaccagaag gaggaggtgc agctgctggt gttcggcctg     300
accgccaaca gcgacaccca cctgctgcag ggccagagcc tgaccctgac cctggagagc     360
ccccccggca gcagccccag cgtgcagtgc agaagccccg gcggcaagaa catccagggc     420
ggcaagaccc tgagcgtgag ccagctggag ctgcaggaca gcggcacctg gacctgcacc     480
gtgctgcagg accagaagac cgtggagttc aagatcgaca tcgtggtgct ggcc           534
```

<210> SEQ ID NO 24
<211> LENGTH: 178
<212> TYPE: PRT
<213> ORGANISM: Artificial sequence
<220> FEATURE:
<223> OTHER INFORMATION: Synthetic sequence

<400> SEQUENCE: 24

```
Lys Lys Val Val Leu Gly Lys Lys Gly Asp Thr Val Glu Leu Thr Cys
  1               5                  10                  15

Thr Ala Ser Gln Lys Lys Ser Ile Gln Phe His Trp Lys Asn Ser Asn
             20                  25                  30

Gln Ile Lys Ile Leu Gly Asn Gln Gly Ser Phe Leu Thr Lys Gly Pro
         35                  40                  45

Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80
```

```
Thr Tyr Ile Cys Glu Val Glu Asp Gln Lys Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Val
            115                 120                 125

Gln Cys Arg Ser Pro Gly Gly Lys Asn Ile Gln Gly Gly Lys Thr Leu
            130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala

<210> SEQ ID NO 25
<211> LENGTH: 534
<212> TYPE: DNA
<213> ORGANISM: Artificial sequence
<220> FEATURE:
<223> OTHER INFORMATION: Synthetic sequence

<400> SEQUENCE: 25
aagaaggtgg tgctgggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gagtggacag cagaagaagc     180
ctgtgggacc agggcaactt ccccctgatc atcaagaacc tgaagatcga ggacagcgac     240
acctacatct gcgaggtgga ggaccagaag gaggaggtgg agctgctggt gttcggcctg     300
accgccaaca gcgacaccca cctgctggag ggccagagcc tgaccctgac cctggagagc     360
cccccggca gcagcccag cgtgcagtgc agaagccccg gcggcaagaa catccagggc      420
ggcaagaccc tgagcgtgag ccagctggag ctgcaggaca gcggcacctg gacctgcacc     480
gtgctgcagg accagaagac cgtggagttc aagatcgaca tcgtggtgct ggcc           534

<210> SEQ ID NO 26
<211> LENGTH: 178
<212> TYPE: PRT
<213> ORGANISM: Artificial sequence
<220> FEATURE:
<223> OTHER INFORMATION: Synthetic sequence

<400> SEQUENCE: 26

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Val Asp Ser Arg Arg Ser Leu Trp Asp Gln
        50                  55                  60

Gly Asn Phe Pro Leu Ile Ile Ser Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110
```

```
Ser Leu Thr Leu Thr Leu Glu Ser Pro Pro Gly Ser Ser Pro Ser Val
            115                 120                 125

Gln Cys Arg Ser Pro Gly Gly Lys Asn Ile Gln Gly Gly Lys Thr Leu
        130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala

<210> SEQ ID NO 27
<211> LENGTH: 534
<212> TYPE: DNA
<213> ORGANISM: Artificial sequence
<220> FEATURE:
<223> OTHER INFORMATION: Synthetic sequence

<400> SEQUENCE: 27
aagaaggtgg tgctgggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gtggacag cagaagaagc       180 ctgtgggacc agggcaactt ccccctgatc atcagcaacc tgaagatcga ggacagcgac     240
acctacatct gcgaggtgga ggaccagaag gaggaggtgc agctgctggt gttcggcctg     300
accgccaaca gcgacaccca cctgctgcag ggccagagcc tgaccctgac cctggagagc     360
ccccccggca gcagccccag cgtgcagtgc agaagcccg gcggcaagaa catccagggc      420
ggcaagaccc tgagcgtgag ccagctggag ctgcaggaca gcggcacctg gacctgcacc     480
gtgctgcagg accagaagac cgtggagttc aagatcgaca tcgtggtgct ggcc           534

<210> SEQ ID NO 28
<211> LENGTH: 178
<212> TYPE: PRT
<213> ORGANISM: Artificial sequence
<220> FEATURE:
<223> OTHER INFORMATION: Synthetic sequence

<400> SEQUENCE: 28

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Ser Leu Trp Asp Gln
50                  55                  60

Gly Asn Phe Pro Leu Ile Ile Lys Asn Leu Glu Ile Glu Asp Ser Asp
65                  70                  75                  80

Thr Tyr Ile Cys Glu Val Asp Gln Lys Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Gly Gly Lys Asn Ile Gln Gly Gly Lys Thr Leu
        130                 135                 140
```

```
Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala

<210> SEQ ID NO 29
<211> LENGTH: 534
<212> TYPE: DNA
<213> ORGANISM: Artificial sequence
<220> FEATURE:
<223> OTHER INFORMATION: Synthetic sequence

<400> SEQUENCE: 29
aagaaggtgg tgctgggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gagtggacag cagaagaagc     180
ctgtgggacc agggcaactt ccccctgatc atcaagaacc tggagatcga ggacagcgac     240
acctacatct gcgaggtgga ggaccagaag gaggaggtgc agctgctggt gttcggcctg     300
accgccaaca gcgacaccca cctgctgcag ggccagagcc tgaccctgac cctggagagc     360
cccccgggca gcagcccag cgtgcagtgc agaagccccg gcggcaagaa catccagggc     420
ggcaagaccc tgagcgtgag ccagctggag ctgcaggaca gcggcacctg gacctgcacc     480
gtgctgcagg accagaagac cgtggagttc aagatcgaca tcgtggtgct ggcc           534

<210> SEQ ID NO 30
<211> LENGTH: 178
<212> TYPE: PRT
<213> ORGANISM: Artificial sequence
<220> FEATURE:
<223> OTHER INFORMATION: Synthetic sequence

<400> SEQUENCE: 30

Asn Glu Val Val Leu Gly Glu Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Val Asp Ser Arg Arg Ser Leu Trp Asp Gln
        50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Gly Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175
```

Leu Ala

<210> SEQ ID NO 31
<211> LENGTH: 534
<212> TYPE: DNA
<213> ORGANISM: Artificial sequence
<220> FEATURE:
<223> OTHER INFORMATION: Synthetic sequence

<400> SEQUENCE: 31

```
aacgaggtgg tgctgggcga ggagggcgac accgtggagc tgacctgcac cgccagccag      60
aagaagagca tccagttcca ctggaagaac agcaaccaga tcaagatcct gggcaaccag     120
ggcagcttcc tgaccaaggg ccccagcaag ctgaacgaca gagtggacag cagaagaagc     180
ctgtgggacc agggcaactt ccccctgatc atcaagaacc tgaagatcga ggacagcgac     240
acctacatct gcgaggtgga ggaccagaag gaggaggtgc agctgctggt gttcggcctg     300
accgccaaca gcgacaccca cctgctgcag ggccagagcc tgaccctgac cctggagagc     360
ccccccggca gcagccccag cgtgcagtgc agaagccccg gcggcaagaa catccagggc     420
ggcaagaccc tgagcgtgag ccagctggag ctgcaggaca gcggcacctg gacctgcacc     480
gtgctgcagg accagaagac cgtggagttc aagatcgaca tcgtggtgct ggcc            534
```

<210> SEQ ID NO 32
<211> LENGTH: 179
<212> TYPE: PRT
<213> ORGANISM: Artificial sequence
<220> FEATURE:
<223> OTHER INFORMATION: Synthetic sequence

<400> SEQUENCE: 32

```
Gly Asn Glu Val Val Leu Gly Glu Gly Asp Thr Val Glu Leu Thr
1               5                  10                  15

Cys Thr Ala Ser Gln Lys Lys Ser Ile Gln Phe His Trp Lys Asn Ser
            20                  25                  30

Asn Gln Ile Lys Ile Leu Gly Asn Gln Gly Ser Phe Leu Thr Lys Gly
        35                  40                  45

Pro Ser Lys Leu Asn Asp Arg Val Asp Ser Arg Arg Ser Leu Trp Asp
    50                  55                  60

Gln Gly Asn Phe Pro Leu Ile Ile Lys Asn Leu Lys Ile Glu Asp Ser
65                  70                  75                  80

Asp Thr Tyr Ile Cys Glu Val Glu Asp Gln Lys Glu Glu Val Gln Leu
                85                  90                  95

Leu Val Phe Gly Leu Thr Ala Asn Ser Asp Thr His Leu Leu Gln Gly
            100                 105                 110

Gln Ser Leu Thr Leu Thr Leu Glu Ser Pro Pro Gly Ser Ser Pro Ser
        115                 120                 125

Val Gln Cys Arg Ser Pro Gly Gly Lys Asn Ile Gln Gly Gly Lys Thr
    130                 135                 140

Leu Ser Val Ser Gln Leu Glu Leu Gln Asp Ser Gly Thr Trp Thr Cys
145                 150                 155                 160

Thr Val Leu Gln Asp Gln Lys Thr Val Glu Phe Lys Ile Asp Ile Val
                165                 170                 175

Val Leu Ala
```

<210> SEQ ID NO 33
<211> LENGTH: 534
<212> TYPE: DNA

<213> ORGANISM: Artificial sequence
<220> FEATURE:
<223> OTHER INFORMATION: Synthetic sequence

<400> SEQUENCE: 33

| | | | | | |
|---|---|---|---|---|---|
| aacgaggtgg | tgctgggcga | ggagggcgac | accgtggagc | tgacctgcac | cgccagccag | 60 |
| aagaagagca | tccagttcca | ctggaagaac | agcaaccaga | tcaagatcct | gggcaaccag | 120 |
| ggcagcttcc | tgaccaaggg | ccccagcaag | ctgaacgaca | gagtggacag | cagaagaagc | 180 |
| ctgtgggacc | agggcaactt | cccctgatc | atcaagaacc | tgaagatcga | ggacagcgac | 240 |
| acctacatct | gcgaggtgga | ggaccagaag | gaggaggtgc | agctgctggt | gttcggcctg | 300 |
| accgccaaca | gcgacaccca | cctgctgcag | ggccagagcc | tgaccctgac | cctggagagc | 360 |
| cccccggca | gcagcccag | cgtgcagtgc | agaagccccg | gcggcaagaa | catccagggc | 420 |
| ggcaagaccc | tgagcgtgag | ccagctggag | ctgcaggaca | gcggcacctg | gacctgcacc | 480 |
| gtgctgcagg | accagaagac | cgtggagttc | aagatcgaca | tcgtggtgct | ggcc | 534 |

<210> SEQ ID NO 34
<211> LENGTH: 3409
<212> TYPE: DNA
<213> ORGANISM: Artificial sequence
<220> FEATURE:
<223> OTHER INFORMATION: Synthetic sequence

<400> SEQUENCE: 34

| | | | | | |
|---|---|---|---|---|---|
| gcgcgctcgc | tcgctcactg | aggccgcccg | ggcaaagccc | gggcgtcggg | cgacctttgg | 60 |
| tcgcccggcc | tcagtgagcg | agcgagcgcg | cagagaggga | gtggccaact | ccatcactag | 120 |
| gggttccttg | tagttaatga | ttaacccgcc | atgctaatta | tctacgtagc | catgtctagg | 180 |
| gtcgttacat | aacttacggt | aaatggcccg | cctggctgac | cgcccaacga | cccccgccca | 240 |
| ttgacgtcaa | taatgacgta | tgttcccata | gtaacgccaa | tagggacttt | ccattgacgt | 300 |
| caatgggtgg | agtatttacg | gtaaactgcc | cacttggcag | tacatcaagt | gtatcatatg | 360 |
| ccaagtacgc | cccctattga | cgtcaatgac | ggtaaatggc | ccgcctggca | ttatgcccag | 420 |
| tacatgacct | tatgggactt | tcctacttgg | cagtacatct | acgtattagt | catcgctatt | 480 |
| accatggtga | tgcggttttg | gcagtacatc | aatgggcgtg | gatagcggtt | tgactcacgg | 540 |
| ggatttccaa | gtctccaccc | cattgacgtc | aatgggagtt | tgttttggca | ccaaaatcaa | 600 |
| cgggactttc | caaaatgtcg | taacaactcc | gccccattga | cgcaaatggg | cggtaggcgt | 660 |
| gtacggtggg | aggtctatat | aagcagagct | cgtttagtga | accgtcagat | cgcctggaga | 720 |
| cgccatccac | gctgttttga | cctccataga | agacaccggg | accgatccag | cctccggact | 780 |
| ctagaggatc | cggtactcga | ggaactgaaa | accagaaag | ttaactggta | agtttagtct | 840 |
| ttttgtcttt | tatttcaggt | cccggatccg | gtggtggtgc | aaatcaaaga | actgctcctc | 900 |
| agtggatgtt | gcctttactt | ctaggcctgt | acggaagtgt | tacttctgct | ctaaaagctg | 960 |
| cggaattgta | cccgcggccg | cagcgctcca | ccatgaacag | aggcgtgccc | ttcagacacc | 1020 |
| tgctgctggt | gctgcagctg | gccctgctgc | ccgccgccac | ccagggcaag | aaggtggtgc | 1080 |
| tgggcaagaa | gggcgacacc | gtggagctga | cctgcaccgc | cagccagaag | aagagcatcc | 1140 |
| agttccactg | gaagaacagc | aaccagatca | agatcctggg | caaccagggc | agcttcctga | 1200 |
| ccaagggccc | cagcaagctg | aacgacagag | tggacagcag | aagaagcctg | tgggaccagg | 1260 |
| gcaacttccc | cctgatcatc | aagaacctga | agatcgagga | cagcgacacc | tacatctgcg | 1320 |
| aggtggagga | ccagaaggag | gaggtgcagc | tgctggtgtt | cggcctgacc | gccaacagcg | 1380 |

```
acacccacct gctgcagggc cagagcctga ccctgaccct ggagagcccc cccggcagca  1440
gccccagcgt gcagtgcaga agccccggcg gcaagaacat ccagggcggc aagaccctga  1500
gcgtgagcca gctggagctg caggacagcg gcacctggac ctgcaccgtg ctgcaggacc  1560
agaagaccgt ggagttcaag atcgacatcg tggtgctggc cgagcccaag agcagcgaca  1620
agacccacac ctgccccccc tgccccgccc ccgagctgct gggcggcccc agcgtgttcc  1680
tgttcccccc caagcccaag gacacccctg atgatcagcag aaccccccgag gtgacctgcg  1740 tggtggtgga cgtgagccac gaggacccccg aggtgaagtt caactggtac gtggacggcg  1800
tggaggtgca caacgccaag accaagccca gagaggagca gtacaacagc acctacagag  1860
tggtgagcgt gctgaccgtg ctgcaccagg actggctgaa cggcaaggag tacaagtgca  1920
aggtgagcaa caaggccctg cccgccccca tcgagaagac catcagcaag gccaagggcc  1980
agcccagaga gccccaggtg tacaccctgc ccccagcag agacgagctg accaagaacc  2040
aggtgagcct gacctgcctg gtgaagggct tctaccccag cgacatcgcc gtggagtggg  2100
agagcaacgg ccagcccgag aacaactaca agaccacccc ccccgtgctg gacagcgacg  2160
gcagcttctt cctgtacagc aagctgaccg tggacaagag cagatggcag cagggcaacg  2220
tgttcagctg cagcgtgatg cacgaggccc tgcacaacca ctacacccag aagagcctga  2280
gcctgagccc cggcaagggc ggcggcggcg cgactacta cgactacgac ggcggctact  2340
actacgacgg cgactgagcg gccgcaatca acctctggat tacaaaattt gtgaaagatt  2400
gactggtatt cttaactatg ttgctccttt tacgctatgt ggatacgctg ctttaatgcc  2460
tttgtatcat gctattgctt cccgtatggc tttcattttc tcctccttgt ataaatcctg  2520
gttgctgtct ctttatgagg agttgtggcc cgttgtcagg caacgtggcg tggtgtgcac  2580
tgtgtttgct gacgcaaccc ccactggttg gggcattgcc accacctgtc agctcctttc  2640
cgggactttc gctttccccc tccctattgc cacggcggaa ctcatcgccg cctgccttgc  2700
ccgctgctgg acagggctc ggctgttggg cactgacaat tccgtggtgt tgtcggggaa  2760
atcatcgtcc tttccttggc tgctcgcctg tgttgccacc tggattctgc gcgggacgtc  2820
cttctgctac gtcccttcgg ccctcaatcc agcggacctt ccttcccgcg gcctgctgcc  2880
ggctctgcgg cctcttccgc gtcttcgcct tcgccctcag acgagtcgga tctccctttg  2940
ggccgcctcc ccgcctgggg gatccagaca tgataagata cattgatgag tttggacaaa  3000
ccacaactag aatgcagtga aaaaaatgct ttatttgtga aatttgtgat gctattgctt  3060
tatttgtaac cattataagc tgcaataaac aagttaacaa caacaattgc attcatttta  3120
tgtttcaggt tcaggggag gtgtgggagg ttttttcgga tcctctagag tcgaccagag  3180
catggctacg tagataagta gcatggcggg ttaatcatta actacaagga acccctagtg  3240
atggagttgg ccactccctc tctgcgcgct cgctcgctca ctgaggccgg gcgaccaaag  3300
gtcgcccgac gcccgggctt tgcccgggcg gcctcagtga gcgagcgagc gcgccagctg  3360
cattaatgaa tcggccaacg cgcggggaga ggcggtttgc gtattgggc  3409
```

<210> SEQ ID NO 35
<211> LENGTH: 609
<212> TYPE: DNA
<213> ORGANISM: Artificial sequence
<220> FEATURE:
<223> OTHER INFORMATION: Synthetic sequence

<400> SEQUENCE: 35

```
atgaaccggg gagtcccttt taggcacttg cttctggtgc tgcaactggc gctcctccca    60
gcagccactc agggaaagaa agtggtgctg ggcaaaaaag gggatacagt ggaactgacc   120
tgtacagctt cccagaagaa gagcatacaa ttccactgga aaaactccaa ccagataaag   180
attctgggaa atcagggctc cttcttaact aaaggtccat ccaagctgaa tgatcgcgct   240
gactcaagaa gaagcctttg ggaccaagga aactttcccc tgatcatcaa gaatcttaag   300
atagaagact cagatactta catctgtgaa gtggaggacc agaaggagga ggtgcaattg   360
ctagtgttcg gattgactgc caactctgac acccacctgc ttcagggca gagcctgacc   420 ctgaccttgg agagcccccc tggtagtagc ccctcagtgc aatgtaggag tccaagggt   480 aaaaacatac agggggggaa gaccctctcc gtgtctcagc tggagctcca ggatagtggc   540
acctggacat gcactgtctt gcagaaccag aagaaggtgg agttcaaaat agacatcgtg   600
gtgctagct                                                           609
```

<210> SEQ ID NO 36
<211> LENGTH: 178
<212> TYPE: PRT
<213> ORGANISM: Artificial sequence
<220> FEATURE:
<223> OTHER INFORMATION: Synthetic sequence

<400> SEQUENCE: 36

Lys Lys Val Val Leu Ala Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Leu
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Leu Glu Phe Lys Ile Asp Ile Val Val
                165                 170                 175

Leu Ala

<210> SEQ ID NO 37
<211> LENGTH: 534
<212> TYPE: DNA
<213> ORGANISM: Artificial sequence
<220> FEATURE:
<223> OTHER INFORMATION: Synthetic sequence

<400> SEQUENCE: 37

```
aagaaggtgg tgctggccaa gaagggcgat accgtggagc tgacctgcac cgccagccag    60
```

```
aagaagaaca tccagttcca ctggaagaac agcaaccaga tcaagatcct gggcaaccag    120
ggcagcttcc tgaccaaggg cccaagcaag ctgaacgata gagtggatag cagaagaagc    180
ctgtgggatc agggcaactt cccactgatc atcaagaacc tgaagatcga ggatagcgat    240
acctacatct gcgaggtgga ggatcagaag gaggaggtgc agctgctggt gttcggcctg    300
accgccaaca gcgataccca cctgctgcag ggccagagcc tgaccctgac cctggagagc    360
ccaccaggca gcagcccaag cctgcagtgc agaagcccaa gaggcaagaa catccagggc    420
ggcaagaccc tgagcgtgag ccagctggag ctgcaggata gcggcacctg gacctgcacc    480
gtgctgcaga accagaagaa gctggagttc aagatcgata tcgtggtgct ggcc          534
```

```
<210> SEQ ID NO 38
<211> LENGTH: 178
<212> TYPE: PRT
<213> ORGANISM: Artificial sequence
<220> FEATURE:
<223> OTHER INFORMATION: Synthetic sequence

<400> SEQUENCE: 38
```

```
Lys Lys Val Val Leu Ala Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Leu
        115                 120                 125

Gln Cys Arg Ser Pro Arg Gly Lys Asn Ile Gln Gly Gly Lys Thr Leu
    130                 135                 140

Ser Ile Ser Gln Leu Glu Leu Gln Asp Ser Gly Thr Trp Thr Cys Thr
145                 150                 155                 160

Val Leu Gln Asn Gln Lys Lys Leu Glu Phe Lys Ile Asp Ile Val Val
                165                 170                 175

Leu Ala
```

```
<210> SEQ ID NO 39
<211> LENGTH: 534
<212> TYPE: DNA
<213> ORGANISM: Artificial sequence
<220> FEATURE:
<223> OTHER INFORMATION: Synthetic sequence

<400> SEQUENCE: 39
```

```
aagaaggtgg tgctggccaa gaagggcgat accgtggagc tgacctgcac cgccagccag     60
aagaagaaca tccagttcca ctggaagaac agcaaccaga tcaagatcct gggcaaccag    120
ggcagcttcc tgaccaaggg cccaagcaag ctgaacgata gagtggatag cagaagaagc    180
ctgtgggatc agggcaactt cccactgatc atcaagaacc tgaagatcga ggatagcgat    240
```

```
acctacatct gcgaggtgga ggatcagaag gaggaggtgc agctgctggt gttcggcctg    300
accgccaaca gcgatacccca cctgctgcag ggccagagcc tgaccctgac cctggagagc   360
ccaccaggca gcagcccaag cctgcagtgc agaagcccaa gaggcaagaa catccagggc   420
ggcaagaccc tgagcatcag ccagctggag ctgcaggata gcggcacctg gacctgcacc   480
gtgctgcaga accagaagaa gctggagttc aagatcgata tcgtggtgct ggcc          534
```

<210> SEQ ID NO 40
<211> LENGTH: 178
<212> TYPE: PRT
<213> ORGANISM: Artificial sequence
<220> FEATURE:
<223> OTHER INFORMATION: Synthetic sequence

<400> SEQUENCE: 40

```
Lys Lys Val Val Leu Gly Lys Lys Gly Asp Thr Val Glu Leu Thr Cys
 1               5                  10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Ser Asn Leu Glu Ile Glu Asp Ser Asp
65                  70                  75                  80

Thr Tyr Ile Cys Glu Val Glu Asp Gln Lys Glu Glu Val Glu Leu Val
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Val
        115                 120                 125

Gln Cys Arg Ser Pro Gly Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asp Gln Lys Thr Val Glu Phe Lys Ile Asp Ile Val Val
                165                 170                 175

Leu Ala
```

<210> SEQ ID NO 41
<211> LENGTH: 534
<212> TYPE: DNA
<213> ORGANISM: Artificial sequence
<220> FEATURE:
<223> OTHER INFORMATION: Synthetic sequence

<400> SEQUENCE: 41

```
aagaaggtgg tgctgggcaa gaagggcgat accgtggagc tgacctgcac cgccagccag    60
aagaagaaca tccagttcca ctggaagaac agcaaccaga tcaagatcct gggcaaccag   120
ggcagcttcc tgaccaaggg cccaagcaag ctgaacgata gagtggatag cagaagaagc   180
ctgtgggatc agggcaactt cccactgatc atcagcaacc tggagatcga ggatagcgat   240
acctacatct gcgaggtgga ggatcagaag gaggaggtgg agctggtggt gttcggcctg   300
accgccaaca gcgatacccca cctgctggag ggccagagcc tgaccctgac cctggagagc   360
ccaccaggca gcagcccaag cgtgcagtgc agaagcccag gcggcaagaa catccagggc   420
```

```
ggcaagaccc tgagcgtgag ccagctggag ctgcaggata gcggcacctg gacctgcacc    480
gtgctgcagg atcagaagac cgtggagttc aagatcgata tcgtggtgct ggcc          534
```

<210> SEQ ID NO 42
<211> LENGTH: 178
<212> TYPE: PRT
<213> ORGANISM: Artificial sequence
<220> FEATURE:
<223> OTHER INFORMATION: Synthetic sequence

<400> SEQUENCE: 42

```
Lys Lys Val Val Leu Ala Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Asp Gln Lys Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Leu
        115                 120                 125

Gln Cys Arg Ser Pro Gly Gly Lys Asn Ile Gln Gly Gly Lys Thr Leu
    130                 135                 140

Ser Ile Ser Gln Leu Glu Leu Gln Asp Ser Gly Thr Trp Thr Cys Thr
145                 150                 155                 160

Val Leu Gln Asn Gln Lys Lys Leu Glu Phe Lys Ile Asp Ile Val Val
                165                 170                 175

Leu Ala
```

<210> SEQ ID NO 43
<211> LENGTH: 534
<212> TYPE: DNA
<213> ORGANISM: Artificial sequence
<220> FEATURE:
<223> OTHER INFORMATION: Synthetic sequence

<400> SEQUENCE: 43

```
aagaaggtgg tgctggccaa gaagggcgat accgtggagc tgacctgcac cgccagccag    60
aagaagaaca tccagttcca ctggaagaac agcaaccaga tcaagatcct gggcaaccag   120
ggcagcttcc tgaccaaggg cccaagcaag ctgaacgata gagtggatag cagaagaagc   180
ctgtgggatc agggcaactt ccccactgat catcaagaacc tgaagatcga ggatagcgat   240
acctacatct gcgaggtgga ggatcagaag gaggaggtgc agctgctggt gttcggcctg   300
accgccaaca gcgataccca cctgctgcag ggccagagcc tgaccctgac cctggagagc   360
ccaccaggca gcagcccaag cctgcagtgc agaagcccag cggcaagaa catccagggc   420 ggcaagaccc tgagcatcag ccagctggag ctgcaggata gcggcacctg gacctgcacc   480
gtgctgcaga accagaagaa gctggagttc aagatcgata tcgtggtgct ggcc          534
```

<210> SEQ ID NO 44

<211> LENGTH: 178
<212> TYPE: PRT
<213> ORGANISM: Artificial sequence
<220> FEATURE:
<223> OTHER INFORMATION: Synthetic sequence

<400> SEQUENCE: 44

```
Lys Lys Val Val Leu Ala Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Ser Asn Leu Glu Ile Glu Asp Ser Asp
65                  70                  75                  80

Thr Tyr Ile Cys Glu Val Glu Asp Gln Lys Glu Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Leu
        115                 120                 125

Gln Cys Arg Ser Pro Gly Gly Lys Asn Ile Gln Gly Gly Lys Thr Leu
    130                 135                 140

Ser Ile Ser Gln Leu Glu Leu Gln Asp Ser Gly Thr Trp Thr Cys Thr
145                 150                 155                 160

Val Leu Gln Asp Gln Lys Thr Leu Glu Phe Lys Ile Asp Ile Val Val
                165                 170                 175

Leu Ala
```

<210> SEQ ID NO 45
<211> LENGTH: 534
<212> TYPE: DNA
<213> ORGANISM: Artificial sequence
<220> FEATURE:
<223> OTHER INFORMATION: Synthetic sequence

<400> SEQUENCE: 45

```
aagaaggtgg tgctggccaa gaagggcgat accgtggagc tgacctgcac cgccagccag      60
aagaagaaca tccagttcca ctggaagaac agcaaccaga tcaagatcct gggcaaccag     120
ggcagcttcc tgaccaaggg cccaagcaag ctgaacgata gagtggatag cagaagaagc     180
ctgtgggatc agggcaactt cccactgatc atcagcaacc tggagatcga ggatagcgat     240
acctacatct gcgaggtgga ggatcagaag gaggaggtgg agctgctggt gttcggcctg     300
accgccaaca gcgatacccc cctgctggag gccagagcc tgaccctgac cctggagagc     360
ccaccaggca gcagcccaag cctgcagtgc agaagcccag gcggcaagaa catccagggc     420
ggcaagaccc tgagcatcag ccagctggag ctgcaggata gcggcacctg gacctgcacc     480
gtgctgcagg atcagaagac cctggagttc aagatcgata tcgtggtgct ggcc           534
```

<210> SEQ ID NO 46
<211> LENGTH: 25
<212> TYPE: PRT
<213> ORGANISM: Artificial sequence
<220> FEATURE:
<223> OTHER INFORMATION: Synthetic sequence

```
<400> SEQUENCE: 46

Met Asn Arg Gly Val Pro Phe Arg His Leu Leu Val Leu Gln Leu
1               5                   10                  15

Ala Leu Leu Pro Ala Ala Thr Gln Gly
            20                  25

<210> SEQ ID NO 47
<211> LENGTH: 75
<212> TYPE: DNA
<213> ORGANISM: Artificial sequence
<220> FEATURE:
<223> OTHER INFORMATION: Synthetic sequence

<400> SEQUENCE: 47
atgaacagag gcgtgccctt cagacacctg ctgctggtgc tgcagctggc cctgctgccc        60
gccgccaccc agggc                                                       75

<210> SEQ ID NO 48
<211> LENGTH: 178
<212> TYPE: PRT
<213> ORGANISM: Pan troglodytes

<400> SEQUENCE: 48

Lys Lys Val Val Leu Gly Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Thr Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Thr Leu Ile Ile Lys Asn Leu Lys Ile Glu Asp Ser Asp
65                  70                  75                  80

Thr Tyr Ile Cys Glu Val Gly Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 49
<211> LENGTH: 178
<212> TYPE: PRT
<213> ORGANISM: Pan paniscus

<400> SEQUENCE: 49

Lys Lys Val Val Leu Gly Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30
```

```
Gln Thr Lys Ile Leu Gly Asn Gln Gly Ser Phe Leu Thr Lys Gly Pro
             35                  40                  45

Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Gly Asp Gln Lys Glu Val Gln Leu Leu
                 85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
             115                 120                 125

Gln Cys Arg Ser Pro Arg Gly Lys Asn Ile Gln Gly Gly Lys Thr Leu
         130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 50
<211> LENGTH: 178
<212> TYPE: PRT
<213> ORGANISM: Gorilla gorilla

<400> SEQUENCE: 50

Asn Lys Val Val Leu Gly Lys Lys Gly Asp Thr Val Glu Leu Asn Cys
 1               5                  10                  15

Thr Ala Ser Gln Lys Lys Ser Ile Gln Phe His Trp Lys Asn Ser Asn
             20                  25                  30

Gln Met Lys Ile Leu Gly Asn Gln Gly Ser Phe Leu Thr Lys Gly Pro
             35                  40                  45

Ser Lys Leu Ser Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Gly Gln Lys Glu Glu Val Gln Leu Leu
                 85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
             115                 120                 125

Gln Cys Arg Ser Pro Arg Gly Lys Asn Ile Gln Gly Gly Lys Thr Leu
         130                 135                 140

Ser Val Ser Gln Leu Glu Leu Gln Asp Ser Gly Thr Trp Thr Cys Thr
145                 150                 155                 160

Val Leu Gln Asn Gln Glu Lys Val Glu Phe Lys Ile Asp Ile Val Val
                165                 170                 175

Leu Ala

<210> SEQ ID NO 51
<211> LENGTH: 178
<212> TYPE: PRT
<213> ORGANISM: Bornean orangutan

<400> SEQUENCE: 51
```

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Thr Lys Ile Leu Gly Asn Gln Gly Ser Phe Leu Thr Lys Gly Pro
                35                  40                  45

Ser Lys Leu Ser Asn Arg Ala Asp Ser Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
                100                 105                 110

Ser Leu Thr Leu Ala Leu Glu Ser Pro Pro Gly Ser Ser Pro Ser Val
                115                 120                 125

Gln Cys Arg Ser Pro Thr Gly Lys Asn Ile Gln Ala Gly Lys Thr Leu
130                 135                 140

Ser Val Ser Gln Leu Glu Leu Gln Asp Ser Gly Thr Arg Thr Cys Ala
145                 150                 155                 160

Val Leu Gln Asp Gln Lys Lys Val Glu Phe Lys Ile Asp Ile Val Val
                165                 170                 175

Leu Ala

<210> SEQ ID NO 52
<211> LENGTH: 178
<212> TYPE: PRT
<213> ORGANISM: white-cheeked gibbon

<400> SEQUENCE: 52

Lys Lys Val Val Leu Gly Lys Lys Gly Asp Thr Val Glu Leu Thr Cys
1               5                   10                  15

Thr Ala Ser Pro Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
                35                  40                  45

Ser Lys Leu Ser Asp Arg Ala Asp Ser Arg Lys Ser Leu Trp Asp Gln
    50                  55                  60

Arg Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
                100                 105                 110

Ser Leu Thr Leu Thr Leu Glu Gly Pro Pro Gly Ser Ser Pro Ser Val
                115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asp Gln Lys Lys Val Glu Phe Lys Ile Asp Ile Val Val
                165                 170                 175

Leu Ala

<210> SEQ ID NO 53
<211> LENGTH: 178
<212> TYPE: PRT
<213> ORGANISM: Agile gibbon

<400> SEQUENCE: 53

Lys Lys Val Val Leu Gly Lys Lys Gly Asp Thr Val Glu Leu Thr Cys
1               5                   10                  15

Thr Ala Ser Pro Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Arg Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Pro Gln Leu Glu Leu Gln Asp Ser Gly Thr Trp Thr Cys Thr
145                 150                 155                 160

Val Leu Gln Asp Gln Lys Lys Val Glu Phe Lys Ile Asp Ile Val Val
                165                 170                 175

Leu Ala

<210> SEQ ID NO 54
<211> LENGTH: 178
<212> TYPE: PRT
<213> ORGANISM: Siamang

<400> SEQUENCE: 54

Lys Lys Val Val Leu Gly Lys Lys Gly Asp Thr Val Glu Leu Thr Cys
1               5                   10                  15

Ile Ala Ser Pro Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Gly Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Pro Gln Leu Glu Leu Gln Asp Ser Gly Thr Trp Thr Cys Thr

```
                145                 150                 155                 160
Val Leu Gln Asp Gln Lys Lys Val Glu Phe Lys Ile Asp Ile Val Val
                    165                 170                 175

Leu Ala

<210> SEQ ID NO 55
<211> LENGTH: 178
<212> TYPE: PRT
<213> ORGANISM: Colobus monkey

<400> SEQUENCE: 55

Lys Asn Val Val Leu Gly Lys Lys Gly Asp Thr Val Glu Leu Thr Cys
1               5                   10                  15

Asn Ala Pro Ser Lys Lys Asn Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
        50                  55                  60

Gly Cys Phe Ser Met Ile Ile Lys Asn Leu Lys Ile Glu Asp Ser Asp
65                  70                  75                  80

Thr Tyr Ile Cys Glu Val Glu Asp Lys Lys Glu Glu Val Glu Leu Leu
                85                  90                  95

Val Phe Gly Leu Thr Ala Ser Ser Asp Thr His Leu Leu Gln Gly Gln
            100                 105                 110

Ser Leu Thr Leu Thr Leu Glu Ser Pro Pro Gly Thr Ser Pro Ser Val
        115                 120                 125

Gln Cys Arg Ser Pro Arg Gly Lys Asn Ile Gln Gly Gly Lys Thr Leu
    130                 135                 140

Ser Val Pro Gln Leu Glu Arg Gln Asp Ser Gly Thr Trp Thr Cys Thr
145                 150                 155                 160

Val Ser Gln Asp Gln Lys Arg Val Glu Phe Lys Ile Asp Ile Val Val
                165                 170                 175

Leu Ala

<210> SEQ ID NO 56
<211> LENGTH: 178
<212> TYPE: PRT
<213> ORGANISM: Colobus guereza

<400> SEQUENCE: 56

Lys Asn Val Val Leu Gly Lys Lys Gly Asp Thr Val Glu Leu Thr Cys
1               5                   10                  15

Asn Ala Pro Ser Lys Lys Asn Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
        50                  55                  60

Gly Cys Phe Ser Met Ile Ile Lys Asn Leu Lys Ile Glu Asp Ser Asp
65                  70                  75                  80

Thr Tyr Ile Cys Glu Val Glu Asp Lys Lys Glu Glu Val Glu Leu Leu
                85                  90                  95

Val Phe Gly Leu Thr Ala Ser Ser Asp Thr His Leu Leu Gln Gly Gln
            100                 105                 110
```

```
Ser Leu Thr Leu Thr Leu Glu Ser Pro Pro Gly Thr Ser Pro Ser Val
            115                 120                 125

Gln Cys Arg Ser Pro Arg Gly Lys Asn Ile Gln Gly Gly Lys Thr Leu
        130                 135                 140

Ser Val Pro Gln Leu Glu Arg Gln Asp Ser Gly Thr Trp Thr Cys Thr
145                 150                 155                 160

Val Ser Gln Asp Gln Lys Arg Val Glu Phe Lys Ile Asp Ile Val Val
                165                 170                 175

Leu Ala

<210> SEQ ID NO 57
<211> LENGTH: 178
<212> TYPE: PRT
<213> ORGANISM: Angolan colobus

<400> SEQUENCE: 57

Lys Asn Val Val Leu Gly Lys Lys Gly Asp Thr Val Glu Leu Thr Cys
1               5                   10                  15

Asn Ala Pro Pro Lys Lys Asn Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
        50                  55                  60

Gly Cys Phe Ser Met Ile Ile Lys Asn Leu Lys Ile Glu Asp Ser Asp
65                  70                  75                  80

Thr Tyr Ile Cys Glu Val Glu Asp Lys Lys Glu Val Glu Leu Leu
                85                  90                  95

Val Phe Gly Leu Thr Ala Ser Asp Thr His Leu Leu Gln Gly Gln
                100                 105                 110

Ser Leu Thr Leu Thr Leu Glu Ser Pro Pro Gly Thr Ser Pro Ser Val
            115                 120                 125

Gln Cys Arg Ser Pro Arg Gly Lys Asn Ile Gln Gly Gly Lys Thr Leu
        130                 135                 140

Ser Val Pro Gln Leu Glu Arg Gln Asp Ser Gly Thr Trp Thr Cys Thr
145                 150                 155                 160

Ile Ser Gln Asp Gln Lys Arg Val Glu Phe Lys Ile Asp Ile Val Val
                165                 170                 175

Leu Ala

<210> SEQ ID NO 58
<211> LENGTH: 176
<212> TYPE: PRT
<213> ORGANISM: African green monkey

<400> SEQUENCE: 58

Val Val Leu Gly Lys Lys Gly Asp Thr Val Glu Leu Thr Cys Asn Ala
1               5                   10                  15

Ser Gln Lys Thr Thr Thr Gln Phe His Trp Lys Asn Ser Asn Gln Thr
                20                  25                  30

Lys Ile Leu Gly Lys Gln Gly Ser Phe Leu Thr Lys Gly Ser Ser Lys
            35                  40                  45

Leu Arg Asp Arg Ile Asp Ser Arg Lys Ser Leu Trp Asp Gln Gly Cys
        50                  55                  60

Phe Ser Met Ile Ile Lys Asn Leu Lys Ile Glu Asp Ser Glu Thr Tyr
65                  70                  75                  80
```

Ile Cys Glu Val Glu Asn Lys Lys Glu Val Leu Leu Val Phe
            85                  90                  95

Gly Leu Thr Ala Asn Ser Asp Thr His Leu Leu Gln Gly Gln Ser Leu
            100                 105                 110

Thr Leu Thr Leu Glu Ser Pro Pro Gly Ser Ser Pro Ser Val Lys Cys
            115                 120                 125

Arg Ser Pro Arg Gly Lys Asn Ile Gln Val Gly Arg Thr Leu Ser Val
130                 135                 140

Pro Gln Leu Glu Arg Gln Asp Ser Gly Thr Trp Thr Cys Thr Val Ser
145                 150                 155                 160

Gln Asp Gln Asn Thr Val Glu Phe Lys Ile Asp Ile Val Val Leu Ala
                165                 170                 175

<210> SEQ ID NO 59
<211> LENGTH: 178
<212> TYPE: PRT
<213> ORGANISM: Vervet monkey

<400> SEQUENCE: 59

Lys Lys Val Val Leu Gly Lys Lys Gly Asp Thr Val Glu Leu Thr Cys
1               5                   10                  15

Asn Ala Ser Gln Lys Thr Thr Thr Gln Phe His Trp Lys Asn Ser Asn
            20                  25                  30

Gln Thr Lys Ile Leu Gly Lys Gln Gly Ser Phe Leu Thr Lys Gly Ser
            35                  40                  45

Ser Lys Leu Arg Asp Arg Ile Asp Ser Arg Lys Ser Leu Trp Asp Gln
50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asn Lys Lys Glu Val Glu Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Lys Cys Arg Ser Pro Arg Gly Lys Asn Ile Gln Val Gly Arg Thr Leu
            130                 135                 140

Ser Val Pro Gln Leu Glu Arg Gln Asp Ser Gly Thr Trp Thr Cys Thr
145                 150                 155                 160

Val Ser Gln Asp Gln Asn Thr Val Glu Phe Lys Ile Asp Ile Val Val
                165                 170                 175

Leu Ala

<210> SEQ ID NO 60
<211> LENGTH: 178
<212> TYPE: PRT
<213> ORGANISM: Sabaeus monkey

<400> SEQUENCE: 60

Lys Lys Val Val Leu Gly Lys Lys Gly Asp Thr Val Glu Leu Thr Cys
1               5                   10                  15

Asn Ala Ser Gln Asn Thr Thr Thr Gln Phe His Trp Lys Asn Ser Asn
            20                  25                  30

Gln Ile Lys Ile Leu Gly Lys Gln Gly Ser Phe Leu Thr Lys Gly Ser
            35                  40                  45

```
Ser Lys Leu Arg Asp Arg Ile Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asn Lys Lys Glu Glu Val Glu Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Lys Cys Arg Ser Pro Arg Gly Lys Asn Ile Gln Gly Gly Arg Thr Leu
130                 135                 140

Ser Val Pro Gln Leu Glu Arg Gln Asp Ser Gly Thr Trp Thr Cys Thr
145                 150                 155                 160

Val Ser Gln Asp Gln Asn Thr Val Glu Phe Lys Ile Asp Ile Val Val
                165                 170                 175

Leu Ala

<210> SEQ ID NO 61
<211> LENGTH: 176
<212> TYPE: PRT
<213> ORGANISM: Tantalus monkey

<400> SEQUENCE: 61

Val Val Leu Gly Lys Lys Gly Asp Thr Val Glu Leu Thr Cys Asn Ala
1               5                   10                  15

Ser Gln Asn Thr Thr Thr Gln Phe His Trp Lys Asn Ser Asn Gln Ile
                20                  25                  30

Lys Ile Leu Gly Lys Gln Gly Ser Phe Leu Thr Lys Gly Ser Ser Lys
            35                  40                  45

Leu Arg Asp Arg Ile Asp Ser Arg Lys Ser Leu Trp Asp Gln Gly Cys
        50                  55                  60

Phe Ser Met Ile Ile Lys Asn Leu Lys Ile Glu Asp Ser Glu Thr Tyr
65                  70                  75                  80

Ile Cys Glu Val Glu Asn Lys Lys Glu Glu Val Glu Leu Leu Val Phe
                85                  90                  95

Gly Leu Thr Ala Asn Ser Asp Thr His Leu Leu Gln Gly Gln Ser Leu
            100                 105                 110

Thr Leu Thr Leu Glu Ser Pro Pro Gly Ser Ser Pro Ser Val Lys Cys
        115                 120                 125

Arg Ser Pro Arg Gly Lys Asn Ile Gln Gly Gly Arg Thr Leu Ser Val
130                 135                 140

Pro Gln Leu Glu Arg Gln Asp Ser Gly Thr Trp Thr Cys Thr Val Ser
145                 150                 155                 160

Gln Asp Gln Asn Thr Val Glu Phe Lys Ile Asp Ile Val Val Leu Ala
                165                 170                 175

<210> SEQ ID NO 62
<211> LENGTH: 176
<212> TYPE: PRT
<213> ORGANISM: Red guenon

<400> SEQUENCE: 62

Val Val Leu Gly Lys Lys Gly Asp Thr Val Glu Leu Thr Cys Asn Ala
1               5                   10                  15

Ser Gln Lys Thr Thr Thr Gln Phe His Trp Lys Asn Ser Asn Gln Met
```

```
                    20                  25                  30
Lys Ile Leu Gly Lys Gln Gly Ser Phe Leu Thr Lys Gly Pro Ser Lys
                35                  40                  45

Leu Arg Asp Arg Thr Asp Ser Arg Lys Ser Leu Trp Asp Gln Gly Cys
 50                  55                  60

Phe Ser Met Ile Ile Lys Asn Leu Lys Ile Glu Asp Ser Glu Thr Tyr
 65                  70                  75                  80

Ile Cys Glu Val Glu Asp Lys Lys Glu Val Glu Leu Leu Val Phe
                 85                  90                  95

Gly Leu Thr Ala Asn Ser Asp Thr His Leu Leu Gln Gly Gln Ser Leu
                100                 105                 110

Thr Leu Thr Leu Glu Ser Pro Pro Gly Ser Ser Pro Ser Val Lys Cys
                115                 120                 125

Arg Ser Pro Arg Gly Lys Asn Ile Gln Gly Gly Arg Thr Leu Ser Val
                130                 135                 140

Pro Gln Leu Glu Arg Gln Asp Ser Gly Thr Trp Thr Cys Thr Val Ser
145                 150                 155                 160

Gln Asp Gln Asn Thr Val Glu Phe Lys Ile Asp Ile Val Val Leu Ala
                165                 170                 175
```

<210> SEQ ID NO 63
<211> LENGTH: 178
<212> TYPE: PRT
<213> ORGANISM: Sooty mangabey

<400> SEQUENCE: 63

```
Lys Asn Val Val Leu Gly Lys Lys Gly Asp Thr Val Glu Leu Ala Cys
 1               5                  10                  15

Asn Ala Ser Gln Lys Lys Ser Thr Gln Phe His Trp Lys Asn Ser Lys
                20                  25                  30

Gln Ile Lys Ile Leu Gly Asn Gln Gly Ser Phe Leu Thr Lys Gly Ser
                35                  40                  45

Ser Lys Leu Ser Asp Arg Ala Asp Ser Arg Lys Ser Leu Trp Asp Gln
 50                  55                  60

Gly Cys Phe Ser Met Ile Ile Lys Asn Leu Lys Ile Glu Asp Ser Glu
 65                  70                  75                  80

Thr Tyr Ile Cys Glu Val Glu Asn Lys Lys Glu Glu Val Glu Leu Leu
                 85                  90                  95

Val Phe Gly Leu Thr Ala Asn Ser Asp Thr His Leu Leu Glu Gly Gln
                100                 105                 110

Ser Leu Thr Leu Thr Leu Glu Ser Pro Pro Gly Ser Ser Pro Ser Val
                115                 120                 125

Lys Cys Arg Ser Pro Arg Gly Lys Asn Ile Gln Gly Gly Arg Thr Leu
                130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala
```

<210> SEQ ID NO 64
<211> LENGTH: 178
<212> TYPE: PRT
<213> ORGANISM: Mandrill

<400> SEQUENCE: 64

```
Lys Asn Val Val Leu Gly Lys Lys Gly Asp Thr Val Glu Leu Thr Cys
1               5                   10                  15

Asn Ala Ser Gln Lys Lys Asn Thr Pro Phe His Trp Lys Asn Ser Lys
            20                  25                  30

Gln Ile Lys Ile Leu Gly Lys Gln Ser Ser Phe Leu Thr Lys Gly Pro
            35                  40                  45

Ser Lys Leu Ser Asp Arg Ile Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Glu Leu Leu
                85                  90                  95

Val Phe Gly Leu Thr Ala Asn Ser Asp Thr His Leu Leu Glu Gly Gln
                100                 105                 110

Ser Leu Thr Leu Thr Leu Glu Ser Pro Pro Gly Ser Ser Pro Ser Val
                115                 120                 125

Lys Cys Arg Ser Pro Arg Gly Lys Asn Ile Gln Gly Gly Arg Thr Leu
    130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala

<210> SEQ ID NO 65
<211> LENGTH: 178
<212> TYPE: PRT
<213> ORGANISM: Black snub-nose monkey

<400> SEQUENCE: 65

Lys Lys Val Val Leu Gly Lys Lys Gly Asp Thr Val Glu Leu Thr Cys
1               5                   10                  15

Ser Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Glu Leu Leu
                85                  90                  95

Val Phe Gly Leu Thr Ala Asn Ser Asp Thr His Leu Leu Gln Gly Gln
                100                 105                 110

Ser Leu Thr Leu Thr Leu Glu Ser Pro Pro Gly Ser Ser Pro Ser Val
                115                 120                 125

Gln Cys Arg Ser Pro Arg Gly Lys Asn Ile Gln Gly Gly Lys Thr Leu
    130                 135                 140

Ser Val Pro Gln Leu Glu Arg Gln Asp Ser Gly Ile Trp Thr Cys Thr
145                 150                 155                 160

Val Ser Gln Asp Gln Lys Thr Val Glu Phe Lys Ile Asp Ile Met Val
                165                 170                 175

Leu Ala
```

<210> SEQ ID NO 66
<211> LENGTH: 178
<212> TYPE: PRT
<213> ORGANISM: Golden snub-nose monkey

<400> SEQUENCE: 66

```
Lys Lys Val Val Leu Gly Lys Lys Gly Asp Thr Val Glu Leu Thr Cys
1               5                   10                  15

Ser Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Glu Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Pro Gln Leu Glu Arg Gln Asp Ser Gly Ile Trp Thr Cys Thr
145                 150                 155                 160

Val Ser Gln Asp Gln Lys Thr Val Glu Phe Lys Ile Asp Ile Met Val
                165                 170                 175

Leu Ala
```

<210> SEQ ID NO 67
<211> LENGTH: 178
<212> TYPE: PRT
<213> ORGANISM: Leaf monkey

<400> SEQUENCE: 67

```
Lys Lys Val Val Leu Gly Lys Lys Gly Asp Thr Val Glu Leu Thr Cys
1               5                   10                  15

Ser Ala Ser Gln Lys Lys Asn Ile Gln Phe His Trp Lys Asn Ser Lys
            20                  25                  30

Gln Ile Lys Ile Leu Gly Asn Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Lys Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Pro Gln Leu Glu Arg Gln Asp Ser Gly Ile Trp Thr Cys Thr
```

```
                    145                 150                 155                 160

Val Ser Gln Asp Gln Lys Thr Val Glu Phe Lys Ile Asp Ile Val Val
                    165                 170                 175

Leu Ala

<210> SEQ ID NO 68
<211> LENGTH: 178
<212> TYPE: PRT
<213> ORGANISM: Francoi's langur

<400> SEQUENCE: 68

Lys Lys Val Val Leu Gly Lys Lys Gly Asp Thr Val Glu Leu Thr Cys
1               5                   10                  15

Ser Ala Ser Gln Lys Lys Asn Ile Gln Phe His Trp Lys Asn Ser Lys
                20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
        50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Lys Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Pro Gln Leu Glu Arg Gln Asp Ser Gly Ile Trp Thr Cys Thr
145                 150                 155                 160

Val Ser Gln Asp Gln Lys Thr Val Glu Phe Lys Ile Asp Ile Val Val
                    165                 170                 175

Leu Ala

<210> SEQ ID NO 69
<211> LENGTH: 178
<212> TYPE: PRT
<213> ORGANISM: Pig-tailed macaque

<400> SEQUENCE: 69

Lys Lys Val Val Leu Gly Lys Lys Gly Asp Thr Val Glu Leu Thr Cys
1               5                   10                  15

Asn Ala Ser Gln Lys Lys Asn Thr Gln Phe His Trp Lys Asn Ser Asp
                20                  25                  30

Gln Ile Lys Ile Leu Gly Ile Gln Gly Ser Phe Leu Thr Lys Gly Pro
            35                  40                  45

Ser Lys Leu Ser Asp Arg Ala Asp Ser Arg Lys Ser Leu Trp Asp Gln
        50                  55                  60

Gly Cys Phe Ser Met Ile Ile Lys Asn Leu Lys Ile Glu Asp Ser Asn
65                  70                  75                  80

Thr Tyr Ile Cys Glu Val Glu Asn Lys Lys Glu Glu Val Glu Leu Leu
                85                  90                  95

Val Phe Gly Leu Thr Ala Asn Ser Asp Thr His Leu Leu Glu Gly Gln
            100                 105                 110
```

```
Ser Leu Thr Leu Thr Leu Glu Ser Pro Pro Gly Ser Ser Pro Ser Val
            115                 120                 125

Lys Cys Arg Ser Pro Gly Gly Lys Asn Ile Gln Gly Gly Arg Thr Leu
130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala

<210> SEQ ID NO 70
<211> LENGTH: 178
<212> TYPE: PRT
<213> ORGANISM: Rhesus macaque

<400> SEQUENCE: 70

Lys Lys Val Val Leu Gly Lys Lys Gly Asp Thr Val Glu Leu Thr Cys
1               5                   10                  15

Asn Ala Ser Gln Lys Lys Asn Thr Gln Phe His Trp Lys Asn Ser Asn
            20                  25                  30

Gln Ile Lys Ile Leu Gly Ile Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Asp
65                  70                  75                  80

Thr Tyr Ile Cys Glu Val Glu Asn Lys Lys Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Val
            115                 120                 125

Lys Cys Arg Ser Pro Gly Gly Lys Asn Ile Gln Gly Gly Arg Thr Leu
130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala

<210> SEQ ID NO 71
<211> LENGTH: 178
<212> TYPE: PRT
<213> ORGANISM: Cynomolgus macaque

<400> SEQUENCE: 71

Lys Lys Val Val Leu Gly Lys Lys Gly Asp Thr Val Glu Leu Thr Cys
1               5                   10                  15

Asn Ala Ser Gln Lys Lys Asn Thr Gln Phe His Trp Lys Asn Ser Asn
            20                  25                  30

Gln Ile Lys Ile Leu Gly Ile Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Asp
65                  70                  75                  80
```

Thr Tyr Ile Cys Glu Val Glu Asn Lys Lys Glu Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Val
        115                 120                 125

Lys Cys Arg Ser Pro Gly Gly Lys Asn Ile Gln Gly Gly Arg Thr Leu
    130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala

<210> SEQ ID NO 72
<211> LENGTH: 178
<212> TYPE: PRT
<213> ORGANISM: Japanese macaque

<400> SEQUENCE: 72

Lys Lys Val Val Leu Gly Lys Lys Gly Asp Thr Val Glu Leu Thr Cys
1               5                   10                  15

Asn Ala Ser Gln Lys Lys Asn Thr Gln Phe His Trp Lys Asn Ser Asn
            20                  25                  30

Gln Ile Lys Ile Leu Gly Ile Gln Gly Ser Phe Leu Thr Lys Gly Pro
        35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Asp
65                  70                  75                  80

Thr Tyr Ile Cys Glu Val Glu Asn Lys Lys Glu Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Ser Ser Pro Ser Val
        115                 120                 125

Lys Cys Arg Ser Pro Gly Gly Lys Asn Ile Gln Gly Gly Arg Thr Ile
    130                 135                 140

Ser Val Pro Gln Leu Glu Arg Gln Asp Ser Gly Thr Trp Thr Cys Thr
145                 150                 155                 160

Val Ser Gln Asp Gln Lys Thr Val Glu Phe Lys Ile Asp Ile Val Val
                165                 170                 175

Leu Ala

<210> SEQ ID NO 73
<211> LENGTH: 178
<212> TYPE: PRT
<213> ORGANISM: Wolf's guenon

<400> SEQUENCE: 73

Lys Lys Val Val Leu Gly Lys Lys Gly Gly Thr Val Glu Leu Thr Cys
1               5                   10                  15

Asn Ala Thr Gln Lys Lys Asn Thr Gln Phe His Trp Lys His Ser Asn
            20                  25                  30

Gln Ile Lys Ile Leu Gly Asn Gln Gly Ser Phe Leu Thr Lys Gly Pro

```
                35                  40                  45
Ser Lys Leu Ser Asp Arg Ala Asp Ser Arg Lys Ser Leu Trp Asp Gln
     50                  55                  60
Gly Cys Phe Ser Met Ile Ile Lys Asn Leu Lys Ile Glu Asp Ser Glu
 65                  70                  75                  80
Thr Tyr Ile Cys Glu Val Glu Asp Lys Lys Glu Glu Val Glu Leu Leu
                 85                  90                  95
Val Phe Gly Leu Thr Ala Asn Ser Asp Thr His Leu Leu Gln Gly Gln
                100                 105                 110
Ser Leu Thr Leu Thr Leu Glu Ser Pro Pro Gly Ser Ser Pro Ser Val
                115                 120                 125
Lys Cys Arg Ser Pro Arg Gly Lys Asn Ile Gln Arg Gly Arg Thr Leu
                130                 135                 140
Ser Val Pro Gln Leu Glu Arg Gln Asp Ser Gly Thr Trp Thr Cys Thr
145                 150                 155                 160
Val Ser Gln Asp Gln Lys Thr Val Glu Phe Asn Ile Asp Ile Val Val
                165                 170                 175
Leu Ala

<210> SEQ ID NO 74
<211> LENGTH: 178
<212> TYPE: PRT
<213> ORGANISM: Talapoin

<400> SEQUENCE: 74

Lys Lys Val Val Leu Gly Lys Lys Gly Asp Thr Val Glu Leu Thr Cys
 1               5                  10                  15
Asn Ala Ser Gln Lys Lys Asn Thr Gln Phe His Trp Lys Asn Ser Asn
                20                  25                  30
Gln Ile Lys Ile Leu Gly Asn Gln Gly Ser Phe Leu Thr Lys Gly Pro
                35                  40                  45
Ser Lys Leu Ser Asp Arg Ala Asp Ser Arg Lys Ser Leu Trp Asp Gln
     50                  55                  60
Gly Cys Phe Ser Met Ile Ile Lys Asn Leu Lys Ile Glu Asp Ser Glu
 65                  70                  75                  80
Thr Tyr Ile Cys Glu Val Glu Asp Lys Lys Glu Glu Val Glu Leu Leu
                 85                  90                  95
Val Phe Gly Leu Thr Ala Asn Ser Asp Thr His Leu Leu Gln Gly Gln
                100                 105                 110
Ser Leu Thr Leu Thr Leu Glu Ser Pro Pro Gly Ser Ser Pro Ser Val
                115                 120                 125
Lys Cys Arg Ser Pro Arg Gly Lys Asn Ile Gln Gly Gly Arg Thr Leu
                130                 135                 140
Ser Val Pro Gln Leu Glu Arg Gln Asp Ser Gly Thr Trp Thr Cys Thr
145                 150                 155                 160
Val Ser Gln Asp Gln Lys Thr Val Glu Phe Lys Ile Asp Ile Val Val
                165                 170                 175
Leu Ala

<210> SEQ ID NO 75
<211> LENGTH: 178
<212> TYPE: PRT
<213> ORGANISM: Gray-cheeked mangabey

<400> SEQUENCE: 75
```

```
Lys Lys Val Val Leu Gly Lys Lys Gly Asp Thr Val Glu Leu Thr Cys
1               5                   10                  15

Asn Ala Ser Gln Lys Lys Ser Thr Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Thr Ser Pro Ser Val
            115                 120                 125

Lys Cys Arg Ser Pro Arg Gly Lys Asn Ile Gln Val Gly Arg Thr Leu
            130                 135                 140

Ser Val Pro Gln Leu Glu Arg Gln Asp Ser Gly Thr Trp Thr Cys Asn
145                 150                 155                 160

Val Ser Gln Asp Gln Lys Thr Val Glu Phe Lys Ile Asp Ile Val Val
                165                 170                 175

Leu Ala

<210> SEQ ID NO 76
<211> LENGTH: 178
<212> TYPE: PRT
<213> ORGANISM: Olive baboon

<400> SEQUENCE: 76

Lys Lys Val Val Leu Gly Lys Lys Gly Asp Thr Val Glu Leu Thr Cys
1               5                   10                  15

Asn Ala Ser Gln Lys Lys Ser Thr Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Ser Asp Arg Ala Asp Ser Arg Lys Ser Leu Trp Asp Gln
    50                  55                  60

Gly Cys Phe Ser Met Ile Ile Lys Asn Leu Lys Ile Glu Asp Ser Glu
65                  70                  75                  80

Thr Tyr Ile Cys Glu Val Glu Asp Lys Lys Glu Glu Val Glu Leu Leu
                85                  90                  95

Val Phe Gly Leu Thr Ala Asn Ser Asp Thr His Leu Leu Glu Gly Gln
            100                 105                 110

Ser Leu Thr Leu Thr Leu Glu Ser Pro Pro Gly Thr Ser Pro Ser Val
            115                 120                 125

Lys Cys Arg Ser Pro Arg Gly Lys Asn Ile Gln Gly Gly Arg Thr Leu
            130                 135                 140

Ser Val Pro Gln Leu Glu Arg Gln Asp Ser Gly Thr Trp Thr Cys Asn
145                 150                 155                 160

Val Ser Gln Asp Gln Lys Thr Val Glu Phe Lys Ile Asp Ile Val Val
                165                 170                 175

Leu Ala
```

```
<210> SEQ ID NO 77
<211> LENGTH: 177
<212> TYPE: PRT
<213> ORGANISM: Coppery_titi

<400> SEQUENCE: 77
```

Lys Thr Val Val Leu Gly Lys Lys Gly Glu Thr Val Glu Leu Ser Cys
1               5                   10                  15

Glu Thr Ser Leu Lys Lys Thr Leu Gln Phe Tyr Trp Lys Thr Ser Asp
            20                  25                  30

Gln Ile Lys Ile Leu Gly Ile Gln Gly Phe Leu Leu Thr Lys Gly Gln
        35                  40                  45

Ser Lys Leu Ala Asp Arg Ile Asp Ser Lys Ser Ser Trp Asp Arg
50                  55                  60

Gly Ser Phe Pro Leu Ile Ile Lys Asn Val Gln Val Glu Asp Ser Glu
65                  70                  75                  80

Thr Tyr Ile Cys Glu Val Glu Ser Lys Lys Glu Glu Val Glu Leu Gln
                85                  90                  95

Val Phe Gly Leu Thr Ala Thr Pro Asp Thr His Leu Leu Gln Gly Gln
            100                 105                 110

Asn Leu Thr Leu Thr Leu Glu Ser Pro Pro Gly Ser Ser Pro Ser Val
        115                 120                 125

Glu Cys Thr Ser Pro Arg Gly Lys Arg Ile Ser Gly Met Lys Thr Leu
130                 135                 140

Phe Leu Ser Gln Leu Val Ile Gln Asp Ser Gly Thr Gly Lys Cys Ala
145                 150                 155                 160

Leu Cys Gln His Arg Glu Leu Val Phe Gln Ile Asn Ile Val Val Leu
                165                 170                 175

Ala

```
<210> SEQ ID NO 78
<211> LENGTH: 177
<212> TYPE: PRT
<213> ORGANISM: Marmoset

<400> SEQUENCE: 78
```

Lys Thr Val Val Leu Gly Lys Lys Gly Glu Met Val Glu Leu Pro Cys
1               5                   10                  15

Glu Thr Ser Leu Lys Lys Leu Gln Phe His Trp Lys Thr Ser Asn
            20                  25                  30

Gln Ile Lys Ile Leu Gly Ile Gln Gly Ser Phe Val Thr Lys Gly Gln
        35                  40                  45

Ser Lys Leu Ala Asn Arg Ile Asp Ser Lys Gln Ser Ser Trp Asp Arg
50                  55                  60

Gly Ser Phe Pro Leu Ile Arg Asn Val Gln Val Glu Asp Ser Glu
65                  70                  75                  80

Thr Tyr Ile Cys Glu Val Glu Ser Lys Lys Glu Glu Val Glu Leu Gln
                85                  90                  95

Val Phe Gly Leu Thr Val Asn Pro Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Glu Cys Met Ser Pro Arg Gly Lys Thr Ile Arg Gly Met Lys Thr Leu
130                 135                 140

Phe Met Ser Gln Leu Glu Ile Gln Asp Ser Gly Thr Trp Lys Cys Thr
145                 150                 155                 160

```
Val Ser Gln His Leu Glu Leu Val Phe Lys Ile Asn Ile Val Val Leu
            165                 170                 175
Ala

<210> SEQ ID NO 79
<211> LENGTH: 177
<212> TYPE: PRT
<213> ORGANISM: Squirrel monkey

<400> SEQUENCE: 79

Lys Thr Val Val Leu Gly Lys Lys Gly Glu Val Glu Leu Pro Cys
1               5                   10                  15

Glu Thr Ser Leu Lys Lys Asn Val Pro Phe His Trp Lys Thr Ser Asp
            20                  25                  30

Arg Ile Lys Ile Leu Gly Val Gln Asn Tyr Phe Val Thr Arg Gly Gln
        35                  40                  45

Ser Lys Leu Thr Asp Arg Ile Asp Ser Lys Arg Ser Ser Trp Asp Arg
    50                  55                  60

Gly Ser Phe Pro Leu Leu Ile Lys Asp Ala Arg Ile Glu Asp Ser Glu
65                  70                  75                  80

Thr Tyr Ile Cys Glu Val Glu Ser Lys Lys Glu Val Glu Leu Gln
                85                  90                  95

Val Phe Gly Leu Thr Ala Asn Pro Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Glu Cys Thr Ser Pro Arg Gly Lys Arg Ile Arg Gly Arg Lys Thr Leu
    130                 135                 140

Ser Val Ser Gln Leu Gly Ile Pro Asp Ser Gly Thr Trp Lys Cys Thr
145                 150                 155                 160

Val Phe Gln His Leu Glu Leu Val Phe Glu Ile Asn Ile Val Val Leu
                165                 170                 175

Ala

<210> SEQ ID NO 80
<211> LENGTH: 177
<212> TYPE: PRT
<213> ORGANISM: Bolivian squirrel monkey

<400> SEQUENCE: 80

Lys Thr Val Val Leu Gly Lys Lys Gly Glu Val Glu Leu Pro Cys
1               5                   10                  15

Glu Thr Ser Leu Lys Lys Asn Val Pro Phe His Trp Lys Thr Ser Asp
            20                  25                  30

Gln Ile Lys Ile Leu Gly Val Gln Asn Tyr Phe Val Thr Arg Gly Gln
        35                  40                  45

Ser Lys Leu Thr Asp Arg Ile Asp Ser Lys Lys Ser Ser Trp Asp Arg
    50                  55                  60

Gly Ser Phe Pro Leu Leu Ile Lys Asp Ala Arg Ile Glu Asp Ser Glu
65                  70                  75                  80

Thr Tyr Ile Cys Glu Val Glu Ser Lys Lys Glu Val Glu Leu Gln
                85                  90                  95

Val Phe Gly Leu Thr Ala Asn Pro Asp Thr His Leu Leu Gln Gly Gln
            100                 105                 110

Ser Leu Thr Leu Thr Leu Glu Ser Pro Pro Gly Ser Ser Pro Ser Val
```

```
                    115                 120                 125
Glu Cys Thr Ser Pro Arg Gly Lys Arg Ile Arg Gly Arg Lys Thr Leu
            130                 135                 140

Ser Val Ser Gln Leu Gly Ile Pro Asp Ser Gly Thr Trp Lys Cys Thr
145                 150                 155                 160

Val Phe Gln His Leu Glu Leu Val Phe Glu Ile Asn Ile Val Val Leu
                165                 170                 175

Ala

<210> SEQ ID NO 81
<211> LENGTH: 177
<212> TYPE: PRT
<213> ORGANISM: Howler monkey

<400> SEQUENCE: 81

Lys Thr Val Val Leu Gly Arg Lys Gly Glu Thr Val Glu Leu Ser Cys
1               5                   10                  15

Glu Thr Ser Pro Lys Lys Asn Leu Gln Phe His Trp Lys Thr Ser Asn
            20                  25                  30

Gln Ile Lys Ile Leu Gly Val Gln Gly Ser Ser Leu Thr Lys Gly Gln
        35                  40                  45

Ser Lys Leu Ala Asp Arg Ile Asp Ser Lys Lys Ser Ser Trp Asp Arg
    50                  55                  60

Gly Ser Phe Pro Leu Ile Ile Lys Asn Val Gln Val Glu Asp Ser Glu
65                  70                  75                  80

Thr Tyr Ile Cys Glu Val Glu Ser Lys Lys Glu Glu Val Glu Leu Gln
                85                  90                  95

Val Phe Gly Leu Thr Ala Asn Pro Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Glu Cys Thr Ser Pro Arg Gly Lys Arg Ile Gln Gly Met Lys Ser Leu
    130                 135                 140

Ser Leu Ser Gln Leu Glu Ile Gln Asp Ser Gly Thr Trp Lys Cys Thr
145                 150                 155                 160

Val Ser Gln His Pro Gln Leu Val Phe Lys Ile Asn Ile Val Val Leu
                165                 170                 175

Ala

<210> SEQ ID NO 82
<211> LENGTH: 177
<212> TYPE: PRT
<213> ORGANISM: Bolivian red howler monkey

<400> SEQUENCE: 82

Lys Thr Val Val Leu Gly Arg Lys Gly Glu Thr Val Glu Leu Ser Cys
1               5                   10                  15

Glu Thr Ser Pro Lys Lys Asn Leu Gln Phe His Trp Lys Thr Ser Asn
            20                  25                  30

Gln Ile Lys Ile Leu Gly Val Gln Gly Ser Ser Leu Thr Lys Gly Gln
        35                  40                  45

Ser Lys Leu Ala Asp Arg Ile Asp Ser Lys Lys Ser Ser Trp Asp Arg
    50                  55                  60

Gly Ser Phe Pro Leu Ile Ile Lys Asn Val Gln Val Glu Asp Ser Glu
65                  70                  75                  80
```

```
Thr Tyr Ile Cys Glu Val Glu Ser Lys Lys Glu Val Glu Leu Gln
                85                  90                  95

Val Phe Gly Leu Thr Ala Asn Pro Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Glu Cys Thr Ser Pro Arg Gly Lys Arg Ile Gln Gly Met Lys Ser Leu
        130                 135                 140

Ser Leu Ser Gln Leu Glu Ile Gln Asp Ser Gly Thr Trp Lys Cys Thr
145                 150                 155                 160

Val Ser Gln His Pro Gln Leu Val Phe Lys Ile Asn Ile Val Val Leu
                165                 170                 175

Ala

<210> SEQ ID NO 83
<211> LENGTH: 177
<212> TYPE: PRT
<213> ORGANISM: Panamanian white throated capuchin

<400> SEQUENCE: 83

Lys Thr Val Val Leu Gly Lys Lys Gly Glu Met Val Glu Leu Pro Cys
1               5                   10                  15

Glu Thr Ser Leu Lys Lys Asn Thr Gln Phe His Trp Lys Thr Ser Asp
                20                  25                  30

Gln Ile Lys Ile Leu Gly Ile Gln Asn Ser Phe Leu Thr Arg Gly Gln
            35                  40                  45

Ser Lys Leu Ala Asp Arg Ile Asp Ser Lys Lys Ser Ser Trp Asp Arg
    50                  55                  60

Gly Ser Phe Pro Leu Leu Ile Lys Asn Val Arg Val Glu Asp Ser Glu
65                  70                  75                  80

Thr Tyr Ile Cys Glu Val Glu Gly Lys Lys Glu Glu Val Glu Leu Gln
                85                  90                  95

Val Phe Gly Leu Thr Ala Asn Pro Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Glu Cys Thr Ser Pro Arg Gly Lys Arg Ile Gln Gly Met Lys Thr Leu
        130                 135                 140

Ser Leu Ser Gln Leu Glu Ile Gln Asp Ser Gly Thr Trp Lys Cys Thr
145                 150                 155                 160

Val Ser Gln His Leu Glu Leu Val Phe Glu Ile Asn Ile Val Val Leu
                165                 170                 175

Ala

<210> SEQ ID NO 84
<211> LENGTH: 177
<212> TYPE: PRT
<213> ORGANISM: Nancy Ma's owl monkey

<400> SEQUENCE: 84

Lys Thr Val Val Leu Gly Glu Lys Gly Glu Thr Val Glu Leu Pro Cys
1               5                   10                  15

Glu Thr Ser Leu Lys Lys Asn Val Gln Phe His Trp Lys Thr Ser Asp
                20                  25                  30

Gln Ile Lys Ile Leu Gly Asn Gln Gly Ser Phe Leu Thr Arg Gly Gln
            35                  40                  45
```

```
Ser Lys Leu Ala Asp Arg Ile Asp Ser Lys Lys Ser Ser Trp Asp Arg
    50                  55                  60

Gly Ser Phe Pro Leu Ile Ile Lys Asn Val Gln Val Glu Asp Ser Glu
65                  70                  75                  80

Thr Tyr Ile Cys Glu Val Glu Arg Lys Lys Glu Glu Val Glu Leu Gln
                85                  90                  95

Val Phe Gly Leu Thr Ala Ser Pro Asp Thr Asn Leu Leu Gln Gly Gln
            100                 105                 110

Ser Leu Thr Leu Thr Leu Glu Ser Pro Pro Gly Ser Ser Pro Ser Val
        115                 120                 125

Glu Cys Thr Ser Pro Arg Gly Lys Arg Ile Gln Gly Met Lys Asn Leu
    130                 135                 140

Ser Val Ser Gln Leu Glu Ile Gln Asp Ser Gly Thr Trp Lys Cys Thr
145                 150                 155                 160

Val Ser Gln Arg Pro Glu Leu Leu Phe Lys Ile Asn Val Val Val Leu
                165                 170                 175

Ala
```

<210> SEQ ID NO 85
<211> LENGTH: 177
<212> TYPE: PRT
<213> ORGANISM: Azara's owl monkey

<400> SEQUENCE: 85

```
Lys Thr Val Val Leu Gly Glu Lys Gly Glu Thr Val Glu Leu Pro Cys
1               5                   10                  15

Glu Thr Ser Leu Lys Lys Asn Val Gln Phe His Trp Lys Thr Ser Asp
                20                  25                  30

Gln Ile Lys Ile Leu Gly Asn Gln Gly Ser Phe Leu Thr Arg Gly Gln
            35                  40                  45

Ser Lys Leu Ala Asp Arg Ile Asp Ser Lys Lys Ser Ser Trp Asp Arg
        50                  55                  60

Gly Ser Phe Pro Leu Ile Ile Lys Asn Val Gln Val Glu Asp Ser Glu
65                  70                  75                  80

Thr Tyr Ile Cys Glu Val Glu Arg Lys Lys Glu Glu Val Glu Leu Gln
                85                  90                  95

Val Phe Gly Leu Thr Ala Ser Pro Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Glu Cys Thr Ser Pro Arg Gly Lys Arg Ile Gln Gly Met Lys Thr Leu
    130                 135                 140

Ser Val Ser Gln Leu Glu Ile Gln Asp Ser Gly Thr Trp Lys Cys Thr
145                 150                 155                 160

Val Ser Gln His Pro Glu Leu Leu Phe Lys Ile Asn Val Val Val Leu
                165                 170                 175

Ala
```

<210> SEQ ID NO 86
<211> LENGTH: 177
<212> TYPE: PRT
<213> ORGANISM: Spix's owl monkey

<400> SEQUENCE: 86

```
Lys Thr Val Val Leu Gly Glu Lys Gly Glu Thr Val Glu Leu Pro Cys
```

```
            1               5                  10                  15
          Glu Thr Ser Leu Lys Lys Asn Val Gln Phe His Trp Lys Thr Ser Asp
                          20                  25                  30
          Gln Ile Lys Ile Leu Gly Ile Gln Gly Ser Phe Leu Thr Arg Gly Gln
                          35                  40                  45
          Ser Lys Leu Ala Asp Arg Ile Asp Ser Lys Lys Ser Ser Trp Asp Arg
                          50                  55                  60
          Gly Ser Phe Pro Leu Ile Ile Lys Asn Val Gln Val Glu Asp Ser Glu
          65                  70                  75                  80
          Thr Tyr Ile Cys Glu Val Glu Arg Lys Lys Glu Glu Val Glu Leu Gln
                          85                  90                  95
          Val Phe Gly Leu Thr Ala Ser Pro Asp Thr His Leu Leu Gln Gly Gln
                         100                 105                 110
          Ser Leu Thr Leu Thr Leu Glu Ser Pro Pro Gly Ser Ser Pro Ser Val
                         115                 120                 125
          Glu Cys Thr Ser Pro Arg Gly Lys Arg Ile Gln Gly Met Lys Thr Leu
                         130                 135                 140
          Ser Val Ser Gln Leu Glu Ile Gln Asp Ser Gly Thr Trp Lys Cys Thr
          145                 150                 155                 160
          Val Ser Gln His Pro Glu Leu Leu Phe Lys Ile Asn Val Val Leu
                         165                 170                 175
          Ala
```

<210> SEQ ID NO 87
<211> LENGTH: 178
<212> TYPE: PRT
<213> ORGANISM: Tarsier

<400> SEQUENCE: 87

```
          Lys Glu Val Val Leu Ala Lys Lys Gly Glu Thr Gly Glu Leu Pro Cys
          1               5                  10                  15
          Gln Gly Ser Pro Lys Lys Ser Met Ser Phe Ser Trp Lys Tyr Ser Asn
                          20                  25                  30
          Gln Val Met Ile Leu Arg Asn Gln Gly Ser Phe Trp Ile Thr Gly Ser
                          35                  40                  45
          Ser Arg Leu Lys Pro Arg Val Glu Ser Lys Lys Ser Leu Trp Asp Gln
                          50                  55                  60
          Gly Ser Phe Pro Leu Ile Ile Arg Asn Leu Glu Val Gly Asp Ser Gly
          65                  70                  75                  80
          Thr Tyr Ile Cys Glu Val Gln Asp Arg Lys Thr Glu Val Glu Leu Leu
                          85                  90                  95
          Val Phe Ala Leu Thr Ala Asn Ser Asn Thr Arg Leu Leu Gln Gly Gln
                         100                 105                 110
          Ser Leu Thr Leu Ser Leu Glu Gly Pro Gln Gly Arg Asn Pro Ser Leu
                         115                 120                 125
          Gln Cys Gln Gly Pro Gly Asn Lys Lys Ile Ser Gly Val Gly Ser Leu
                         130                 135                 140
          Ser Leu Ser Gln Leu Gly Pro Gln His Ser Gly Arg Trp Thr Cys Ala
          145                 150                 155                 160
          Val Ser Gln Asp Gln Lys Thr Leu Glu Phe Ser Lys Asp Val Val Val
                         165                 170                 175
          Leu Val
```

<210> SEQ ID NO 88

```
<211> LENGTH: 178
<212> TYPE: PRT
<213> ORGANISM: Sunda flying lemur

<400> SEQUENCE: 88
```

Lys Glu Val Ile Leu Gly Lys Lys Gly Asp Met Val Glu Leu Pro Cys
1               5                   10                  15

Lys Ala Ser Glu Lys Arg Tyr Leu Leu Phe Ser Trp Lys His Ser Asp
            20                  25                  30

Gln Ile Lys Ile Leu Gly Asn Gln Gly Ser Phe Trp Ile Thr Gly Ser
        35                  40                  45

Ser Lys Leu Lys His Arg Val Glu Ser Arg Lys Asn Leu Trp Asp Gln
50                  55                  60

Gly Ser Phe Pro Leu Val Ile Lys Asn Leu Glu Val Glu Asp Ser Gly
65                  70                  75                  80

Met Tyr Ile Cys Glu Val Glu Asn Arg Lys Ile Glu Val Glu Leu Leu
                85                  90                  95

Val Phe Gly Leu Ile Ala Asn Ser Asp Thr Arg Leu Leu Gln Gly Gln
            100                 105                 110

Ser Leu Thr Leu Thr Leu Glu Ser Pro Pro Asp Ser Asn Pro Ser Val
        115                 120                 125

Gln Trp Lys Ser Pro Gly Asn Lys His Thr Asn Gly Val Lys Thr Leu
130                 135                 140

Ser Val Ser Gln Leu Gly Ser Gln Glu Ser Gly Thr Trp Thr Cys Thr
145                 150                 155                 160

Val Ser Lys Asp Gln Lys Thr Leu Ala Leu Asn Ile Asn Ile Leu Val
                165                 170                 175

Leu Ala

```
<210> SEQ ID NO 89
<211> LENGTH: 179
<212> TYPE: PRT
<213> ORGANISM: Gray mouse lemur

<400> SEQUENCE: 89
```

Lys Glu Val Val Leu Gly Arg Lys Gly Asp Thr Val Glu Leu Pro Cys
1               5                   10                  15

Lys Ala Ser Gln Lys Lys Ala Ile Pro Phe Ala Trp Lys His Ser Asn
            20                  25                  30

Gln Thr Arg Ile Leu Gly Lys Gln Gly Ser Ser Phe Glu Thr Thr
        35                  40                  45

Gly Pro Ser Met Met Lys Asn Arg Val Glu Ser Lys Lys Asn Leu Trp
50                  55                  60

Asp Gln Gly Ser Phe Pro Leu Val Ile Lys Asn Leu Glu Met Lys Asp
65                  70                  75                  80

Ser Gly Ser Tyr Ile Cys Glu Val Glu Asp Lys Lys Glu Val Glu Leu
                85                  90                  95

Leu Val Phe Gly Leu Thr Ala Asn Ser Gly Thr Arg Val Leu His Gly
            100                 105                 110

Gln Ser Leu Thr Leu Thr Leu Glu Ser Pro Arg Gly Ser Ser Pro Ser
        115                 120                 125

Val His Cys Lys Ser Pro Gly Asn Lys Asn Ile Asn Gly Val Ser Leu
130                 135                 140

Leu Ser Leu Pro Gln Leu Gly Ile Gln Asp Ser Gly Thr Trp Thr Cys
145                 150                 155                 160

```
Thr Val Ser Gln Asp Arg Gln Thr Leu Ala Phe Lys Ile His Ile Ser
                165                 170                 175

Val Leu Ala

<210> SEQ ID NO 90
<211> LENGTH: 179
<212> TYPE: PRT
<213> ORGANISM: Coquerel's sifaka

<400> SEQUENCE: 90

Lys Glu Val Val Leu Gly Arg Lys Gly Asp Thr Val Glu Leu Pro Cys
1               5                   10                  15

Lys Ala Ser Gln Lys Lys Ser Met Pro Phe Ala Trp Lys His Ser Asn
                20                  25                  30

Gln Thr Arg Ile Leu Gly Lys Gln Gly Ser Ser Tyr Phe Glu Thr Thr
            35                  40                  45

Gly Pro Ser Met Met Lys Asn Arg Val Glu Ser Lys Lys Asn Leu Trp
        50                  55                  60

Asp Gln Gly Ser Phe Pro Leu Ile Ile Lys Asn Leu Glu Met Gln Asp
65                  70                  75                  80

Ser Gly Thr Tyr Ile Cys Glu Val Glu Asp Lys Lys Glu Val Glu Leu
                85                  90                  95

Leu Val Phe Gly Leu Thr Ala Asn Ser Gly Thr Arg Val Leu His Gly
                100                 105                 110

Gln Ser Leu Thr Leu Thr Leu Glu Ser Pro Arg Gly Ser Ser Pro Ser
            115                 120                 125

Val Gln Cys Lys Ser Pro Arg Asn Lys Asn Ile Asn Gly Val Ser Val
        130                 135                 140

Leu Ser Val Ser Gln Leu Gly Leu Gln Asp Ser Gly Thr Trp Thr Cys
145                 150                 155                 160

Thr Val Ser Gln Asp Arg His Thr Leu Ala Phe Lys Ile His Ile Ser
                165                 170                 175

Val Leu Ala
```

CD4 MUTEINS AND METHODS OF USING THE SAME

CROSS-REFERENCE TO RELATED APPLICATIONS

The subject patent application claims the benefit of priority to U.S. Provisional Patent Application No. 62/645,903 (filed Mar. 21, 2018). The full disclosure of the priority application is incorporated herein by reference in its entirety and for all purposes.

STATEMENT OF GOVERNMENT SUPPORT

This invention was made with government support under grant numbers AI091476, AI129868, AI100263 and AI129980 awarded by The National Institutes of Health. The government has certain rights in the invention.

FIELD OF THE INVENTION

The invention relates generally to proteins including CD4 and their use in the treatment of HIV.

BACKGROUND

Polypeptides derived from CD4, a transmembrane receptor for human immunodeficiency virus (HIV) expressed on permissive host CD4+ T cells, can be deployed to inhibit HIV infection. Such CD4-derived polypeptides can intercede to block or "neutralize" HIV infection by binding to virus particles, thereby impeding recognition of CD4 on permissive host cells. Soluble forms of CD4 (sCD4) were first proposed as an approach to inhibit HIV infection in the nineteen eighties (Hussey, R. E. et al. (1988) NATURE, 331(6151): 78-81; Deen, K. C. et al. (1988) NATURE, 331 (6151): 82-4; Smith, D. H. et al. (1987) SCIENCE, 238(4834): 1704-7; Fisher, R. A. et al. (1988) NATURE, 331(6151): 76-8; Watanabe, M. et al. (1989) NATURE, 337(6204): 267-70; Traunecker, A. et al. (1988) NATURE, 331(6151): 84-6). However, the short half-life of sCD4 in plasma dampened enthusiasm for its use as a recombinant protein therapeutic drug for treating HIV infection (Watanabe et al. (1989), supra; Schooley, R. T. et al. (1990) ANN. INTERN. MED., 112(4): 247-53). Furthermore, a substantial proportion of the HIV strains isolated directly from patients (i.e., primary isolates) are resistant to neutralization by sCD4 (Ashkenazi, A. et al. (1991) PROC. NATL. ACAD. SCI. USA, 88(16): 7056-60; Daar, E. S. et al. (1990) PROC. NATL. ACAD. SCI. USA, 87(17): 6574-8; O'Brien, W. A. et al. (1992) J. VIROL., 66(5): 3125-30.

Previous improvements to the half-life of sCD4 have been made by adding an immunoglobulin (Ig) fragment crystallizable (Fc) (Capon, D. J. et al. (1989) NATURE, 337(6207): 525-31; Chamow, S. M. et al. (1992) INT. J. CANCER SUPPL., 7: 69-72; Byrn, R. A. et al. (1990) NATURE, 344(6267): 667-70). Forms of sCD4 containing an immunoglobulin Fc have been termed CD4-Ig. Despite this approach, the half-life of human CD4-Ig still fell short of that which would be expected for a conventional antibody (Hodges, T. L. et al. (1991) ANTIMICROB. AGENTS CHEMOTHER., 35(12): 2580-6; Kahn, J. O. et al. (1990) ANN. INTERN. MED., 112(4): 254-61; Chamow, S. M. et al. (1994) BIOCONJUG. CHEM., 5(2): 133-40). The suboptimal pharmacokinetic properties of CD4-Ig have limited its utility in therapeutic settings.

Although developments have been made to date, there is still an ongoing need for new and effective therapies for treating and managing HIV and AIDS.

SUMMARY OF THE INVENTION

The invention is based, in part, upon the discovery of proteins comprising both human CD4 domain 1 and CD4 domain 2 (CD4 D1D2) that have greater stability and/or activity than proteins comprising the naturally occurring human CD4 D1D2. In certain embodiments, the proteins exhibit higher aggregation temperatures, e.g., as measured by dynamic light scattering (DLS) in a thermal scan assay, and/or longer plasma half-lives compared to proteins comprising the naturally occurring human CD4 D1D2. Furthermore, it is contemplated that the proteins described herein may be suitable for the treatment of HIV in human subjects.

In one aspect, the invention provides a protein comprising a human CD4 domain 1 and domain 2 (CD4 D1D2) mutein, wherein the CD4 D1D2 mutein is at least 90% identical to wild-type human CD4 D1D2 (SEQ ID NO: 1), and comprises at least one substitution of a. a basic amino acid in wild-type human CD4 D1D2 (SEQ ID NO: 1) by an uncharged amino acid;
b. a basic amino acid in wild-type human CD4 D1D2 (SEQ ID NO: 1) by an acidic amino acid;
c. an uncharged amino acid in wild-type human CD4 D1D2 (SEQ ID NO: 1) by an acidic amino acid; or
d. a glycine or an amino acid with a buried hydrophobic side chain in wild-type human CD4 D1D2 (SEQ ID NO: 1) by a hydrophobic amino acid that has a larger volume than the amino acid that is replaced;

wherein the substitution is at a position that is non-identical to wild-type human CD4 D1D2 (SEQ ID NO: 1) in a non-human primate CD4 D1D2.

In another aspect, the invention provides a protein comprising a CD4 D1D2 mutein, wherein the CD4 D1D2 mutein is at least 90% identical to wild-type human CD4 D1D2 (SEQ ID NO: 1), and comprises at least one substitution at a position corresponding to K1, K2, V4, L5, G6, K7, K8, D10, T11, V12, L14, T15, T17, A18, S19, Q20, K21, K22, S23, I24, Q25, H27, N30, N32, I34, K35, I36, L37, N39, G41, S42, L44, K46, P48, K50, L51, N52, D53, A55, D56, R58, R59, S60, L61, Q64, G65, N66, F67, P68, L69, I70, I71, K72, K73, L74, K75, I76, E77, D80, T81, V86, E87, D88, Q89, E91, V93, Q94, L95, L96, V97, F98, G99, T101, A102, N103, S104, D105, H107, L108, Q110, S113, L114, L116, T117, L118, S120, P121, P122, G123, S124, S125, V128, Q129, C130, R131, S132, P133, R134, G135, N137, I138, Q139, G140, G141, K142, T143, L144, S145, V146, S147, L149, E150, L151, Q152, D153, G155, T156, W157, T158, T160, V161, L162, Q163, N164, Q165, K166, K167, V168, E169, F170, K171, I172, D173, I174, V175, V176, or A178 of wild-type human CD4 D1D2 (SEQ ID NO: 1).

In certain embodiments, the CD4 D1D2 mutein comprises at least one substitution of an amino acid in wild-type human CD4 D1D2 (SEQ ID NO: 1) by an amino acid at a corresponding position in a non-human primate CD4 D1D2. For example, in certain embodiments, the CD4 D1D2 mutein comprises at least one substitution at a position corresponding to K1, K2, V4, G6, K7, D10, T11, V12, T15, T17, A18, S19, Q20, K21, K22, S23, I24, Q25, H27, N30, N32, I34, K35, N39, G41, S42, L44, K46, P48, K50, L51, N52, D53, A55, D56, R58, S60, L61, Q64, G65, N66, P68, L69, I70, K72, K73, L74, K75, I76, E77, D80, T81, E87, D88, Q89, E91, Q94, L96, G99, T101, A102, N103, S104, D105, H107, L108, Q110, S113, T117, S120, P122, G123, S124, S125, V128, Q129, C130, R131, S132, R134, G135, N137, I138, Q139, G140, G141, K142, T143, L144, S145, V146, S147, E150, L151, Q152, D153, T156, W157, T158, T160, V161, L162, Q163, N164, Q165, K166, K167, V168, E169, F170, K171, I172, D173, I174, V175, or A178 of wild-type human CD4 D1D2 (SEQ ID NO: 1), e.g., by an amino acid at a corresponding position in a non-human primate CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape, old world monkey, or new world monkey CD4 D1D2. For example, in certain embodiments, the CD4 D1D2 mutein comprises at least one substitution at a position corresponding to K1, K2, K7, D10, T11, T15, T17, A18, S19, Q20, K21, K22, S23, I24, Q25, H27, N30, N32, I34, N39, G41, S42, L44, K46, P48, N52, D53, A55, R59, L61, Q64, G65, N66, P68, L69, I70, K72, K73, L74, K75, I76, D80, E87, D88, Q89, Q94, L96, A102, N103, S104, Q110, S113, T117, S120, S124, Q129, R131, R134, N137, Q139, G140, G141, K142, T143, L144, S145, V146, S147, E150, L151, Q152, T156, W157, T158, T160, V161, L162, N164, Q165, K166, K167, V168, K171, D173, I174, or V175 of wild-type human CD4 D1D2 (SEQ ID NO: 1), e.g., by an amino acid at a corresponding position in an ape, old world monkey, or new world monkey CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape or old world monkey CD4 D1D2. For example, in certain embodiments, the CD4 D1D2 mutein comprises at least one substitution at a position corresponding to K2, D10, T15, T17, S19, Q20, K21, K22, S23, I24, Q25, N30, N32, I34, N39, P48, N52, D53, A55, R59, G65, N66, P68, L69, D80, E87, D88, Q89, Q94, Q110, T117, S120, S124, Q129, R134, G140, K142, L144, S147, L151, T156, W157, T160, V161, L162, N164, K166, or K167 of wild-type human CD4 D1D2 (SEQ ID NO: 1), e.g., by an amino acid at a corresponding position in an ape or old world monkey CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape CD4 D1D2. For example, in certain embodiments, the CD4 D1D2 mutein comprises at least one substitution at a position corresponding to K1, T15, T17, Q20, 34, N52, D53, A55, R59, G65, P68, E87, D88, T117, S120, R134, G140, S147, W157, T160, N164, or K166 of wild-type human CD4 D1D2 (SEQ ID NO: 1), e.g., by an amino acid at a corresponding position in an ape CD4 D1D2.

In certain embodiments, the CD4 D1D2 mutein comprises at least one substitution of an amino acid in wild-type human CD4 D1D2 (SEQ ID NO: 1) by an amino acid at a corresponding position in an old world monkey CD4 D1D2. For example, in certain embodiments, the CD4 D1D2 mutein comprises at least one substitution at a position corresponding to K2, D10, T15, T17, S19, Q20, K21, K22, S23, I24, Q25, N30, N32, I34, N39, P48, N52, A55, R59, N66, P68, L69, D80, D88, Q89, Q94, Q110, 5124, Q129, R134, G140, K142, L144, 5147, L151, T156, T160, V161, L162, N164, K166, or K167 of wild-type human CD4 D1D2 (SEQ ID NO: 1), e.g., by an amino acid at a corresponding position in an old world monkey CD4 D1D2.

In certain embodiments, the CD4 D1D2 mutein comprises at least one substitution of a glycine or a hydrophobic amino acid in wild-type human CD4 D1D2 (SEQ ID NO: 1) by a hydrophobic amino acid that has a larger volume, for example, side chain volume, than the amino acid that is replaced. For example, in certain embodiments, the CD4 D1D2 mutein comprises at least one substitution of an amino acid at a position corresponding to L5, G6, V12, L14, A18, I24, I36, L37, L44, L51, A55, G65, F67, P68, L69, V93, G99, I71, L74, V86, V93, L95, L96, V97, F98, A102, L108, L114, L116, L118, P121, V128, P133, I138, G141, L144, V146, L149, G155, V161, V168, F170, I172, I174, or V176 of wild-type human CD4 D1D2 (SEQ ID NO: 1), e.g., by a hydrophobic amino acid having a larger volume than the amino acid that is replaced. In certain embodiments, the CD4 D1D2 mutein comprises at least one substitution of an amino acid at a position corresponding to G6, A55, L116, V128, V146, V168, or V176 of wild-type human CD4 D1D2 (SEQ ID NO: 1), e.g., by a hydrophobic amino acid having a larger volume than the amino acid that is replaced. In certain embodiments, the CD4 D1D2 mutein comprises at least one substitution of an amino acid at a position corresponding to G6, I24, L44, L51, A55, L69, G99, A102, V128, G141, V146, V161, and V168 of wild-type human CD4 D1D2 (SEQ ID NO: 1), e.g., by a hydrophobic amino acid having a larger volume than the amino acid that is replaced.

In certain embodiments, the CD4 D1D2 mutein comprises at least one substitution that results in a protein with a decrease in net positive charge. For example, in certain embodiments, the CD4 D1D2 mutein comprises at least one substitution of a basic amino acid in wild-type human CD4 D1D2 (SEQ ID NO: 1) by an uncharged amino acid or a basic amino acid in wild-type human CD4 D1D2 (SEQ ID NO: 1) by an acidic amino acid. For example, in certain embodiments, the CD4 D1D2 mutein comprises at least one substitution of an amino acid at a position corresponding to K1, K2, K7, K21, K22, K35, K46, K50, R58, R59, K72, K75, R131, R134, K142, K166, K167, or K171 of wild-type human CD4 D1D2 (SEQ ID NO: 1) e.g., by G, A, S, T, N, Q, H, or Y.

In certain embodiments, the CD4 D1D2 mutein comprises at least one substitution of an uncharged amino acid in wild-type human CD4 D1D2 (SEQ ID NO: 1) by an acidic amino acid. For example, in certain embodiments, the CD4 D1D2 mutein comprises at least one substitution of an amino acid at a position corresponding to V4, T11, T15, T17, S19, Q20, S23, Q25, H27, N30, N32, I34, S42, P48, N52, 560, L61, Q64, N66, I70, I76, T81, Q89, Q94, T101, N103, S104, H107, Q110, S113, T117, S120, P122, G123, S124, S125, Q129, G135, N137, Q139, G140, T143, 5145, 5147, L151, Q152, T156, T158, T160, L162, Q163, N164, Q165, V175, or A178 of wild-type human CD4 D1D2 (SEQ ID NO: 1), e.g., by D or E.

In certain embodiments, the CD4 D1D2 mutein comprises at least one substitution in the CD4 D1 domain, for example, one or more of the substitutions described herein, and at least one substitution in the CD4 D2 domain, for example, one or more of the substitutions described herein. In certain embodiments, the CD4 D1D2 mutein comprises one, two, three, four, five, six, seven, eight, nine, ten, eleven, twelve, thirteen, fourteen, fifteen, sixteen, seventeen, eighteen, nineteen, or twenty substitutions. In certain embodiments, the CD4 D1D2 mutein is at least 91%, 92%, 93%, 94%, 95%, 96%, 97%, 98%, or 99% identical to wild-type human CD4 D1D2 (SEQ ID NO: 1).

In certain embodiments, the CD4 D1D2 mutein comprises fewer than ten, nine, eight, seven, six, five, four, three, two, or one substitutions at amino acid positions with surface-exposed side chains in wild-type human CD4 D1D2 (SEQ ID NO: 1).

In certain embodiments, the CD4 D1D2 mutein comprises at least one substitution at a position corresponding to K2, G6, K8, T15, T17, K21, S23, A55, I70, K72, K75, Q94, L96, Q110, L116, V128, R134, K142, V146, N164, K166, K167, V168, or V176 of wild-type human CD4 D1D2 (SEQ ID NO: 1).

In certain embodiments, the CD4 D1D2 mutein comprises at least one substitution at a position corresponding to K1, K2, L5, G6, K7, K8, T15, T17, K21, K22, S23, A55, I70, K72, K75, Q94, L96, G99, A102, Q110, R134, K142, N164, K166, K167, or K171 of wild-type human CD4 D1D2 (SEQ ID NO: 1).

In certain embodiments, the CD4 D1D2 mutein comprises at least one substitution at a position corresponding to G6, S23, A55, K72, K75, Q94, L96, Q110, L116, V128, R134, V146, N164, K167, V168, or V176 of wild-type human CD4 D1D2 (SEQ ID NO: 1).

In certain embodiments, the CD4 D1D2 mutein comprises at least one substitution at a position corresponding to L5, K8, S23, A55, K75, Q94, L96, Q110, R134, N164, or K167 of wild-type human CD4 D1D2 (SEQ ID NO: 1). For example, the CD4 D1D2 mutein may comprise at least one substitution at a position corresponding to G6, S23, A55, K72, K75, Q94, L96, Q110, V128, R134, V146, N164, K167, or V168 of wild-type human CD4 D1D2 (SEQ ID NO: 1), at least one substitution at a position corresponding to L5, S23, A55, L96, R134, N164, or K167 of wild-type human CD4 D1D2 (SEQ ID NO: 1), at least one substitution at a position corresponding to K72, K75, Q94, Q110, L116, V128, R134, V146, N164, K167, V168, or V176 of wild-type human CD4 D1D2 (SEQ ID NO: 1), at least one substitution at a position corresponding to S23, A55, R134, N164, or K167 of wild-type human CD4 D1D2 (SEQ ID NO: 1), or at least one substitution at a position corresponding to S23, A55, R134, N164, or K167 of wild-type human CD4 D1D2 (SEQ ID NO: 1), at least one substitution at a position corresponding to A55, R134, N164, or K167 of wild-type human CD4 D1D2 (SEQ ID NO: 1). In certain embodiments, the CD4 D1D2 mutein comprises at least one substitution at a position corresponding to G6, S23, A55, V128, V146, or V168 of wild-type human CD4 D1D2 (SEQ ID NO: 1), at least one substitution at a position corresponding to K2, K7, K8, T17, I70, K72, Q94, Q110, R134, K142, N164, or K167 of wild-type human CD4 D1D2 (SEQ ID NO: 1).

In certain embodiments, the CD4 D1D2 mutein comprises substitutions at the following positions: A55 and K72; A55 and K75; A55 and Q94; A55 and Q110; A55 and L116; A55 and V128; A55 and R134; A55 and V146; A55 and N164; A55 and K167; A55 and V168; S23 and K72; S23 and K75; S23 and Q94; S23 and Q110; S23 and L116; S23 and V128; S23 and R134; S23 and V146; S23 and N164; S23 and K167; S23 and V168; G6 and K72; G6 and K75; G6 and Q94; G6 and Q110; G6 and L116; G6 and V128; G6 and R134; G6 and V146; G6 and N164; G6 and K167; G6 and V168; K72 and K75; K72 and Q94; K72 and Q110; K72 and L116; K72 and V128; K72 and R134; K72 and V146; K72 and N164; K72 and K167; K72 and V168; K75 and 94; K75 and Q110; K75 and L116; K75 and V128; K75 and R134; K75 and V146; K75 and N164; K75 and K167; K75 and V168; Q94 and Q110; Q94 and L116; Q94 and V128; Q94 and R134; Q94 and V146; Q94 and N164; Q94 and K167; Q94 and V168; Q110 and L116; Q110 and V128; Q110 and R134; Q110 and V146; Q110 and N164; Q110 and K167; Q110 and V168; L116 and V128; L116 and R134; L116 and V146; L116 and N164; L116 and K167; L116 and V168; V128 and R134; V128 and V146; V128 and N164; V128 and K167; V128 and V168; V146 and N164; V146 and K167; V146 and V168; or N164 and K167. In certain embodiments, the CD4 D1D2 mutein comprises substitutions at the following positions: S23, A55, and K72; S23, A55, and K75; S23, A55, and Q94; S23, A55, and Q110; S23, A55, and L116; S23, A55, and V128; S23, A55, and R134; S23, A55, and V146; S23, A55, and N164; S23, A55, and K167; S23, A55, and V168; G6, S23, and K72; G6, S23, and K75; G6, S23, and Q94; G6, S23, and Q110; G6, S23, and L116; G6, S23, and V128; G6, S23, and R134; G6, S23, and V146; G6, S23, and N164; G6, S23, and K167; G6, S23, and V168; G6, A55, and K72; G6, A55, and K75; G6, A55, and Q94; G6, A55, and Q110; G6, A55, and L116; G6, A55, and V128; G6, A55, and R134; G6, A55, and V146; G6, A55, and N164; G6, A55, and K167; G6, A55, and V168; G6, S23, A55, and K72; G6, S23, A55, and K75; G6, S23, A55, and Q94; G6, S23, A55, and Q110; G6, S23, A55, and L116; G6, S23, A55, and V128; G6, S23, A55, and R134; G6, S23, A55, and V146; G6, S23, A55, and N164; G6, S23, A55, and K167; or G6, S23, A55, and V168.

In certain embodiments, the CD4 D1D2 mutein comprises substitutions at the following positions: R134, N164, and K167; K72, R134, and K167; K75, R134, and K167; Q94, R134, and K167; Q110, R134, and K167; Q94, Q110, and R134; Q94, Q110, and N164; Q94, Q110, and 167; Q94, Q110, R134, and K167; K72, K75, and R134; K72, K75, and N164; K72, K75, and K167; K72, K75, R134, and K167; V128, V168, and R134; V128, V168, and N164; V128, V168, and K167; V128, V168, and V146; V128, V168, and L116; V128, V168, and K72; V128, V168, and K75; V128, V168, and Q94; V128, V168, and Q110; V146, R134, and K167; V146, R134, and N164; R134, K142, N164, and K167; I70, R134, N164, and K167; K72, R134, N164, and K167; Q94, R134, N164, and K167; Q110, R134, N164, and K167; Q94, Q110, R134, and K167; Q94, Q110, R134, N164, and K167; K72, Q94, Q110, R134, N164, and K167; K75, Q94, Q110, R134, N164, and K167; K72, K75, Q94, Q110, R134, N164, and K167; V128, V168, R134, and K72; V128, V168, R134, and K75; V128, V168, R134, and Q94; V128, V168, R134, and Q110; V128, V168, R134, and L116; V128, V168, R134, and V146; V128, V168, R134, and N164; V128, V168, R134, and K167; V128, V168, V146, and K72; V128, V168, V146, and K75; V128, V168, V146, and Q94; V128, V168, V146, and Q110; V128, V168, V146, and N164; or V128, V168, V146, and K167.

In certain embodiments, the CD4 D1D2 mutein comprises substitutions at the following positions: G6, A55, V128, and V168; G6, A55, V146, and V168; G6, A55, V128, and V146; G6, A55, V128, V146, and V168; G6, S23, A55, V128, and V168; G6, S23, A55, V128, V146, and V168; G6, S23, A55, V128, R134, V146, and V168; A55, V128, V168, and K72; A55, V128, V168, and K75; A55, V128, V168, and Q94; A55, V128, V168, and Q110; A55, V128, V168, and L116; A55, V128, V168, and R134; A55, V128, V168, and V146; A55, V128, V168, and K167; S23, V128, V168, and K72; S23, V128, V168, and K75; S23, V128, V168, and Q94; S23, V128, V168, and Q110; S23, V128, V168, and L116; S23, V128, V168, and R134; S23, V128, V168, and V146; S23, V128, V168, and K167; S23, A55, R134, and K167; S23, A55, R134, N164, and K167; S23, A55, K72, R134, and K167; S23, A55, K75, R134, and K167; S23, A55, Q94, R134, and K167; S23, A55, L96, R134, and K167; S23, A55, Q110, R134, and K167; S23, K72, K75, R134, and K167; S23, K72, K75, R134, N164, and K167; S23, A55, K72, K75, R134, and K167; S23, A55, K72, K75, R134, N164, and K167; S23, A55, K72, K75, L96, R134, N164, and K167; S23, A55, K72, K75, Q94, R134, N164, and K167; S23, A55, K72, K75, Q110, R134, N164, and K167; S23, A55, K72, K75, Q94, Q110, R134, N164, and K167; S23, A55, K72, K75, Q94, L96, Q110, R134, N164, and K167; G6, S23, A55, K72, K75, Q94, Q110, R134, N164, and K167; S23, A55, K72, K75, Q94, Q110, V128, R134, and K167; S23, A55, K72, K75, Q94, Q110, R134, V146, and K167; S23, A55, K72, K75, Q94, Q110, R134, K167, V168; S23, A55, K72, K75, Q94, Q110, V128, R134, K167, V168; S23, A55, K72, K75, Q94, Q110, V128, R134, V146, K167, V168; S23, A55, K72, K75, Q94, Q110, V128, R134, N164, K167, V168; S23, A55, K72, K75, Q94, Q110, V128, R134, V146, N164, K167, V168; G6, S23, A55, K72, K75, Q94, Q110, V128, R134, and K167; G6, S23, A55, K72, K75, Q94, Q110, R134, V146, and K167; G6, S23, A55, K72, K75, Q94, Q110, R134, K167, V168; G6, S23, A55, K72, K75, Q94, Q110, V128, R134, K167, V168; G6, S23, A55, K72, K75, Q94, Q110, V128, R134, V146, K167, V168; G6, S23, A55, K72, K75, Q94, Q110, V128, R134, N164, K167, V168; G6, S23, A55, K72, K75, Q94, Q110, V128, R134, V146, N164, K167, V168; G6, S23, A55, K72, V128, and V168; G6, S23, A55, K75, V128, and V168; G6, S23, A55, Q94, V128, and V168; G6, S23, A55, Q110, V128, and V168; G6, S23, A55, V128, N164, and V168; G6, S23, A55, V128, K167, and V168; A55, R134, N164, and K167; L5, S23, A55, L96, and R134; L5, S23, A55, L96, and N164; L5, S23, A55, L96, and K167; S23, A55, R134, N164, and K167; G6, S23, A55, R134, N164, and K167; S23, A55, L96, R134, N164, and K167; L5, S23, A55, R134, N164, and K167; or L5, S23, A55, L96, R134, N164, and K167.

In certain embodiments, the CD4 D1D2 mutein comprises substitutions at the following positions: A55, R134, N164, and K167; S23, A55, R134, N164, and K167; L5, S23, A55, L96, R134, N164, and K167; A55, V128, and V168; S23, A55, V128, and V168; G6, S23, A55, V128, and V168; G6, S23, A55, V128, V146, and V168; S23, A55, K72, K75, Q94, Q110, R134, and K167; G6, S23, A55, K72, K75, Q94, Q110, R134, and K167; S23, A55, K72, K75, Q94, L96, Q110, R134, and K167; S23, A55, K72, K75, Q94, Q110, R134, N164, and K167; S23, A55, K72, K75, R134, and K167; or S23, A55, K72, K75, V128, R134, K167, and V168.

In certain embodiments, the CD4 D1D2 mutein comprises substitutions at the following positions: R134 and K167; R134 and N164; N164 and K167; A55 and R134; A55 and N164; A55 and K167; S23 and R134; S23 and N164; S23 and K167; K72 and K75; K75 and R134; K75 and N164; K75 and K167; K75 and Q94; K75 and Q110; S23 and K75; A55 and K75; Q94 and Q110; S23 and A55; L5 and S23; K2 and N164; K2 and K167; K7 and K8; K7 and A55; K8 and N164; K8 and K167; K8 and A55; T17 and N164; T17 and K167; I70 and N164; I70 and K167; A55 and I70; A55 and K72; K72 and N164; K72 and K167; Q94 and N164; Q94 and K167; Q110 and N164; Q110 and K167; K142 and K167; R134, N164, and K167; A55, R134, and N164; A55, R134, and K167; A55, N164, and K167; A55, K7, and K8; S23, R134, and N164; S23, R134, and K167; S23, N164, and K167; S23, A55, and R134; S23, A55, and N164; S23, A55, and K167; K75, R134, and N164; K75, R134, and K167; K75, N164, and K167; K75, Q94, and Q110; A55, K75, and R134; L5, A55, and L96; A55, R134, N164, and K167; A55, K75, R134, and K167; L5, S23, A55, and L96; R134, K142, N164, and K167; K7, R134, N164, and K167; K8, R134, N164, and K167; K72, R134, N164, and K167; K75, R134, N164, and K167; T17, R134, N164, and K167; I70, R134, N164, and K167; Q94, R134, N164, and K167; Q110, R134, N164, and K167; Q94, Q110, R134, and N164; S23, A55, R134, N164, and K167; Q94, Q110, R134, N164, and K167; Q94, Q110, R134, K142, and K167; Q94, Q110, K142, N164, and K167; K7, K8, R134, N164, and K167. S23, A55, L96, R134, N164, and K167; K75, Q94, Q110, R134, N164, and K167; or K72, K75, Q94, Q110, R134, N164, and K167.

In certain embodiments, the CD4 D1D2 mutein comprises substitutions at the following positions: R134 and K167; R134 and N164; N164 and K167; Q94 and Q110; K2 and N164; K2 and K167; K7 and K8; K8 and N164; K8 and K167; T17 and N164; T17 and K167; I70 and N164; I70 and K167; K72 and N164; K72 and K167; K75 and R134; K75 and N164; K75 and K167; K75 and Q94; K75 and Q110; Q94 and N164; Q94 and K167; Q110 and N164; Q110 and K167; K142 and K167; R134, N164, and K167; K75, Q94, and Q110; K7, R134, N164, and K167; K8, R134, N164, and K167; T17, R134, N164, and K167; R134, K142, N164, and K167; I70, R134, N164, and K167; K72, R134, N164, and K167; Q94, R134, N164, and K167; Q110, R134, N164, and K167; Q94, Q110, R134, and N164; Q94, Q110, R134, N164, and K167; Q94, Q110, R134, K142, and K167; Q94, Q110, K142, N164, and K167; K75, Q94, Q110, R134, N164, and K167; K72, K75, Q94, Q110, R134, N164, and K167; or K7, K8, R134, N164, and K167.

In certain embodiments, the CD4 D1D2 mutein comprises substitutions at the following positions: R134, N164, and K167; A55, R134, and N164; A55, R134, and K167; A55, N164, and K167; L5, A55, and L96; A55, R134, N164, and K167; L5, S23, A55, and L96; S23, A55, R134, N164, and K167; S23, A55, L96, R134, N164, and K167; L5, S23, A55, R134, N164, and K167; or L5, S23, A55, L96, R134, N164, and K167. In certain embodiments, the CD4 D1D2 mutein comprises substitutions at the following positions: L5, A55, and L96; A55, R134, N164, and K167; S23, A55, R134, N164, and K167; or L5, S23, A55, L96, R134, N164, and K167.

In certain embodiments, the CD4 D1D2 mutein comprises substitutions at the following positions: R134 and K167; R134 and N164; N164 and K167; A55 and R134; A55 and N164; A55 and K167; S23 and R134; S23 and N164; S23 and K167; K72 and K75; K75 and R134; K75 and N164; K75 and K167; K75 and Q94; K75 and Q110; S23 and K75; A55 and K75; Q94 and Q110; S23 and A55; L5 and S23; K2 and N164; K2 and K167; K7 and K8; K7 and A55; K8 and N164; K8 and K167; K8 and A55; T17 and N164; T17 and K167; I70 and N164; I70 and K167; A55 and I70; A55 and K72; K72 and N164; K72 and K167; Q94 and N164; Q94 and K167; Q110 and N164; Q110 and K167; K142 and K167; R134, N164, and K167; A55, R134, and N164; A55, R134, and K167; A55, N164, and K167; A55, K7, and K8; S23, R134, and N164; S23, R134, and K167; S23, N164, and K167; S23, A55, and R134; S23, A55, and N164; S23, A55, and K167; K75, R134, and N164; K75, R134, and K167; K75, N164, and K167; K75, Q94, and Q110; A55, K75, and R134; L5, A55, and L96; A55, R134, N164, and K167; A55, K75, R134, and K167; L5, S23, A55, and L96; R134, K142, N164, and K167; K7, R134, N164, and K167; K8, R134, N164, and K167; K72, R134, N164, and K167; K75, R134, N164, and K167; T17, R134, N164, and K167; I70, R134, N164, and K167; Q94, R134, N164, and K167; Q110, R134, N164, and K167; Q94, Q110, R134, and N164; S23, A55, R134, N164, and K167; Q94, Q110, R134, N164, and K167; Q94, Q110, R134, K142, and K167; Q94, Q110, K142, N164, and K167; K7, K8, R134, N164, and K167; S23, A55, L96, R134, N164, and K167; K75, Q94, Q110, R134, N164, and K167; or K72, K75, Q94, Q110, R134, N164, and K167.

In certain embodiments, the CD4 D1D2 mutein comprises substitutions at the following positions: R134 and K167; R134 and N164; N164 and K167; Q94 and Q110; K2 and N164; K2 and K167; K7 and K8; K8 and N164; K8 and K167; T17 and N164; T17 and K167; I70 and N164; I70 and K167; K72 and N164; K72 and K167; K75 and R134; K75 and N164; K75 and K167; K75 and Q94; K75 and Q110; Q94 and N164; Q94 and K167; Q110 and N164; Q110 and K167; K142 and K167; R134, N164, and K167; K75, Q94, and Q110; K7, R134, N164, and K167; K8, R134, N164, and K167; T17, R134, N164, and K167; R134, K142, N164, and K167; I70, R134, N164, and K167; K72, R134, N164, and K167; Q94, R134, N164, and K167; Q110, R134, N164, and K167; Q94, Q110, R134, and N164; Q94, Q110, R134, N164, and K167; Q94, Q110, R134, K142, and K167; Q94, Q110, K142, N164, and K167; K75, Q94, Q110, R134, N164, and K167; K72, K75, Q94, Q110, R134, N164, and K167; or K7, K8, R134, N164, and K167.

In certain embodiments, the CD4 D1D2 mutein comprises substitutions at the following positions: R134, N164, and K167; A55, R134, and N164; A55, R134, and K167; A55, N164, and K167; L5, A55, and L96; A55, R134, N164, and K167; L5, S23, A55, and L96; S23, A55, R134, N164, and K167; S23, A55, L96, R134, N164, and K167; L5, S23, A55, R134, N164, and K167; or L5, S23, A55, L96, R134, N164, and K167. In certain embodiments, the CD4 D1D2 mutein comprises substitutions at the following positions: L5, A55, and L96; A55, R134, N164, and K167; S23, A55, R134, N164, and K167; or L5, S23, A55, L96, R134, N164, and K167.

In certain embodiments, the CD4 D1D2 mutein comprises at least one substitution of a basic amino acid in wild-type human CD4 D1D2 (SEQ ID NO: 1) by an uncharged amino acid; a basic amino acid in wild-type human CD4 D1D2 (SEQ ID NO: 1) by an acidic amino acid; or an uncharged amino acid in wild-type human CD4 D1D2 (SEQ ID NO: 1) by an acidic amino acid.

In certain embodiments, the CD4 D1D2 mutein comprises at least one substitution of a glycine or a hydrophobic amino acid in wild-type human CD4 D1D2 (SEQ ID NO: 1) by a hydrophobic amino acid that has a larger volume than the amino acid that is replaced.

In certain embodiments, the CD4 D1D2 mutein comprises at least one substitution of an amino acid in wild-type human CD4 D1D2 (SEQ ID NO: 1) by an amino acid at a corresponding position in a non-human primate CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape, old world monkey, or new world monkey CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape or old world monkey CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape CD4 D1D2.

In certain embodiments, the CD4 D1D2 mutein comprises at least one substitution of an amino acid in wild-type human CD4 D1D2 (SEQ ID NO: 1) by an amino acid at a corresponding position in an old world monkey CD4 D1D2.

In certain embodiments, the CD4 D1D2 mutein comprises at least one of: a substitution of K1 by N (K1N); a substitution of K2 by E (K2E), N (K2N) or T (K2T); a substitution of L5 by Y (L5Y), I (L5I), E (L5E), W (L5W), V (L5V), F (L5F), or T (L5T); a substitution of K7 by E (K7E); a substitution of K8 by E (K8E); a substitution of T15 by N (T15N) or E (T15E); a substitution of T17 by N (T17N) or E (T17E); a substitution of S23 by N (S23N), T (S23T), K (S23K), Y (S23Y), or A (S23A); a substitution of A55 by V (A55V), I (A55I), P (A55P), L (A55L), M (A55M), F (A55F), Y (A55Y), W (A55W) or T (A55T); a substitution of I70 by E (I70E), L (I70L), or V (I70V); a substitution of K72 by S (K72S); a substitution of K75 by E (K75E) or Q (K75Q); a substitution of Q94 by E (Q94E); a substitution of L96 by V (L96V), Q (L96Q), T (L96T), I (L96I), or Y (L96Y); a substitution of Q110 by E (Q110E) or H (Q110H); a substitution of L116 by F (L116F) or W (L116W); a substitution of V128 by I (V128I) or L (V128L); a substitution of R134 by G (R134G) or T (R134T); a substitution of K142 by R (K142R), G (K142G), or S (K142S); a substitution of V146 by I (V146I), L (V146L), F (V146F), or W (V146W); a substitution of N164 by D (N164D), H (N164H), R (N164R), or E (N164E); a substitution of K167 by T (K167T), R (K167R), or L (K167L); a substitution of V168 by I (V168I) or L (V168L); and a substitution of V176 by I (V176I).

In certain embodiments the CD4 D1D2 mutein comprises at least one of the K2E, K7E, K8E, T17N, T17E, A55V, I70E, K72S, K75E, Q94E, Q110E, R134G, K142R, N164D, and K167T substitutions. For example, in certain embodiments, the CD4 D1D2 mutein comprises the following substitutions: K2E and N164D; K2E and K167T; K7E and K8E; K8E and N164D; K8E and K167T; T17N and N164D; T17N and K167T; T17E and N164D; T17N and K167T; I70E and N164D; I70E and K167T; K72S and N164D; K72S and K167T; Q94E and Q110E; Q94E and N164D; Q94E and K167T; Q110E and N164D; Q110E and K167T; R134G and N164D; R134G and K167T; K142R and K167T; N164D and K167T; R134G, N164D and K167T; K2E, R134G, N164D, and K167T; K8E, R134G, N164D, and K167T; T17N, R134G, N164D, and K167T; T17E, R134G, N164D, and K167T; A55V, R134G, N164D, and K167T; I70E, R134G, N164D, and K167T; K72S, R134G, N164D, and K167T; K75E, Q94E, and Q110E; or K72S, K75E, Q94E, Q110E, R134G, N164D, and K167T.

In certain embodiments, the CD4 D1D2 mutein comprises at least one of the L5Y, K8E, S23N, A55V, K75E, Q94E, L96V, Q110E, R134G, N164D, and K167T substitutions, at least one of the L5Y, S23N, A55V, L96V, R134G, N164D, and K167T substitutions, at least one of the S23N, A55V, R134G, N164D, and K167T substitutions, or at least one of the A55V, R134G, N164D, and K167T substitutions. For example, in certain embodiments, the CD4 D1D2 mutein comprises the following substitution(s): A55V; L5Y, A55V, and L96V; A55V, R134G, N164D, and K167T; S23N, A55V, R134G, N164D, and K167T; L5Y, A55V, L96V, R134G, N164D, and K167T; or L5Y, S23N, A55V, L96V, R134G, N164D, and K167T.

In certain embodiments, the CD4 D1D2 mutein comprises at least one of the G6A, S23N, A55V, K72S, K75E, K75Q, Q94E, Q110E, V128L, R134G, V146I, N164D, K167T, and V168L substitutions.

In certain embodiments, the CD4 D1D2 mutein comprises at least one of the K72S, K75E, K75Q, Q94E, Q110E, V128L, R134G, V146I, N164D, K167T, and V168L substitutions.

In certain embodiments, the CD4 D1D2 mutein comprises at least one of the K72S, K75E, K75Q, Q94E, Q110E, R134G, N164D, and K167T substitutions.

In certain embodiments, the CD4 D1D2 mutein comprises at least one of the L116F, V128L, V146I, and V168L substitutions.

In certain embodiments, the CD4 D1D2 mutein comprises the following substitutions: A55V and K72S; A55V and K75E; A55V and K75Q; A55V and Q94E; A55V and Q110E; A55V and L116F; A55V and V128L; A55V and R134G; A55V and V146I; A55V and N164D; A55V and K167T; A55V and V168L; S23N and K72S; S23N and K75E; S23N and K75Q; S23N and Q94E; S23N and Q110E; S23N and L116F; S23N and V128I; S23N and R134G; S23N and V146I; S23N and N164D; S23N and K167T; S23N and V168L; G6A and K72S; G6A and K75E; G6A and K75Q; G6A and Q94E; G6A and Q110E; G6A and L116F; G6A and V128L; G6A and R134G; G6A and V146I; G6A and N164D; G6A and K167T; G6A and V168L; K72S and K75E; K72S and K75Q; K72S and Q94E; K72S and Q110E; K72S and L116F; K72S and V128L; K72S and R134G; K72S and V146I; K72S and N164D; K72S and K167T; K72S and V168L; K75E and Q94E; K75E and Q110E; K75E and L116F; K75E and V128L; K75E and R134G; K75E and V146I; K75E and N164D; K75E and K167T; K75E and V168L; K75Q and Q94E; K75Q and Q110E; K75Q and L116F; K75Q and V128L; K75Q and R134G; K75Q and V146I; K75Q and N164D; K75Q and K167T; K75Q and V168L; Q94E and Q110E; Q94E and L116F; Q94E and V128L; Q94E and R134G; Q94E and V146I; Q94E and N164D; Q94E and K167T; Q94E and V168L; Q110E and L116F; Q110E and V128L; Q110E and R134G; Q110E and V146I; Q110E and N164D; Q110E and K167T; Q110E and V168L; L116F and V128L; L116F and R134G; L116F and V146I; L116F and N164D; L116F and K167T; L116F and V168L; V128L and R134G; V128L and V146I; V128L and N164D; V128L and K167T; V128L and V168L; V146I and N164D; V146I and K167T; V146I and V168L; or N164D and K167T.

In certain embodiments, the CD4 D1D2 mutein comprises the A55V substitution.

In certain embodiments, the CD4 D1D2 mutein comprises the S23N substitution.

In certain embodiments, the CD4 D1D2 mutein comprises the L5Y, A55V, and L96V substitutions.

In certain embodiments, the CD4 D1D2 mutein comprises the A55V, R134G, N164D, and K167T substitutions.

In certain embodiments, the CD4 D1D2 mutein comprises the S23N, A55V, R134G, N164D, and K167T substitutions.

In certain embodiments, the CD4 D1D2 mutein comprises the L5Y, A55V, L96V, R134G, N164D, and K167T substitutions.

In certain embodiments, the CD4 D1D2 mutein comprises the L5Y, S23N, A55V, L96V, R134G, N164D, and K167T substitutions.

In certain embodiments, the CD4 D1D2 mutein comprises the Q40A substitution.

In certain embodiments, the CD4 D1D2 mutein comprises the amino acid sequence of SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 36, SEQ ID NO: 38, SEQ ID NO: 40, SEQ ID NO: 42, or SEQ ID NO: 44, or an amino acid sequence that has at least 90%, 95%, 96%, 97%, 98%, or 99% sequence identity to SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 36, SEQ ID NO: 38, SEQ ID NO: 40, SEQ ID NO: 42, or SEQ ID NO: 44.

In certain embodiments, the CD4 D1D2 mutein comprises a leader sequence comprising the amino acid sequence of SEQ ID NO: 46, which is encoded by the nucleotide sequence of SEQ ID NO: 47. In certain embodiments, the leader sequence has at least 90%, 95%, 96%, 97%, 98%, or 99% sequence identity to SEQ ID NO: 46.

In certain embodiments, the CD4 D1D2 mutein does not include a substitution of an amino acid residue in wild-type human CD4 D1D2 (SEQ ID NO: 1) that contacts gp120. For example, in certain embodiments, the CD4 D1D2 mutein does not include a substitution at a position corresponding to N32, K35, L44, K46, or R59 of wild-type human CD4 D1D2 (SEQ ID NO: 1).

In certain embodiments, the CD4 D1D2 mutein does not include a substitution of an amino acid residue that forms a salt bridge in wild-type human CD4 D1D2 (SEQ ID NO: 1). For example, in certain embodiments, the CD4 D1D2 mutein does not include a substitution at a position corresponding to K1, K2, K50, D56, R58, R59, K72, E77, E91, R131, D153, K167, E169, or K171 of wild-type human CD4 D1D2 (SEQ ID NO: 1).

In certain embodiments, the CD4 D1D2 mutein does not include a substitution at a position corresponding to F98 of wild-type human CD4 D1D2 (SEQ ID NO: 1), e.g., the CD4 D1D2 mutein does not include a substitution of F98 by valine (F98V). In certain embodiments, the CD4 D1D2 mutein does not include a substitution at a position corresponding to I76 of wild-type human CD4 D1D2 (SEQ ID NO: 1), e.g., the CD4 D1D2 mutein does not include a substitution of I76 by proline (I76P).

In certain embodiments, the CD4 D1D2 mutein comprises at least one amino acid substitution, for example, one or more of the substitutions described herein, that increases the aggregation temperature of the protein, as measured by dynamic light scattering (DLS). In certain embodiments, the CD4 D1D2 mutein comprises at least one amino acid substitution, for example, one or more of the substitutions described herein, that decreases the $IC_{50}$ of the protein for HIV infection of a $CD4^+$ $CCR5^+$ cell line.

In certain embodiments, the protein has an aggregation temperature of at least 60° C., as measured by dynamic light scattering (DLS), or an aggregation temperature at least 7° C. higher than the aggregation temperature of a corresponding protein comprising a wild-type human CD4 D1D2, as measured by dynamic light scattering (DLS). In certain embodiments, the protein has a plasma half-life of at least 12 hours, 24 hours, 1 day, 1.5 days, 2 days, 2.5 days, 3 days, 3.5 days, 4 days, 4.5 days, 5 days, 5.5 days, 6 days, 6.5 days, 7 days, 7.5 days, 8 days, 8.5 days, 9 days, 9.5 days, or 10 days. In certain embodiments, the protein has a plasma half-life of at least 12 hours. In certain embodiments, the protein has a plasma half-life of at least 3 days.

In certain embodiments, the CD4 D1D2 mutein comprises at least one amino acid substitution that increases the melting temperature of the protein, as measured by a dye intercalation assay.

In certain embodiments, the CD4 D1D2 mutein comprises at least one amino acid substitution that increases the amount of the CD4 D1D2 mutein that is expressed.

In certain embodiments, the protein further comprises a primate lentivirus envelope glycoprotein binding moiety. The binding moiety may, for example, comprise at least one sulfotyrosine, and/or comprise the amino acid sequence of SEQ ID NO: 2, SEQ ID NO: 3, SEQ ID NO: 4, SEQ ID NO: 5, SEQ ID NO: 6, or SEQ ID NO: 7.

In certain embodiments, the protein further comprises an immunoglobulin Fc domain. In certain embodiments, the Fc domain is a human IgG1 or IgG2 Fc domain, e.g., an IgG1 Fc domain. In certain embodiments, the Fc domain comprises a substitution or deletion at C220. In certain embodiments, the Fc domain comprises at least one of a M252Y, S254T, T256E, M428L, H433K, N434S, and N434F substitution. For example, the Fc domain may comprise the M252Y, S254T, and T256E substitutions, or the M428L and N434S substitutions.

In certain embodiments, the protein is not identical to a naturally-occurring, wild-type non-human primate protein. In certain embodiments, the CD4 D1D2 mutein is not identical to a corresponding portion of a wild-type non-human primate protein.

In certain embodiments, the protein does not comprise a CD4 domain 3 (D3) and/or a domain 4 (D4) region, e.g., a human CD4 D3 and/or D4 region.

In another aspect, the invention provides an isolated nucleic acid comprising a nucleotide sequence encoding any of the foregoing proteins. In another aspect, the invention provides an expression vector comprising any of the foregoing nucleic acids. In certain embodiments, the expression vector is a viral vector, e.g., an adeno-associated virus (AAV) vector. In another aspect, the invention provides a host cell comprising any of the foregoing expression vectors. In another aspect, the invention provides a pharmaceutical composition comprising any of the foregoing proteins or any of the foregoing expression vectors.

In another aspect, the invention provides a method of treating an HIV infection in a subject in need thereof. The method comprises administering to the subject an effective amount of any of the foregoing proteins, any of the foregoing expression vectors, or any of the foregoing pharmaceutical compositions.

These and other aspects and features of the invention are described in the following detailed description and claims.

DESCRIPTION OF THE DRAWINGS

The invention can be more completely understood with reference to the following drawings.

FIG. 4 is a sequence alignment of primate CD4 D1D2 amino acid sequences (SEQ ID NOs:1 and 48-90). The amino acid sequences of apes (SEQ ID NOs:1 and 48-54, respectively), old world monkeys (SEQ ID NOs:55-76, respectively), new world monkeys (SEQ ID NOs:77-86, respectively), and prosimians CD4 D1D2 (SEQ ID NOs:87-90, respectively) were aligned. Positions of non-identity with human CD4 D1D2 (SEQ ID NO:1) are indicated in bold. The numbering corresponds to human CD4 D1D2. Thus, a two amino acid indel preceding F43 in prosimians is treated here as a deletion, with the numbering skipping over this indel. The signal peptide present on CD4 pre-proteins is not shown or included in the numbering. An X indicates a position where no data is currently available. Alignments for amino acids 1-58 (FIG. 4A), 59-118 (FIG. 4B), and 119-178 (FIG. 4C) are shown. CD4 domain 1 (D1) corresponds to amino acids 1-98, and CD4 domain 2 (D2) corresponds to amino acids 99-178.

FIG. 15 is a series of bar graphs showing the results of dye intercalation thermal scan assays for CD4 muteins containing combinations of amino acid substitutions. The 50% melting temperatures of eCD4-Ig proteins containing mim6 sulfopeptides in SYPRO Orange dye intercalation assays are shown in FIG. 15A-C. The 50% melting temperatures for CD4-Ig proteins lacking sulfopeptides in an Applied Biosystems Protein Thermal Shift assay are shown in FIG. 15D. All of the variants shown here have the C220S substitution in the hinge.

FIG. 17 is a series of bar graphs showing the protein expression yield for different eCD4-Ig proteins. Each panel of FIG. 17A-H represents a separate protein expression yield experiment. Two controls are shown in black. These two controls are eCD4-Ig protein with a wild-type human CD4 D1D2 (SEQ ID NO:1), and eCD4-Ig containing the substitutions G6A/S23N/A55V/V128L/V168L. All other variants are shown in gray. All of the variants shown include the C220S substitution in the hinge, and an IgG1 Fc. The variants in FIG. 17A-G all are all eCD4-Ig proteins containing the mim6 sulfopeptide, whereas the variants in FIG. 17H are all CD4-Ig proteins lacking a sulfopeptide.

FIG. 18 is a series of line graphs showing pharmacokinetics in human FcRn transgenic mice of wild-type CD4-Ig or the indicated CD4-Ig or eCD4-Ig variants with substitutions that improve conformational stability. The data shown in FIGS. 18A-C were collected in parallel, and can be compared directly, and are only separated into three panels for clarity. FIG. 18A depicts the pharmacokinetics of CD4-Ig variants (not including a sulfopeptide) that contain either a wild-type human CD4 D1D2 sequence, or a CD4 D1D2 sequence with mutations at positions R134/N164/K167 or K72/K75/Q94/Q110/R134/N164/K167. The half-life of wild-type CD4-Ig was 2.4 days, whereas the half-life of R134G/N164D/K167T CD4-Ig was 4.2 days, and the half-life of K72S/K75E/Q94E/Q110E/R134G/N164D/K167T CD4-Ig was 8.6 days. FIG. 18B depicts the pharmacokinetics of CD4-Ig (not including a sulfopeptide) and eCD4-Ig (including a sulfopeptide) proteins containing substitutions at the positions R134/N164/K167. FIG. 18C depicts the pharmacokinetics of CD4-Ig (not including a sulfopeptide) and eCD4-Ig (including a sulfopeptide) proteins with substitutions at positions K72/K75/Q94/Q110/R134/N164/K167, and an eCD4-Ig protein with substitutions at positions Q94/Q110/R134/N164/K167.

FIG. 20 depicts a pharmacokinetics experiment in wild-type BALB/cJ mice evaluating variants of eCD4-Ig containing the substitutions G6A/S23N/A55V/V128L/V168L. The pharmacokinetics of eCD4-Ig variants containing G6A/S23N/A55V/V128L/V168L were compared against a control containing S23N/A55V/K72S/K75E/Q94E/L96V/Q110E/R134G/N164D/K167T (FIG. 20A). The surface charge substitutions R134G, N164D, and K167T were introduced individually and in combination into the G6A/S23N/A55V/V128L/V168L background. Thus, the additional variants tested in this pharmacokinetics experiment were G6A/S23N/A55V/V128L/R134G/V168L, G6A/S23N/A55V/V128L/K176T/V168L, and G6A/S23N/A55V/V128L/R134G/N164D/K167T/V168L. The half-lives calculated from protein concentrations on days 1 and 5 were compared (FIG. 20B). The only significant difference in half-life (P=0.03, 2-tailed parametric t test) was between the eCD4-Ig variant containing S23N/A55V/K72S/K75E/Q94E/L96V/Q110E/R134G/N164D/K167T and the eCD4-Ig variant containing G6A/S23N/A55V/V128L/R134G/V168L.

DETAILED DESCRIPTION

Figure 1:
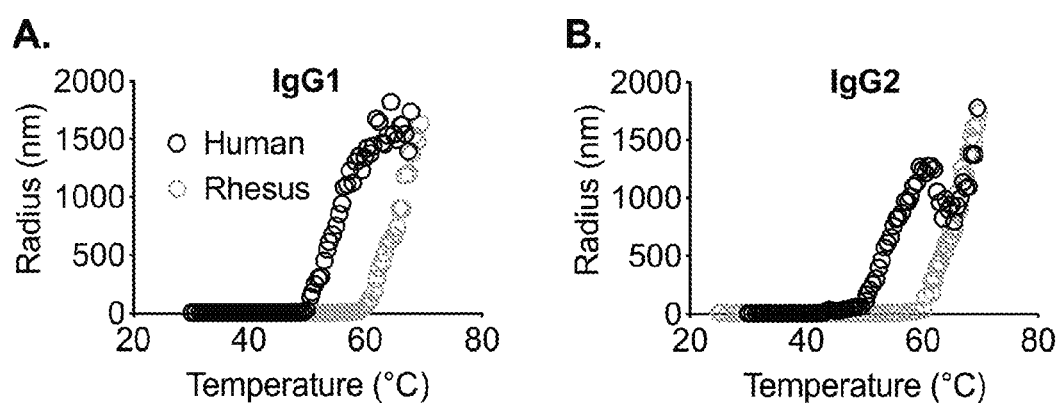
FIG. 1 depicts thermal scan assay results for eCD4-Ig proteins with wild-type human CD4 D1D2 or wild-type rhesus CD4 D1D2. A graph showing particle radius as a function of temperature for eCD4-IgG1 with wild-type human CD4 D1D2 or eCD4-IgG1 with wild-type rhesus macaque CD4 D1D2 is shown in FIG. 1A. A graph showing radius as a function of temperature for eCD4-IgG2 with wild-type human CD4 D1D2 or eCD4-IgG2 with rhesus macaque CD4 D1D2 is shown in FIG. 1B. Aggregation was measured by dynamic light scattering (DLS), with increasing particle radius, shown in nanometers (nm), indicating protein aggregation. The 50% aggregation temperatures for eCD4-Ig proteins based on wild-type human CD4 D1D2 were 51° C. (IgG1) and 53° C. (IgG2). The aggregation temperatures for eCD4-Ig based on wild-type rhesus CD4 D1D2 were 62° C. (IgG1) and 67° C. (IgG2).

The invention is based, in part, upon the discovery of proteins comprising both human CD4 domain 1 and CD4 domain 2 (CD4 D1D2) that have greater stability and/or activity than proteins comprising the naturally occurring human CD4 D1D2. In certain embodiments, the proteins exhibit higher production yields; higher aggregation temperatures, e.g., as measured by dynamic light scattering (DLS) in a thermal scan assay; higher melting temperatures, e.g., as measured by dye intercalation assay; and/or longer plasma half-lives compared to proteins comprising the naturally occurring human CD4 D1D2. Furthermore, it is contemplated that the proteins described herein may be suitable for the treatment of HIV in human subjects.

Various features and aspects of the invention are discussed in more detail below.

I. Proteins

In one aspect, the invention provides a protein comprising a human CD4 D1D2 mutein, wherein the CD4 D1D2 mutein is at least 90% identical to wildtype human CD4 D1D2 (SEQ ID NO: 1), and comprises at least one substitution at a position corresponding to K1, K2, V4, L5, G6, K7, K8, D10, T11, V12, L14, T15, T17, A18, S19, Q20, K21, K22, S23, I24, Q25, H27, N30, N32, I34, K35, I36, L37, N39, G41, S42, L44, K46, P48, K50, L51, N52, D53, A55, D56, R58, R59, S60, L61, Q64, G65, N66, F67, P68, L69, I70, I71, K72, K73, L74, K75, I76, E77, D80, T81, V86, E87, D88, Q89, E91, V93, Q94, L95, L96, V97, F98, G99, T101, A102, N103, S104, D105, H107, L108, Q110, S113, L114, L116, T117, L118, S120, P121, P122, G123, S124, S125, V128, Q129, C130, R131, S132, P133, R134, G135, N137, I138, Q139, G140, G141, K142, T143, L144, S145, V146, S147, L149, E150, L151, Q152, D153, G155, T156, W157, T158, T160, V161, L162, Q163, N164, Q165, K166, K167, V168, E169, F170, K171, I172, D173, I174, V175, V176, or A178 of wild-type human CD4 D1D2 (SEQ ID NO: 1). As used herein, the term "mutein" refers to a protein with an amino acid sequence that differs from a wild type amino acid sequence.

In certain embodiments, the CD4 D1D2 mutein comprises at least one substitution of an amino acid in wild-type human CD4 D1D2 (SEQ ID NO: 1) by an amino acid at a corresponding position in a non-human primate CD4 D1D2. For example, in certain embodiments, the CD4 D1D2 mutein comprises at least one substitution at a position corresponding to K1, K2, V4, G6, K7, D10, T11, V12, T15, T17, A18, S19, Q20, K21, K22, S23, I24, Q25, H27, N30, N32, I34, K35, N39, G41, 542, L44, K46, P48, K50, L51, N52, D53, A55, D56, R58, R59, 560, L61, Q64, G65, N66, P68, L69, I70, K72, K73, L74, K75, I76, E77, D80, T81, E87, D88, Q89, E91, Q94, L96, G99, T101, A102, N103, S104, D105, H107, L108, Q110, S113, T117, S120, P122, G123, S124, S125, V128, Q129, C130, R131, S132, R134, G135, N137, I138, Q139, G140, G141, K142, T143, L144, S145, V146, S147, E150, L151, Q152, D153, T156, W157, T158, T160, V161, L162, Q163, N164, Q165, K166, K167, V168, E169, F170, K171, I172, D173, I174, V175, or A178 of wild-type human CD4 D1D2 (SEQ ID NO: 1), e.g., by an amino acid at a corresponding position in a non-human primate CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape, old world monkey, or new world monkey CD4 D1D2. For example, in certain embodiments, the CD4 D1D2 mutein comprises at least one substitution at a position corresponding to K1, K2, K7, D10, T11, T15, T17, A18, S19, Q20, K21, K22, S23, I24, Q25, H27, N30, N32, I34, N39, G41, S42, L44, K46, P48, N52, D53, A55, R59, L61, Q64, G65, N66, P68, L69, I70, K72, K73, L74, K75, I76, D80, E87, D88, Q89, Q94, L96, A102, N103, S104, Q110, S113, T117, S120, S124, Q129, R131, R134, N137, Q139, G140, G141, K142, T143, L144, 5145, V146, 5147, E150, L151, Q152, T156, W157, T158, T160, V161, L162, N164, Q165, K166, K167, V168, K171, D173, I174, or V175 of wild-type human CD4 D1D2 (SEQ ID NO: 1), e.g., by an amino acid at a corresponding position in an ape, old world monkey, or new world monkey CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape or old world monkey CD4 D1D2. For example, in certain embodiments, the CD4 D1D2 mutein comprises at least one substitution at a position corresponding to K2, D10, T15, T17, S19, Q20, K21, K22, S23, I24, Q25, N30, N32, I34, N39, P48, N52, D53, A55, R59, G65, N66, P68, L69, D80, E87, D88, Q89, Q94, Q110, T117, S120, S124, Q129, R134, G140, K142, L144, S147, L151, T156, W157, T160, V161, L162, N164, K166, or K167 of wild-type human CD4 D1D2 (SEQ ID NO: 1), e.g., by an amino acid at a corresponding position in an ape or old world monkey CD4 D1D2.

In certain embodiments, the CD4 D1D2 mutein comprises at least one substitution of an amino acid in wild-type human CD4 D1D2 (SEQ ID NO: 1) by an amino acid at a corresponding position in an ape CD4 D1D2. For example, in certain embodiments, the CD4 D1D2 mutein comprises at least one substitution at a position corresponding to K1, T15, T17, Q20, 34, N52, D53, A55, R59, G65, P68, E87, D88, T117, S120, R134, G140, S147, W157, T160, N164, or K166 of wild-type human CD4 D1D2 (SEQ ID NO: 1), e.g., by an amino acid at a corresponding position in an ape CD4 D1D2.

In certain embodiments, the CD4 D1D2 mutein comprises at least one substitution of an amino acid in wild-type human CD4 D1D2 (SEQ ID NO: 1) by an amino acid at a corresponding position in an old world monkey CD4 D1D2. For example, in certain embodiments, the CD4 D1D2 mutein comprises at least one substitution at a position corresponding to K2, D10, T15, T17, S19, Q20, K21, K22, S23, I24, Q25, N30, N32, I34, N39, P48, N52, A55, R59, N66, P68, L69, D80, D88, Q89, Q94, Q110, S124, Q129, R134, G140, K142, L144, S147, L151, T156, T160, V161, L162, N164, K166, or K167 of wild-type human CD4 D1D2

(SEQ ID NO: 1), e.g., by an amino acid at a corresponding position in an old world monkey CD4 D1D2.

Exemplary non-human primates (NHPs), including apes, old world monkeys, new world monkeys, and prosimians are listed in FIG. 4, along with a sequence alignment between the wild-type human CD4 D1D2 (SEQ ID NO: 1) amino acid sequence and exemplary NHP CD4 D1D2 amino acid sequences.

In certain embodiments, the CD4 D1D2 mutein comprises at least one substitution of a glycine or a hydrophobic amino acid in wild-type human CD4 D1D2 (SEQ ID NO: 1) by a hydrophobic amino acid that has a larger volume, for example, side chain volume, than the amino acid that is replaced. The hydrophobic amino acid may, e.g., be a buried hydrophobic amino acid. As used herein, the amino acids A, V, P, L, I, M, F, Y, and W are considered hydrophobic amino acids, and the relative volume of glycine and the hydrophobic amino acids is as follows: G<A<V<P<L=I<M<F<Y<W. For example, in certain embodiments, the CD4 D1D2 mutein comprises at least one substitution of an amino acid at a position corresponding to L5, G6, V12, L14, A18, I24, I36, L37, L44, L51, A55, G65, F67, P68, L69, V93, G99, I71, L74, V86, V93, L95, L96, V97, F98, A102, L108, L114, L116, L118, P121, V128, P133, I138, G141, L144, V146, L149, G155, V161, V168, F170, I172, I174, or V176 of wild-type human CD4 D1D2 (SEQ ID NO: 1), e.g., by a hydrophobic amino acid having a larger volume than the amino acid being replaced. In certain embodiments, the CD4 D1D2 mutein comprises at least one substitution of an amino acid at a position corresponding to G6, I24, L44, L51, A55, L69, G99, A102, V128, G141, V146, V161, and V168 of wild-type human CD4 D1D2 (SEQ ID NO: 1), e.g., by a hydrophobic amino acid having a larger volume than the amino acid that is replaced. In certain embodiments, the CD4 D1D2 mutein comprises one or more amino acid substitutions identified in Table 1.

TABLE 1

| Wild-type Human CD4 D1D2 (SEQ ID NO: 1) Amino Acid | Substitution at Specified Position |
|---|---|
| L5 | M, F, Y, or W |
| G6 | A, V, P, L, I, M, F, Y, or W |
| V12 | P, L, I, M, F, Y, or W |
| L14 | M, F, Y, or W |
| A18 | V, P, L, I, M, F, Y, or W |
| I24 | M, F, Y, or W |
| I36 | M, F, Y, or W |
| L37 | M, F, Y, or W |
| L44 | M, F, Y, or W |
| L51 | M, F, Y, or W |
| A55 | V, P, L, I, M, F, Y, or W |
| G65 | A, V, P, L, I, M, F, Y, or W |
| F67 | Y, or W |
| P68 | L, I, M, F, Y, or W |
| L69 | M, F, Y, or W |
| I71 | M, F, Y, or W |
| L74 | M, F, Y, or W |
| V86 | P, L, I, M, F, Y, or W |
| V93 | P, L, I, M, F, Y, or W |
| L95 | M, F, Y, or W |
| L96 | M, F, Y, or W |
| V97 | P, L, I, M, F, Y, or W |
| F98 | Y, or W |
| G99 | A, V, P, L, I, M, F, Y, or W |
| A102 | V, P, L, I, M, F, Y, or W |
| L108 | M, F, Y, or W |
| L114 | M, F, Y, or W |
| L116 | M, F, Y, or W |
| L118 | M, F, Y, or W |

TABLE 1-continued

| Wild-type Human CD4 D1D2 (SEQ ID NO: 1) Amino Acid | Substitution at Specified Position |
|---|---|
| P121 | L, I, M, F, Y, or W |
| V128 | P, L, I, M, F, Y, or W |
| P133 | L, I, M, F, Y, or W |
| I138 | M, F, Y, or W |
| G141 | A, V, P, L, I, M, F, Y, or W |
| L144 | M, F, Y, or W |
| V146 | P, L, I, M, F, Y, or W |
| L149 | M, F, Y, or W |
| G155 | A, V, P, L, I, M, F, Y, or W |
| V161 | P, L, I, M, F, Y, or W |
| V168 | P, L, I, M, F, Y, or W |
| F170 | Y, or W |
| I172 | M, F, Y, or W |
| I174 | M, F, Y, or W |
| V176 | P, L, I, M, F, Y, or W |

In certain embodiments, the CD4 D1D2 mutein comprises at least one substitution of a glycine or a hydrophobic amino acid in wild-type human CD4 D1D2 (SEQ ID NO: 1) by a hydrophobic amino acid that has a larger volume, for example, side chain volume, than the amino acid that is replaced, and is also at a corresponding position in a non-human primate CD4 D1D2. For example, in certain embodiments, the CD4 D1D2 mutein comprises at least one of: a substitution of G6 by A (G6A); a substitution of 124 by M (124M); a substitution of L44 by W (L44W); a substitution of L51 by M (L51M); a substitution of A55 by V (A55V) or I (A55I); a substitution of L69 by M (L69M); a substitution of G99 by A (G99A); a substitution of A102 by V (A102V); a substitution of V128 by L (V128L); a substitution of G141 by V (G141V) or M (G141M); a substitution of V146 by I (V146I) or M (V146M); a substitution of V161 by I (V1611) or L (V161L); and a substitution of V168 by L (V168L).

In certain embodiments, the CD4 D1D2 mutein comprises at least one substitution that results in a protein with a decrease in net positive charge. For example, in certain embodiments, the CD4 D1D2 mutein comprises at least one substitution of a basic amino acid in wild-type human CD4 D1D2 (SEQ ID NO: 1) by an uncharged amino acid or a basic amino acid in wild-type human CD4 D1D2 (SEQ ID NO: 1) by an acidic amino acid. In certain embodiments, the uncharged amino acid is an uncharged, polar amino acid (G, S, T, N, Q, and H), A or Y.

As used herein, the amino acids G, A, S, T, N, Q, H, Y, L, I, V, M, F, W, P, and C are considered to be uncharged amino acids, the amino acids G, S, T, N, Q, and H are considered to be uncharged, polar amino acids, the amino acids D and E and are considered to be acidic amino acids, and the amino acids K and R are considered to be basic amino acids.

For example, in certain embodiments, the CD4 D1D2 mutein comprises at least one substitution of an amino acid at a position corresponding to K1, K2, K7, K21, K22, K35, K46, K50, R58, R59, K72, K75, R131, R134, K142, K166, K167, or K171 of wild-type human CD4 D1D2 (SEQ ID NO: 1) e.g., by G, A, S, T, N, Q, H, or Y. In certain embodiments, the CD4 D1D2 mutein comprises one or more amino acid substitutions identified in Table 2. In certain embodiments the CD4 D1D2 mutein comprises one or more substitutions identified in Table 3 of a basic amino acid in wild-type human CD4 D1D2 (SEQ ID NO: 1) by an acidic amino acid.

TABLE 2

| Wild-type Human CD4 D1D2 (SEQ ID NO: 1) Amino Acid | Substitution at Specified Position |
|---|---|
| K1 | G, A, S, T, N, Q, H, or Y |
| K2 | G, A, S, T, N, Q, H, or Y |
| K7 | G, A, S, T, N, Q, H, or Y |
| K21 | G, A, S, T, N, Q, H, or Y |
| K22 | G, A, S, T, N, Q, H, or Y |
| K35 | G, A, S, T, N, Q, H, or Y |
| K46 | G, A, S, T, N, Q, H, or Y |
| K50 | G, A, S, T, N, Q, H, or Y |
| R58 | G, A, S, T, N, Q, H, or Y |
| R59 | G, A, S, T, N, Q, H, or Y |
| K72 | G, A, S, T, N, Q, H, or Y |
| K75 | G, A, S, T, N, Q, H, or Y |
| R131 | G, A, S, T, N, Q, H, or Y |
| R134 | G, A, S, T, N, Q, H, or Y |
| K142 | G, A, S, T, N, Q, H, or Y |
| K166 | G, A, S, T, N, Q, H, or Y |
| K167 | G, A, S, T, N, Q, H, or Y |
| K171 | G, A, S, T, N, Q, H, or Y |

TABLE 3

| Wild-type Human CD4 D1D2 (SEQ ID NO: 1) Amino Acid | Substitution at Specified Position |
|---|---|
| K1 | D or E |
| K2 | D or E |
| K7 | D or E |
| K21 | D or E |
| K22 | D or E |
| K35 | D or E |
| K46 | D or E |
| K50 | D or E |
| R58 | D or E |
| R59 | D or E |
| K72 | D or E |
| K75 | D or E |
| R131 | D or E |
| R134 | D or E |
| K142 | D or E |
| K166 | D or E |
| K167 | D or E |
| K171 | D or E |

In certain embodiments, the CD4 D1D2 mutein comprises at least one substitution of a basic amino acid in wild-type human CD4 D1D2 (SEQ ID NO: 1) by an uncharged or acidic amino acid that is also at a corresponding position in a non-human primate CD4 D1D2. For example, in certain embodiments, the CD4 D1D2 mutein comprises at least one of a substitution of K1 by N (K1N); a substitution of K2 by N (K2N), T (K2T), or E (K2E); a substitution of K7 by E (M7E); a substitution of K21 by N (K21N); a substitution of K22 by T (K22T); a substitution of K46 by T (K46T); a substitution of R59 by Q (R59Q); a substitution of K75 by Q (K75Q) or E (K75E); a substitution of R131 by T (R131T) or Q (R131Q); a substitution of R134 by T (R134T) or G (R134G); a substitution of K142 by G (K142G) or S (K142S); a substitution of K166 by N (K166N), Q (K166Q), H (K166H), or E (K166E); a substitution of K167 by T (K167T); and a substitution of K171 by Q (K171Q), S (K171S), N (K171N), or E (K171E).

In certain embodiments, the CD4 D1D2 mutein comprises at least one substitution of an uncharged amino acid in wild-type human CD4 D1D2 (SEQ ID NO: 1) by an acidic amino acid. For example, in certain embodiments, the CD4 D1D2 mutein comprises at least one substitution of an amino acid at a position corresponding to V4, T11, T15, T17, S19, Q20, S23, Q25, H27, N30, N32, I34, S42, P48, N52, S60, L61, Q64, N66, I70, I76, T81, Q89, Q94, T101, N103, S104, H107, Q110, S113, T117, S120, P122, G123, S124, S125, Q129, G135, N137, Q139, G140, T143, S145, S147, L151, Q152, T156, T158, T160, L162, Q163, N164, Q165, V175, or A178 of wild-type human CD4 D1D2 (SEQ ID NO: 1), e.g., by D or E. In certain embodiments, the CD4 D1D2 mutein comprises one or more amino acid substitutions identified in Table 4.

TABLE 4

| Wild-type Human CD4 D1D2 (SEQ ID NO: 1) Amino Acid | Substitution at Specified Position |
|---|---|
| V4 | D or E |
| T11 | D or E |
| T15 | D or E |
| T17 | D or E |
| S19 | D or E |
| Q20 | D or E |
| S23 | D or E |
| Q25 | D or E |
| H27 | D or E |
| N30 | D or E |
| N32 | D or E |
| I34 | D or E |
| S42 | D or E |
| P48 | D or E |
| N52 | D or E |
| S60 | D or E |
| L61 | D or E |
| Q64 | D or E |
| N66 | D or E |
| I70 | D or E |
| I76 | D or E |
| T81 | D or E |
| Q89 | D or E |
| Q94 | D or E |
| T101 | D or E |
| N103 | D or E |
| S104 | D or E |
| H107 | D or E |
| Q110 | D or E |
| S113 | D or E |
| T117 | D or E |
| S120 | D or E |
| P122 | D or E |
| G123 | D or E |
| S124 | D or E |
| S125 | D or E |
| Q129 | D or E |
| G135 | D or E |
| N137 | D or E |
| Q139 | D or E |
| G140 | D or E |
| T143 | D or E |
| S145 | D or E |
| S147 | D or E |
| L151 | D or E |
| Q152 | D or E |
| T156 | D or E |
| T158 | D or E |
| T160 | D or E |
| L162 | D or E |
| Q163 | D or E |
| N164 | D or E |
| Q165 | D or E |
| V175 | D or E |
| A178 | D or E |

In certain embodiments, the CD4 D1D2 mutein comprises at least one substitution of an uncharged amino acid in wild-type human CD4 D1D2 (SEQ ID NO: 1) by an acidic amino acid that is also at a corresponding position in a non-human primate CD4 D1D2. For example, in certain embodiments, the CD4 D1D2 mutein comprises at least one of: a substitution of T17 by E (T17E); a substitution of N32 by D (N32D); a substitution of Q94 by E (Q94E); a substitution of Q110 by E (Q110E); a substitution of G123 by D (G123D); a substitution of Q129 by E (Q129E); and a substitution of N164 by D (N164D).

In certain embodiments, the CD4 D1D2 mutein comprises at least one substitution in the CD4 D1 domain (corresponding to amino acid residues 1 to 98 of SEQ ID NO: 1), for example, one or more of the substitutions described herein, and at least one substitution in the CD4 D2 domain (corresponding to amino acid residues 99 to 178 of SEQ ID NO: 1), for example, one or more of the substitutions described herein.

In certain embodiments, the CD4 D1D2 mutein comprises one, two, three, four, five, six, seven, eight, nine, ten, eleven, twelve, thirteen, fourteen, fifteen, sixteen, seventeen, eighteen, nineteen, or twenty substitutions. In certain embodiments, the CD4 D1D2 mutein is at least 91%, 92%, 93%, 94%, 95%, 96%, 97%, 98%, or 99% identical to wild-type human CD4 D1D2 (SEQ ID NO: 1).

In certain embodiments, the CD4 D1D2 mutein comprises fewer than ten, nine, eight, seven, six, five, four, three, two, or one substitution at amino acid positions with surface-exposed side chains in wild-type human CD4 D1D2 (SEQ ID NO: 1).

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. Usa 87:2264-2268; Altschul, (1993) J. Mol. Evol. 36, 290-300; Altschul et al., (1997) Nucleic Acids Res. 25:3389-3402, incorporated by reference) are tailored for sequence similarity searching. For a discussion of basic issues in searching sequence databases, see Altschul et al., (1994) Nature Genetics 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. Usa 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In certain embodiments, the CD4 D1D2 mutein comprises at least one substitution at a position corresponding to K1, K2, L5, G6, K7, K8, T15, T17, K21, K22, S23, A55, I70, K72, K75, Q94, L96, G99, A102, Q110, R134, K142, N164, K166, K167, or K171 of wild-type human CD4 D1D2 (SEQ ID NO: 1). In certain embodiments, the CD4 D1D2 mutein comprises at least one substitution at a position corresponding to L5, K8, S23, A55, K75, Q94, L96, Q110, R134, N164, or K167 of wild-type human CD4 D1D2 (SEQ ID NO: 1). For example, the CD4 D1D2 mutein may comprise at least one substitution at a position corresponding to L5, S23, A55, L96, R134, N164, or K167 of wild-type human CD4 D1D2 (SEQ ID NO: 1), at least one substitution at a position corresponding to S23, A55, R134, N164, or K167 of wild-type human CD4 D1D2 (SEQ ID NO: 1), or at least one substitution at a position corresponding to A55, R134, N164, or K167 of wild-type human CD4 D1D2 (SEQ ID NO: 1). In certain embodiments, the CD4 D1D2 mutein comprises at least one substitution at a position corresponding to K2, K7, K8, T17, I70, K72, Q94, Q110, R134, K142, N164, or K167 of wild-type human CD4 D1D2 (SEQ ID NO: 1).

In certain embodiments, the CD4 D1D2 mutein comprises substitutions at the following positions: R134 and K167; R134 and N164; N164 and K167; A55 and R134; A55 and N164; A55 and K167; S23 and R134; S23 and N164; S23 and K167; K72 and K75; K75 and R134; K75 and N164; K75 and K167; K75 and Q94; K75 and Q110; S23 and K75; A55 and K75; Q94 and Q110; S23 and A55; L5 and S23; K2 and N164; K2 and K167; K7 and K8; K7 and A55; K8 and N164; K8 and K167; K8 and A55; T17 and N164; T17 and K167; 170 and N164; I70 and K167; A55 and I70; A55 and K72; K72 and N164; K72 and K167; Q94 and N164; Q94 and K167; Q110 and N164; Q110 and K167; K142 and K167; R134, N164, and K167; A55, R134, and N164; A55, R134, and K167; A55, N164, and K167; A55, K7, and K8; S23, R134, and N164; S23, R134, and K167; S23, N164, and K167; S23, A55, and R134; S23, A55, and N164; S23, A55, and K167; K75, R134, and N164; K75, R134, and K167; K75, N164, and K167; K75, Q94, and Q110; A55, K75, and R134; L5, A55, and L96; A55, R134, N164, and K167; A55, K75, R134, and K167; L5, S23, A55, and L96; R134, K142, N164, and K167; K7, R134, N164, and K167; K8, R134, N164, and K167; K72, R134, N164, and K167; K75, R134, N164, and K167; T17, R134, N164, and K167; I70, R134, N164, and K167; Q94, R134, N164, and K167; Q110, R134, N164, and K167; Q94, Q110, R134, and N164; S23, A55, R134, N164, and K167; Q94, Q110, R134, N164, and K167; Q94, Q110, R134, K142, and K167; Q94, Q110, K142, N164, and K167; K7, K8, R134, N164, and K167; S23, A55, L96, R134, N164, and K167; K75, Q94, Q110, R134, N164, and K167; K72, K75, Q94, Q110, R134, N164, and K167; or K2, T17, K21, K72, K75, Q94, Q110, R134, N164, and K167.

In certain embodiments, the CD4 D1D2 mutein comprises substitutions at the following positions: R134 and K167; R134 and N164; N164 and K167; Q94 and Q110; K2 and N164; K2 and K167; K7 and K8; K8 and N164; K8 and K167; T17 and N164; T17 and K167; I70 and N164; I70 and K167; K72 and N164; K72 and K167; K75 and R134; K75 and N164; K75 and K167; K75 and Q94; K75 and Q110; Q94 and N164; Q94 and K167; Q110 and N164; Q110 and K167; K142 and K167; R134, N164, and K167; K75, Q94, and Q110; K7, R134, N164, and K167; K8, R134, N164, and K167; T17, R134, N164, and K167; R134, K142, N164, and K167; I70, R134, N164, and K167; K72, R134, N164, and K167; Q94, R134, N164, and K167; Q110, R134, N164, and K167; Q94, Q110, R134, and N164; Q94, Q110, R134, N164, and K167; Q94, Q110, R134, K142, and K167; Q94, Q110, K142, N164, and K167; K75, Q94, Q110, R134, N164, and K167; K72, K75, Q94, Q110, R134, N164, and K167; or K7, K8, R134, N164, and K167.

In certain embodiments, the CD4 D1D2 mutein comprises substitutions at the following positions: R134, N164, and K167; A55, R134, and N164; A55, R134, and K167; A55, N164, and K167; L5, A55, and L96; A55, R134, N164, and K167; L5, S23, A55, and L96; S23, A55, R134, N164, and K167; S23, A55, L96, R134, N164, and K167; L5, S23, A55, R134, N164, and K167; or L5, S23, A55, L96, R134, N164, and K167. In certain embodiments, the CD4 D1D2 mutein comprises substitutions at the following positions: L5, A55, and L96; A55, R134, N164, and K167; S23, A55, R134, N164, and K167; or L5, S23, A55, L96, R134, N164, and K167.

In certain embodiments, the CD4 D1D2 mutein comprises at least one of: a substitution of K1 by N (K1N); a substitution of K2 by E (K2E), N (K2N) or T (K2T); a substitution of L5 by Y (L5Y), I (L5I), E (L5E), W (L5W), V (L5V), F (L5F), or T (L5T); a substitution of K7 by E (7); a substitution of K8 by E (K8E); a substitution of T15 by N (T15N) or E (T15E); a substitution of T17 by N (T17N) or E (T17E); a substitution of S23 by N (S23N), T (S23T), K (S23K), Y (S23Y), or A (S23A); a substitution of A55 by V (A55V), I (A55I), P (A55P), L (A55L), M (A55M), F (A55F), Y (A55Y), W (A55W) or T (A55T); a substitution of I70 by E (I70E), L (I70L), or V (I70V); a substitution of K72 by S (K72S); a substitution of K75 by E (K75E) or Q (K75Q); a substitution of Q94 by E (Q94E); a substitution of L96 by V (L96V), Q (L96Q), T (L96T), I (L96I), or Y (L96Y); a substitution of Q110 by E (Q110E) or H (Q110H); a substitution of R134 by G (R134G) or T (R134T); a substitution of K142 by R (K142R), G (K142G), or S (K142S); a substitution of N164 by D (N164D), H (N164H), R (N164R), or E (N164E); and a substitution of K167 by T (K167T), R (K167R), or L (K167L).

In certain embodiments the CD4 D1D2 mutein comprises at least one of the K2E, K7E, K8E, T17N, T17E, A55V, I70E, K72S, K75E, Q94E, Q110E, R134G, K142R, N164D, and K167T substitutions. For example, in certain embodiments, the CD4 D1D2 mutein comprises the following substitutions: K2E and N164D; K2E and K167T; K7E and K8E; K8E and N164D; K8E and K167T; T17N and N164D; T17N and K167T; T17E and N164D; T17N and K167T; I70E and N164D; I70E and K167T; K72S and N164D; K72S and K167T; Q94E and Q110E; Q94E and N164D; Q94E and K167T; Q110E and N164D; Q110E and K167T; R134G and N164D; R134G and K167T; K142R and K167T; N164D and K167T; R134G, N164D and K167T; K2E, R134G, N164D, and K167T; K8E, R134G, N164D, and K167T; T17N, R134G, N164D, and K167T; T17E, R134G, N164D, and K167T; A55V, R134G, N164D, and K167T; I70E, R134G, N164D, and K167T; K72S, R134G, N164D, and K167T; K75E, Q94E, and Q110E; or K72S, K75E, Q94E, Q110E, R134G, N164D, and K167T.

In certain embodiments, the CD4 D1D2 mutein comprises at least one of the L5Y, K8E, S23N, A55V, K75E, Q94E, L96V, Q110E, R134G, N164D, and K167T substitutions, at least one of the L5Y, S23N, A55V, L96V, R134G, N164D, and K167T substitutions, at least one of the S23N, A55V, R134G, N164D, and K167T substitutions, or at least one of the A55V, R134G, N164D, and K167T substitutions. For example, in certain embodiments, the CD4 D1D2 mutein comprises the following substitution(s): A55V; L5Y, A55V, and L96V; A55V, R134G, N164D, and K167T; S23N, A55V, R134G, N164D, and K167T; L5Y, A55V, L96V, R134G, N164D, and K167T; or L5Y, S23N, A55V, L96V, R134G, N164D, and K167T.

In certain embodiments, the CD4 D1D2 mutein comprises the amino acid sequence of SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 36, SEQ ID NO: 38, SEQ ID NO: 40, SEQ ID NO: 42, SEQ ID NO: 44, or an amino acid sequence that has at least 90%, 95%, 96%, 97%, 98%, or 99% sequence identity to SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 36, SEQ ID NO: 38, SEQ ID NO: 40, SEQ ID NO: 42, or SEQ ID NO: 44.

In certain embodiments, the CD4 D1D2 mutein comprises a leader sequence comprising the amino acid sequence of SEQ ID NO: 46, which is encoded by the nucleotide sequence of SEQ ID NO: 47. In certain embodiments, the leader sequence has at least 90%, 95%, 96%, 97%, 98%, or 99% sequence identity to SEQ ID NO: 46.

In certain embodiments, the CD4 D1D2 mutein does not include a substitution of an amino acid residue in wild-type human CD4 D1D2 (SEQ ID NO: 1) that contacts gp120. For example, in certain embodiments, the CD4 D1D2 mutein does not include a substitution at a position corresponding to N32, K35, L44, K46, or R59 of wild-type human CD4 D1D2 (SEQ ID NO: 1) and the naturally occurring amino acid is retained.

In certain embodiments, the CD4 D1D2 mutein does not include a substitution of an amino acid residue that forms a salt bridge in wild-type human CD4 D1D2 (SEQ ID NO: 1). For example, in certain embodiments, the CD4 D1D2 mutein does not include a substitution at a position corresponding to K1, K2, K50, D56, R58, R59, K72, E77, E91, R131, D153, K167, E169, or K171 of wild-type human CD4 D1D2 (SEQ ID NO: 1) and the naturally occurring amino acid is retained.

In certain embodiments, the CD4 D1D2 mutein does not include a substitution at a position corresponding to F98 of wild-type human CD4 D1D2 (SEQ ID NO: 1), e.g., the CD4 D1D2 mutein does not include a substitution of F98 by valine (F98V). In certain embodiments, the CD4 D1D2 mutein does not include a substitution at a position corresponding to 176 of wild-type human CD4 D1D2 (SEQ ID NO: 1), e.g., the CD4 D1D2 mutein does not include a substitution of 176 by proline (176P).

In certain embodiments, the CD4 D1D2 mutein comprises at least one amino acid substitution, for example, one or more of the substitutions described herein, that increases the aggregation temperature of the protein. In certain embodiments, the protein has an aggregation temperature of at least 60° C., 61° C., 62° C., 63° C., 64° C., 65° C., 66° C., 67° C., 68° C., 69° C., or 70° C. In certain embodiments, the protein has an aggregation temperature at least 7° C., 8° C., 9° C., 10° C., 11° C., or 12° C. higher than the aggregation temperature of a corresponding protein comprising a wild-type human CD4 D1D2. Aggregation temperature can be measured by any method known in the art, including by dynamic light scattering (DLS) in a thermal scan assay as described in Examples 1 and 2 herein.

In certain embodiments, the CD4 D1D2 mutein comprises at least one amino acid substitution, for example, one or more of the substitutions described herein, that increases the melting temperature of the protein. In certain embodiments, the protein has a melting temperature of at least 50.3° C., 51° C., 52° C., 53° C., 53° C., 54° C., 55° C., 56° C., 57° C., 58° C., 59° C., or 60° C., 61° C., 62° C., 63° C., 64° C., 65° C., 66° C. In certain embodiments, the protein has a melting temperature at least 0.1° C., 1° C., 2° C., 3° C. 0.4° C., 5° C., 6° C., 7° C., 8° C., 9° C., 10° C., 11° C., 12° C., 13° C., 14° C., 15° C., or 16° C. higher than the melting temperature of a corresponding protein comprising a wild-type human CD4 D1D2. Melting temperature can be measured by any method known in the art, including by a thermal scan assay using, e.g., dye intercalation, as described in Example 3 herein. In certain embodiments, the CD4 D1D2 mutein comprises at least one amino acid substitution, for example, one or more of the substitutions described herein, that increases the yield of the CD4 D1D2 mutein. In certain embodiments, the protein is produced at a yield that is between about 1.1 and 5 times, about 1.5 and 5 times, about 2 and 5 times, about 3 and 5 times, about 4 and 5 times, about 1.1 and 4 times, about 1.5 and 4 times, about 2 and 4 times about 4 and 4 times, about 1.1 and 3 times, about 1.5 and 3 times, about 2 and 3 times, about 1.1 and 2 times about 1.5 and 2 times, or about 1.1 and 1.5 times the yield of a corresponding protein comprising a wild-type human CD4 D1D2. In certain embodiments, the protein is produced at ayield that is at least about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, about 350%, about 400%, about 450% higher than the yield of a corresponding protein comprising a wild-type human CD4 D1D2.

In certain embodiments, the CD4 D1D2 mutein comprises at least one amino acid substitution, for example, one or more of the substitutions described herein, that increases neutralization of a virus, e.g., HIV, by the CD4 D1D2 mutein. For example, in certain embodiments, the CD4 D1D2 mutein comprises at least one amino acid substitution that decreases the $IC_{50}$ of the protein for HIV infection of a $CD4^+$ $CCR5^+$ cell. Viral neutralization can be measured by any method known in the art, including by incubating a protein comprising the CD4 D1D2 mutein with virus and CD4+ CCR5+ TZM-bl cells, which express firefly luciferase upon viral infection, as described in Example 5 herein.

In certain embodiments, the protein has a plasma half-life of at least 12 hours, 24 hours, 1 day, 1.5 days, 2 days, 2.5 days, 3 days, 3.5 days, 4 days, 4.5 days, 5 days, 5.5 days, 6 days, 6.5 days, 7 days, 7.5 days, 8 days, 8.5 days, 9 days, 9.5 days, or 10 days, e.g., in the plasma of a mouse (e.g., a human FcRn transgenic mouse), rat, rhesus macaque, or human. For example, in certain embodiments, the protein has a plasma half-life of at least 12 hours in a rat. In certain embodiments, the protein has a plasma half of at least 3 days in a human FcRn transgenic mouse.

In certain embodiments, a protein comprising a CD4 D1D2 mutein further comprises a primate lentivirus envelope glycoprotein binding moiety. The binding moiety may, for example, comprise a peptide mimetic of CCR5, the co-receptor for HIV. In certain embodiments, the binding moiety comprises at least one sulfotyrosine. In certain embodiments, the binding moiety comprises the amino acid sequence of SEQ ID NO: 2, SEQ ID NO: 3, SEQ ID NO: 4, SEQ ID NO: 5, SEQ ID NO: 6, or SEQ ID NO: 7. In certain embodiments, a tyrosine residue in any one of SEQ ID NO: 2, SEQ ID NO: 3, SEQ ID NO: 4, SEQ ID NO: 5, SEQ ID NO: 6, or SEQ ID NO: 7 is sulfated.

Alternatively or in addition, in certain embodiments, a protein comprising a CD4 D1D2 mutein further comprises an immunoglobulin Fc domain. As used herein, unless otherwise indicated, the term "immunoglobulin Fc domain" refers to a fragment of an immunoglobulin heavy chain constant region. An immunoglobulin Fc domain may include, e.g., immunoglobulin CH2 and CH3 domains. An immunoglobulin Fc domain may include, e.g., immunoglobulin CH2 and CH3 domains and an immunoglobulin hinge region. In certain embodiments, the immunoglobulin hinge region comprises a substitution or deletion of C220, e.g., C220S. Boundaries between immunoglobulin hinge regions, CH2, and CH3 domains are well known in the art, and can be found, e.g., in the PROSITE database (available on the World Wide Web at prosite.expasy.org).

In certain embodiments, the immunoglobulin Fc domain is derived from a human IgG1, IgG2, IgG3, IgG4, IgA1, IgA2, IgD, IgE, and IgM Fc domain. In certain embodiments, the immunoglobulin Fc domain is derived from a human IgG1 isotype or another isotype that directs antibody-dependent cell-mediated cytotoxicity (ADCC) and/or complement mediated cytotoxicity (CDC). In certain embodiments, the immunoglobulin Fc domain is derived from a human IgG1 isotype. In certain embodiments, the immunoglobulin Fe domain is derived from a human IgG2 isotype or another isotype that elicits little or no antibody-dependent cell-mediated cytotoxicity (ADCC) and/or complement mediated cytotoxicity (CDC). In certain embodiments, the immunoglobulin Fc domain is derived from a human IgG3 isotype. In certain embodiments, the immunoglobulin Fc domain is derived from a human IgG4 isotype.

In certain embodiments, the Fc domain comprises a substitution, for example, one or more of the substitutions described herein, that increases the stability and/or half-life of the Fc domain. For example, in certain embodiments, the Fc domain comprises at least one of a M252Y, S254T, T256E, M428L, H433K, N434S, and N434F substitution. For example, the Fc domain may comprise the M252Y, S254T, and T256E substitutions, or the M428L and N434S substitutions. All Fc domain residue numbers are according to conventional human IgG numbering (Hessell et al. (2007) NATURE, 449(7158):101-4).

In certain embodiments, a protein comprising a CD4 D1D2 mutein further comprises an immunoglobulin Fc domain and/or a primate lentivirus envelope glycoprotein binding moiety. In certain embodiments, the CD4 D1D2 mutein is linked or fused directly to the Fc domain and/or envelope glycoprotein binding moiety. In other embodiments, the CD4 D1D2 mutein can be covalently bound to the Fc domain and/or envelope glycoprotein binding moiety by a linker.

II. Protein Production

Methods for producing proteins of the invention are known in the art. For example, DNA molecules encoding a protein comprising a CD4 mutein can be chemically synthesized using the sequence information provided herein. Synthetic DNA molecules can be ligated to other appropriate nucleotide sequences, including, e.g., expression control sequences, to produce conventional gene expression constructs encoding the desired protein.

Nucleic acids encoding a desired protein comprising a CD4 mutein can be incorporated (ligated) into expression vectors, which can be introduced into host cells through conventional transfection or transformation techniques. Transformed host cells can be grown under conditions that permit the host cells to express the genes that encode the protein.

Nucleic acids encoding a CD4 mutein may be generated by mutating a nucleotide sequence encoding the wild-type human CD4 D1D2 (SEQ ID NO: 35) using methods known in the art. Furthermore, in certain embodiments, nucleic acids encoding a protein of the invention may be codon optimized for expression in a heterologous cell, e.g., an *E. coli* cell, CHO cell, etc., using methods known in the art.

Exemplary nucleotide sequences encoding CD4 muteins disclosed herein include SEQ ID NO: 9 (encoding the amino acid sequence depicted in SEQ ID NO: 8), SEQ ID NO: 11 (encoding the amino acid sequence depicted in SEQ ID NO: 10), SEQ ID NO: 13 (encoding the amino acid sequence depicted in SEQ ID NO: 12), SEQ ID NO: 15 (encoding the amino acid sequence depicted in SEQ ID NO: 14), SEQ ID NO: 17 (encoding the amino acid sequence depicted in SEQ ID NO: 16), SEQ ID NO: 19 (encoding the amino acid sequence depicted in SEQ ID NO: 18), SEQ ID NO: 21 (encoding the amino acid sequence depicted in SEQ ID NO: 20), SEQ ID NO: 23 (encoding the amino acid sequence depicted in SEQ ID NO: 22), SEQ ID NO: 25 (encoding the amino acid sequence depicted in SEQ ID NO: 24), SEQ ID NO: 27 (encoding the amino acid sequence depicted in SEQ ID NO: 26), SEQ ID NO: 29 (encoding the amino acid sequence depicted in SEQ ID NO: 28), SEQ ID NO: 31 (encoding the amino acid sequence depicted in SEQ ID NO: 30), SEQ ID NO: 33 (encoding the amino acid sequence depicted in SEQ ID NO: 32), SEQ ID NO: 37 (encoding the amino acid sequence depicted in SEQ ID NO: 36), SEQ ID NO: 39 (encoding the amino acid sequence depicted in SEQ ID NO: 38), SEQ ID NO: 41 (encoding the amino acid sequence depicted in SEQ ID NO: 40), SEQ ID NO: 43 (encoding the amino acid sequence depicted in SEQ ID NO: 42), and SEQ ID NO: 45 (encoding the amino acid sequence depicted in SEQ ID NO: 44).

Specific expression and purification conditions will vary depending upon the expression system employed. For example, if a gene is to be expressed in *E. coli*, it can be cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

A protein can be produced by growing (culturing) a host cell transfected with an expression vector encoding such protein, under conditions that permit expression of the protein. Following expression, the protein can be harvested and purified or isolated using techniques known in the art, e.g., Protein A purification.

III. Expression Vectors

In another aspect, the invention provides an isolated nucleic acid comprising a nucleotide sequence encoding any of the foregoing proteins. In another aspect, the invention provides an expression vector comprising any of the foregoing nucleic acids. In certain embodiments, the expression vector is a viral vector, e.g., an adeno-associated virus (AAV) vector.

Adeno-associated virus (AAV) is a small, nonenveloped icosahedral virus of the genus *Dependoparvovirus* and family Parvovirus. AAV has a single-stranded linear DNA genome of approximately 4.7 kb. AAV includes numerous serologically distinguishable types including serotypes AAV-1 to AAV-12, as well as more than 100 serotypes from nonhuman primates (See, e.g., Srivastava (2008) J. CELL BIOCHEM., 105(1): 17-24, and Gao et al. (2004) J. VIROL., 78(12), 6381-6388). AAV is capable of infecting both dividing and quiescent cells of several tissue types, with different AAV serotypes exhibiting different tissue tropism.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous protein of interest. In this case the rep and cap proteins are provided in trans on, for example, a plasmid. In order to produce an AAV vector, a host cell line permissive of AAV replication must express the rep and cap genes, the ITR-flanked expression cassette, and helper functions provided by a helper virus, for example AV genes Ela, E1b55K, E2a, E4orf6, and VA (Weitzman et al., Adeno-associated virus biology. Adeno-Associated Virus: Methods and Protocols, pp. 1-23, 2011). Methods for generating and purifying AAV vectors have been described in detail (See e.g., Mueller et al., (2012) CURRENT PROTOCOLS IN MICROBIOLOGY, 14D.1.1-14D.1.21, Production and Discovery of Novel Recombinant Adeno-Associated Viral Vectors). Numerous cell types are suitable for producing AAV vectors, including HEK293 cells, COS cells, HeLa cells, BHK cells, Vero cells, as well as insect cells (See e.g. U.S. Pat. Nos. 6,156,303, 5,387,484, 5,741,683, 5,691,176, 5,688,676, 8,163,543, U.S. Publication No. 20020081721, PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the present invention. Similarly, it is contemplated that any AV type may be used, and a person of skill in the art will be able to identify AAV and AV types suitable for the production of their desired recombinant AAV vector (rAAV). AAV and AV particles may be purified, for example by affinity chromatography, iodixonal gradient, or CsCl gradient.

AAV vectors may have single-stranded genomes that are 4.7 kb in size, or are larger or smaller than 4.7 kb, including oversized genomes that are as large as 5.2 kb, or as small as 3.0 kb. Further, vector genomes may be substantially self-complementary, so that within the virus the genome is substantially double stranded. AAV vectors containing genomes of all types are suitable for use in the method of the present invention.

Exemplary AAV vectors are described in Gardner, M. R. et al. (2015) NATURE, 519(7541): 87-91. An exemplary AAV vector nucleotide sequence is depicted in SEQ ID NO: 34.

IV. Pharmaceutical Compositions

For therapeutic use, a protein or expression vector disclosed herein preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (See *Remington's Pharmaceutical Sciences*, 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1: 10-29).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (-)-3-hydroxybutyric acid. Sustained release compositions may also include liposomes that can be prepared by any of several methods known in the art.

Pharmaceutical compositions containing a protein or expression vector disclosed herein can be presented in a dosage unit form and can be prepared by any suitable method. A pharmaceutical composition should be formulated to be compatible with its intended route of administration. Examples of routes of administration are intravenous (IV), subcutaneous, intradermal, inhalation, transdermal, topical, transmucosal, intrathecal and rectal administration. An exemplary route of administration is IV infusion. Useful formulations can be prepared by methods known in the pharmaceutical art. For example, see *Remington's Pharmaceutical Sciences*, 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. In certain embodiments, administration will be parenteral administration. In certain embodiments, the pharmaceutical composition is administered subcutaneously, and in certain embodiments intravenously.

Preparations for parenteral administration include sterile aqueous or non-aqueous solutions, suspensions, and emulsions.

In certain embodiments, a therapeutically effective amount of active component is in the range of 0.1 mg/kg to 100 mg/kg, e.g., 1 mg/kg to 100 mg/kg, 1 mg/kg to 50 mg/kg, 1 mg/kg to 40 mg/kg, 1 mg/kg to 30 mg/kg, 1 mg/kg to 20 mg/kg, 1 mg/kg to 10 mg/kg, 1 mg/kg to 5 mg/kg, 50 mg/kg, 40 mg/kg, 30 mg/kg, 20 mg/kg, 10 mg/kg, 7.5 mg/kg, 5 mg/kg, or 2.5 mg/kg. In certain embodiments, a therapeutically effective amount of a viral vector is in the range of $10^2$ to $10^{15}$ vector genome (vg) copies, e.g., $10^2$ to $10^{10}$, $10^2$ to $10^5$, $10^5$ to $10^{15}$, $10^5$ to $10^{10}$, $10^{10}$ to $10^{15}$, $10^{10}$ to $10^{14}$, $10^{10}$ to $10^{12}$, or $10^{12}$ to $10^{14}$ vg copies. The amount administered will depend on variables such as the type and extent of disease or indication to be treated, the overall health of the patient, the in vivo potency of the active component, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 30 mg/kg. Dosing frequency can vary, depending on factors such as route of administration, dosage amount, serum half-life of the antibody, and the disease being treated. Exemplary dosing frequencies are once per day, once per week and once every two weeks. An exemplary route of administration is parenteral, e.g., intravenous infusion. In certain embodiments, a protein or expression vector disclosed herein is lyophilized, and then reconstituted in buffered saline, at the time of administration.

V. Therapeutic Uses

The proteins, expression vectors, compositions and methods disclosed herein can be used to treat human immunodeficiency virus (HIV) infection in a subject. The invention provides a method of treating a HIV infection in a subject. The method comprises administering to the subject an effective amount of a protein, expression vector or pharmaceutical composition disclosed herein, either alone or in a combination with another therapeutic agent, to treat the HIV infection in the subject. The invention also provides a method of blocking the entry of HIV into a host cell, e.g., a human host cell. The method comprises exposing the host cell to an effective amount of a protein, expression vector or pharmaceutical composition disclosed herein, either alone or in a combination with another therapeutic agent, to block the entry of HIV into the host cell. The invention also provides a method of causing the killing of a host cell, e.g., a human host cell, infected with HIV. The method comprises exposing the host cell to an effective amount of a protein, expression vector or pharmaceutical composition disclosed herein, either alone or in a combination with another therapeutic agent, to cause the killing of the infected host cell. The invention also provides a method of causing the inactivation of a viral particle, e.g., an HIV viral particle. The method comprises exposing the viral particle to an effective amount of a protein, expression vector or pharmaceutical composition disclosed herein, either alone or in a combination with another therapeutic agent, to cause the inactivation of the viral particle. The invention also provides a method of clearing virus particles from the plasma of a subject, e.g., HIV virus particles. The method comprises exposing the subject to an effective amount of a protein, expression vector or pharmaceutical composition disclosed herein, either alone or in a combination with another therapeutic agent, to clear virus particles from the plasma of a subject.

The term "effective amount" as used herein refers to the amount of an active agent (e.g., a protein comprising a mutant CD4 D1D2 or a viral vector expressing a protein comprising a mutant CD4 D1D2 according to the present invention) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a method or composition described herein is administered in combination with a nucleoside/nucleotide reverse transcriptase inhibitor (e.g., lamivudine, abacavir, zidovudine, stavudine, didanosine, emtricitabine, and tenofovir), a non-nucleoside reverse transcriptase inhibitor (e.g., delavirdine, efavirenz, etravirine, and nevirapine), a protease inhibitor (e.g., amprenavir, fosamprenavir, atazanavir, darunavir, indinavir, lopinavir, ritonavir, nelfinavir, saquinavir, and tipranavir), a fusion or entry inhibitor (e.g., enfuvirtide and maraviroc), integrase inhibitors (e.g., raltegravir and cabotegravir), or any combination thereof. In certain embodiments, a method or composition described herein is administered in combination with a latency-reversing agent (LRA), for example, a HDAC inhibitor (e.g., vorinostat) or a TLR7 agonist (e.g., GS-9620, e.g., as described in U.S. Patent Publication No. US20160008374A1).

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1—Non-Human Primate eCD4-Ig Exhibits Greater Stability than Human eCD4-Ig CD4-Ig is a fusion of domains 1 and 2 of CD4 (CD4 D1D2) and an antibody Fc domain. eCD4-Ig is a fusion of CD4 D1D2, an antibody Fc domain, and a tyrosine-sulfated peptide (sulfopeptide) that resembles tyrosine-sulfated regions of HIV and SIV coreceptors (Gardner, M. R. et al. (2015) NATURE, 519 (7541): 87-91). This Example describes measurement of the aggregation temperatures of eCD4-Ig variants including human CD4 D1D2 or non-human primate (NHP) CD4 D1D2.

Conformational stability of a protein (the protein's resistance to unfolding) is an important attribute among protein therapeutics. Partial unfolding can allow the therapeutic protein to adhere non-specifically to other molecules in vivo which in turn can diminish the half-life of the therapeutic protein.

Conformational stability can be measured by dynamic light scattering (DLS), which is an approach for measuring particle size in solution, which can in turn be used to measure particle size under different conditions (Nobbmann, U. et al. (2007) BIOTECHNOL. GENET. ENG. REV., 24: 117-28). The movement of particles due to Brownian motion is faster for small particles than for large particles. DLS is able to calculate particle size by detecting particle movement. Since soluble protein molecules are smaller than aggregates of the same protein, an increase in particle size detected by DLS indicates protein aggregation. A thermal scan DLS assay detects the formation of aggregates as the temperature of a protein sample is slowly increased. In this assay, proteins with greater conformational stability begin to aggregate at comparatively high temperatures, whereas proteins with lower conformational stability begin to aggregate at comparatively low temperatures.

Typically, an aggregation temperature of 60° C. or greater is desirable for a recombinant protein therapeutic. As shown in FIG. 1A, an eCD4-Ig variant with the IgG1 Fc domain and the wild-type human CD4 D1D2 had an aggregation temperature of 51° C. As shown in FIG. 1B, an eCD4-Ig variant with the IgG2 Fc domain and the wild-type human CD4 D1D2 had an aggregation temperature of 53° C. As shown in FIG. 1A, an eCD4-Ig variant with the IgG1 Fc domain and the wild-type rhesus macaque CD4 D1D2 had an aggregation temperature of 62° C., which is 9° C. higher than that of the corresponding eCD4-Ig variant with human CD4 D1D2. As shown in FIG. 1B, an eCD4-Ig variant with the IgG2 Fc domain and the wild-type rhesus macaque CD4 D1D2 had an aggregation temperature of 67° C., which is 14° C. higher than that of the corresponding eCD4-Ig variant with human CD4 D1D2.

Thus, eCD4-Ig based on wild-type rhesus CD4 D1D2 exhibits improved conformational stability relative to eCD4-Ig based on wild-type human CD4 D1D2.

Figure 2:
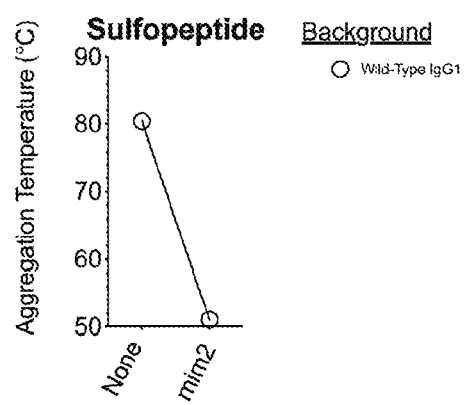
FIG. 2 is a graph showing aggregation temperature for CD4-Ig proteins with or without a CCR5 mimetic sulfopeptide "mim2." Each protein tested had wild-type human CD4 D1D2 fused to human IgG1 Fc, and was identical except for the presence or absence of the sulfopeptide.

The aggregation temperature was also measured for CD4-Ig (without a sulfopeptide) and eCD4-Ig (with a "mim2" (SEQ ID NO:3) sulfopeptide), each including wild-type human CD4 D1D2. As shown in FIG. 2, CD4-Ig had an aggregation temperature of 80.4° C., whereas eCD4-Ig had an aggregation temperature of 51° C. Therefore, the presence of an additional binding moiety (e.g., a sulfopeptide) can greatly reduce the conformational stability of CD4-Ig.

Example 2—Identification of Amino Acid Substitutions that Improve the Stability of Human CD4 D1D2 Using DLS Assays This Example describes the identification of amino acid substitutions that increase the aggregation temperature of proteins including human CD4 D1D2, e.g., CD4-Ig and eCD4-Ig.

Figure 3:
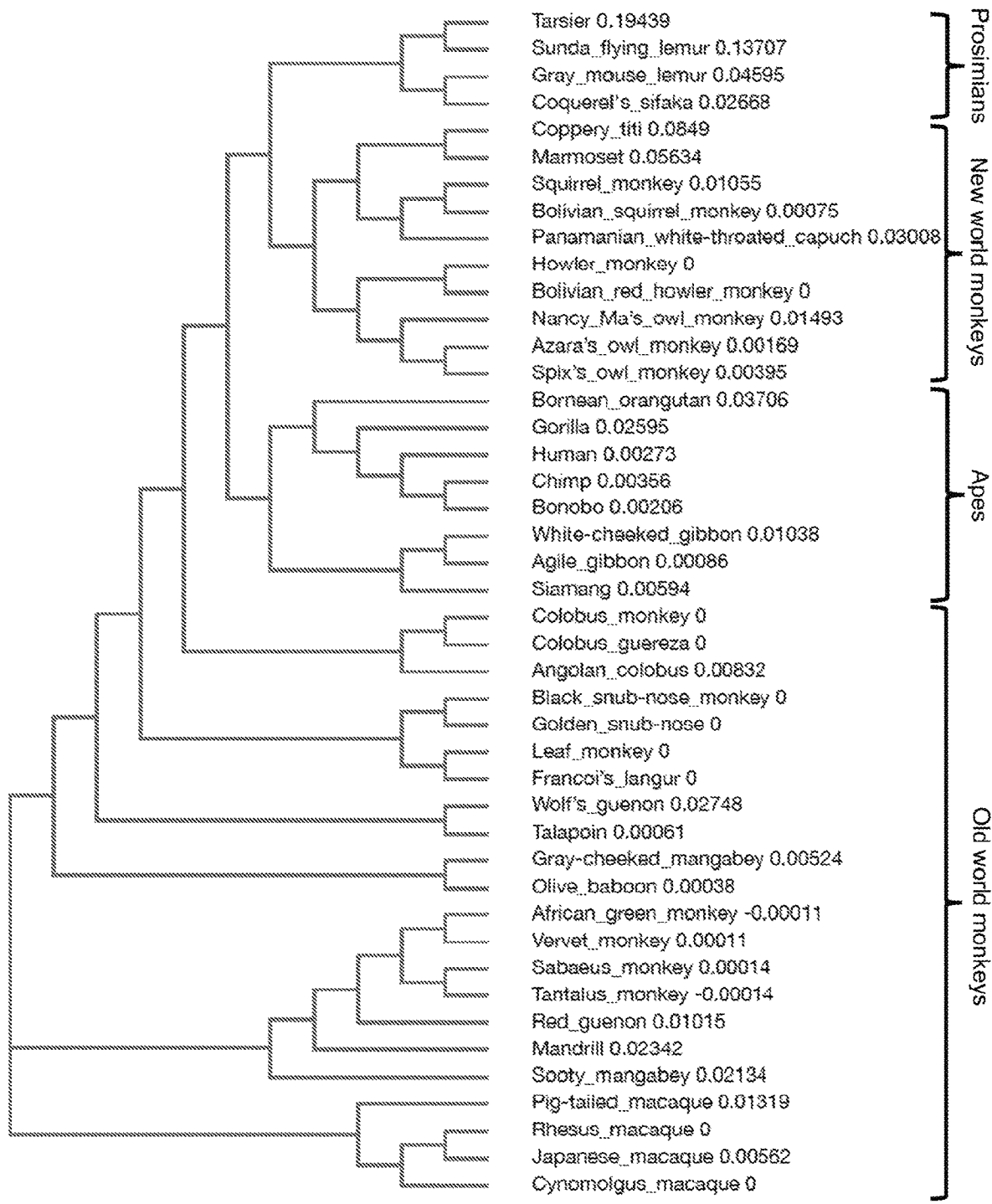
FIG. 3 is a phylogenetic tree showing relatedness of primate CD4 D1D2 amino acid sequences. The human CD4 D1D2 sequence groups with that of other apes. Consistent with their evolutionary relationships, the CD4 D1D2 sequences of prosimians, new world monkeys, and old world monkeys each form distinct groups.

In order to identify amino acid substitutions that could confer improved conformational stability on human eCD4-Ig, human CD4 D1D2 was compared to CD4 D1D2 from various non-human primate (NHP) species. The human CD4 D1D2 amino acid sequence was aligned to the CD4 D1D2 amino acid sequences of various ape, monkey, and prosimian species, including: chimpanzee, bonobo, gorilla, Bornean orangutan, white-cheeked gibbon, agile gibbon, siamang, Colobus monkey, Colobus guereza, Angolan colobus, African green monkey, vervet monkey, Sabaeus monkey, Tantalus monkey, red guenon, sooty mangabey, mandrill, black snub-nose monkey, golden snub-nose monkey, leaf monkey, pig-tailed macaque, rhesus macaque, cynomolgus macaque, Japanese macaque, Wolf's guenon, Talapoin, gray-cheeked mangabey, olive baboon, coppery titi, marmoset, common squirrel monkey, Bolivian squirrel monkey, howler monkey, Bolivian red howler monkey, Panamanian white-throated capuchin, Nancy Ma's owl monkey, Azara's owl monkey, tarsier, Sunda flying lemur, gray mouse lemur, and Coquerel's sifaka (FIGS. 3 and 4). Among these NHP species, the CD4 D1D2 sequence of humans is most similar that of other apes, second most similar to that of old-world monkeys, third most similar to that of new world monkeys, and least similar to that of prosimians (FIG. 3). Rhesus and human CD4 D1D2 were found to be 88% identical, with differences at positions T17, S23, I24, N39, N52, R59, N66, P68, L69, D88, Q89, Q94, Q110, Q129, R134, K142, L144, 5147, L151, L162, N164, and K167. Chimpanzee and human CD4 D1D2 were found to be 98% identical, with differences at positions 134, A55, P68, and E87.

To determine whether certain substitutions stabilize the hydrophobic cores of CD4 domain 1 (D1) and domain 2 (D2), we substituted a glycine or a hydrophobic amino acid in wild-type human CD4 D1D2 (SEQ ID NO: 1) with a hydrophobic amino acid that has a larger volume, for example, side chain volume, than the amino acid that is replaced. The hydrophobic amino acid was in certain instances a buried hydrophobic amino acid. In this experiment, the amino acids A, V, P, L, I, M, F, Y, and W were considered hydrophobic amino acids, and the relative volume of glycine and the hydrophobic amino acids was considered to be as follows: G<A<V<P<L=I<M<F<Y<W. For example, positions G6, I24, L44, L51, A55, L69, G99, A102, V128, G141, V146, V161, and V168 are each observed as hydrophobic amino acids of larger volume in NHP CD4 D1D2 than in human CD4 D1D2 (FIG. 4). Without wishing to be bound by theory, it was hypothesized that certain amino acid substitutions within the hydrophobic core of the protein, where a glycine or a hydrophobic amino acid is replaced with a hydrophobic amino acid of larger volume than the amino acid that is replaced, would increase conformational stability. Thus, the conformational stability of CD4 D1D2 can be improved through the strategy of stabilizing the hydrophobic core of the protein. To analyze potential substitutions, a computer software program was developed for visualizing spaces within the hydrophobic core of the protein. The program allowed virtual tomographic sectioning and editing of Protein Data Bank (PDB) structures. For example, note the empty space within the hydrophobic pocket bounded by L100, L144, V161, and F170 and surrounding V128 (FIG. 5A). Modeling the substitution V128L fills most of this hydrophobic pocket (FIG. 5B). Likewise, note the hydrophobic pocket bounded by L5, V161, F170, and K7 surrounding V168 (FIG. 5C). This hydrophobic pocket is filled by the substitution V168L (FIG. 5D). In addition to modeling V128 and V168 shown here, this tool allowed for the modeling of substitutions at, e.g., G6, A55, and V146. Thus, the structure of human CD4 D1D2 was analyzed to identify spaces, and substitutions that might fill these spaces, thereby stabilizing the hydrophobic cores of CD4 D1 and D2.

Based on these comparisons, a mutagenic analysis was conducted to identify mutations that confer the superior aggregation temperature of NHP eCD4-Ig upon human eCD4-Ig. Substitutions were evaluated using the DLS thermal scan assay, as described in Example 1. Substitutions were evaluated individually and/or in combination with mutations at other positions in CD4 D1D2 (i.e., in different mutational backgrounds). Unless indicated otherwise, eCD4-Ig variants that were tested included the sulfopeptide mim1 (SEQ ID NO: 2), mim2 (SEQ ID NO: 3), mim4 (SEQ ID NO: 4), mim5 (SEQ ID NO:5) or mim6 (SEQ ID NO: 6). Unless indicated otherwise, eCD4-Ig variants that were tested included the included IgG1 or IgG2 Fc domains, with or without a C220S substitution.

Figure 6:
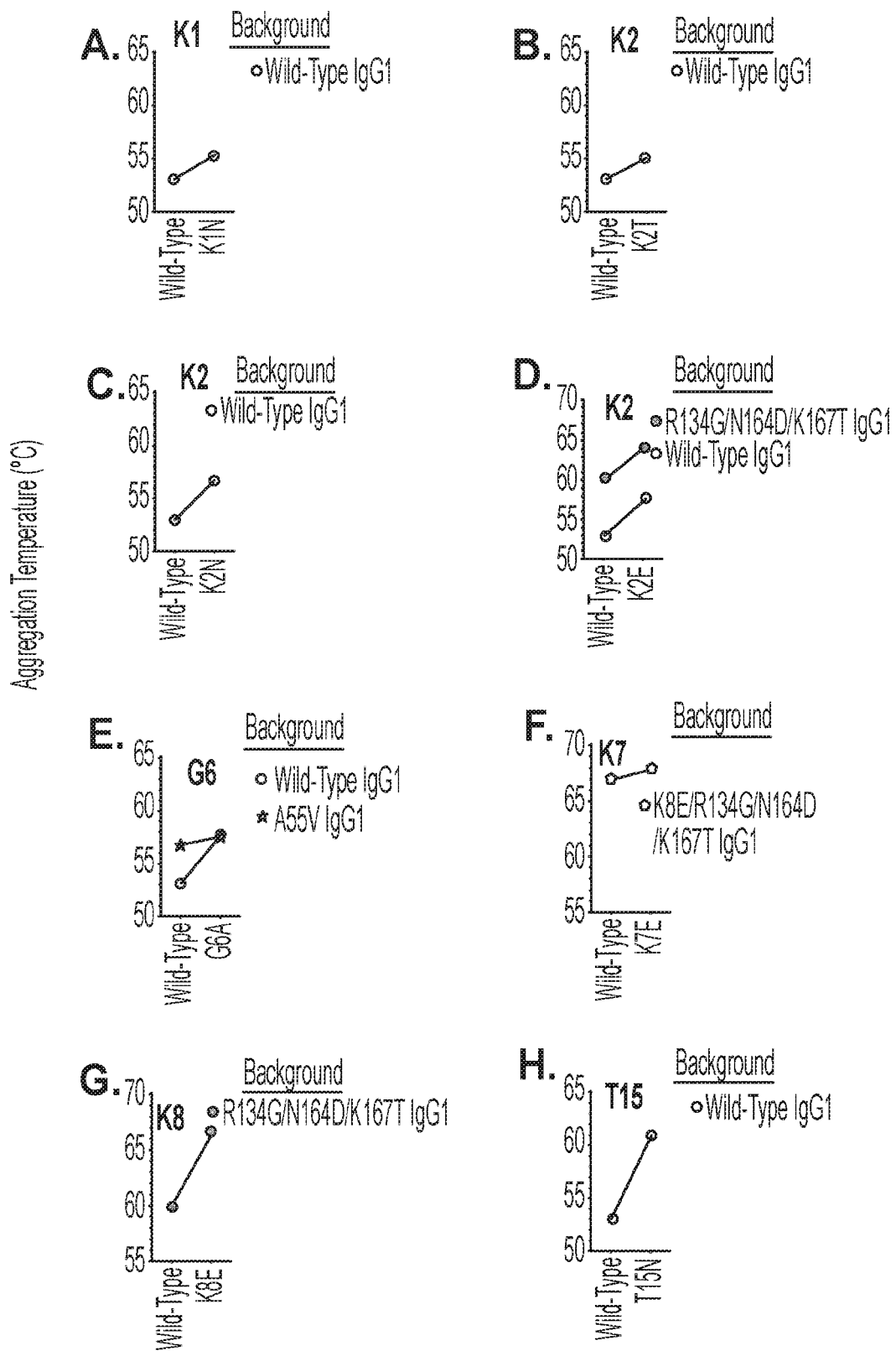
FIG. 6 is a series of graphs showing 50% aggregation temperatures of eCD4-Ig variants with substitutions at one or more positions that differ among human versus NHP CD4 D1D2. Using a DLS thermal scan assay, aggregation temperatures of eCD4-Ig with and without the indicated amino acid substitutions were measured. 'Background' indicates the mutational background in which a substitution was tested (i.e., if the substitution was evaluated in an eCD4-Ig variant with one or more additional substitutions present). Several of the substitutions were evaluated in more than one mutational background. Multiple substitutions are indicated as a list with each substitution separated by a backslash. The x-axis of each graph indicates if the eCD4-Ig variant had the indicated substitution, or a wild-type amino acid residue at the substitution position ("wild-type"). The isotype of the Fc domain in the eCD4-Ig protein (IgG1 or IgG2) is indicated. Black lines with black open or filled symbols indicate IgG1, whereas gray lines with gray open or filled symbols indicate IgG2.

K1 in human CD4 D1D2 (SEQ ID NO:1) is an N in gorillas (FIG. 4A), which are apes. Introducing K1N into eCD4-Ig based on wild-type human CD4 D1D2 background (SEQ ID NO:1) increased the aggregation temperature of eCD4-Ig by 2.3° C., as measured in a dynamic light scattering (DLS) assay for thermal stability (FIG. 6A).

K2 in human CD4 D1D2 (SEQ ID NO:1) is an N in several old world monkeys, including Colobuses, the sooty mangabey, and mandrill, a T in the new world monkeys, and an E in prosimians (FIG. 4A). In a wild-type human CD4 DID background, K2T, K2N, and K2E increased the aggregation temperature of eCD4-Ig by 3° C., 3.7° C., and 4.6° C. respectively (FIG. 6B-D). The K2E substitution in an R134G/N164D/K167T background increased aggregation temperatures by 3.9° C. (FIG. 6D). These results suggest that substitutions at position K2 in human CD4 D1D2 (SEQ ID NO:1), e.g., substitution by E (K2E), increase the aggregation temperature of proteins including CD4 D1D2, e.g., eCD4-Ig.

G6 in human CD4 D1D2 (SEQ ID NO:1) is an A in the tarsier, a prosimian (FIG. 4A). Introducing G6A into a wild-type human CD4 D1D2 (SEQ ID NO: 1) background increased the aggregation temperature of eCD4-Ig by 4.6° C. In an A55V background, introducing G6A increased the aggregation temperature of eCD4-Ig by 0.8° C. (FIG. 6E).

K7 in human CD4 D1D2 (SEQ ID NO:1) is an E in several new world monkeys, including Nancy Ma's owl monkey, Azara's owl monkey, and Spix's owl monkey (FIG. 4A). It also can be an R in several other new world monkeys and in prosimians. The K7E substitution modestly improved conformational stability (FIG. 6F). These results suggest that substitutions at position K7 in human CD4 D1D2 (SEQ ID NO: 1), e.g., substitution by E (K7E), increase the aggregation temperature of proteins including CD4 D1D2, e.g., eCD4-Ig.

Due to its proximity to K7, substitutions at K8 in human CD4 D1D2 (SEQ ID NO:1) were also evaluated. Substitution of K8 by E in human CD4 D1D2 (SEQ ID NO:1)

dramatically improved conformational stability (FIG. 6G). These results suggest that substitutions at position K8 in human CD4 D1D2 (SEQ ID NO:1), e.g., substitution by E (K8E), increase the aggregation temperature of proteins including CD4 D1D2, e.g., eCD4-Ig.

T15 in human CD4 D1D2 (SEQ ID NO:1) is an N in the gorilla (an ape), an A in the sooty mangabey (an old world monkey), a P in prosimians and certain new world monkeys, and an S in the remaining new world monkeys. T15N creates an N-X-T consensus motif for N-linked glycosylation (FIG. 4A). The introduction of T15N in human CD4 D1D2 (SEQ ID NO:1) increased the aggregation temperature of eCD4-Ig by 7.9° C. (FIG. 6H).

T17 in human CD4 D1D2 (SEQ ID NO:1) is an N in most old world monkeys, including rhesus macaques. The presence of the N creates an N-X-T consensus motif for N-linked glycosylation (FIG. 4A). Introducing the T17N substitution in human eCD4-Ig increased the aggregation temperature of eCD4-Ig (FIG. 6I). T17 in human CD4 D1D2 (SEQ ID NO:1) is also an E in all of the new world monkeys, and the T17E substitution conferred a modest improvement in conformational stability (FIG. 6J). These results suggest that substitutions at position T17 in human CD4 D1D2 (SEQ ID NO:1), e.g., substitution by N (T17N) or E (T17E), increase the aggregation temperature of proteins including CD4 D1D2, e.g., eCD4-Ig.

K21 in human CD4 D1D2 (SEQ ID NO:1) is an N in sabaeus and tantalus monkeys (FIG. 4A), which are old world monkeys. Introducing K21N into eCD4-Ig with a wild-type human CD4 D1D2 background increased its aggregation temperature by 11° C. (FIG. 6K).

K22 in human CD4 D1D2 (SEQ ID NO:1) is a T in several old world monkeys, including African green monkeys, vervet monkeys, sabaeus monkeys, tantalus monkeys, and the red guenon (FIG. 4A). Introducing K21T into eCD4-Ig with a wild-type human CD4 D1D2 background increased its aggregation temperature by 6.3° C. (FIG. 6L).

S23 in human CD4 D1D2 (SEQ ID NO:1) is an N in various old and new world monkeys, including rhesus macaques, is a T in certain other old and new world monkeys, and is an S, Y, or A in prosimians (FIG. 4A). S23N increased aggregation temperatures by 10.1° C. and 4.8° C. in eCD4-Ig molecules based on wild-type human CD4 D1D2 (SEQ ID NO:1) and human CD4 D1D2 containing the substitutions G6A/A55V/V128L/V168L, respectively (FIG. 6M). S23T increased aggregation temperatures by 2.3° C. in a background containing G6A/A55V/V128L/V168L (FIG. 6N).

G38 in human CD4 D1D2 (SEQ ID NO:1) is an in the Sunda flying lemur, a prosimian. Changing G38A in a wild-type human CD4 D1D2 (SEQ ID NO:1) background reduced the aggregation temperature of eCD4-Ig by 9° C.

L51 in human CD4 D1D2 (SEQ ID NO:1) is an M in certain prosimians (FIG. 4A). Changing L51 to an I increased the aggregation temperature of eCD4-Ig by 1.8° C. and 2.2° C. in a wild-type human CD4 D1D2 (SEQ ID NO:1) and G6A/A55V background, respectively (FIG. 6P).

A55 in human CD4 D1D2 (SEQ ID NO:1) is a V in chimpanzees, as well as in bonobos and prosimians (FIG. 4A). This position is an I in all of the new world monkeys, and several old world monkeys, including African green monkeys, vervet monkeys, sabeus monkeys, tantalus monkeys, and mandrills. The red guenon, an old world monkey, is the lone outlier with a threonine at this position. Mutating A55 in human eCD4-Ig to V (A55V) in a wild-type human CD4 D1D2 background increased its aggregation temperature by 5.7° C., and mutating A55 in human eCD4-Ig to a V (A55V) in a R134G/N164D/K1K67T mutational background increased aggregation temperature by 4.9° C. (FIG. 6Q). However, in the context of G6A, the aggregation temperature of eCD4-Ig was unchanged. Mutating A55 to an I in the context of an eCD4-Ig with a wild-type human CD4 D1D2 (SEQ ID NO:1) increased its aggregation temperature by 7.1° C. (FIG. 6R). These results suggest that substitutions at position A55 in human CD4 D1D2 (SEQ ID NO:1), e.g., substitution by V (A55V) or I (A55I), increase the aggregation temperature of proteins including CD4 D1D2, e.g., eCD4-Ig.

A55 is a buried hydrophobic amino acid. Without wishing to be bound by theory, it is contemplated that the presence of a bulky hydrophobic amino acid at this position improves the stability of the hydrophobic core of CD4 D1, thereby improving its overall conformational stability. As a result, substitutions of buried glycine residues or buried hydrophobic residues in CD4 D1D2 by a hydrophobic amino acid that has a larger volume than the amino acid that is replaced may increase the aggregation temperature of proteins including CD4 D1D2, e.g., eCD4-Ig. For example, the following positions are buried glycine residues or buried hydrophobic residues in CD4 D2D2, which can be replaced by a hydrophobic amino acid of greater volume: L5, G6, V12, L14, A18, I24, I36, L37, L44, L51, A55, G65, F67, P68, L69, V93, G99, I71, L74, V86, V93, L95, L96, V97, F98, A102, L108, L114, L116, L118, P121, V128, P133, I138, G141, L144, V146, L149, G155, V161, V168, F170, I172, I174, or V176 of wild-type human CD4 D1D2 (SEQ ID NO: 1). Several of these positions also differ in NHPs, including G6, I24, L44, L51, A55, L69, G99, A102, V128, G141, V146, V161, and V168 of wild-type human CD4 D1D2 (SEQ ID NO: 1).

I70 in human CD4 D1D2 (SEQ ID NO:1) is substituted with other amino acids in new world monkeys and prosimians (FIG. 4B). Introducing the amino acid substitution I70E improved conformational stability by 2° C. in a R134G/N164D/K167T eCD4-Ig background (FIG. 6S). These results suggest that substitutions at position I70 in human CD4 D1D2 (SEQ ID NO: 1), e.g., substitution by E (I70E), increase the aggregation temperature of proteins including CD4 D1D2, e.g., eCD4-Ig.

K72 in human CD4 D1D2 (SEQ ID NO:1) is substituted with other amino acids in new world monkeys and prosimians (FIG. 4B). Introducing the amino acid substitution K72S improved conformational stability in a wild-type human CD4 D1D2 (SEQ ID NO:1) background and an R134G/N164D/K167T eCD4-Ig background by 1.3° C. and 3° C., respectively (FIG. 6T). These results suggest that substitutions at position K72 in human CD4 D1D2 (SEQ ID NO:1), e.g., substitution by S (K72S), increase the aggregation temperature of proteins including CD4 D1D2, e.g., eCD4-Ig.

K75 in human CD4 D1D2 (SEQ ID NO:1) is substituted with other amino acids in NHPs, including E in prosimians and Q in various new world monkeys (FIG. 4B). K75E increased the aggregation temperature of eCD4-Ig with a wild-type human CD4 D1D2 background (SEQ ID NO:1) by 4.1° C. (FIG. 6U). Likewise, K75Q increased the aggregation temperature of eCD4-Ig with a wild-type human CD4 D1D2 background (SEQ ID NO:1) by 3° C. (FIG. 6V).

Substitution of V86 in human CD4 D1D2 (SEQ ID NO:1) with an L in the context of a wild-type human CD4 D1D2 (SEQ ID NO:1) background or a G6A/A55V background did not substantially affect the aggregation temperature of eCD4-Ig (FIG. 6W).

Substitution of V93 in human CD4 D1D2 (SEQ ID NO:1) with an I in the context of a wild-type human CD4 D1D2 (SEQ ID NO:1) background modestly increased the aggregation temperature of eCD4-Ig by 0.2° C., but decreased the aggregation temperature by 9.25° C. in a G6A/A55V background (FIG. 6X).

Q94 in human CD4 D1D2 (SEQ ID NO:1) is only a Q in apes and humans, and is an E in old world primates, new world primates, and prosimians (FIG. 4B). Q94E modestly decreased the aggregation temperature of eCD4-Ig in an R134G background (FIG. 6U).

Substitution of V97 in human CD4 D1D2 (SEQ ID NO:1) with an I in the context of a G6A/A55V background modestly decreased the aggregation temperature of eCD4-Ig (FIG. 6Z).

A102 in human CD4 D1D2 (SEQ ID NO:1) is a V in the squirrel monkey, a new world monkey (FIG. 4B). A102V increased the aggregation temperature of eCD4-Ig with a wild-type human CD4 D1D2 background (SEQ ID NO:1) by 1.1° C. (FIG. 6AA).

Q110 in human CD4 D1D2 (SEQ ID NO:1) is an E in certain old world primates, including rhesus macaques, and is an H in certain prosimians (FIG. 4B). Q110E did not change the aggregation temperature of eCD4-Ig in a Q94E/R134G/N164D/K167T background (FIG. 6BB).

Despite apparently not varying among primates, position L116 of human CD4 D1D2 (SEQ ID NO:1) was of interest, due to being adjacent to a hydrophobic pocket bounded by L116, C130, V146, W157, and C159. Substitution of L116 in human CD4 D1D2 (SEQ ID NO:1) with an F (a hydrophobic amino acid of larger volume than the amino acid that is replaced) in the context of a G6A/S23N/A55V/V128L/V168L background increased the aggregation temperature of eCD4-Ig by 7.2° C. (FIG. 6CC). However, in a G6A/S23N/A55V/V128L/V146I/V168L background, L116F resulted in a 0.4° C. decrease in aggregation temperature. Likewise, substitution of L116 with a W (another hydrophobic amino acid of larger volume than the amino acid that is replaced) increased the aggregation temperature of eCD4-Ig in a G6A/S23N/A55V/V128L/V168L background by 1.4° C. but decreased the aggregation temperature in a G6A/S23N/A55V/V128L/V146I/V168L background by 6° C. (FIG. 6DD). These results suggest that substitutions at position L116 in human CD4 D1D2 (SEQ ID NO:1), e.g., substitution by F or W (L116F or L116W), increase the aggregation temperature of proteins including CD4 D1D2, e.g., eCD4-Ig, although not in combination with V146I.

Figure 5:
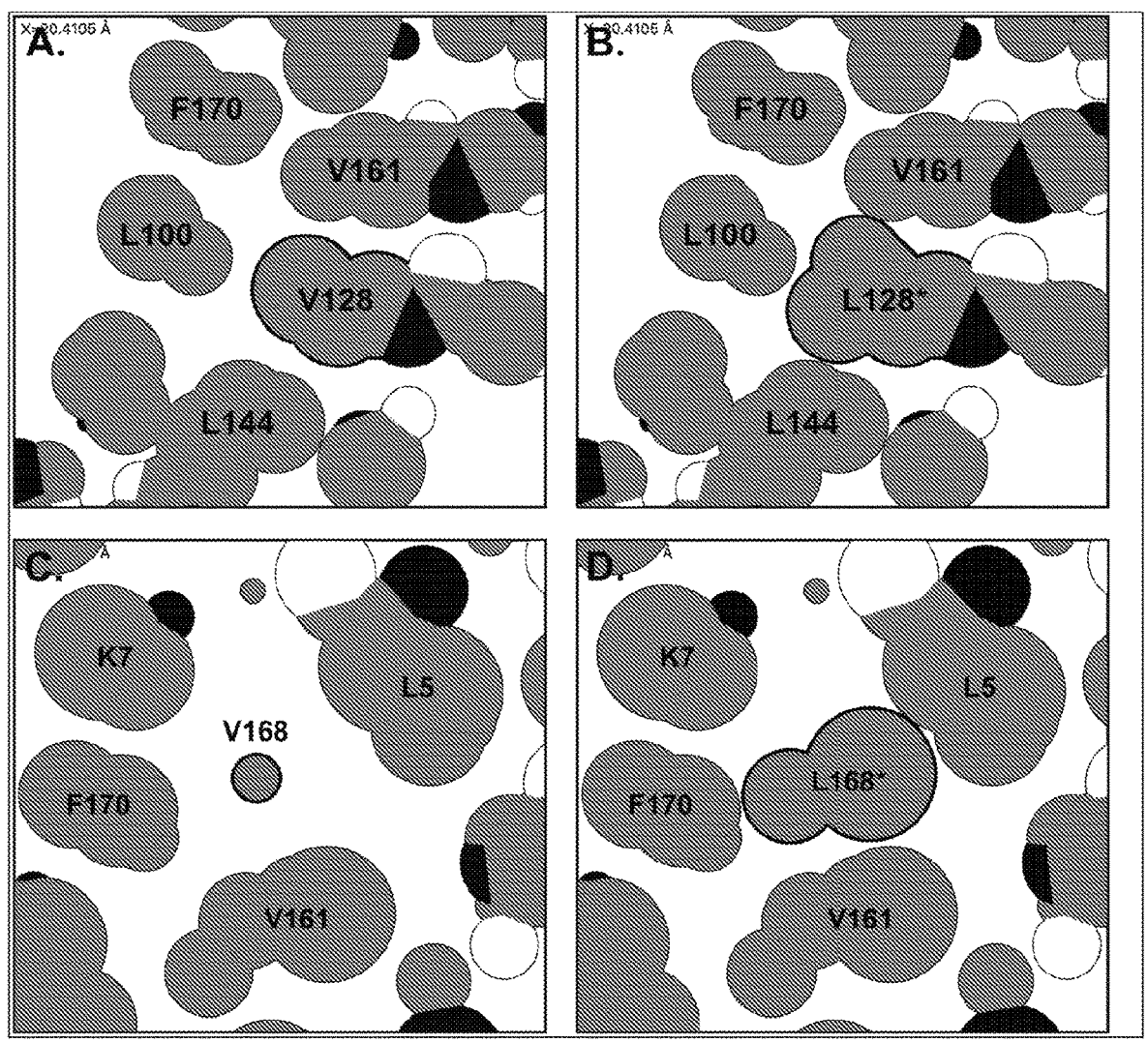
FIG. 5 is a computer-generated visual representation of certain mutations that stabilize the hydrophobic core of CD4 domain 2. To better visualize the interior of CD4 a tool was developed that allows virtual tomographic sectioning and editing of protein data bank (PDB) structures. This computational tool was used to analyze substitutions of a glycine or buried hydrophobic amino acid with a larger hydrophobic amino acid within the hydrophobic core of CD4 D1 and D2. This figure shows two space-filling mutations, which replace a buried hydrophobic amino acid with a hydrophobic amino acid of larger volume than the one which is replaced. Shown here are 2D sections of the human CD4 crystal structure 3CD4 with either wild-type V128 (FIG. 5A) or the substitution V128L (FIG. 5B) modeled at position 128. Note how the V128L substitution fills the hydrophobic pocket bounded by L100, L144, V161, and F170. Also shown here is a 2D section of the same CD4 crystal structure, revealing a space surrounding V168 bounded by L5, K7, V161, and F170 (FIG. 5C), and the substitution V168L (FIG. 5D), which mostly fills this hydrophobic pocket. Carbon atoms are shown in gray, oxygen atoms are shown in white, and nitrogen atoms are shown in black.

V128 in human CD4 D1D2 (SEQ ID NO:1) is an L in the tarsier, a prosimian (FIG. 4C). Substitution of V128 with an I (a hydrophobic amino acid of larger volume than the amino acid that is replaced) increased the aggregation temperature of eCD4-Ig in a wild-type human CD4 D1D2 (SEQ ID NO:1) background by 1.6° C. (FIG. 6EE). Using a computational tool developed for visualizing and editing protein structures, the substitution V128L was modeled (FIG. 5). V128L (a substitution with a hydrophobic amino acid of larger volume than the amino acid that is replaced) fills the hydrophobic pocket bounded by L100, L144, V161, and F170 to a greater extent than the wild-type V128. V128L increased the aggregation temperature of eCD4-Ig with a wild-type human CD4 D1D2 (SEQ ID NO:1) background by 2.7° C. (FIG. 6FF). These results suggest that substitutions at position V128, particularly with a hydrophobic amino acid of greater volume than V, increase the conformational stability and aggregation temperature of proteins including CD4 D1D2, e.g., eCD4-Ig.

R134 in human CD4 D1D2 (SEQ ID NO:1) is a T in the Bornean orangutan (an ape), but is a G in macaques (old world monkeys), tarsiers (prosimians), Sunda flying lemurs (prosimians), and gray mouse lemurs (prosimians) (FIG. 4C). Including a R134G substitution in eCD4-Ig with a wild-type human CD4 D1D2 (SEQ ID NO:1) background increased the aggregation temperature by 4.1° C. (FIG. 6GG). Additionally, including the R134G substitution in different mutational backgrounds (e.g., K167T or Q94E/Q110E/K142R/N164D) greatly improved the conformational stability of human eCD4-Ig (FIG. 6GG). These results suggest that substitutions at position R134 in human CD4 D1D2 (SEQ ID NO:1), e.g., substitution by G (R134G), increase the aggregation temperature of proteins including CD4 D1D2, e.g., eCD4-Ig.

G140 in human CD4 D1D2 (SEQ ID NO:1) is an A in the Bornean orangutan (an ape), and a V or an R in several old world monkeys. Substituting G140 with an A in a wild-type human CD4 D1D2 (SEQ ID NO:1) background increased the aggregation temperature of eCD4-Ig by 7.8° C. (FIG. 6HH).

K142 in human CD4 D1D2 (SEQ ID NO:1) is an R in various old and new world monkeys, including the rhesus macaque, and can be a G or S in prosimians (FIG. 4C). In various background contexts K142R did not increase the aggregation temperature of eCD4-Ig (FIG. 6II).

V146 in human CD4 D1D2 (SEQ ID NO:1) is an L or M in various new world monkeys and prosimians (FIG. 4C). V146 also is adjacent to a hydrophobic pocket in the structure of CD4 D2 bounded by L116, C130, V146, W157, and C159. Substitution of V146 with an L (a hydrophobic amino acid of larger volume than the amino acid that is replaced) in a G6A/S23N/A55V/V128L/V146L background increased the aggregation temperature of eCD4-Ig by 2.2° C. (FIG. 6JJ). However, substitution of V146 with an I (a hydrophobic amino acid of larger volume than the amino acid that is replaced) increased the aggregation temperature of eCD4-Ig with a G6A/S23N/A55V/V128L/V146L background by 7.6° C. (FIG. 6KK). Likewise, substitution of V146 with an F or a W (each a hydrophobic amino acid of larger volume than the amino acid that is replaced) increased the aggregation temperature of eCD4-Ig with a background of G6A/S23N/A55V/V128L/V146L by 3.6° C. and 4.1° C., respectively (FIGS. 6LL & MM). Without the intention of being bound by any particular theory, these results suggest that filling the hydrophobic pocket in the structure of CD4 D2 that is bounded by L116, C130, V146, W157, and C159 by substituting V146 with a hydrophobic amino acid of larger volume than the amino acid that is replaced (e.g., V146I, V146F, V146L, V146W, V146M, and V146P) can increase protein stability, as measured in thermal stability assays such as DLS.

N164 in human CD4 D1D2 (SEQ ID NO:1) is a D in the apes other than chimpanzees, bonobos, and gorillas, as well as in the old world monkeys and prosimians (FIG. 4C). This D is probably ancestral, whereas the N present in certain apes and the H present in new world monkeys are probably derived. The aggregation temperature of human eCD4-Ig with and without a N164D substitution was measured in combination with several other substitutions (R134G, R134G/K167T, and Q94E/Q110E/R134G/K142R/K167T) (FIG. 6NN). In each of these mutational backgrounds, N164D conferred improved conformational stability on eCD4-Ig. These results suggest that substitutions at position N164 in human CD4 D1D2 (SEQ ID NO:1), e.g., substitution by D (N164D), increase the aggregation temperature of proteins including CD4 D1D2, e.g., eCD4-Ig.

K167 in human CD4 D1D2 (SEQ ID NO: 1) is a T in all of the old world monkeys, except for the Colobuses, and in all of the prosimians. In the Colobuses, this position is an R, and in the new world monkeys it is a L. Mutating K167 in human eCD4-Ig, e.g., to T (K167T), improved conformational stability (FIG. 6OO). This improvement in conformational stability was observed in three different mutational backgrounds (R134G, Q94E/Q110E/R134G/K142R/N164D, and Q94E/Q110E/R134G/N164D). These results suggest that substitutions at position K167 in human CD4 D1D2 (SEQ ID NO:1), e.g., substitution by T (K167T), increase the aggregation temperature of proteins including CD4 D1D2, e.g., eCD4-Ig.

V168 in human CD4 D1D2 (SEQ ID NO:1) is an L in owl monkeys, which are new world primates, and in prosimians (FIG. 4C). Using a computational tool developed for visualizing and editing protein structures, the substitution V168L was modeled. Substitution of V168 with an L (a hydrophobic amino acid of larger volume than the amino acid that is replaced) increased the aggregation temperature of eCD4-Ig in a wild-type human CD4 D1D2 (SEQ ID NO:1) background by 0.8° C. (FIG. 6PP). Thus, substitutions at position V168, particularly with a hydrophobic amino acid of greater volume than V, increase the conformational stability and aggregation temperature of proteins including CD4 D1D2, e.g., eCD4-Ig.

V176 in human CD4 D1D2 (SEQ ID NO:1) was substituted with an I. In a wild-type human CD4 D1D2 (SEQ ID NO:1) background, V176I increased the aggregation temperature of eCD4-Ig by 9.2° C.

Figure 7:
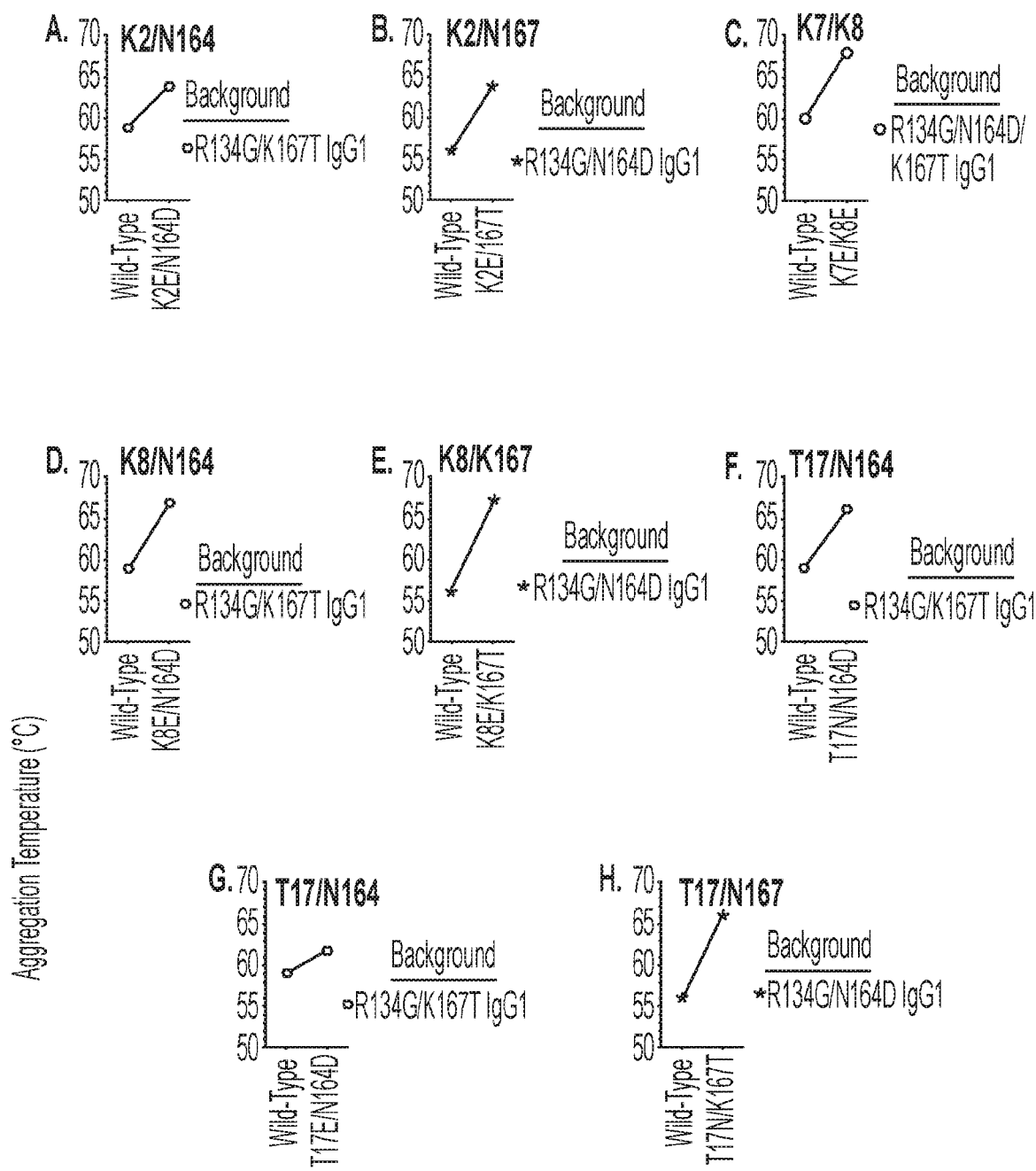
FIG. 7 is a series of graphs showing 50% aggregation temperatures of eCD4-Ig variants with the indicated combinations of substitutions. Using a DLS thermal scan assay, aggregation temperatures of eCD4-Ig with and without the indicated amino acid substitutions were measured. Background indicates the mutational background in which substitutions were tested (i.e., if the substitutions were evaluated in an eCD4-Ig variant with one or more additional substitutions present). Several of the substitutions were evaluated in more than one mutational background. Multiple substitutions are indicated as a list with each substitution separated by a backslash. The x-axis of each graph indicates if the eCD4-Ig variant had the indicated substitutions, or a wild-type amino acid residue at the substitution positions ("wild-type"). The isotype of the Fc domain in the eCD4-Ig protein (IgG1 or IgG2) is indicated. Black lines and black open or filled symbols indicate IgG1, whereas gray lines and gray open or filled symbols indicate IgG2.

The following combinations of substitutions increased aggregation temperature in the backgrounds tested: K2E/N164D (FIG. 7A); K2E/K167T (FIG. 7B); K7E/K8E (FIG. 7C); K8E/N164D (FIG. 7D); K8E/K167T (FIG. 7E); T17N/N164D (FIG. 7F); T17N/K167T (FIG. 7G); T17E/N164D (FIG. 7H); T17E/K167T (FIG. 7I); I70E/N164D (FIG. 7J); I70E/K167T (FIG. 7K); K72S/N164D (FIG. 7L); K72S/K167T (FIG. 7M); Q94E/Q110E (FIG. 7N); Q94E/N164D (FIG. 7P); Q94E/K167T (FIG. 7Q); Q110E/N164D (FIG. 7S); Q110E/K167T (FIG. 7T); R134G/N164D (FIG. 7V); R134G/K167T (FIG. 7W); K142R/N164D (FIG. 7X); K142E/K167T (FIG. 7Y); N164D/K167T (FIG. 7Z), and K166N/K167T (FIG. 7AA).

The following combinations of substitutions decreased aggregation temperature in the backgrounds tested: Q94/R134 (FIG. 7O), Q110/R134 (FIG. 7R), R134/K142 (FIG. 7U), and K142/N164 (FIG. 7X). Surprisingly, despite Q94E and Q110E not individually increasing aggregation temperatures, substituting the combination Q94/Q110 did generally increase aggregation temperatures (FIG. 7N).

Aggregation temperatures were also compared for proteins with and without combinations of three, four, or five positions substituted. The combinations of positions substituted included R134/N164/K167 (FIG. 7A), R134/K142/N164/K167 (FIG. 7B), T17/R134/N164/K167 (FIG. 7C), Q94/R134/N164/K167 (FIG. 7D), Q94/Q110/R134/N164/K167 (FIG. 7E), Q110/R134/N164/K167 (FIG. 7F), Q94/Q110/R134/K142/K167 (FIG. 7G), Q94/Q110/R134/N164 (FIG. 7H), Q94/Q110/K142/K167 (FIG. 7I), and K75/Q94/Q110 (FIG. 7J). All of these combinations of substitutions significantly improved conformational stability.

Figure 8:
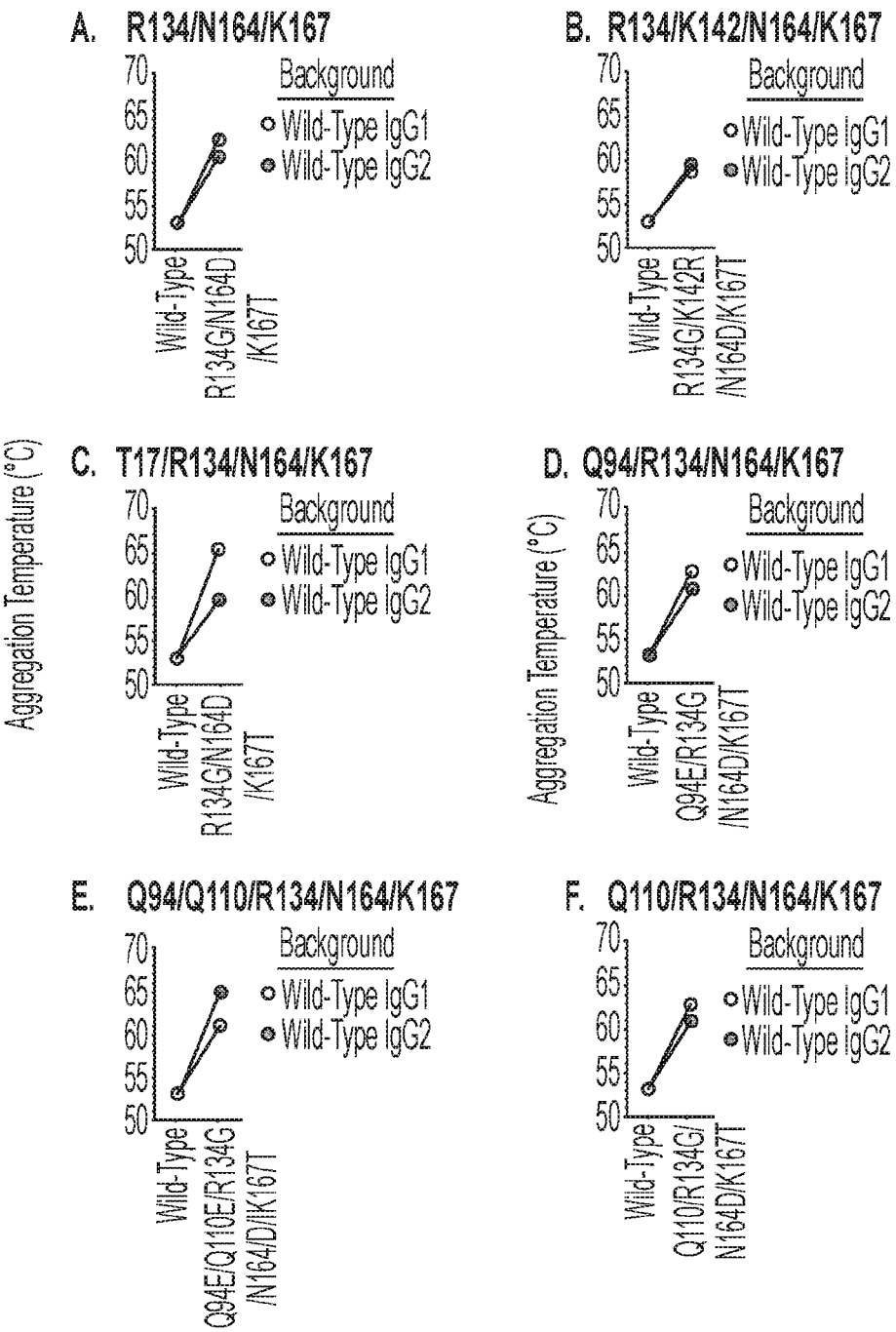
FIG. 8 is a series of graphs showing 50% aggregation temperatures of eCD4-Ig variants with the indicated combinations of more than two substitutions. Using a DLS thermal scan assay, aggregation temperatures of eCD4-Ig with and without the indicated amino acid substitutions were measured. Background indicates the mutational background in which substitutions were tested (i.e., if the substitutions were evaluated in an eCD4-Ig variant with one or more additional substitutions present). Several of the substitutions were evaluated in more than one mutational background. Multiple substitutions are indicated as a list with each substitution separated by a backslash. The x-axis of each graph indicates if the eCD4-Ig variant had the indicated substitutions, or a wild-type amino acid residue at the substitution positions ("wild-type"). The isotype of the Fc domain in the eCD4-Ig protein (IgG1 or IgG2) is indicated.

Substitutions at the three positions R134/N164/K167 in an otherwise wild-type human CD4 D1D2 (SEQ ID NO:1) background increased the aggregation temperature of eCD4-Ig by ten degrees, from 53° C. to 63° C. (FIG. 8A). Specifically, this eCD4-Ig variant contained the amino acid substitutions R134G/K164D/K167T. These results suggest that substitutions at positions R134, K164, and K167 in human CD4 D1D2 (SEQ ID NO:1), e.g., R134G, K164D, and K167T substitutions, increase the aggregation temperature of proteins including CD4 D1D2, e.g., eCD4-Ig. These results also show that the superior conformational stability of NHP CD4 D1D2 to human CD4 D1D2 can be reproduced with a minimal number of substitutions. Due to the improved conformational stability of eCD4-Ig variants containing R134G/K164D/K167T, a number of other substitutions were evaluated in this mutational background.

The amino acid substitutions and combinations thereof that improved the conformational stability of human CD4 D1D2 often resulted in a net loss in positive charge. For instance, K72S, R134G, and K167T each substitute a positively charged basic amino acid by an uncharged amino acid. T17E, I70E, Q94E, Q110E, and N164D each substitute an uncharged amino acid by a negatively charged acidic amino acid. Likewise, K2E, K7E, K8E, and K75E each substitute a positively charged basic amino acid by a negatively charged acidic amino acid. These results suggest that substitutions that lead to a net loss of positive charge or gain of negative charge increase the aggregation temperature of proteins including CD4 D1D2, e.g., eCD4-Ig.

Furthermore, it was observed that many of the amino acid substitutions that improved conformational stability did not disrupt salt bridges. Positions involved in potential salt bridges were identified by analyzing existing x-ray crystal structures of human CD4. The potential salt bridges (each salt bridge indicated by a hyphen) were: K1-E91, K2-E91, K7-D10, K8-E119, K29-K85, K50-E77, R54-D78, R58-E13, R59-D56, K72-D56, K89-E85, R131-E169, K136-D153, K167-E169, and K171-E169. Among the positions that differ in human versus NHP CD4 D1D2, those involved in potential salt bridges are: K1, K2, K50, D56, R58, R59, K72, E77, E91, R131, D153, K167, E169, and K171. Improved conformational stability was observed in CD4-derived polypeptides with substitutions at positions T17, A55, I70, K75, Q94, Q110, R134, and N164, none of which are involved in salt bridges. These results suggest that substitutions that improve conformational stability of proteins including CD4 D1D2, e.g., eCD4-Ig, are often not involved in salt bridges.

Figure 9:
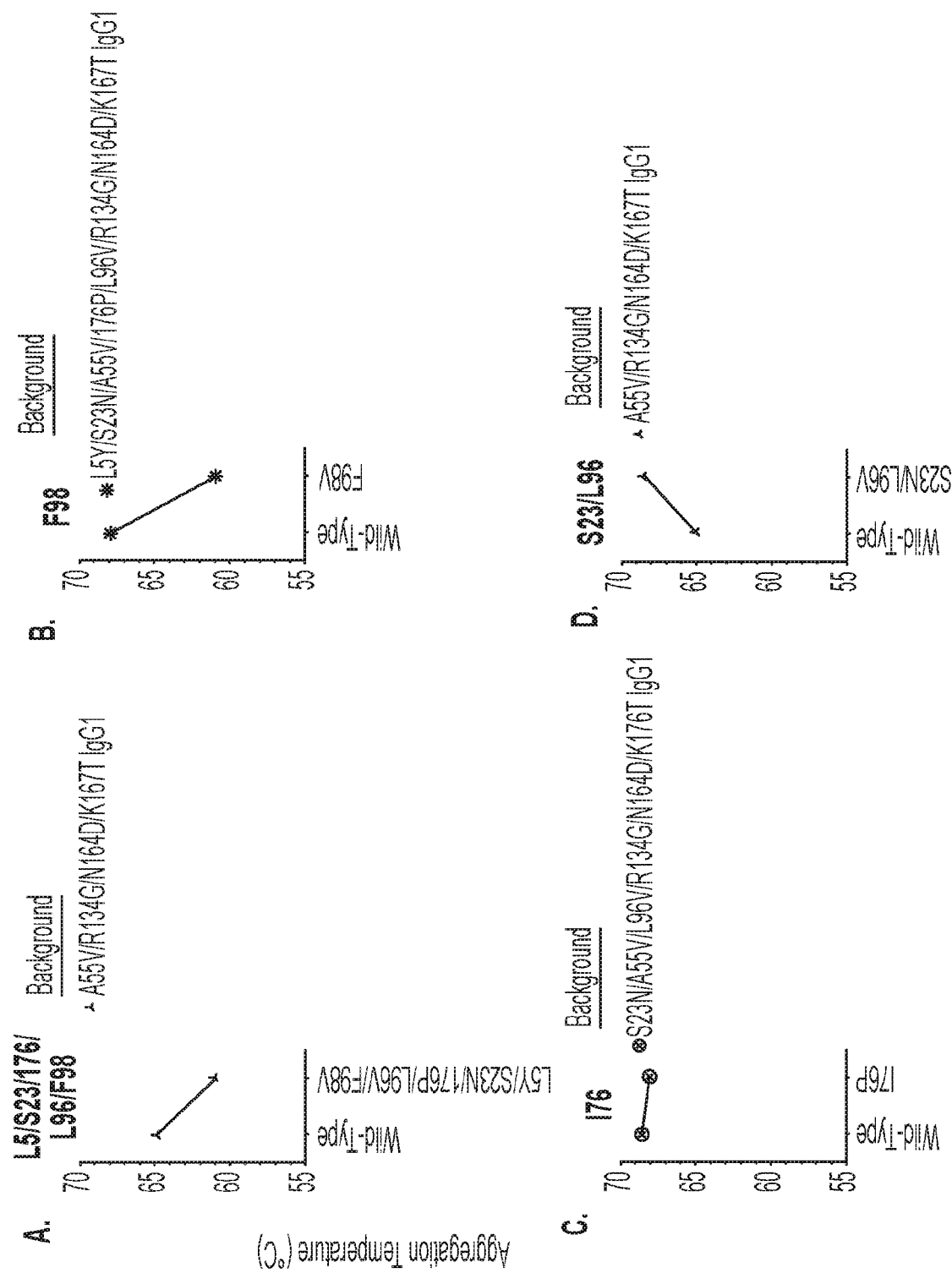
FIG. 9 is a series of graphs showing 50% aggregation temperatures of eCD4-Ig variants with the indicated substitutions. Using a DLS thermal scan assay, aggregation temperatures of eCD4-Ig with and without the indicated amino acid substitutions were measured. Background indicates the mutational background in which substitutions were tested (i.e., if the substitutions were evaluated in an eCD4-Ig variant with one or more additional substitutions present). Multiple substitutions are indicated as a list with each substitution separated by a backslash. The x-axis of each graph indicates if the eCD4-Ig variant had the indicated substitutions, or a wild-type amino acid residue at the substitution positions ("wild-type").

Combinations of substitutions including A55V were investigated further, in the context of mutant forms of eCD4-Ig containing substitutions at positions L5, I76, L96, and F98 (FIG. 9). It was found that substituting A55V together with all four of these other substitutions (L5Y, I76P, L96V, and F98V) decreased the conformational stability of eCD4-Ig (FIG. 9A). When evaluated individually, F98V led to a substantial loss of conformational stability (FIG. 9B). Without wishing to be bound by theory, it is possible that the F98V substitution destabilized the interface between domain 1 and domain 2. When the substitution I76P, which is also a position at the interface between domains 1 and domain 2, was reverted to wild-type, it was found that I76P is modestly detrimental to conformational stability in the context of CD4 D1D2 (FIG. 9C). Surprisingly, it was found that the presence of the pair of substitutions S23N/L96V significantly improved conformational stability (FIG. 9D). Thus, A55V and S23N improved conformational stability in the context of CD4 D1D2, whereas I76P and F98V were detrimental to conformational stability.

Figure 10:
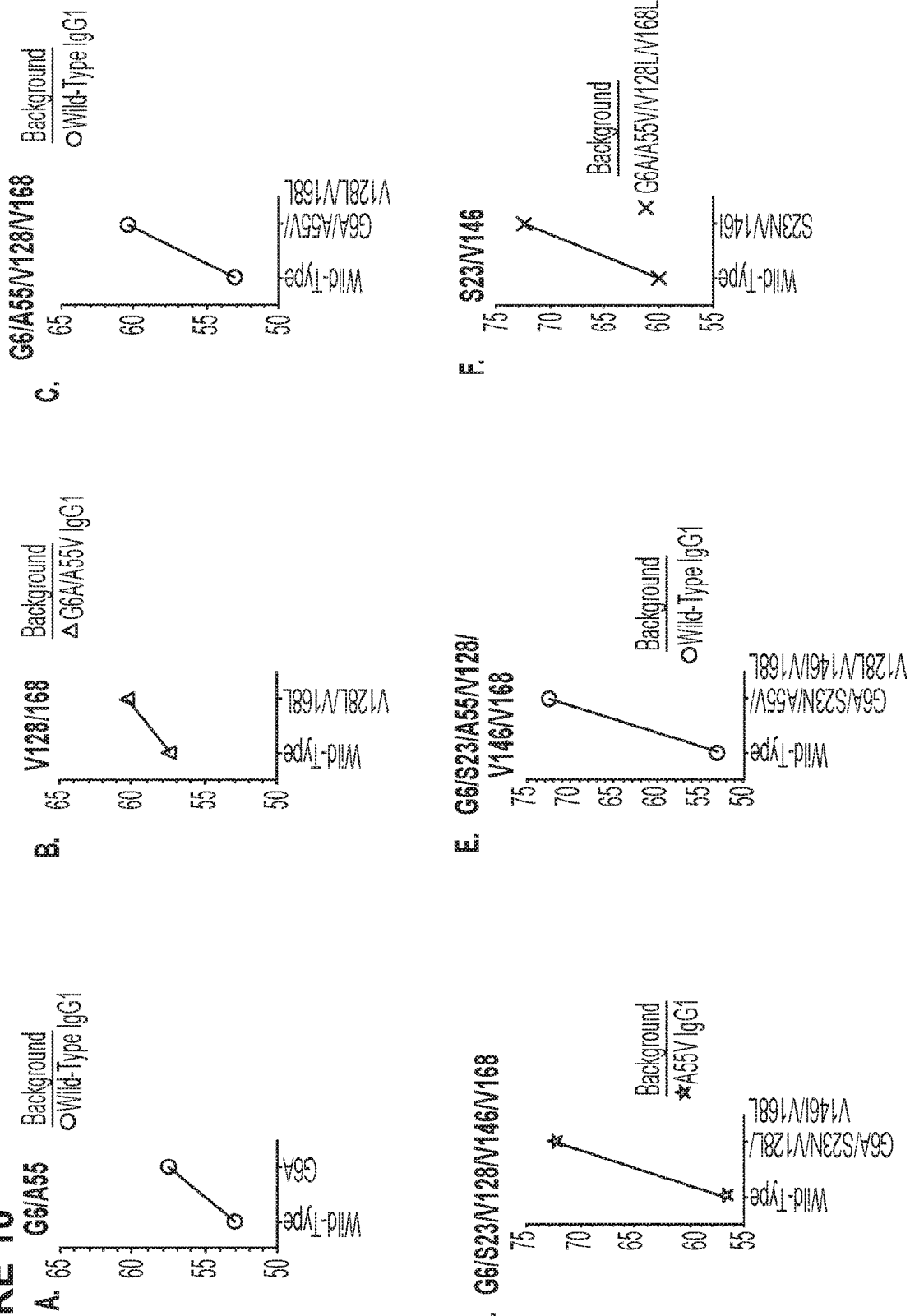
FIG. 10 is a series of graphs showing 50% aggregation temperatures of eCD4-Ig variants with the indicated combinations of substitutions. Using a DLS thermal scan assay, aggregation temperatures of eCD4-Ig with and without the indicated amino acid substitutions were measured. Background indicates the mutational background in which substitutions were tested (i.e., if the substitutions were evaluated in an eCD4-Ig variant with one or more additional substitutions present). Several of the substitutions were evaluated in more than one mutational background. Multiple substitutions are indicated as a list with each substitution separated by a backslash. The x-axis of each graph indicates if the eCD4-Ig variant had the indicated substitutions, or a wild-type amino acid residue at the substitution positions ("wild-type").

Substitutions that replace a glycine or buried hydrophobic amino acid with a different hydrophobic amino acid of larger volume than the amino acid that is replaced were combined, and the aggregation temperatures of the resulting eCD4-Ig proteins were measured (FIG. 10). For instance, combining G6A and A55V increased the aggregation temperature of eCD4-Ig with a wild-type human CD4 D1D2 (SEQ ID NO:1) background by 4.5° C. (FIG. 10A). Combining V128L and V128L increased the aggregation temperature of eCD4-Ig with a G6A/A55V background by 2.9° C. (FIG. 10B). Combining G6A, A55V, V128L, and V168L increased the aggregation temperature of eCD4-Ig with a wild-type human CD4 D1D2 (SEQ ID NO:1) background by 7.4° C. (FIG. 10C). Combining G6A, S23N, V128L, V146I, and V168L increased the aggregation temperature of eCD4-Ig with an A55V background by 15.7° C. (FIG. 10D). Combining G6A, S23N, A55V, V128L, V146I, and V168L increased the aggregation temperature of eCD4-Ig with a wild-type human CD4 D1D2 (SEQ ID NO:1) background by 19.4° C. (FIG. 10E). Combining S23N and V146I increased the aggregation temperature of eCD4-Ig with a G6A/A55V/V128L/V168L background by 7.4° C. (FIG. 10F). Combining S23N, V128L, and V168L increased the aggregation temperature of eCD4-Ig with a G6A/A55V background by 7.3° C. (FIG. 10G). Combining S23N, A55V, V128L, V146I, and V168L increased the aggregation temperature of eCD4-Ig with a G6A background by 14.8° C. (FIG. 10H). Combining S23N, V128L, V146I, and V128L increased the aggregation temperature of eCD4-Ig with a G6A/A55V background by 14.9° C. (FIG. 10I). Combining G6A, S23N, A55V, L116F, V128L, and V168L increased the aggregation temperature of eCD4-Ig with a wild-type human CD4 D1D2 (SEQ ID NO:1) background by 19° C. (FIG. 10J). Combining G6A, S23N, A55V, V128L, V146F and V168L increased the aggregation temperature of eCD4-Ig with a wild-type human CD4 D1D2 (SEQ ID NO:1) background by 15.4° C. (FIG. 10K). Combining G6A, S23N, A55V, V128L, V146W and V168L increased the aggregation temperature of eCD4-Ig with a wild-type human CD4 D1D2 (SEQ ID NO:1) background by 15.9° C. (FIG. 10L). Thus, combinations of substitutions that replaced a glycine or buried hydrophobic amino acid with a hydrophobic amino acid of larger volume than the amino acid that is replaced resulted in substantial increases in the aggregation temperature of a CD4 D1D2-containing protein, e.g., eCD4-Ig.

Figure 11:
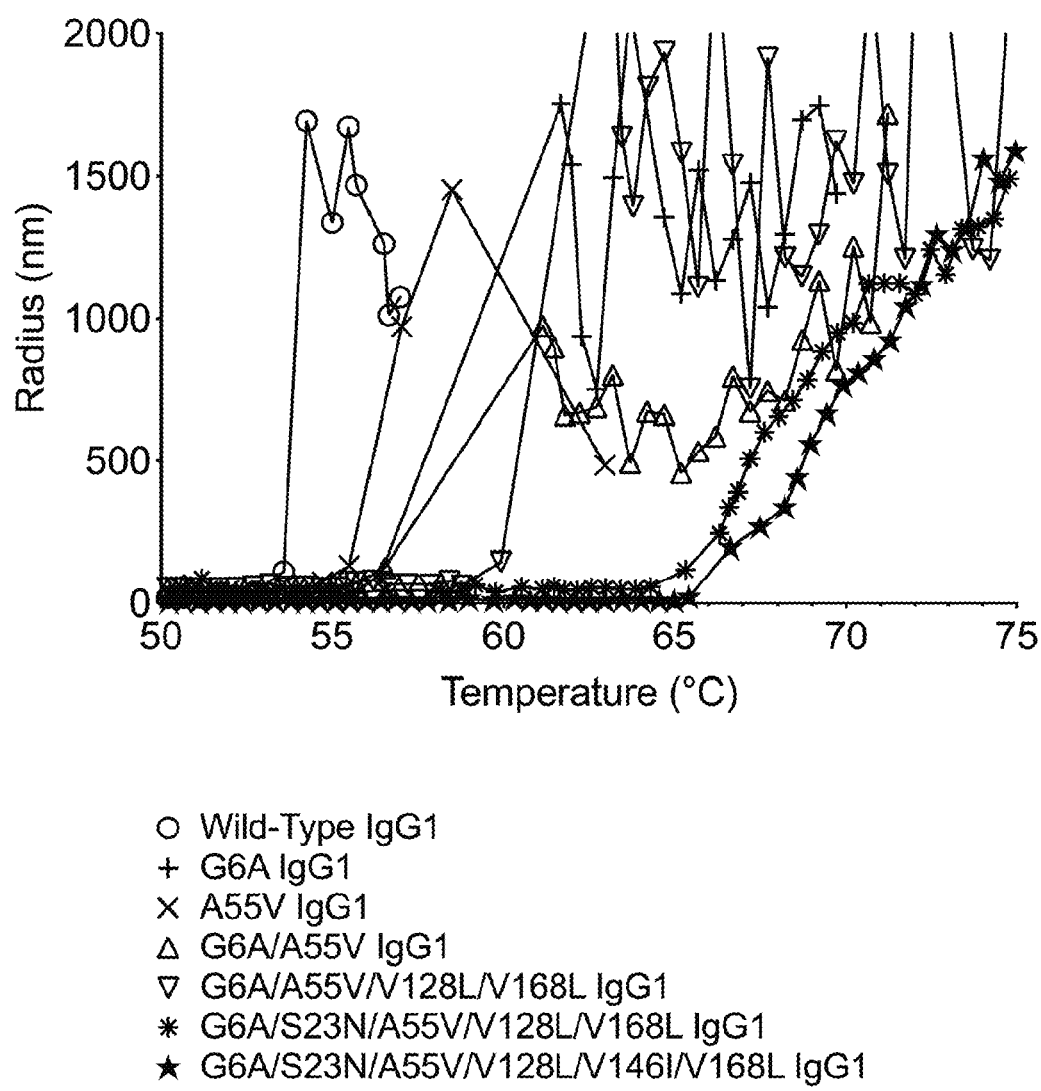
FIG. 11 is a line graph showing the primary data for the DLS thermal scan assay for eCD4-Ig variants with the indicated substitutions or combinations thereof. The y-axis shows the average radius of the material detected by DLS, as the assay scans temperatures along the x-axis (50 to 75° C. shown).

To further illustrate the increased aggregation temperatures conferred by substituting a glycine or buried hydrophobic amino acid with an amino acid of larger volume than the amino acid that is replaced, the primary thermal scan data from DLS assays is presented for certain examples (FIG. 11). In these examples, the addition of G6A, A55V, G6A/A55V, V128L/V168L, S23N, and V146I progressively improved the thermal stability of eCD4-Ig.

Figure 12:
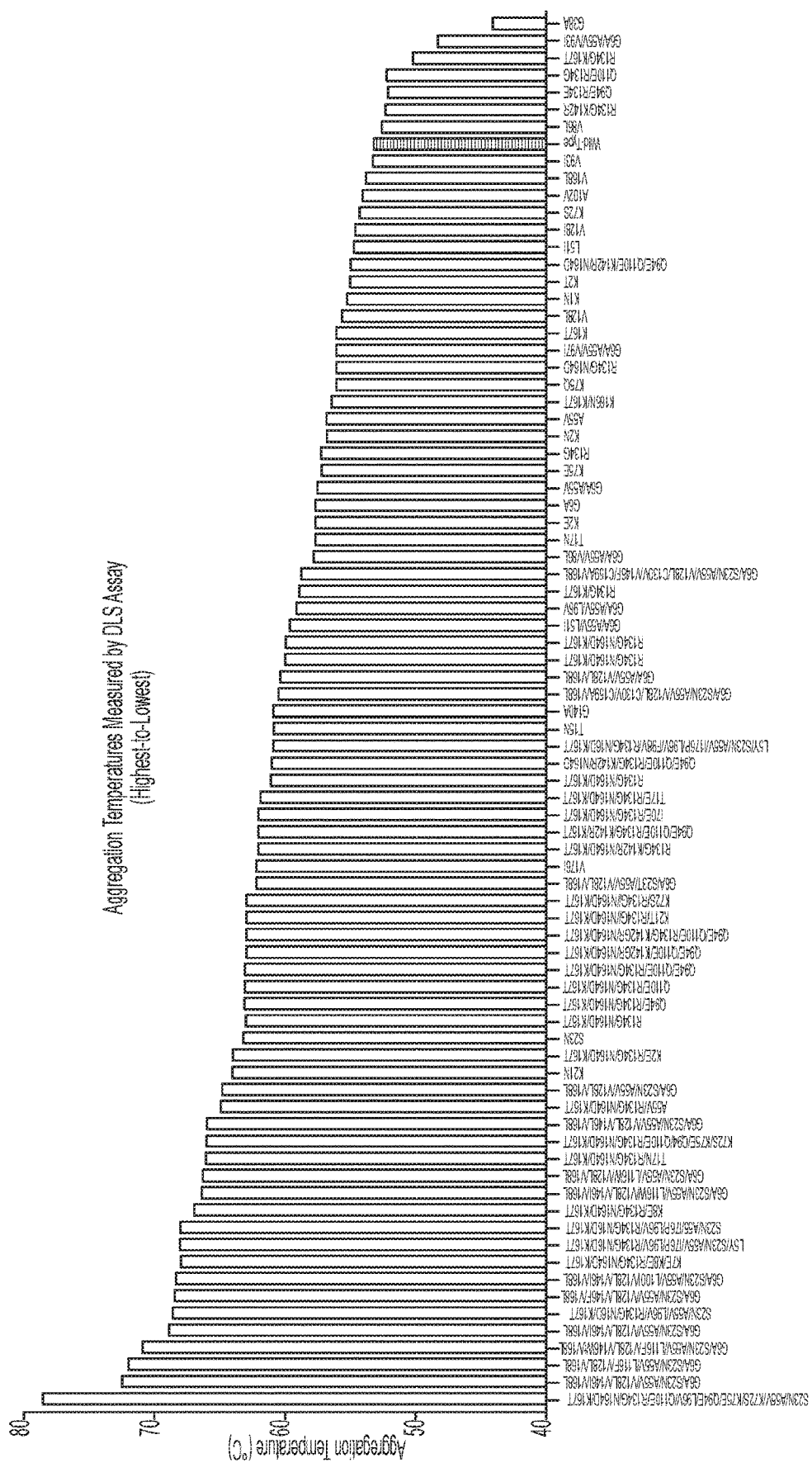
FIG. 12 is a bar graph showing the 50% aggregation temperatures of eCD4-Ig variants as measured by the DLS thermal scan assay with the indicated combinations of substitutions. The aggregation temperatures are ordered from highest to lowest. The control protein with the wild-type human CD4 D1D2 (SEQ ID NO:1) is shown in black, and the variants with substitutions are shown in gray. The data are presented for eCD4-Ig variants having the C220S substitution in the hinge, an IgG1 Fc domain, and either mim2 or mim6 as the sulfopeptide.

Aggregation temperatures for eCD4-Ig proteins measured by the DLS thermal scan assay described in this example are depicted in descending order, from highest-to-lowest temperatures (FIG. 12).

Thermal scan assay results for CD4-Ig and eCD4-Ig protein variants described in this Example are summarized in Table 5. All IgG1 Fc domains included the C220S substitution in the hinge region, except those marked with an * (standard IgG1 numbering).

TABLE 5

| Substitutions in human CD4 D1D2 (SEQ ID NO: 1) | Sulfopeptide | Aggregation temperature (° C.) IgG1 | IgG2 |
|---|---|---|---|
| None (wild-type) | none | 80.4* | |
| None (wild-type) | mim2 | 51* | |
| None (wild-type) | mim2 | 53 | 53 |
| None (wild-type) | mim6 | 53 | |
| K1N | mim6 | 55.3 | |
| K2T | mim6 | 55 | |
| K2N | mim6 | 56.7 | |
| K2E | mim6 | 57.6 | |
| G6A | mim6 | 57.6 | |
| T15N | mim6 | 60.9 | |
| T17N | mim6 | 57.7 | |
| K21N | mim6 | 64 | |
| S23N | mim6 | 63.1 | |
| G38A | mim6 | 44 | |
| L51I | mim6 | 54.8 | |
| A55V | mim2 | 56.7* | |
| A55V | mim6 | 56.7 | |
| K72S | mim6 | 54.3 | |
| K75E | mim6 | 57.1 | |
| K75Q | mim6 | 56 | |
| V86L | mim6 | 52.5 | |
| V93I | mim6 | 53.2 | |
| A102V | mim6 | 54.1 | |
| V128I | mim6 | 54.6 | |
| V128L | mim6 | 55.7 | |
| R134G | mim2 | 57.1 | |
| G140A | mim6 | 60.8 | |
| K167T | mim2 | 56 | |
| V168L | mim6 | 53.8 | |
| V176I | mim6 | 62.2 | |
| G6A/A55V | mim6 | 57.5 | |
| R134G/K142R | mim2 | 52 | |
| R134G/N164D | mim2 | 56 | |
| R134G/K167T | mim2 | 58.9 | 57 |
| R134G/K167T | mim4 | 50 | 56 |
| Q94E/R134E | mim2 | 52 | |
| Q110E/R134G | mim2 | 52 | |
| K166N/K167T | mim6 | 56.4 | |
| G6A/A55V/L51I | mim6 | 59.7 | |
| G6A/A55V/V86L | mim6 | 57.8 | |
| G6A/A55V/V93I | mim6 | 48.25 | |
| G6A/A55V/L96V | mim6 | 59.2 | |
| G6A/A55V/V97I | mim6 | 56 | |
| R134G/N164D/K167T | mim2 | 63 | 61 |
| R134G/N164D/K167T | mim4 | 61 | 57 |
| R134G/N164D/K167T | mim5 | 60 | 62 |
| R134G/N164D/K167T | none | 82.7 | |
| R134G/N164D/K167T | mim6 | 60 | 61 |
| T17N/R134G/N164D/K167T | mim2 | 66 | 60 |
| A55V/R134G/N164D/K167T | mim6 | 64.9 | |
| R134G/K142R/N164D/K167T | mim2 | 62 | 60 |
| Q94E/R134G/N164D/K167T | mim2 | 63 | 61 |
| Q110E/R134G/N164D/K167T | mim2 | 63 | 61 |
| Q94E/Q110E/K142R/N164D | mim2 | 55 | |
| Q94E/Q110E/R134G/N164D/K167T | mim2 | 63 | 65 |
| Q94E/Q110E/R134G/K142R/K167T | mim2 | 62 | |
| Q94E/Q110E/R134G/K142R/N164D | mim2 | 61 | |
| Q94E/Q110E/K142R/N164D/K167T | mim2 | 63 | |
| Q94E/Q110E/R134G/K142R/N164D/K167T | mim2 | 63 | 61.5 |
| K2E/R134G/N164D/K167T | mim6 | 63.9 | |
| K7E/K8E/R134G/N164D/K167T | mim6 | 68 | |
| K8E/R134G/N164D/K167T | mim6 | 67 | |
| T17E/R134G/N164D/K167T | mim6 | 61.8 | |
| K21T/R134G/N164D/K167T | mim6 | 63 | |
| I70E/R134G/N164D/K167T | mim6 | 62 | |
| K72S/R134G/N164D/K167T | mim6 | 63 | |
| K72S/K75E/Q94E/Q110E/R134G/N164D/K167T | none | 87.1 | |
| K72S/K75E/Q94E/Q110E/R134G/N164D/K167T | mim6 | 66 | |
| L5Y/S23N/A55V/I76P/L96V/F98V/R134G/N16D/K167T | mim6 | 61 | |
| L5Y/S23N/A55V/I76P/L96V/R134G/N16D/K167T | mim6 | 68 | |
| S23N/A55V/I76P/L96V/R134G/N16D/K167T | mim6 | 68 | |
| S23N/A55V/L96V/R134G/N16D/K167T | mim6 | 68.5 | |

TABLE 5-continued

| Substitutions in human CD4 D1D2 (SEQ ID NO: 1) | Sulfopeptide | Aggregation temperature (° C.) IgG1 | IgG2 |
|---|---|---|---|
| G6A/A55V/V128L/V168L | mim6 | 60.4 | |
| G6A/S23N/A55V/V128L/V168L | mim6 | 64.8 | |
| G6A/S23T/A55V/V128L/V168L | mim6 | 62.3 | |
| G6A/S23N/A55V/V128L/V146I/V168L | mim6 | 72.4 | |
| G6A/S23N/A55V/V128L/V146L/V168L | mim6 | 66 | |
| G6A/S23N/A55V/V128L/V146F/V168L | mim6 | 68.4 | |
| G6A/S23N/A55V/V128L/V146W/V168L | mim6 | 68.9 | |
| G6A/S23N/A55V/L116F/V128L/V168L | mim6 | 72 | |
| G6A/S23N/A55V/L116W/V128L/V168L | mim6 | 66.2 | |
| G6A/S23N/A55V/L116F/V128L/V146I/V168L | mim6 | 70.9 | |
| G6A/S23N/A55V/L116W/V128L/V146I/V168L | mim6 | 66.4 | |
| G6A/S23N/A55V/L100I/V128L/V146I/V168L | mim6 | 68.4 | |
| G6A/S23N/A55V/V128L/C130V/C159A/V168L | mim6 | 60.5 | |
| G6A/S23N/A55V/V128L/C130V/V146F/C159A/V168L | mim6 | 58.8 | |

Example 3—Identification of Amino Acid Substitutions that Improve the Stability of Human CD4 D1D2 Using Dye Intercalation Assays This Example describes the use of another type of thermal scan assay, based on dye intercalation, to identify substitutions and combinations thereof within CD4 muteins (e.g., CD4-Ig and eCD4-Ig) that increase its conformational stability. Similar to the DLS assay, as the temperature is gradually increased, conformational instability allows dyes to intercalate into the unfolding protein. The intercalated dyes fluoresce, and their light is detected as a quantitative measurement of the extent of protein unfolding or 'melting.' Thus, the data are reported as a 50% melting temperature. Two complementary types of dye intercalation assays were used, one based on SYPRO Orange intercalation, and the other a proprietary dye component of the Applied Biosystems Protein Thermal Shift Assay.

Figure 13:
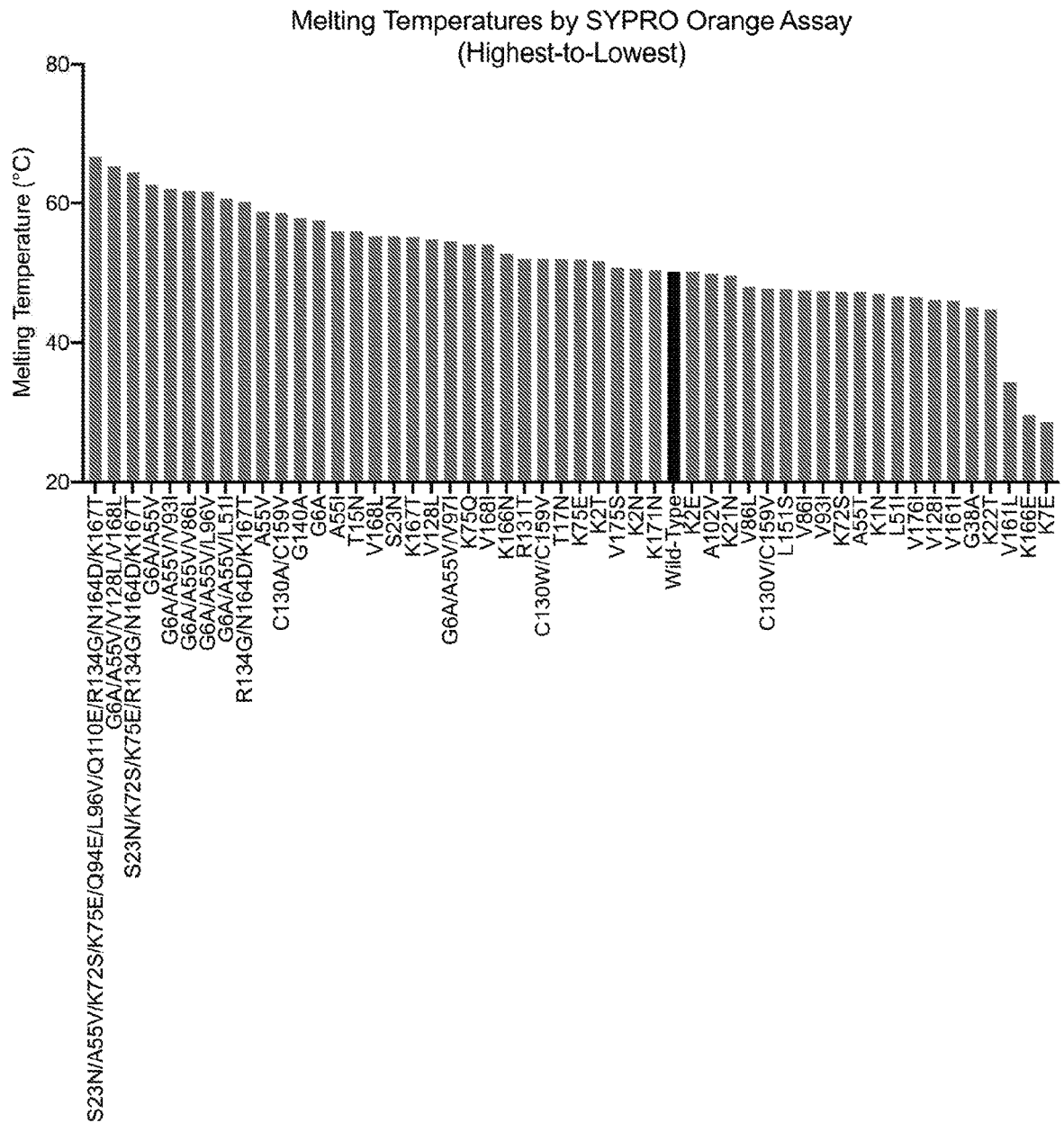
FIG. 13 is a bar graph showing the results of a SYPRO Orange dye intercalation assay. 50% melting temperatures of eCD4-Ig variants as measured by the assay are shown. The melting temperatures are ordered from highest to lowest. The control protein with the wild-type human CD4 D1D2 (SEQ ID NO:1) is shown in black, and the variants with substitutions are shown in gray. The data are presented for eCD4-Ig variants having the C220S substitution in the hinge, an IgG1 Fc domain, and either mim2 or mim6 as the sulfopeptide.
Figure 14:
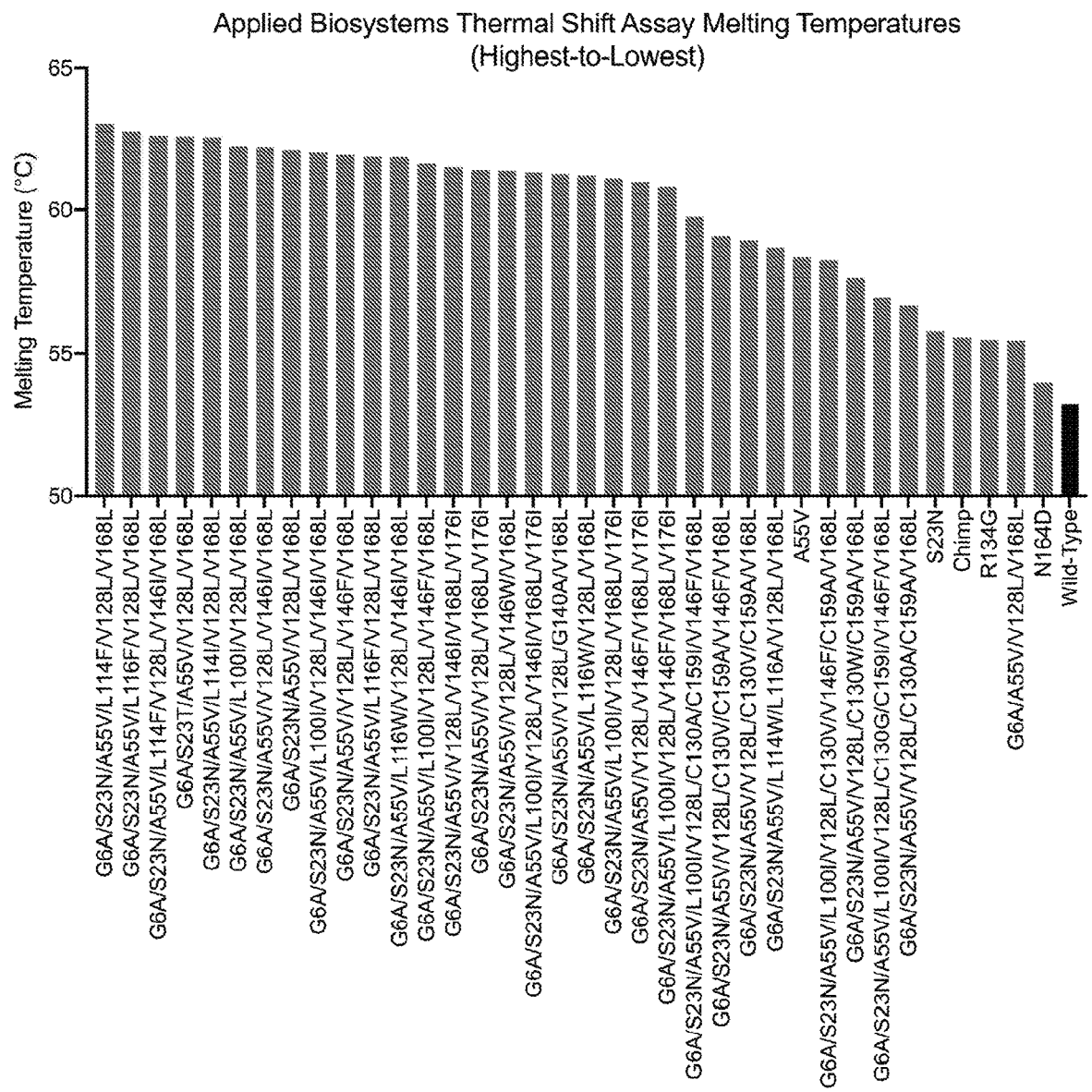
FIG. 14 is a bar graph showing the results of an Applied Biosystems Protein Thermal Shift dye intercalation assay. 50% melting temperatures of eCD4-Ig variants as measured by the assay are shown. The melting temperatures are ordered from highest to lowest. The control protein with the wild-type human CD4 D1D2 (SEQ ID NO:1) is shown in black, and the variants with substitutions are shown in gray. "Chimp" indicates an otherwise-identical eCD4-Ig protein with CD4 D1D2 sequences from chimpanzee CD4. The data are presented for eCD4-Ig variants having the C220S substitution in the hinge, an IgG1 Fc domain, and either mim2 or mim6 as the sulfopeptide.

First, a SYPRO Orange dye intercalation assay was used to identify substitutions and combinations thereof within eCD4-Ig that increase its conformational stability. The melting temperatures from this SYPRO Orange dye intercalation assay are shown (FIG. 13). These results are also listed in Table 6. All of the eCD4-Ig proteins reported here included the mim6 sulfopeptide, the C220S substitution in the hinge region, and an IgG1 Fc.

TABLE 6

| Substitutions in human CD4 D1D2 (SEQ ID NO: 1) | Sulfopeptide | Melting temperature (° C.) |
|---|---|---|
| S23N/A55V/K72S/K75E/Q94E/L96V/Q110E/R134G/N164D/K167T | mim6 | 66.6 |
| G6A/A55V/V128L/V168L | mim6 | 65.3 |
| S23N/K72S/K75E/R134G/N164D/K167T | mim6 | 64.5 |
| G6A/A55V | mim6 | 62.7 |
| G6A/A55V/V93I | mim6 | 62.0 |
| G6A/A55V/V86L | mim6 | 61.7 |
| G6A/A55V/L96V | mim6 | 61.6 |
| G6A/A55V/L51I | mim6 | 60.6 |
| R134G/N164D/K167T | mim6 | 60.1 |
| A55V | mim6 | 58.7 |
| C130A/C159V | mim6 | 58.5 |
| G140A | mim6 | 57.9 |
| G6A | mim6 | 57.6 |
| A55I | mim6 | 56.1 |
| T15N | mim6 | 56.0 |
| V168L | mim6 | 55.3 |
| S23N | mim6 | 55.3 |
| K167T | mim6 | 55.2 |
| V128L | mim6 | 54.7 |
| G6A/A55V/V97I | mim6 | 54.5 |
| K75Q | mim6 | 54.0 |
| V168I | mim6 | 54.0 |
| K166N | mim6 | 52.7 |
| R131T | mim6 | 51.9 |
| C130W/C159V | mim6 | 51.9 |
| T17N | mim6 | 51.8 |
| K75E | mim6 | 51.7 |
| K2T | mim6 | 51.6 |
| V175S | mim6 | 50.7 |
| K2N | mim6 | 50.5 |
| K171N | mim6 | 50.3 |
| Wild-Type | mim6 | 50.2 |
| K2E | mim6 | 50.2 |
| A102V | mim6 | 49.9 |
| K21N | mim6 | 49.7 |
| V86L | mim6 | 48.0 |
| C130V/C159V | mim6 | 47.8 |
| L151S | mim6 | 47.7 |
| V86I | mim6 | 47.4 |
| V93I | mim6 | 47.3 |
| K72S | mim6 | 47.3 |
| A55T | mim6 | 47.1 |
| K1N | mim6 | 46.9 |
| L51I | mim6 | 46.5 |
| V176I | mim6 | 46.5 |
| V128I | mim6 | 45.9 |
| V161I | mim6 | 45.9 |
| G38A | mim6 | 44.9 |
| K22T | mim6 | 44.6 |
| V161L | mim6 | 34.2 |
| K166E | mim6 | 29.5 |
| K7E | mim6 | 28.6 |

Several additional SYPRO Orange dye intercalation assays were performed to compare combinations of substitutions within eCD4-Ig that were of interest for their ability increase the conformational stability of the protein. eCD4-Ig proteins containing the substitutions R134G/N164D/K167T and K72S/K75E/Q94E/Q110E/R134G/N164D/K167T were compared against those containing wild-type human CD4 D1D2 (SEQ ID NO:1) or wild-type rhesus macaque CD4 D1D2 (FIG. 15A). This assay was repeated, now with R134G/N164D/K167T in the context of an IgG2 Fc (FIG. 15B). Next, eCD4-Ig proteins containing the substitutions R134G/N164D/K167T, K72S/K75E/Q94E/Q110E/R134G/N164D/K167T, and S23N/A55V/K72S/K75E/Q94E/L96V/Q110E/R134G/N164D/K167T were compared against the broadly neutralizing antibody 10-1074 and control eCD4-Ig proteins containing wild-type human CD4 D1D2 (SEQ ID NO:1) or wild-type rhesus macaque CD4 D1D2 (FIG. 15C). The eCD4-Ig proteins reported in FIG. 15A-C all included the mim6 sulfopeptide and the C220S substitution in the hinge region.

Two among the most conformationally-stable CD4 muteins were compared for thermal stability using the Applied Biosystems Protein Thermal Shift Assay. In this experiment, the CD4 muteins were CD4-Ig proteins lacking sulfopeptides. The combinations of substitutions compared were G6A/S23N/A55V/V128L/V168L (average melting temperature 68.5° C.) and S23N/A55V/K72S/K75E/Q94E/

L96V/Q110E/R134G/N164D/K167T V168L (average melting temperature 66.1° C.) (FIG. 15D). Both of these proteins were substantially more stable than CD4-Ig with a wild-type human CD4 D1D2 (SEQ ID NO:1) (average melting temperature 53.3° C.). Although the stabilization of G6A/S23N/ A55V/V128L/V168L relies upon substituting a glycine or buried hydrophobic amino acid with a hydrophobic amino acid of greater volume to a greater extent than S23N/A55V/ K72S/K75E/Q94E/L96V/Q110E/R134G/N164D/K167T V168L, these approaches for protein stabilization are complementary. Moreover, FIG. 15D shows that either set of substitutions substantially stabilize the CD4 mutein, regardless of the presence or absence of a sulfopeptide. Each of these proteins included the C220S substitution in the hinge region.

Thus, in this example, numerous substitutions within human CD4 D1D2 (SEQ ID NO:1) and combinations of substitutions that increase protein stability were identified, as measured using different dye intercalation assays.

Example 4—Identification of Amino Acid Substitutions that Improve the Expression of Human CD4 D1D2

This example describes the identification of substitutions in human CD4 D1D2 (SEQ ID NO:1) and combinations thereof that increase the expression of CD4 muteins, e.g., CD4-Ig and eCD4-Ig. High protein yield is a desirable property in at least three ways: First, the proportion of translated protein that folds properly and does not aggregate prior to secretion from the producer cell will be reflected in protein yields. Thus, measuring protein yield is an alternative approach for measuring proper protein folding and stability. Indeed, protein stability assays (e.g., DLS) are used to identify substitutions that increase protein expression. Second, the greater the yield of a recombinant protein therapeutic, the fewer resources needed to produce the same amount of protein, and the lower the production cost. Third, when the CD4 mutein is delivered by any gene therapy vector-mediated delivery system (e.g., AAV), higher protein yields would be expected to increase the concentrations of the CD4 mutein present in plasma, or decrease the amount of vector needed to achieve the same concentration of the CD4 mutein in plasma. Since high protein yield is a desirable property, the effects of different substitutions and combinations of substitutions on protein yield were assessed.

Figure 16:
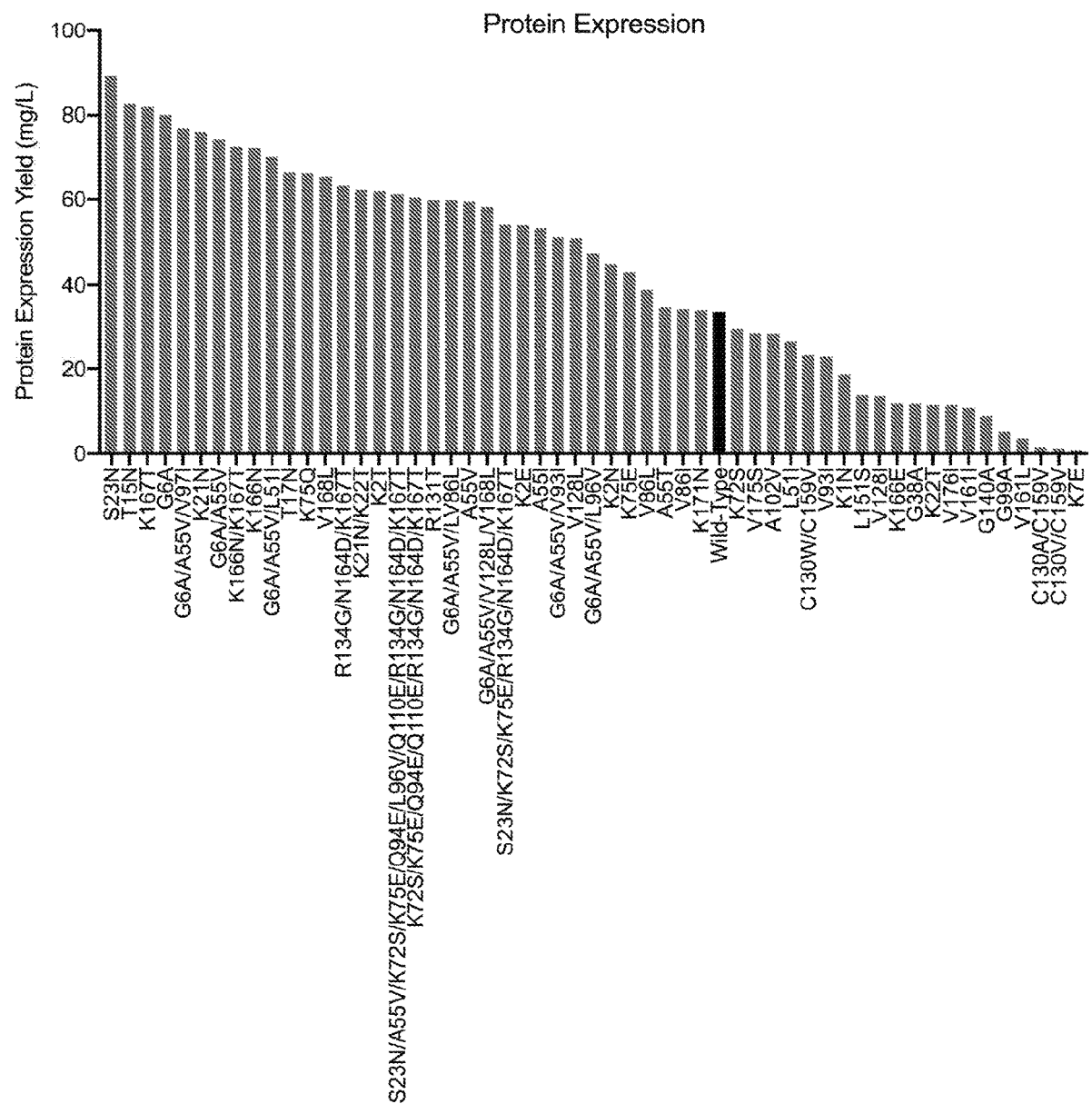
FIG. 16 is a bar graph showing the protein expression yield for different eCD4-Ig proteins. All of the variants shown in this figure include a mim6 sulfopeptide, the C220S substitution in the hinge, and an IgG1 Fc. An eCD4-Ig protein with a wild-type human CD4 D1D2 (SEQ ID NO:1) is shown in black, and all of the variants containing amino acid substitutions are shown in gray.

Various CD4 muteins containing individual substitutions and combinations of substitutions were expressed in Expi293 cells, and cumulative protein yields were compared against eCD4-Ig with a wild-type human CD4 D1D2 (SEQ ID NO:1) (FIG. 16). This analysis showed which substitutions, in general, increase protein yields. The amount of protein expressed in these yield experiments are stated in Table 7.

TABLE 7

| Substitutions in human CD4 D1D2 (SEQ ID NO: 1) | Sulfopeptide | Yield (mg/L) |
| --- | --- | --- |
| S23N | mim6 | 89.4 |
| T15N | mim6 | 82.4 |
| K167T | mim6 | 81.8 |
| G6A | mim6 | 80.1 |
| G6A/A55V/V97I | mim6 | 76.8 |
| K21N | mim6 | 76.0 |
| G6A/A55V | mim6 | 74.0 |

TABLE 7-continued

| Substitutions in human CD4 D1D2 (SEQ ID NO: 1) | Sulfopeptide | Yield (mg/L) |
| --- | --- | --- |
| K166N/K167T | mim6 | 72.5 |
| K166N | mim6 | 72.1 |
| G6A/A55V/L51I | mim6 | 70.0 |
| T17N | mim6 | 66.5 |
| K75Q | mim6 | 66.3 |
| V168L | mim6 | 65.6 |
| R134G/N164D/K167T | mim6 | 63.4 |
| K21N/K22T | mim6 | 62.2 |
| K2T | mim6 | 61.9 |
| S23N/A55V/K72S/K75E/Q94E/L96V/Q110E/R134G/N164D/K167T | mim6 | 61.2 |
| K72S/K75E/Q94E/Q110E/R134G/N164D/K167T | mim6 | 60.4 |
| R131T | mim6 | 59.8 |
| G6A/A55V/LV86L | mim6 | 59.8 |
| A55V | mim6 | 59.4 |
| G6A/A55V/V128L/V168L | mim6 | 58.2 |
| S23N/K72S/K75E/R134G/N164D/K167T | mim6 | 54.2 |
| K2E | mim6 | 54.1 |
| A55I | mim6 | 53.4 |
| G6A/A55V/V93I | mim6 | 51.2 |
| V128L | mim6 | 51.0 |
| G6A/A55V/L96V | mim6 | 47.2 |
| K2N | mim6 | 44.7 |
| K75E | mim6 | 42.9 |
| V86L | mim6 | 38.8 |
| A55T | mim6 | 34.6 |
| V86I | mim6 | 34.2 |
| K171N | mim6 | 34.0 |
| Wild-Type | mim6 | 33.6 |
| K72S | mim6 | 29.5 |
| V175S | mim6 | 28.6 |
| A102V | mim6 | 28.4 |
| L51I | mim6 | 26.6 |
| C130W/C159V | mim6 | 23.2 |
| V93I | mim6 | 22.8 |
| K1N | mim6 | 18.7 |
| L151S | mim6 | 13.8 |
| V128I | mim6 | 13.6 |
| K166E | mim6 | 11.8 |
| G38A | mim6 | 11.8 |
| K22T | mim6 | 11.4 |
| V176I | mim6 | 11.4 |
| V161I | mim6 | 10.8 |
| G140A | mim6 | 8.8 |
| G99A | mim6 | 5.2 |
| V161L | mim6 | 3.6 |
| C130A/C159V | mim6 | 1.4 |
| C130V/C159V | mim6 | 1.2 |
| K7E | mim6 | 0.7 |

Several controlled experiments were designed to specifically address the effects on protein expression of substituting a glycine or buried hydrophobic amino acid with a hydrophobic amino acid of larger volume than the amino acid that is replaced. Mutations at position S23 also were included, due to the substantial impact of mutations on this site on protein stability and yield. Based on the improvements described above for CD4-Ig and eCD4-Ig proteins containing S23N and the combination of G6A/A55V/V128L/ V168L as substitutions of a glycine or buried hydrophobic amino acid with a hydrophobic amino acid of larger volume than the amino acid that is replaced, both G6A/S23N/ A55V/V128L/V168L and wild-type human CD4 D1D2 (SEQ ID NO:1) were included as controls for these protein expression experiments (FIG. 17). Each panel (FIG. 17A-G) represents a separate protein expression experiment with the control proteins expressed in parallel. The following observations were noted: From greatest to least (i.e., where > means "is greater than"), the expression of eCD4-Ig proteins was G6A/S23N/A55V/V128L/V168L>G6A/A55V    >A55V >wild-type human CD4 D1D2 (FIG. 17A). L116W and L116F both improved the expression of eCD4-Ig containing G6A/S23N/A55V/V128L/V168L (FIG. 17B). Substitutions at position S23 other than S23N, e.g., S23T, also increased protein expression (FIGS. 17B & D). Replacement of the C130-C159 disulfide with C130V/C159A improved protein expression (FIG. 17C-D). Substitutions of V146 with a hydrophobic amino acid of larger volume (e.g., V146I, V146L, V146F, and V146W) generally increased protein expression (FIG. 17E-G). Likewise, substitution of L116 with a hydrophobic amino acid of greater volume (e.g., L116F and L116W) generally increased protein expression (FIGS. 17B, D, and G). However the combination of substitutions with a hydrophobic amino acid of larger volume than the amino acid that is replaced at both L116 and V146 tended to not further increase protein expression (FIG. 17G). Thus, combinations of substitutions that maximized protein expression, often 3-4-fold above the expression proteins based on wild-type human CD4 D1D2 (SEQ ID NO:1) sequences, included G6A/S23N/A55V/V128L/V146I/V168L, G6A/S23N/A55V/V128L/V146F/V168L, G6A/S23N/A55V/V128L/V146L/V168L, G6A/S23N/A55V/V128L/V146W/V168L, G6A/S23N/A55V/L116F/V128L/V168L, G6A/S23N/A55V/L116W/V128L/V168L, G6A/S23N/A55V/V128L/C130V/C159A/V168L, G6A/S23N/A55V/L110I/V128L/V168L, and G6A/S23N/A55V/V128L/V168L/V176I. It also was noted that G6A/S23N/A55V/V128L/V168L appeared to rescue the expression of muteins that were poorly expressed in the context of a wild-type human CD4 D1D2 (SEQ ID NO:1) background, e.g., G140A and V176I (FIG. 16) versus (FIGS. 17E & F). The protein expression yields shown in FIG. 17 are stated in Tables 8-15. Protein expression also was compared for CD4-Ig variants lacking a sulfopeptide with wild-type human CD4 D1D2 (SEQ ID NO:1), G6A/S23N/A55V/V128L/V168L, and S23N/A55V/K72S/K75E/Q94E/L96V/Q110E/R134G/N164D/K167T (FIG. 17H). The protein expression yields from FIG. 17H are stated in Table 15. This experiment showed that G6A/S23N/A55V/V128L/V168L expressed more efficiently than otherwise-identical CD4-Ig proteins containing either wild-type or S23N/A55V/K72S/K75E/Q94E/L96V/Q110E/R134G/N164D/K167T CD4 D1D2, and that the enhancement of expression by G6A/S23N/A55V/V128L/V168L was independent of the sulfopeptide. These results show that substituting a glycine or buried hydrophobic amino acid with a hydrophobic amino acid of larger volume than the amino acid that is replaced can increase protein expression, particularly at positions G6, A55, L116, V128, V146, V168, and V176 of human CD4 D1D2. Notably, the side chains of G6A, A55, L116, V128, V146, V168, and V176 are not surface-exposed. Thus, G6A/S23N/A55V/V128L/V168L has just one substitution at a position with a surface-exposed side chain (S23).

TABLE 8

| Substitutions in human CD4 D1D2 (SEQ ID NO: 1) | Sulfopeptide | Yield (mg/L) |
| --- | --- | --- |
| G6A/S23N/A55V/V128L/V168L | mim6 | 36.1 |
| G6A/A55V | mim6 | 27.3 |
| R134G | mim6 | 19.6 |
| N164D | mim6 | 19.0 |
| A55V | mim6 | 16.8 |
| Wild-Type | mim6 | 10.0 |

TABLE 9

| Substitutions in human CD4 D1D2 (SEQ ID NO: 1) | Sulfopeptide | Yield (mg/L) |
| --- | --- | --- |
| G6A/S23N/A55V/L116W/V128L/V168L | mim6 | 67.2 |
| G6A/S23N/A55V/F98W/V128L/V168L | mim6 | 64.5 |
| G6A/S23N/A55V/L116F/V128L/V168L | mim6 | 63.3 |
| G6A/S23T/A55V/V128L/V168L | mim6 | 36.2 |
| G6A/S23N/A55V/V128L/V168L | mim6 | 33.5 |
| G6A/S23N/A55V/L114F/V128L/V168L | mim6 | 29.5 |
| G6A/S23N/A55V/L114I/V128L/V168L | mim6 | 20.4 |
| Wild-Type | mim6 | 15.2 |

TABLE 10

| Substitutions in human CD4 D1D2 (SEQ ID NO: 1) | Sulfopeptide | Yield (mg/L) |
| --- | --- | --- |
| G6A/S23N/A55V/V128L/C130V/V146F/C159A/V168L | mim6 | 99.7 |
| G6A/S23N/A55V/L100I/V128L/C130V/V146F/C159A/V168L | mim6 | 91.1 |
| Chimp CD4 | mim6 | 69.9 |
| G6A/S23N/A55V/V128L/V168L | mim6 | 64.0 |
| G6A/S23N/A55V/V128L/C130A/V146F/C159I/V168L | mim6 | 52.8 |
| G6A/S23N/A55V/V128L/C130G/V146F/C159I/V168L | mim6 | 44.1 |
| Wild-Type | mim6 | 25.4 |
| G6A/S23N/A55V/L116C/V128L/C130A/V146F/V168L | mim6 | 1.9 |
| G6A/S23N/A55V/L116C/V128L/C130A/V168L | mim6 | 1.0 |

TABLE 11

| Substitutions in human CD4 D1D2 (SEQ ID NO: 1) | Sulfopeptide | Yield (mg/L) |
| --- | --- | --- |
| G6A/S23N/A55V/V128L/V146I/V168L | mim6 | 60.5 |
| G6A/S23N/A55V/L116F/V128L/V168L | mim6 | 54.3 |
| G6A/S23N/A55V/V128L/C130W/C159A/V168L | mim6 | 52.2 |
| G6A/S23T/A55V/V128L/V168L | mim6 | 47.7 |
| G6A/S23N/A55V/V128L/C130V/C159A/V168L | mim6 | 45.0 |
| G6A/S23N/A55V/V128L/C130A/C159A/V168L | mim6 | 41.2 |
| G6A/S23N/A55V/V128L/V168L | mim6 | 22.0 |
| Wild-Type | mim6 | 15.9 |

TABLE 12

| Substitutions in human CD4 D1D2 (SEQ ID NO: 1) | Sulfopeptide | Yield (mg/L) |
| --- | --- | --- |
| G6A/S23N/A55V/V128L/V146I/V168L/V176I | mim6 | 34.7 |
| G6A/S23N/A55V/L100I/V128L/V146I/V168L | mim6 | 34.6 |
| G6A/S23N/A55V/L100I/V128L/V146F/V168L | mim6 | 31.9 |
| G6A/S23N/A55V/V128L/V168L | mim6 | 31.7 |
| G6A/S23N/A55V/L100I/V128L/V146I/V168L/V176I | mim6 | 28.4 |
| G6A/S23N/A55V/L114W/L116A/V128L/V168L | mim6 | 27.7 |
| G6A/S23N/A55V/L100I/V128L/V168L/V176I | mim6 | 27.7 |
| G6A/S23N/A55V/L100I/V128L/V146F/V168L/V176I | mim6 | 27.1 |
| G6A/S23N/A55V/V128L/V146F/V168L/V176I | mim6 | 25.5 |
| Wild-Type | mim6 | 12.3 |

TABLE 13

| Substitutions in human CD4 D1D2 (SEQ ID NO: 1) | Sulfopeptide | Yield (mg/L) |
|---|---|---|
| G6A/S23N/A55V/V128L/V146I/V168L | mim6 | 18.8 |
| G6A/S23N/A55V/V128L/G140A/V168L | mim6 | 17.1 |
| G6A/S23N/A55V/V128L/V146L/V168L | mim6 | 17.0 |
| G6A/S23N/A55V/V128L/V146W/V168L | mim6 | 16.9 |
| G6A/S23N/A55V/L110I/V128L/V168L | mim6 | 16.9 |
| G6A/S23N/A55V/V128L/V168L/V176I | mim6 | 15.0 |
| G6A/S23N/A55V/V128L/V168L | mim6 | 12.4 |
| S23N | mim6 | 8.3 |
| Wild-Type | mim6 | 5.7 |

TABLE 14

| Substitutions in human CD4 D1D2 (SEQ ID NO: 1) | Sulfopeptide | Yield (mg/L) |
|---|---|---|
| G6A/S23N/A55V/V128L/V146I/V168L | mim6 | 48.4 |
| G6A/S23N/A55V/L116F/V128L/V168L | mim6 | 40.9 |
| G6A/S23N/A55V/V128L/V146F/V168L | mim6 | 38.4 |
| G6A/S23N/A55V/L116W/V128L/V146I/V168L | mim6 | 38.4 |
| G6A/S23N/A55V/L116F/V128L/V146I/V168L | mim6 | 34.9 |
| G6A/S23N/A55V/V128L/V168L | mim6 | 31.3 |
| Wild-Type | mim6 | 11.6 |

TABLE 15

| Substitutions in human CD4 D1D2 (SEQ ID NO: 1) | Sulfopeptide | Yield (mg/L) |
|---|---|---|
| G6A/S23N/A55V/V128L/V168L | None | 186.1 |
| S23N/A55V/K72S/K75E/Q94E/L96V/Q110E/R134G/N164D/K167T | None | 125.6 |
| Wild-Type | None | 95.0 |

Example 5—Pharmacokinetics of CD4 D1D2 Variants in Human FcRn Transgenic Mice This Example describes the pharmacokinetics in human FcRn transgenic, immunodeficient mice of proteins including CD4 D1D2 variants with improved stability identified in Examples 2-4. In vivo pharmacokinetics (pk) of wild-type human CD4-Ig or variants of human CD4-Ig or eCD4-Ig were measured after intravenous administration in human FcRn transgenic mice.

In a first experiment in human FcRn transgenic mice, the half-life of wild-type human CD4-Ig was 2.4 days, whereas variants of CD4-Ig with substitutions at the positions R134/N164/K167 or K72/K75/Q94/Q110/R134/N164/K16 had half-lives of 4.2 days or 8.6 days, respectively (FIG. 18A). Therefore, substitutions that increased the aggregation temperature of CD4 D1D2 proteins significantly increased half-life in vivo. The half-life of R134/N164/K167 eCD4-Ig was also measured to be 5.5 days (FIG. 18B). Furthermore, the half-lives of eCD4-Ig with substitutions at positions K72/K75/Q94/Q110/R134/N164/K167 and Q94/Q110/R134/N164/K167 were 9.0 and 3.7 days, respectively (FIG. 18C). These results suggest that substitutions which improved the conformational stability of eCD4-Ig in the DLS and dye intercalation thermal scan assays improve the pharmacokinetics of the protein.

Figure 19:
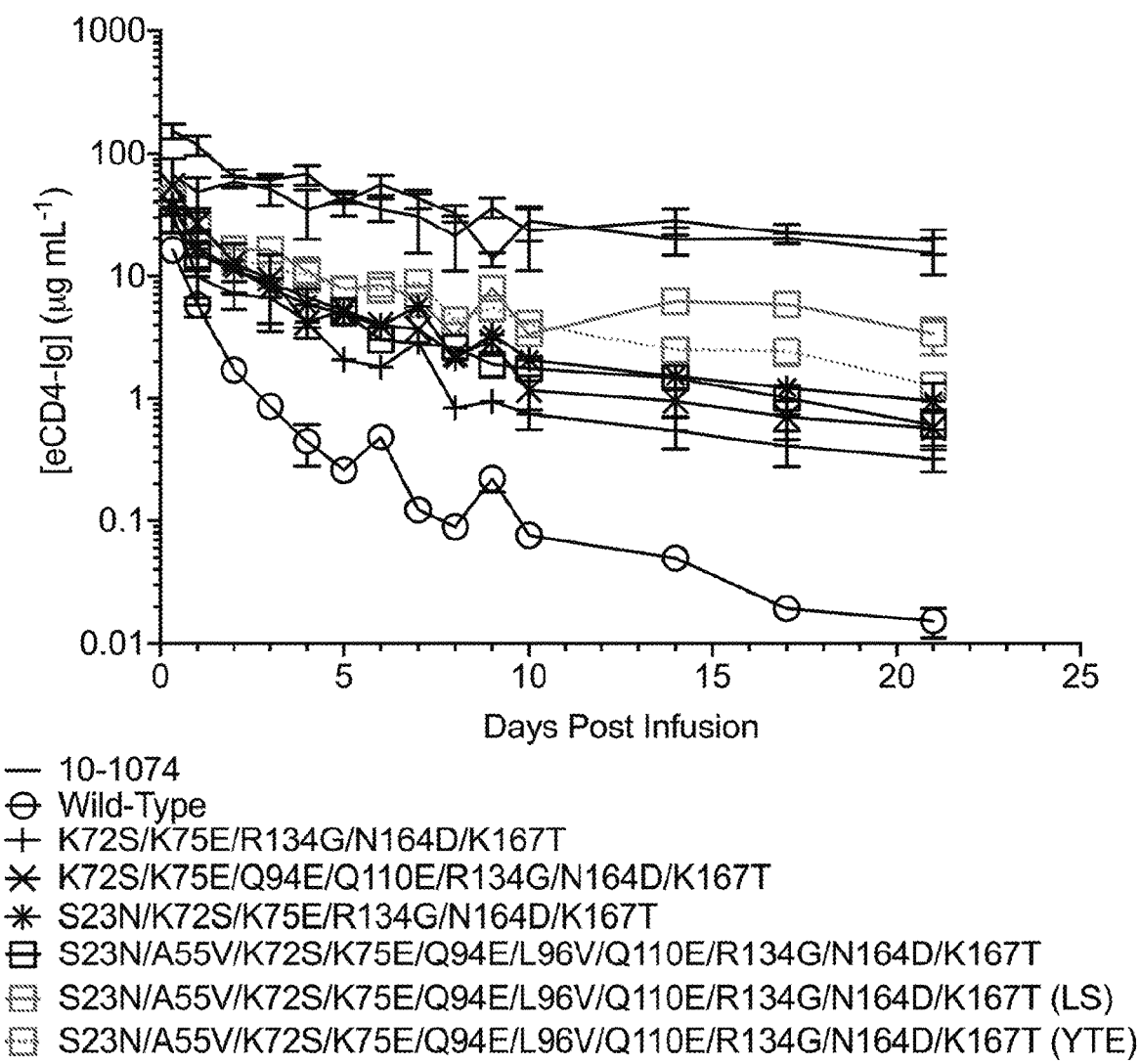
FIG. 19 is a line graph showing the pharmacokinetics in human FcRn transgenic mice of eCD4-Ig with a wild-type human CD4 D1D2 (SEQ ID NO:1) or the indicated substitutions that improve conformational stability or FcRn binding. The broadly neutralizing monoclonal antibody 10-1074 was used as a control in two groups of human FcRn transgenic mice, and each of these two control groups are shown as separate lines. In addition to the wild-type human CD4 D1D2 control, the eCD4-Ig variants evaluated in this pharmacokinetics experiment contained the following combinations of amino acid substitutions: K72S/K75E/R134G/N164D/K167T, K72S/K75E/Q94E/Q110E/R134G/N164D/K167T, S23N/K72S/K75E/R134G/N164D/K167T, and S23N/A55V/K72S/K75E/Q94E/L96V/Q110E/R134G/N164D/K167T. In addition, eCD4-Ig variants with the substitutions S23N/A55V/K72S/K75E/Q94E/L96V/Q110E/R134G/N164D/K167T in CD4 D1D2 were evaluated in the context of an IgG1 Fc containing S254T, and T256E ("YTE"), or M428L and N434S ("LS").

In a second experiment in human FcRn transgenic mice, the pharmacokinetics of eCD4-Ig variants containing additional combinations of mutations were compared (FIG. 19). In this experiment, a control broadly neutralizing antibody known to have a long half-life, 10-1074, was used as a control. 10-1074 (with an IgG1 Fc) had a half-life of 11.6 days. The half-lives for eCD4-Ig variants with a wild-type human IgG1 Fc and the following amino acid substitutions were: 3.5 days for wild-type human CD4 D1D2 (SEQ ID NO:1), 4.6 days for K72S/K75E/R134G/N164D/K167T, 6.1 days for K72S/K75E/Q94E/Q110E/R134G/N164D/K167T, 6.3 days for S23N/A55V/K72S/K75E/Q94E/Q110E/R134G/N164D/K167T, and 6.9 days for S23N/A55V/K72S/K75E/R134G/N164D/K167T (FIG. 19, Table 16). Thus, the half-life of eCD4-Ig was extended by up to two-fold. Additionally, the half-lives of eCD4-Ig proteins containing the Fc domain substitutions M252Y, S254T, and T256E ("YTE"), or M428L and N434S ("LS"), were compared against the half-life of an otherwise-identical variant with a wild-type human IgG1 Fc, in the context of the S23N/A55V/K72S/K75E/Q94E/Q110E/R134G/N164D/K167T substitutions in CD4 D1D2. The eCD4-Ig variant containing the M252Y, S254T, and T256E substitutions in the Fc domain did not appear to substantially change the half-life of eCD4-Ig (6.3 days without the M252Y, S254T, and T256E substitutions, versus 6.0 days with the substitutions) (Table 16). However, the M428L and N434S substitutions in the Fc domain did substantially lengthen the half-life of this eCD4-Ig variant, from 6.3 days without the M428L and N434S substitutions to 10.2 days with the substitutions—a 62% increase (FIG. 19). In comparison to the eCD4-Ig protein with a wild-type human CD4 D1D2 (SEQ ID NO:1) and wild-type human IgG1 Fc domain, the S23N/A55V/K72S/K75E/Q94E/Q110E/R134G/N164D/K167T substitutions in CD4 D1D2 and the M428L and N434S substitutions in the Fc domain increased its half-life from 3.5 days to 10.2 days, or nearly 3-fold.

TABLE 16

| Substitutions in human CD4 D1D2 (SEQ ID NO: 1) | Fc domain (all IgG1) | Average Half-Life (Days) |
|---|---|---|
| Wild-Type | Wild-Type | 3.5 |
| K72S/K75E/R134G/N164D/K167T | Wild-Type | 4.6 |
| K72S/K75E/Q94E/Q110E/R134G/N164D/K167T | Wild-Type | 6.1 |
| S23N/A55V/K72S/K75E/Q94E/Q110E/R134G/N164D/K167T | Wild-Type | 6.3 |
| S23N/A55V/K72S/K75E/R134G/N164D/K167T | Wild-Type | 6.9 |
| S23N/A55V/K72S/K75E/Q94E/Q110E/R134G/N164D/K167T | YTE | 6.0 |
| S23N/A55V/K72S/K75E/Q94E/Q110E/R134G/N164D/K167T | LS | 10.2 |

Example 6—Pharmacokinetics of CD4 D1D2 Variants in Wild-Type Mice

This Example describes the pharmacokinetics of eCD4-Ig proteins with substitutions in CD4 D1D2 in wild-type BALB/cJ mice.

The first goal of this experiment was to determine whether eCD4-Ig variants that are stabilized by substituting a glycine or buried hydrophobic amino acid with a hydrophobic amino acid of larger volume than the amino acid that is replaced generated eCD4-Ig variants that exhibited similar half-lives to eCD4-Ig variants that were stabilized largely by a combination of substitutions that increase its acidity. The control protein tested in this example had a CD4 D1D2 sequence with the following substitutions: S23N/A55V/K72S/K75E/Q94E/Q110E/R134G/N164D/K167T. The pharmacokinetics of this variant, which was largely stabilized through surface changes, was compared to the pharmacokinetics of a variant with the substitutions G6A/S23N/A55V/V128L/V168L (FIG. 20A). Other than S23N, G6A/S23N/A55V/V128L/V168L includes only internal substitutions in the hydrophobic core of the protein.

The second goal of this experiment was to determine whether combining (i) substitutions that render the CD4 mutein more acidic, plus (ii) internal substitutions of a glycine or buried hydrophobic amino acid with a hydrophobic amino acid of larger volume than the amino acid that is replaced, affects the pharmacokinetics of CD4 muteins. To assess the impact on pharmacokinetics of adding surface charge substitutions to this largely internally stabilized variant, eCD4-Ig variants were included in this experiment containing the following combinations of substitutions in CD4 D1D2: G6A/S23N/A55V/V128L/R134G/V168L, G6A/S23N/A55V/V128L/K167T/V168L, and G6A/S23N/A55V/V128L/R134G/N164D/K167T/V168L (FIG. 20A). Half-lives were calculated for the period between days 1 and 5, since mouse antibody responses against these eCD4-Ig proteins were observed in some but not all of these wild-type (i.e., non-immunodeficient) BALB/cJ mice on day 8. The average half-lives are listed in Table 17. This experiment showed that all of the variants that were largely stabilized by the substitution of glycine or a buried hydrophobic amino acid with a hydrophobic amino acid of larger volume than the amino acid that is replaced exhibited at least as long a half-life as the variant containing the substitutions S23N/A55V/K72S/K75E/Q94E/Q110E/R134G/N164D/K167T, which largely render the protein more acidic (FIG. 20B). One of these variants, G6A/S23N/A55V/V128L/R134G/V168L, exhibited a significantly longer half-life than the control variant with the substitutions S23N/A55V/K72S/K75E/Q94E/Q110E/R134G/N164D/K167T (P=0.03, 2-tailed parametric t test). Moreover, this example (e.g., G6A/S23N/A55V/V128L/R134G/V168L versus G6A/S23N/A55V/V128L/V168L) demonstrates that substitutions of a basic amino acid in wild-type human CD4 D1D2 (SEQ ID NO: 1) with an acidic amino acid can be combined with substitutions of a glycine or buried hydrophobic amino acid with a hydrophobic amino acid of larger volume than the amino acid that is replaced to increase the half-life of CD4 muteins in vivo, e.g., eCD4-Ig. In summary, this example shows that CD4 muteins, e.g., eCD4-Ig, containing substitutions of a glycine or buried hydrophobic amino acid with a hydrophobic amino acid of larger volume than the amino acid that is replaced can increase the half-life of the protein in vivo to an extent that is at least great as the other combinations of substitutions characterized herein.

TABLE 17

| Substitutions in human CD4 D1D2 (SEQ ID NO: 1) | Average Half-Life (Days) |
|---|---|
| S23N/A55V/K72S/K75E/Q94E/Q110E/R134G/N164D/K167T | 5.1 |
| G6A/S23N/A55V/V128L/V168L | 6.8 |
| G6A/S23N/A55V/V128L/R134G/V168L | 8.4 |
| G6A/S23N/A55V/V128L/K167T/V168L | 5.8 |
| G6A/S23N/A55V/V128L/R134G/N164D/K167T/V168L | 6.3 |

Example 7—Pharmacokinetics of CD4 D1D2 Variants in Rats

This Example describes the pharmacokinetics in rats of proteins including CD4 D1D2 variants with improved stability identified in Example 2. In vivo pharmacokinetics (pk) of wild-type human CD4-Ig and human eCD4-Ig variants with the substitutions R134G/N164D/K167T were measured after subcutaneous administration of 10 mg/kg protein in rats.

Figure 21:
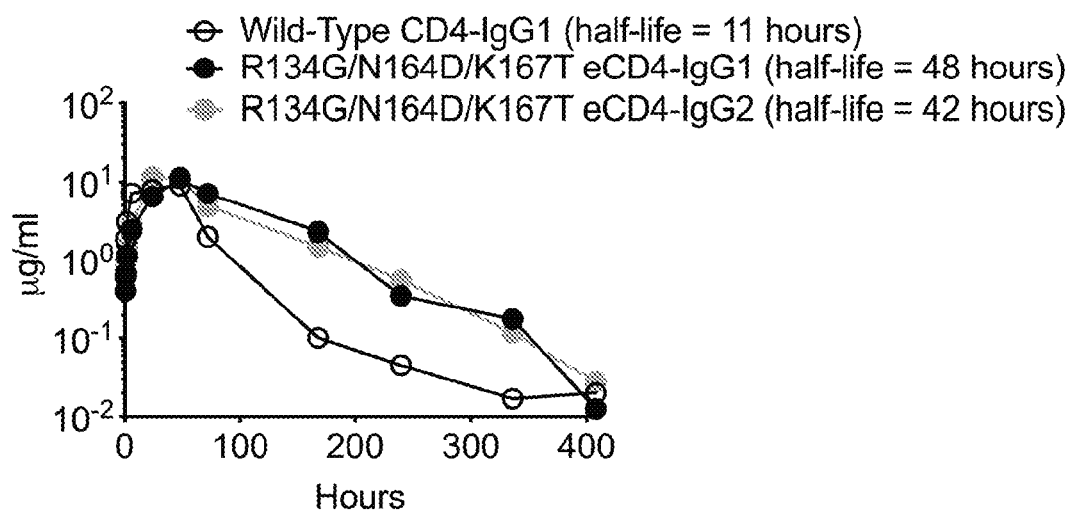
FIG. 21 is a line graph showing pharmacokinetics in rats of wild-type CD4-Ig and eCD4-Ig variants with substitutions that improve conformational stability. Wild-type human CD4-Ig, R134G/N164D/K167T eCD4-IgG1, and R134G/N164D/K167T eCD4-IgG2 were administered to rats subcutaneously at 10 mg/kg. The half-life of wild-type human CD4-Ig was calculated to be 11 hours, whereas the half-lives of R134G/N164D/K167T eCD4-IgG1 and eCD4-IgG2 were calculated to be 48 and 42 hours, respectively.

The half-life of wild-type human CD4-Ig was 11 hours in rats (FIG. 21), consistent with published literature (e.g., Chamow, S. M. et al. (1994) BIOCONJUG. CHEM., 5(2): 133-40). However, variants of eCD4-Ig containing the mutations R134G/N164D/K167T had substantially longer half-lives, e.g., 48 hours for R134G/N164D/K167T eCD4-IgG1 and 42 hours for R134G/N164D/K167T eCD4-IgG2. These results suggest that substitutions, e.g., the R134G/N164D/K167T substitutions, which improved the conformational stability of eCD4-Ig in the DLS thermal scan assay, also improve the pharmacokinetics of the protein.

Example 8—Virus Neutralization by CD4 D1D2 Variants

Figure 22:
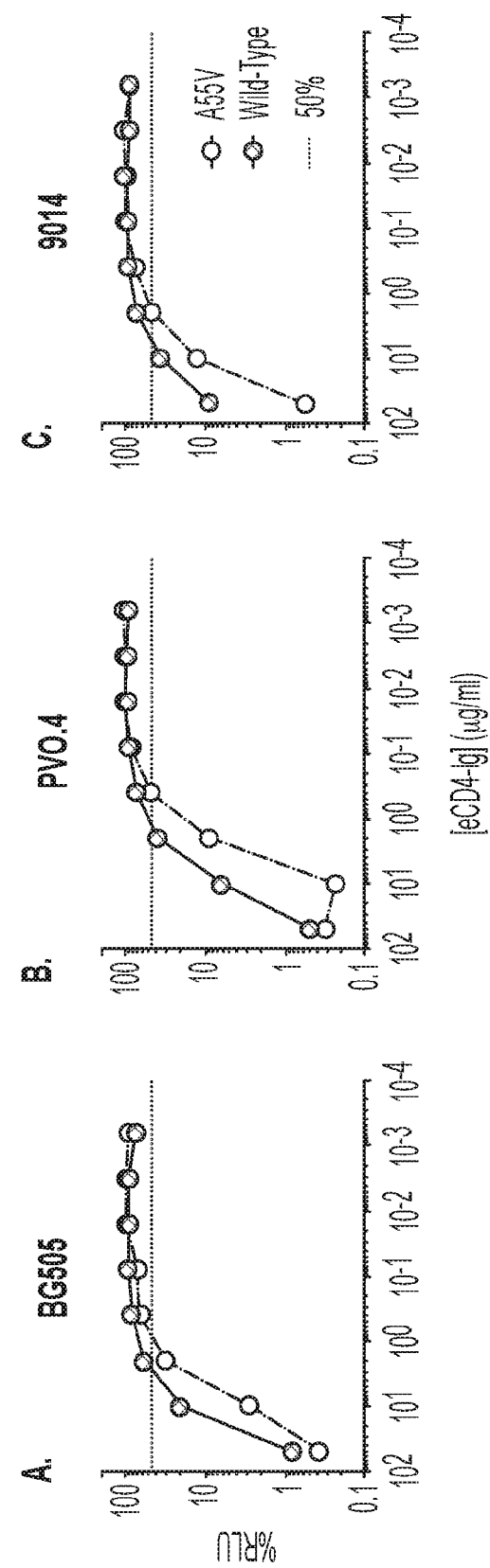
FIG. 22 depicts virus neutralization by eCD4-Ig variants with and without an A55V substitution. Virus neutralization by eCD4-Ig variants with and without the A55V substitution was measured in CD4$^+$ CCR5$^+$ TZM-bl cells, which express firefly luciferase upon infection. R134G/N164D/K167T eCD4-Ig variants with either the wild-type human A55 residue or the A55V substitution were titered over serial 5-fold dilutions. The ability of eCD4-Ig variants with and without the A55V substitution to neutralize infection by BG505 (FIG. 22A), PVO.4 (FIG. 22B), and 9014 (FIG. 22C) pseudoviruses was compared. The percent virus infection, relative to the amount of luciferase expressed in the absence of any eCD4-Ig, is indicated as percent relative light units (% RLU). The dashed line indicates 50% virus infection.
Figure 23:
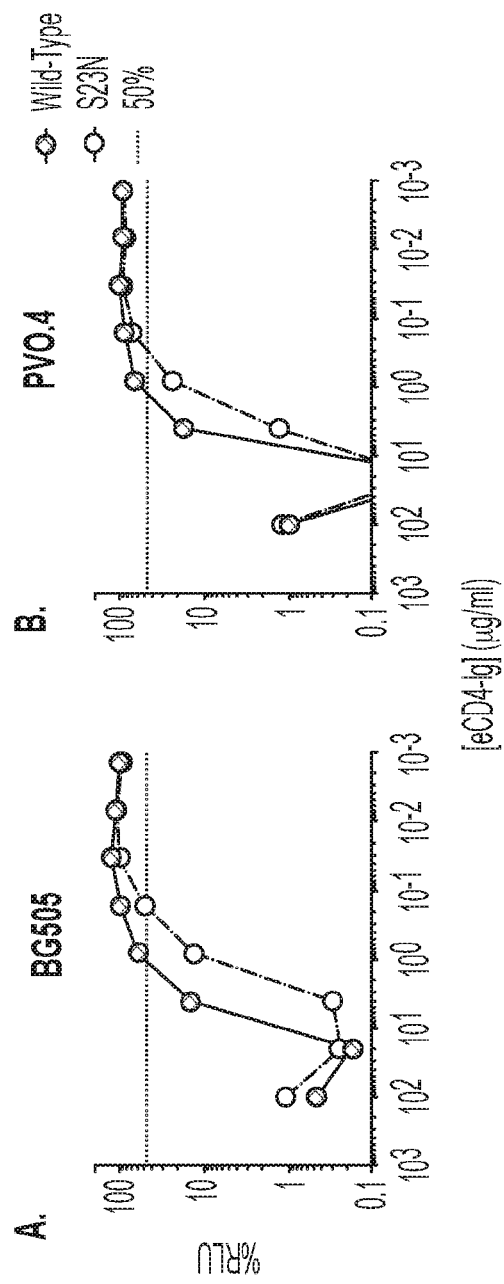
FIG. 23 depicts virus neutralization by eCD4-Ig variants with and without the S23N substitution. Virus neutralization by eCD4-Ig variants with and without the S23N substitution was measured in CD4$^+$ CCR5$^+$ TZM-bl cells, which express firefly luciferase upon infection. L5Y/A55V/I76P/L96V/R134G/N164D/K167T eCD4-Ig variants with either the wild-type human S23 residue or the S23N substitution were titered over serial 5-fold dilutions. The ability of eCD4-Ig variants with and without the S23N substitution to neutralize infection by BG505 (FIG. 23A) and PVO.4 (FIG. 23B) pseudoviruses was compared. The percent virus infection, relative to the amount of luciferase expressed in the absence of any eCD4-Ig, is indicated as percent relative light units (% RLU). The dashed line indicates 50% virus infection.

This Example describes neutralization of virus by proteins including CD4 D1D2 variants with improved stability and pharmacokinetics identified in Examples 2-7.

eCD4-Ig variants with and without the A55V substitution were tested for viral neutralization. The effect of the A55V substitution was tested in the R134G/N164D/K167T mutational background. The A55V mutation improved the potency with which eCD4-Ig neutralizes the infection of three different primary isolates of HIV: BG505 (FIG. 22A), PVO.4 (FIG. 22B) and 9014 (FIG. 22C). eCD4-Ig variants with and without the S23N substitution were also tested for viral neutralization. The effect of the S23N substitution was tested in the L5Y/A55V/I76P/L96V/R134G/N164D/K167T mutational background. The presence of the S23N substitution improved the ability of eCD4-Ig to neutralize two different HIV strains: the clade A virus BG505 (FIG. 23A) and the clade B virus PVO.4 (FIG. 23B). Together, these results suggest that substitutions at positions S23 and A55 in human CD4 D1D2 (SEQ ID NO:1), e.g., the S23N and A55V substitutions, increase viral neutralization by proteins including CD4 D1D2, e.g., eCD4-Ig.

Figure 24:
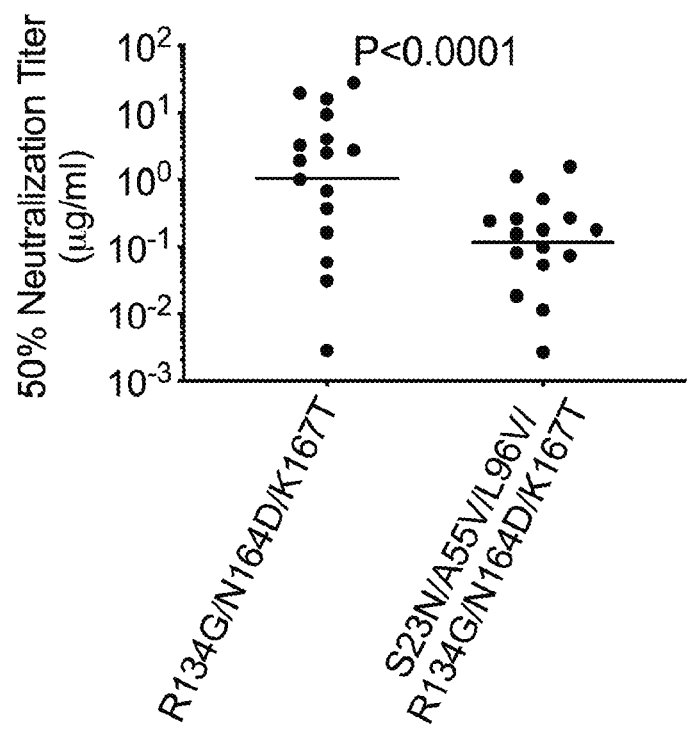
FIG. 24 is a scatter plot depicting virus neutralization by the indicated eCD4-Ig variants. Virus neutralization assays were performed against a panel of test viruses, including 398F1, BG505, 246F3, Tro.11, X2278, 9014, PVO.4, T257-10, CE0217, ZM651, CNE8, CNE55, BJOX2000, CH119, X1634, and 89.6. The target cells were CD4$^+$ CCR5$^+$ TZM-bl cells, which express firefly luciferase upon infection. The percent virus infection, relative to the amount of luciferase expressed in the absence of any eCD4-Ig, is indicated as percent relative light units (% RLU). The dashed line indicates 50% virus infection. In the context of an R134G/N164D/K167T background, the presence of the substitutions S23N/A55V/L96V led to a significant decrease in the concentration of eCD4-Ig needed to inhibit 50% of HIV infection (P<0.0001, Wilcoxon matched pairs test).

The ability of an eCD4-Ig variant containing the substitutions S23N/A55V/L96V/R134G/N164D/K167T (68.5° C. aggregation temperature) to neutralize a panel of test viruses was compared against that of a variant containing the substitutions R134G/N164D/K167T (60° C. aggregation temperature). The test viruses were 398F1, BG505, 246F3, Tro.11, X2278, 9014, PVO.4, T257-10, CE0217, ZM651, CNE8, CNE55, BJOX2000, CH119, X1634, and 89.6. The eCD4-Ig variant with the 68.5° C. aggregation temperature neutralized virus infection significantly better than the eCD4-Ig variant with the 60° C. aggregation temperature (P<0.0001, Wilcoxon matched pairs test) (FIG. 24). The geometric mean concentration of eCD4-Ig needed to neutralize 50% of virus infection was approximately one order of magnitude lower for the variant with the 8.5° C.—higher aggregation temperature.

Figure 25:
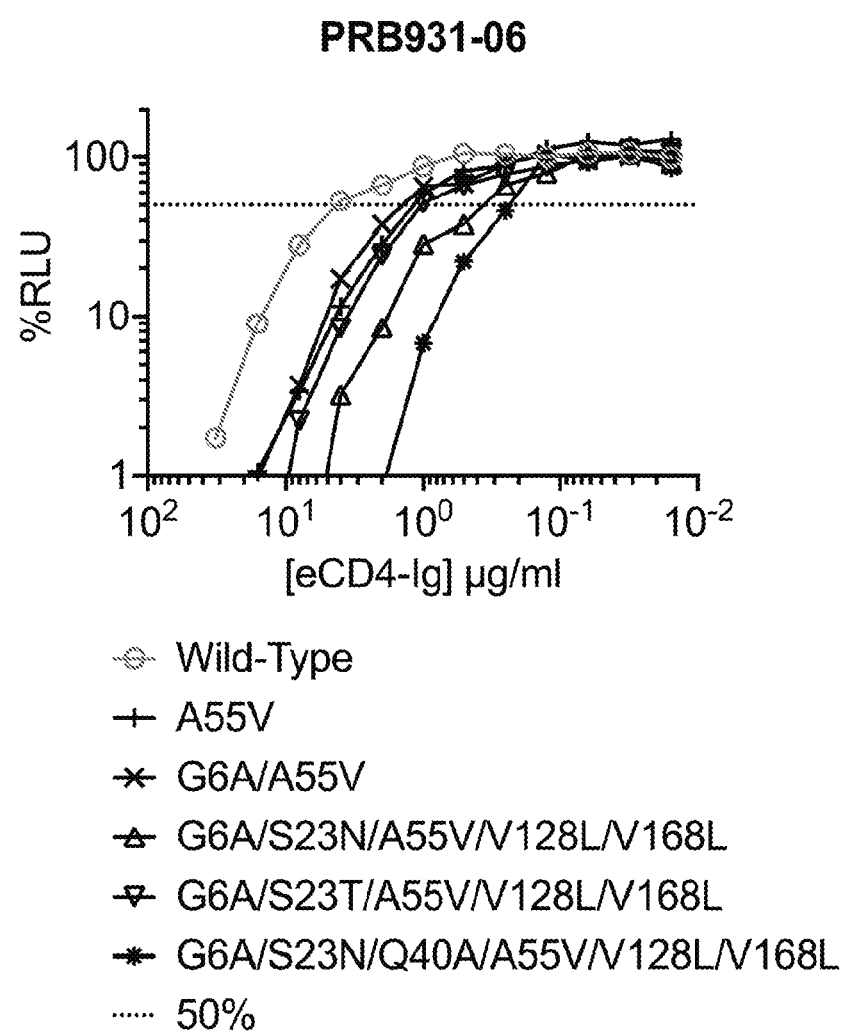
FIG. 25 depicts virus neutralization by eCD4-Ig variants that contain glycine or buried hydrophobic amino acids substituted with a hydrophobic amino acid of larger volume than the amino acid that is replaced. The eCD4-Ig variants tested included a wild-type human CD4 D1D2 (SEQ ID NO:1) control (gray), A55V, G6A/A55V, G6A/S23N/A55V/V128L/V168L, G6A/S23T/A55V/V128L/V168L, and G6A/S23N/Q40A/A55V/V128L/V168L. The test virus is a pseudovirus produced from the envelope glycoprotein of the transmitted/founder (t/f) virus PRB931-06. The target cells were CD4$^+$ CCR5$^+$ TZM-bl cells, which express firefly luciferase upon infection. The percent virus infection, relative to the amount of luciferase expressed in the absence of any eCD4-Ig, is indicated as percent relative light units (% RLU). The dashed line indicates 50% virus infection.

Virus neutralization also was tested for eCD4-Ig variants containing substitutions at glycine or buried hydrophobic amino acids with a hydrophobic amino acid of larger volume than the amino acid that is replaced (FIG. 25). The test virus used in this assay was the transmitted-founder (t/f) virus PRB931-06. The eCD4-Ig variants tested included a wild-type human CD4 D1D2 (SEQ ID NO:1) control (gray), A55V, G6A/A55V, G6A/S23N/A55V/V128L/V168L, G6A/S23N/A55V/V128L/V168L, and G6A/S23N/Q40A/A55V/V128L/V168L. This experiment showed that virus neutralization was highly similar for variants containing A55V, G6A/A55V, and G6A/A55V/S23T/V128L/V168L. However, the inclusion of S23N rather than S23T improved virus neutralization. Furthermore, the neutralization enhancement provided by Q40A was not redundant with the neutralization enhancement provided by S23N and A55V, and the greatest neutralization potency was observed when these three substitutions were combined. Thus, the substitution of glycine or buried hydrophobic amino acids with a hydrophobic amino acid of larger volume than the amino acid that is replaced does not negatively affect virus neutralization.

These results suggest that substitutions in human CD4 D1D2 (SEQ ID NO:1) that increase aggregation temperature also increase viral neutralization by proteins including CD4 D1D2, e.g., eCD4-Ig.

Example 9—Pharmacokinetics of CD4 D1D2 Variants in Rhesus Macaques

This Example describes the pharmacokinetics in rhesus macaques of proteins including CD4 D1D2 variants with improved stability identified in Example 2.

eCD4-Ig variants with the R134G/N164D/K167T substitutions were constructed with IgG1 and IgG2 immunoglobulin Fc regions. Within the IgG1 and IgG2 Fc regions, variants containing the substitutions M428L and N434S (abbreviated: "LS"), were created which have been shown to extend the half-lives of monoclonal antibodies. The pharmacokinetics of these variants were assessed in vivo, in rhesus macaques. The variants tested here had the following aggregation temperatures: R134G/N164D/K167T eCD4-IgG1, 60° C.; R134G/N164D/K167T eCD4-IgG2, 66° C.; R134G/N164D/K167T LS eCD4-IgG1, 68° C.; and R134G/N164D/K167T eCD4-IgG2, 66° C.

Figure 26:
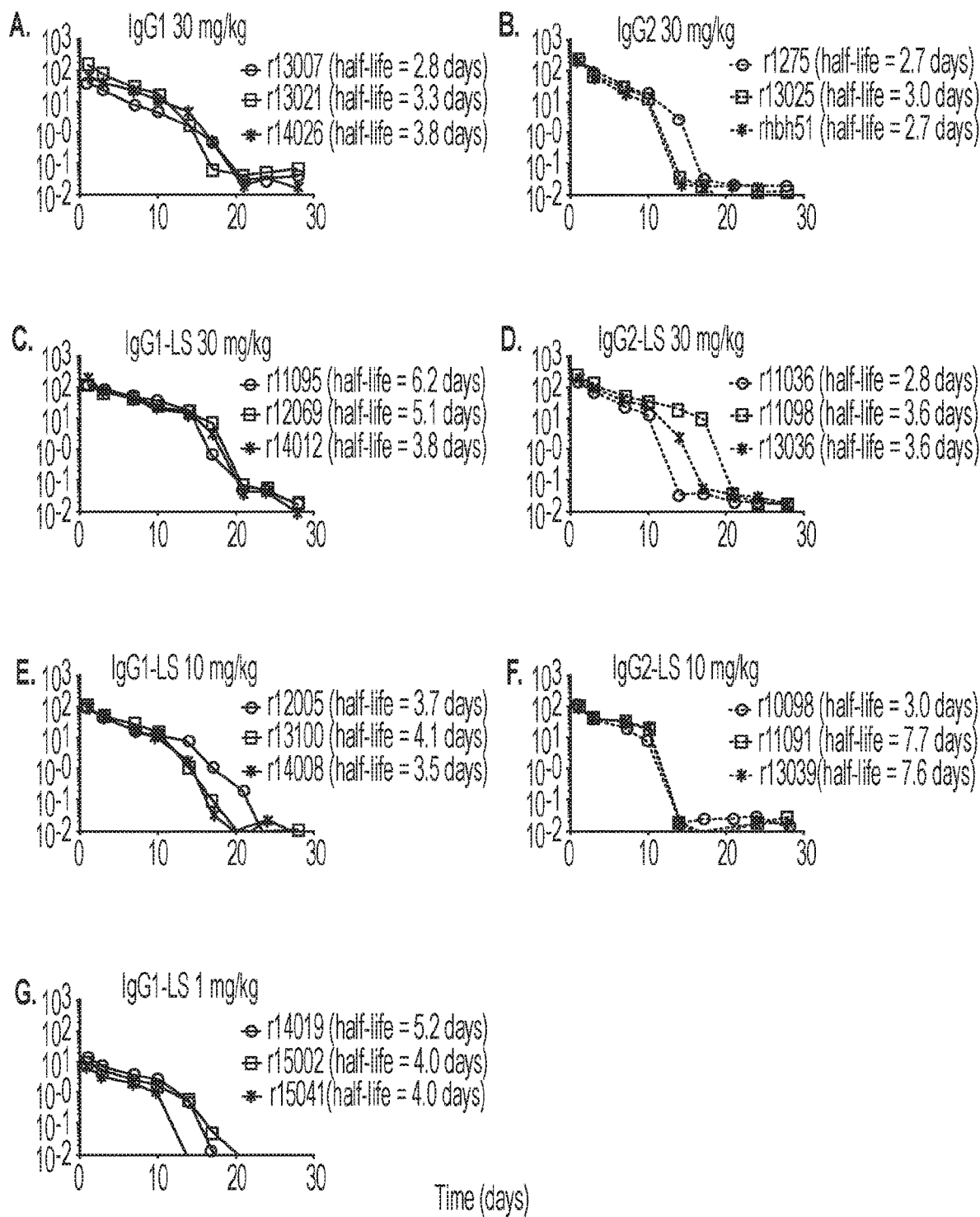
FIG. 26 is a series of line graphs depicting the pharmacokinetics in rhesus macaques of eCD4-Ig variants. The eCD4-Ig variants evaluated in macaques all had the substitutions R134G/N164D/K167T. Where indicated, the eCD4-Ig variants had the "LS" substitutions (M428L and N434S) in the immunoglobulin Fc domain. The half-life of each eCD4-Ig variant in each rhesus macaque is indicated next to the rhesus macaque's number (e.g., animal number r13007, half-life=2.8 days). Groups of three rhesus macaques received intravenous infusions of R134G/N164D/K167T eCD4-IgG1 at 30 mg/kg (FIG. 26A), R134G/N164D/K167T eCD4-IgG2 at 30 mg/kg (FIG. 26B), R134G/N164D/K167T eCD4-IgG1 LS at 30 mg/kg (FIG. 26C), R134G/N164D/K167T eCD4-IgG2 LS at 30 mg/kg (FIG. 26D), R134G/N164D/K167T eCD4-IgG1 LS at 10 mg/kg (FIG. 26E), R134G/N164D/K167T eCD4-IgG2 LS at 10 mg/kg (FIG. 26F), and R134G/N164D/K167T eCD4-IgG1 LS at 1 mg/kg (FIG. 26G). The half-lives were calculated from the first 10 days of data, prior to the potential emergence of anti-drug antibodies. Black symbols indicate plasma eCD4-Ig concentrations in the animals receiving IgG1, whereas gray symbols indicate plasma eCD4-Ig concentrations in the animals receiving IgG2.

Groups of three rhesus macaques received intravenous infusions of R134G/N164D/K167T eCD4-IgG1 at 30 mg/kg (FIG. 26A), R134G/N164D/K167T eCD4-IgG2 at 30 mg/kg (FIG. 26B), R134G/N164D/K167T LS eCD4-IgG1 at 30 mg/kg (FIG. 26C), and R134G/N164D/K167T LS eCD4-IgG2 at 30 mg/kg (FIG. 26D). Each CD4-derived polypeptide tended to exhibit biphasic pharmacokinetic profiles, in which there was a first phase with a half-life of 2.7-6.2 days, and a second phase where plasma concentrations of the polypeptide rapidly declined. Notably, the half-lives observed for R134G/N164D/K167T eCD4-Ig were significantly longer than those reported for CD4-Ig. The presence of the LS substitutions in the IgG1 or IgG2 Fe appeared to modestly lengthen half-life.

Identical pharmacokinetic profiles were observed when the same eCD4-IgG1 proteins were administered to macaques at either 10 mg/kg (FIG. 26E) or at 1 mg/kg (FIG. 26G), as had been observed when they were administered at 30 mg/kg (FIG. 26C). Likewise, identical pharmacokinetic profiles were observed when the same eCD4-IgG2 proteins were administered to macaques at 10 mg/kg (FIG. 26F) as had been observed when they were administered at 30 mg/kg (FIG. 26D).

Example 10—Treatment of Infected Rhesus Macaques with CD4 D1D2 Variants

This Example describes the treatment of SHIV-infected rhesus macaques with proteins including CD4 D1D2 variants with improved stability identified in Example 2.

Figure 27:
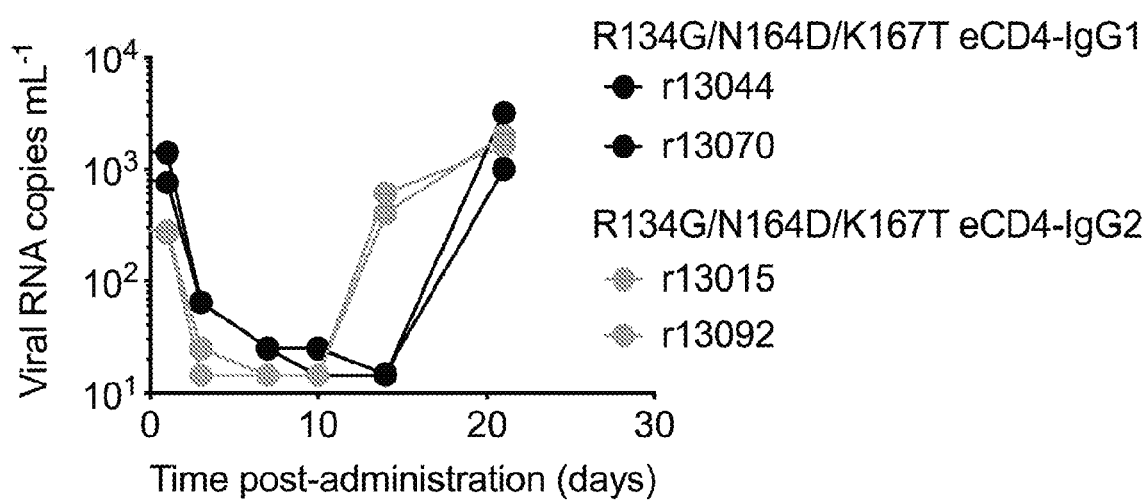
FIG. 27 is a line graph depicting suppression of viral replication in rhesus macaques by eCD4-Ig variants. Rhesus macaques infected with SHIV-AD8 were administered IgG1 or IgG2 forms of R134G/N164D/K167T eCD4-Ig at 30 mg/kg. At various time points thereafter, plasma viral loads were measured (viral RNA copies per mL). Black symbols indicate viral loads in the animals receiving IgG1, whereas gray symbols indicate viral loads in the animals receiving IgG2.

Rhesus macaques infected with SHIV-AD8 were treated with 30 mg/kg intravenously of either the IgG1 or IgG2 forms of R134G/N164D/K167T eCD4-Ig (FIG. 27). Each protein suppressed plasma viral loads by more than one order of magnitude. Viral loads were suppressed to the limit of detection, at least at one time point, in all of the animals. Viral loads rebounded more slowly in the animals that received the IgG1 form of eCD4-Ig, even though these animals started with higher viral loads. These results suggest that proteins, e.g., eCD4-Ig, including the CD4 D1D2 variants described herein, e.g., including the R134G/N164D/K167T substitutions, can suppress virus replication and thereby treat viral infection in primates.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

```
SEQUENCE LISTING
SEQ ID NO: 1:
KKVVLGKKGDTVELTCTASQKKSIQFHWKNSNQIKILGNQGSFLTKGPSKLNDRADSRRSLW

DQGNFPLIIKNLKIEDSDTYICEVEDQKEEVQLLVFGLTANSDTHLLQGQSLTLTLESPPGS

SPSVQCRSPRGKNIQGGKTLSVSQLELQDSGTWTCTVLQNQKKVEFKIDIVVLA

SEQ ID NO:  2:  DYADYDGGYYYDMD

SEQ ID NO:  3:  DYYDYDGGYYYDMD

SEQ ID NO:  4:  DYYDYDGGYYYDDD

SEQ ID NO:  5:  DYYDYDGGYYYDND

SEQ ID NO:  6:  DYYDYDGGYYYDGD

SEQ ID NO:  7:  DYXDYDGGYYYDXD, where X is any amino acid.
```

SEQ ID NO: 8:
KKVVLGKKGDTVELTCTASQKKSIQFHWKNSNQIKILGNQGSFLTKGPSKLNDRADSRRSLW

DQGNFPLIIKNLKIEDSDTYICEVEQKEEVQLLVFGLTANSDTHLLQGQSLTLTLESPPGSS

PSVQCRSPGGKNIQGGKTLSVSQLELQDSGTWTCTVLQDQKTVEFKIDIVVLA

SEQ ID NO: 9:
AAGAAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGCCGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 10:
KKVVLGKKGDTVELTCTASQKKSIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSVQCRSPRGKNIQGGKTLSVSQLELQDSGTWTCTVLQNQKKVEFKIDIVVLA

SEQ ID NO: 11:
AAGAAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCAGAGGCAAGAACATCCAGGGCGGCAAGACCCTGAG

CGTGAGCCAGCTGGAGCTGCAGGACAGCGGCACCTGGACCTGCACCGTGCTGCAGAACCAGA

AGAAGGTGGAGTTCAAGATCGACATCGTGGTGCTGGCC

SEQ ID NO: 12:
KKVVLGKKGDTVELTCTASQKKSIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIVVLA

SEQ ID NO: 13:
AAGAAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 14:
KKVVLGKKGDTVELTCTASQKKNIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIVVLA

SEQ ID NO: 15:
AAGAAGGTGGTGCTGGGCAAGAAGGGCGACACCGTGGAGCTGACCTGCACCGCCAGCCAGAA

GAAGAACATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 16:
NEVVLGKKGDTVELTCTASQKKSIQFHWKNSNQIKILGNQGSFLTKGPSKLNDRADSRRSLW

DQGNFPLIIKNLKIEDSDTYICEVEDQKEEVQLLVFGLTANSDTHLLQGQSLTLTLESPPGS

SPSVQCRSPRGKNIQGGKTLSVSQLELQDSGTWTCTVLQNQKKVEFKIDIVVLA

SEQ ID NO: 17:
AACGAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGCCGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCAGAGGCAAGAACATCCAGGGCGGCAAGACCCTGAG

CGTGAGCCAGCTGGAGCTGCAGGACAGCGGCACCTGGACCTGCACCGTGCTGCAGAACCAGA

AGAAGGTGGAGTTCAAGATCGACATCGTGGTGCTGGCC

SEQ ID NO: 18:
KKVVLGEEGDTVELTCTASQKKSIQFHWKNSNQIKILGNQGSFLTKGPSKLNDRADSRRSLW

DQGNFPLIIKNLKIEDSDTYICEVEDQKEEVQLLVFGLTANSDTHLLQGQSLTLTLESPPGS

SPSVQCRSPRGKNIQGGKTLSVSQLELQDSGTWTCTVLQNQKKVEFKIDIVVLA

SEQ ID NO: 19:
AAGAAGGTGGTGCTGGGCGAGGAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGCCGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCAGAGGCAAGAACATCCAGGGCGGCAAGACCCTGAG

CGTGAGCCAGCTGGAGCTGCAGGACAGCGGCACCTGGACCTGCACCGTGCTGCAGAACCAGA

AGAAGGTGGAGTTCAAGATCGACATCGTGGTGCTGGCC

SEQ ID NO: 20:
NEVVLGKKGDTVELTCTASQKKSIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIVVLA

SEQ ID NO: 21:
AACGAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 22:
KKVVLGEEGDTVELTCTASQKKSIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIVVLA

SEQ ID NO: 23:
AAGAAGGTGGTGCTGGGCGAGGAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 24:
KKVVLGKKGDTVELTCTASQKKSIQFHWKNSNQIKILGNQGSFLTKGPSKLNDRVDSRRSLW

DQGNFPLIIKNLKIEDSDTYICEVEDQKEEVELLVFGLTANSDTHLLEGQSLTLTLESPPGS

SPSVQCRSPGGKNIQGGKTLSVSQLELQDSGTWTCTVLQDQKTVEFKIDIVVLA

SEQ ID NO: 25:
AAGAAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGGAGCTGCTGGTGTTCGGCCTGACCGCCAACA

GCGACACCCACCTGCTGGAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 26:
KKVVLGKKGDTVELTCTASQKKSIQFHWKNSNQIKILGNQGSFLTKGPSKLNDRVDSRRSLW

DQGNFPLIISNLKIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIVVLA

SEQ ID NO: 27:
AAGAAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAGCAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 28:
KKVVLGKKGDTVELTCTASQKKSIQFHWKNSNQIKILGNQGSFLTKGPSKLNDRVDSRRSLW

DQGNFPLIIKNLEIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIWLA

SEQ ID NO: 29:
AAGAAGGTGGTGCTGGGCAAGAAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGGAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 30:
NEVVLGEEGDTVELTCTASQKKSIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSVQCRSPGGKNIQGGKTLSVSQLELQDSGTWTCTVLQDQKTVEFKIDIVVLA

SEQ ID NO: 31:
AACGAGGTGGTGCTGGGCGAGGAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 32:
GNEVVLGEEGDTVELTCTASQKKSIQFHWKNSNQIKILGNQGSFLTKGPSKLNDRVDSRRSL

-continued

WDQGNFPLIIKNLKIEDSDTYICEVEDQKEEVQLLVFGLTANSDTHLLQGQSLTLTLESPPG

SSPSVQCRSPGGKNIQGGKTLSVSQLELQDSGTWTCTVLQDQKTVEFKIDIVVLA

SEQ ID NO: 33:
AACGAGGTGGTGCTGGGCGAGGAGGGCGACACCGTGGAGCTGACCTGCACCGCCAGCCAGAA

GAAGAGCATCCAGTTCCACTGGAAGAACAGCAACCAGATCAAGATCCTGGGCAACCAGGGCA

GCTTCCTGACCAAGGGCCCCAGCAAGCTGAACGACAGAGTGGACAGCAGAAGAAGCCTGTGG

GACCAGGGCAACTTCCCCCTGATCATCAAGAACCTGAAGATCGAGGACAGCGACACCTACAT

CTGCGAGGTGGAGGACCAGAAGGAGGAGGTGCAGCTGCTGGTGTTCGGCCTGACCGCCAACA

GCGACACCCACCTGCTGCAGGGCCAGAGCCTGACCCTGACCCTGGAGAGCCCCCCCGGCAGC

AGCCCCAGCGTGCAGTGCAGAAGCCCCGGCGGCAAGAACATCCAGGGCGGCAAGACCCTGAG

CGTGAGCCAGCTGGAGCTGCAGGACAGCGGCACCTGGACCTGCACCGTGCTGCAGGACCAGA

AGACCGTGGAGTTCAAGATCGACATCGTGGTGCTGGCC

SEQ ID NO: 34:
GCGCGCTCGCTCGCTCACTGAGGCCGCCCGGGCAAAGCCCGGGCGTCGGGCGACCTTTGGTC

GCCCGGCCTCAGTGAGCGAGCGAGCGCGCAGAGAGGGAGTGGCCAACTCCATCACTAGGGGT

TCCTTGTAGTTAATGATTAACCCGCCATGCTAATTATCTACGTAGCCATGTCTAGGGTCGTT

ACATAACTTACGGTAAATGGCCCGCCTGGCTGACCGCCCAACGACCCCCGCCCATTGACGTC

AATAATGACGTATGTTCCCATAGTAACGCCAATAGGGACTTTCCATTGACGTCAATGGGTGG

AGTATTTACGGTAAACTGCCCACTTGGCAGTACATCAAGTGTATCATATGCCAAGTACGCCC

CCTATTGACGTCAATGACGGTAAATGGCCCGCCTGGCATTATGCCCAGTACATGACCTTATG

GGACTTTCCTACTTGGCAGTACATCTACGTATTAGTCATCGCTATTACCATGGTGATGCGGT

TTTGGCAGTACATCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAAAATGTCG

TAACAACTCCGCCCCATTGACGCAAATGGGCGGTAGGCGTGTACGGTGGGAGGTCTATATAA

GCAGAGCTCGTTTAGTGAACCGTCAGATCGCCTGGAGACGCCATCCACGCTGTTTTGACCTC

CATAGAAGACACCGGGACCGATCCAGCCTCCGGACTCTAGAGGATCCGGTACTCGAGGAACT

GAAAAACCAGAAAGTTAACTGGTAAGTTTAGTCTTTTTGTCTTTTATTTCAGGTCCCGGATC

CGGTGGTGGTGCAAATCAAAGAACTGCTCCTCAGTGGATGTTGCCTTTACTTCTAGGCCTGT

ACGGAAGTGTTACTTCTGCTCTAAAAGCTGCGGAATTGTACCCGCGGCCGCAGCGCTCCACC

ATGAACAGAGGCGTGCCCTTCAGACACCTGCTGCTGGTGCTGCAGCTGGCCCTGCTGCCCGC

CGCCACCCAGGGCAAGAAGGTGGTGCTGGGCAAGAAGGGCGACACCGTGGAGCTGACCTGCA

CCGCCAGCCAGAAGAAGAGCATCCAGTTCCACTGGAAGAACAGCAACCAGATCAAGATCCTG

GGCAACCAGGGCAGCTTCCTGACCAAGGGCCCCAGCAAGCTGAACGACAGAGTGGACAGCAG

AAGAAGCCTGTGGGACCAGGGCAACTTCCCCCTGATCATCAAGAACCTGAAGATCGAGGACA

GCGACACCTACATCTGCGAGGTGGAGGACCAGAAGGAGGAGGTGCAGCTGCTGGTGTTCGGC

CTGACCGCCAACAGCGACACCCACCTGCTGCAGGGCCAGAGCCTGACCCTGACCCTGGAGAG

CCCCCCCGGCAGCAGCCCCAGCGTGCAGTGCAGAAGCCCCGGCGGCAAGAACATCCAGGGCG

GCAAGACCCTGAGCGTGAGCCAGCTGGAGCTGCAGGACAGCGGCACCTGGACCTGCACCGTG

CTGCAGGACCAGAAGACCGTGGAGTTCAAGATCGACATCGTGGTGCTGGCCGAGCCCAAGAG

CAGCGACAAGACCCACACCTGCCCCCCCTGCCCCGCCCCCGAGCTGCTGGGCGGCCCCAGCG

TGTTCCTGTTCCCCCCCAAGCCCAAGGACACCCTGATGATCAGCAGAACCCCCGAGGTGACC

-continued

```
TGCGTGGTGGTGGACGTGAGCCACGAGGACCCCGAGGTGAAGTTCAACTGGTACGTGGACGG
CGTGGAGGTGCACAACGCCAAGACCAAGCCCAGAGAGGAGCAGTACAACAGCACCTACAGAG
TGGTGAGCGTGCTGACCGTGCTGCACCAGGACTGGCTGAACGGCAAGGAGTACAAGTGCAAG
GTGAGCAACAAGGCCCTGCCCGCCCCCATCGAGAAGACCATCAGCAAGGCCAAGGGCCAGCC
CAGAGAGCCCCAGGTGTACACCCTGCCCCCCAGCAGAGACGAGCTGACCAAGAACCAGGTGA
GCCTGACCTGCCTGGTGAAGGGCTTCTACCCCAGCGACATCGCCGTGGAGTGGGAGAGCAAC
GGCCAGCCCGAGAACAACTACAAGACCACCCCCCCCGTGCTGGACAGCGACGGCAGCTTCTT
CCTGTACAGCAAGCTGACCGTGGACAAGAGCAGATGGCAGCAGGGCAACGTGTTCAGCTGCA
GCGTGATGCACGAGGCCCTGCACAACCACTACACCCAGAAGAGCCTGAGCCTGAGCCCCGGC
AAGGGCGGCGGCGGCGGCGACTACTACGACTACGACGGCGGCTACTACTACGACGGCGACTG
AGCGGCCGCAATCAACCTCTGGATTACAAAATTTGTGAAAGATTGACTGGTATTCTTAACTA
TGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGCAACCCCCAC
TGGTTGGGGCATTGCCACCACCTGTCAGCTCCTTTCCGGACTTTCGCTTTCCCCCTCCCTA
TTGCCACGGCGGAACTCATCGCCGCCTGCCTTGCCCGCTGCTGGACAGGGGCTCGGCTGTTG
GGCACTGACAATTCCGTGGTGTTGTCGGGGAAATCATCGTCCTTTCCTTGGCTGCTCGCCTG
TGTTGCCACCTGGATTCTGCGCGGGACGTCCTTCTGCTACGTCCCTTCGGCCCTCAATCCAG
CGGACCTTCCTTCCCGCGGCCTGCTGCCGGCTCTGCGGCCTCTTCCGCGTCTTCGCCTTCGC
CCTCAGACGAGTCGGATCTCCCTTTGGGCCGCCTCCCCGCCTGGGGGATCCAGACATGATAA
GATACATTGATGAGTTTGGACAAACCACAACTAGAATGCAGTGAAAAAAATGCTTTATTTGT
GAAATTTGTGATGCTATTGCTTTATTTGTAACCATTATAAGCTGCAATAAACAAGTTAACAA
CAACAATTGCATTCATTTTATGTTTCAGGTTCAGGGGGAGGTGTGGGAGGTTTTTTCGGATC
CTCTAGAGTCGACCAGAGCATGGCTACGTAGATAAGTAGCATGGCGGGTTAATCATTAACTA
CAAGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGCGGCCTCAGTGAGCGAGCGA
GCGCGCCAGCTGCATTAATGAATCGGCCAACGCGCGGGGAGAGGCGGTTTGCGTATTGGGC
```

SEQ ID NO: 35:
```
ATGAACCGGGGAGTCCCTTTTAGGCACTTGCTTCTGGTGCTGCAACTGGCGCTCCTCCCAGC
AGCCACTCAGGGAAAGAAAGTGGTGCTGGCAAAAAAGGGGATACAGTGGAACTGACCTGTA
CAGCTTCCCAGAAGAAGAGCATACAATTCCACTGGAAAAACTCCAACCAGATAAAGATTCTG
GGAAATCAGGGCTCCTTCTTAACTAAAGGTCCATCCAAGCTGAATGATCGCGCTGACTCAAG
AAGAAGCCTTTGGGACCAAGGAAACTTTCCCCTGATCATCAAGAATCTTAAGATAGAAGACT
CAGATACTTACATCTGTGAAGTGGAGGACCAGAAGGAGGAGGTGCAATTGCTAGTGTTCGGA
TTGACTGCCAACTCTGACACCCACCTGCTTCAGGGGCAGAGCCTGACCCTGACCTTGGAGAG
CCCCCCTGGTAGTAGCCCCTCAGTGCAATGTAGGAGTCCAAGGGGTAAAAACATACAGGGGG
GGAAGACCCTCTCCGTGTCTCAGCTGGAGCTCCAGGATAGTGGCACCTGGACATGCACTGTC
TTGCAGAACCAGAAGAAGGTGGAGTTCAAAATAGACATCGTGGTGCTAGCT
```

SEQ ID NO: 36:
```
KKVVLAKKGDTVELTCTASQKKNIQFHWKNSNQIKILGNQGSFLTKGPSKLNDRVDSRRSLW
DQGNFPLIIKNLKIEDSDTYICEVEDQKEEVQLLVFGLTANSDTHLLQGQSLTLTLESPPGS
SPSLQCRSPRGKNIQGGKTLSVSQLELQDSGTWTCTVLQNQKKLEFKIDIVVLA
```

SEQ ID NO: 37:
AAGAAGGTGGTGCTGGCCAAGAAGGGCGATACCGTGGAGCTGACCTGCACCGCCAGCCAGAA

GAAGAACATCCAGTTCCACTGGAAGAACAGCAACCAGATCAAGATCCTGGGCAACCAGGGCA

GCTTCCTGACCAAGGGCCCAAGCAAGCTGAACGATAGAGTGGATAGCAGAAGAAGCCTGTGG

GATCAGGGCAACTTCCCACTGATCATCAAGAACCTGAAGATCGAGGATAGCGATACCTACAT

CTGCGAGGTGGAGGATCAGAAGGAGGAGGTGCAGCTGCTGGTGTTCGGCCTGACCGCCAACA

GCGATACCCACCTGCTGCAGGGCCAGAGCCTGACCCTGACCCTGGAGAGCCCACCAGGCAGC

AGCCCAAGCCTGCAGTGCAGAAGCCCAAGAGGCAAGAACATCCAGGGCGGCAAGACCCTGAG

CGTGAGCCAGCTGGAGCTGCAGGATAGCGGCACCTGGACCTGCACCGTGCTGCAGAACCAGA

AGAAGCTGGAGTTCAAGATCGATATCGTGGTGCTGGCC

SEQ ID NO: 38:
KKVVLAKKGDTVELTCTASQKKNIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSLQCRSPRGKNIQGGKTLSISQLELQDSGTWTCTVLQNQKKLEFKIDIVVLA

SEQ ID NO: 39:
AAGAAGGTGGTGCTGGCCAAGAAGGGCGATACCGTGGAGCTGACCTGCACCGCCAGCCAGAA

GAAGAACATCCAGTTCCACTGGAAGAACAGCAACCAGATCAAGATCCTGGGCAACCAGGGCA

GCTTCCTGACCAAGGGCCCAAGCAAGCTGAACGATAGAGTGGATAGCAGAAGAAGCCTGTGG

GATCAGGGCAACTTCCCACTGATCATCAAGAACCTGAAGATCGAGGATAGCGATACCTACAT

CTGCGAGGTGGAGGATCAGAAGGAGGAGGTGCAGCTGCTGGTGTTCGGCCTGACCGCCAACA

GCGATACCCACCTGCTGCAGGGCCAGAGCCTGACCCTGACCCTGGAGAGCCCACCAGGCAGC

AGCCCAAGCCTGCAGTGCAGAAGCCCAAGAGGCAAGAACATCCAGGGCGGCAAGACCCTGAG

CATCAGCCAGCTGGAGCTGCAGGATAGCGGCACCTGGACCTGCACCGTGCTGCAGAACCAGA

AGAAGCTGGAGTTCAAGATCGATATCGTGGTGCTGGCC

SEQ ID NO: 40:
KKVVLGKKGDTVELTCTASQKKNIQFHWKNSNQIKILGNQGSFLTKGPSKLNDRVDSRRSLW

DQGNFPLIISNLEIEDSDTYICEVEDQKEEVELVVFGLTANSDTHLLEGQSLTLTLESPPGS

SPSVQCRSPGGKNIQGGKTLSVSQLELQDSGTWTCTVLQDQKTVEFKIDIVVLA

SEQ ID NO: 41:
AAGAAGGTGGTGCTGGGCAAGAAGGGCGATACCGTGGAGCTGACCTGCACCGCCAGCCAGAA

GAAGAACATCCAGTTCCACTGGAAGAACAGCAACCAGATCAAGATCCTGGGCAACCAGGGCA

GCTTCCTGACCAAGGGCCCAAGCAAGCTGAACGATAGAGTGGATAGCAGAAGAAGCCTGTGG

GATCAGGGCAACTTCCCACTGATCATCAGCAACCTGGAGATCGAGGATAGCGATACCTACAT

CTGCGAGGTGGAGGATCAGAAGGAGGAGGTGGAGCTGGTGGTGTTCGGCCTGACCGCCAACA

GCGATACCCACCTGCTGGAGGGCCAGAGCCTGACCCTGACCCTGGAGAGCCCACCAGGCAGC

AGCCCAAGCGTGCAGTGCAGAAGCCCAGGCGGCAAGAACATCCAGGGCGGCAAGACCCTGAG

CGTGAGCCAGCTGGAGCTGCAGGATAGCGGCACCTGGACCTGCACCGTGCTGCAGGATCAGA

AGACCGTGGAGTTCAAGATCGATATCGTGGTGCTGGCC

SEQ ID NO: 42:
KKVVLAKKGDTVELTCTASQKKNIQFHWKNSNQIKILGNQGSFLTKGPSKLNDRVDSRRSLW

DQGNFPLIIKNLKIEDSDTYICEVEDQKEEVQLLVFGLTANSDTHLLQGQSLTLTLESPPGS

SPSLQCRSPGGKNIQGGKTLSISQLELQDSGTWTCTVLQNQKKLEFKIDIVVLA

SEQ ID NO: 43:
AAGAAGGTGGTGCTGGCCAAGAAGGGCGATACCGTGGAGCTGACCTGCACCGCCAGCCAGAA

-continued

```
GAAGAACATCCAGTTCCACTGGAAGAACAGCAACCAGATCAAGATCCTGGGCAACCAGGGCA

GCTTCCTGACCAAGGGCCCAAGCAAGCTGAACGATAGAGTGGATAGCAGAAGAAGCCTGTGG

GATCAGGGCAACTTCCCACTGATCATCAAGAACCTGAAGATCGAGGATAGCGATACCTACAT

CTGCGAGGTGGAGGATCAGAAGGAGGAGGTGCAGCTGCTGGTGTTCGGCCTGACCGCCAACA

GCGATACCCACCTGCTGCAGGGCCAGAGCCTGACCCTGACCCTGGAGAGCCCACCAGGCAGC

AGCCCAAGCCTGCAGTGCAGAAGCCCAGGCGGCAAGAACATCCAGGGCGGCAAGACCCTGAG

CATCAGCCAGCTGGAGCTGCAGGATAGCGGCACCTGGACCTGCACCGTGCTGCAGAACCAGA

AGAAGCTGGAGTTCAAGATCGATATCGTGGTGCTGGCC

SEQ ID NO: 44:
KKVVLAKKGDTVELTCTASQKKNIQFHWKNSNQIKILGNQGSFLTKGPSKLNDRVDSRRSLW

DQGNFPLIISNLEIEDSDTYICEVEDQKEEVELLVFGLTANSDTHLLEGQSLTLTLESPPGS

SPSLQCRSPGGKNIQGGKTLSISQLELQDSGTWTCTVLQDQKTLEFKIDIVVLA

SEQ ID NO: 45:
AAGAAGGTGGTGCTGGCCAAGAAGGGCGATACCGTGGAGCTGACCTGCACCGCCAGCCAGAA

GAAGAACATCCAGTTCCACTGGAAGAACAGCAACCAGATCAAGATCCTGGGCAACCAGGGCA

GCTTCCTGACCAAGGGCCCAAGCAAGCTGAACGATAGAGTGGATAGCAGAAGAAGCCTGTGG

GATCAGGGCAACTTCCCACTGATCATCAGCAACCTGGAGATCGAGGATAGCGATACCTACAT

CTGCGAGGTGGAGGATCAGAAGGAGGAGGTGGAGCTGCTGGTGTTCGGCCTGACCGCCAACA

GCGATACCCACCTGCTGGAGGGCCAGAGCCTGACCCTGACCCTGGAGAGCCCACCAGGCAGC

AGCCCAAGCCTGCAGTGCAGAAGCCCAGGCGGCAAGAACATCCAGGGCGGCAAGACCCTGAG

CATCAGCCAGCTGGAGCTGCAGGATAGCGGCACCTGGACCTGCACCGTGCTGCAGGATCAGA

AGACCCTGGAGTTCAAGATCGATATCGTGGTGCTGGCC

SEQ ID NO: 46:
MNRGVPFRHLLLVLQLALLPAATQG

SEQ ID NO: 47:
ATGAACAGAGGCGTGCCCTTCAGACACCTGCTGCTGGTGCTGCAGCTGGCCCTGCTGCCCGC

CGCCACCCAGGGC
```

---

What is claimed is:

1. A protein comprising a human CD4 domain 1 and domain 2 (CD4 D1D2) mutein, wherein the CD4 D1D2 mutein is at least 90% identical to a wild-type human CD4 D1D2 of SEQ ID NO: 1, and comprises at least one substitution in the CD4 domain 1 (D1) and at least one substitution in the CD4 domain 2 (D2), wherein the CD4 D1 corresponds to amino acid residues 1 to 98 of SEQ ID NO: 1 and the CD4 D2 corresponds to amino acid residues 99 to 178 of SEQ ID NO: 1, and wherein each substitution is of (a) a basic amino acid in wild-type human CD4 D1D2 (SEQ ID NO: 1) by an uncharged amino acid;

(b) a basic amino acid in wild-type human CD4 D1D2 (SEQ ID NO: 1) by an acidic amino acid;

(c) an uncharged amino acid in wild-type human CD4 D1D2 (SEQ ID NO: 1) by an acidic amino acid; or (d) a glycine or an amino acid with a buried hydrophobic side chain in wild-type human CD4 D1D2 (SEQ ID NO: 1) by a hydrophobic amino acid that has a larger volume than the amino acid that is replaced;

wherein the CD4 D1D2 mutein is not identical to a naturally-occurring, wild-type non-human primate protein.

2. The protein of claim 1, wherein the CD4 D1D2 mutein comprises at least one substitution at a position corresponding to G6, S23, A55, K72, K75, Q94, L96, Q110, V128, R134, V146, N164, K167, or V168 of wild-type human CD4 D1D2 (SEQ ID NO: 1).

3. The protein of claim 1, wherein the CD4 D1D2 mutein comprises at least one substitution in the CD4 D1 domain and at least one substitution in the CD4 D2 domain.

4. The protein of claim 1, wherein the CD4 D1D2 mutein comprises substitutions at the following positions:

(1) A55 and K72;
(2) A55 and K75;
(3) A55 and Q94;
(4) A55 and Q110;
(5) A55 and L116;
(6) A55 and V128;
(7) A55 and R134;
(8) A55 and V146;
(9) A55 and N164;
(10) A55 and K167;
(11) A55 and V168;
(12) S23 and K72;
(13) S23 and K75;
(14) S23 and Q94;
(15) S23 and Q110;
(16) S23 and L116;
(17) S23 and V128;

(18) S23 and R134;
(19) S23 and V146;
(20) S23 and N164;
(21) S23 and K167; or
(22) S23 and V168.

5. The protein of claim 1, wherein the CD4 D1D2 mutein comprises substitutions at the following positions:
(1) S23, A55, and K72;
(2) S23, A55, and K75;
(3) S23, A55, and Q94;
(4) S23, A55, and Q110;
(5) S23, A55, and L116;
(6) S23, A55, and V128;
(7) S23, A55, and R134;
(8) S23, A55, and V146;
(9) S23, A55, and N164;
(10) S23, A55, and K167;
(11) S23, A55, and V168;
(12) G6, S23, and K72;
(13) G6, S23, and K75;
(14) G6, S23, and Q94;
(15) G6, S23, and Q110;
(16) G6, S23, and L116;
(17) G6, S23, and V128;
(18) G6, S23, and R134;
(19) G6, S23, and V146;
(20) G6, S23, and N164;
(21) G6, S23, and K167;
(22) G6, S23, and V168;
(23) G6, A55, and K72;
(24) G6, A55, and K75;
(25) G6, A55, and Q94;
(26) G6, A55, and Q110;
(27) G6, A55, and L116;
(28) G6, A55, and V128;
(29) G6, A55, and R134;
(30) G6, A55, and V146;
(31) G6, A55, and N164;
(32) G6, A55, and K167;
(33) G6, A55, and V168;
(34) G6, S23, A55, and K72;
(35) G6, S23, A55, and K75;
(36) G6, S23, A55, and Q94;
(37) G6, S23, A55, and Q110;
(38) G6, S23, A55, and L116;
(39) G6, S23, A55, and V128;
(40) G6, S23, A55, and R134;
(41) G6, S23, A55, and V146;
(42) G6, S23, A55, and N164;
(43) G6, S23, A55, and K167; or
(44) G6, S23, A55, and V168.

6. The protein of claim 1, wherein the CD4 D1D2 mutein comprises substitutions at the following positions:
(1) R134, N164, and K167.

7. The protein of claim 1, wherein the CD4 D1D2 mutein comprises substitutions at the following positions:
(1) A55, R134, N164, and K167;
(2) S23, A55, R134, N164, and K167;
(3) A55, V128, and V168;
(4) S23, A55, V128, and V168;
(5) G6, S23, A55, V128, and V168; or
(6) G6, S23, A55, V128, V146, and V168.

8. The protein of claim 1, wherein the CD4 D1D2 mutein comprises substitutions at the following positions:
(1) R134 and K167;
(2) R134 and N164;
(3) N164 and K167;
(4) A55 and R134;
(5) A55 and N164;
(6) A55 and K167;
(7) S23 and R134;
(8) S23 and N164;
(9) S23 and K167; or
(10) S23 and A55.

9. The protein of claim 1, wherein the CD4 D1D2 mutein comprises at least one of the G6A, S23N, A55V, K72S, K75E, K75Q, Q94E, Q110E, V128L, R134G, V146I, N164D, K167T, and V168L substitutions.

10. The protein of claim 9, wherein the CD4 D1D2 mutein comprises at least one of the K72S, K75E, K75Q, Q94E, Q110E, V128L, R134G, V146I, N164D, K167T, and V168L substitutions.

11. The protein of claim 1, wherein the CD4 D1D2 mutein comprises the following substitutions:
(1) A55V and K72S;
(2) A55V and K75E;
(3) A55V and K75Q;
(4) A55V and Q94E;
(5) A55V and Q110E;
(6) A55V and L116F;
(7) A55V and V128L;
(8) A55V and R134G;
(9) A55V and V146I;
(10) A55V and N164D;
(11) A55V and K167T;
(12) A55V and V168L;
(13) S23N and K72S;
(14) S23N and K75E;
(15) S23N and K75Q;
(16) S23N and Q94E;
(17) S23N and Q110E;
(18) S23N and L116F;
(19) S23N and V128I;
(20) S23N and R134G;
(21) S23N and V146I;
(22) S23N and N164D;
(23) S23N and K167T; or
(24) S23N and V168L.

12. The protein of claim 1, wherein the CD4 D1D2 mutein comprises an A55V substitution.

13. The protein of claim 1, wherein the CD4 D1D2 mutein comprises an S23N substitution.

14. The protein of claim 1, wherein the CD4 D1D2 mutein comprises A55V, R134G, N164D, and K167T substitutions.

15. The protein of claim 1, wherein the CD4 D1D2 mutein comprises S23N, A55V, R134G, N164D, and K167T substitutions.

16. The protein of claim 1, wherein the CD4 D1D2 mutein comprises SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 36, SEQ ID NO: 38, SEQ ID NO: 40, SEQ ID NO: 42, or SEQ ID NO: 44.

17. The protein of claim 1, wherein the CD4 D1D2 mutein does not include a substitution of 176 by proline (176P).

18. The protein of claim 1, further comprising a primate lentivirus glycoprotein binding moiety, wherein the binding moiety comprises at least one sulfotyrosine.

19. The protein of claim 18, wherein the binding moiety comprises the amino acid sequence of SEQ ID NO: 2, SEQ ID NO: 3, SEQ ID NO: 4, SEQ ID NO: 5, SEQ ID NO: 6, or SEQ ID NO: 7.

20. The protein of claim 1, further comprising an immunoglobulin Fc domain.

21. A pharmaceutical composition comprising the protein of claim 1.

22. The protein of claim 1, wherein each substitution is at a position that has a different amino acid in the human CD4 D1D2 protein (SEQ ID NO: 1) than in a non-human primate CD4 D1D2 selected from the group consisting of SEQ ID NOs: 48-90.

23. A method of treating an HIV infection in a subject in need thereof, the method comprising administering to the subject an effective amount of the protein of claim 1.

* * * * *